(12) United States Patent
Arnold et al.

(10) Patent No.: US 7,582,637 B2
(45) Date of Patent: Sep. 1, 2009

(54) PYRROLO-PYRIDINE KINASE MODULATORS

(75) Inventors: William D. Arnold, San Diego, CA (US); Pierre-Yves Bounaud, San Diego, CA (US); Andreas Gosberg, San Diego, CA (US); Zhe Li Bounaud, San Diego, CA (US); Ian McDonald, San Diego, CA (US); Ruo W. Steensma, San Diego, CA (US); Mark E. Wilson, San Diego, CA (US)

(73) Assignee: SGX Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 12/040,527

(22) Filed: Feb. 29, 2008

(65) Prior Publication Data

US 2008/0221119 A1 Sep. 11, 2008

Related U.S. Application Data

(62) Division of application No. 11/192,341, filed on Jul. 27, 2005, now Pat. No. 7,361,763.

(60) Provisional application No. 60/683,510, filed on May 19, 2005, provisional application No. 60/591,887, filed on Jul. 27, 2004, provisional application No. 60/591,888, filed on Jul. 27, 2004.

(51) Int. Cl.
A61K 31/497 (2006.01)
A61K 31/44 (2006.01)

(52) U.S. Cl. .................. 514/253.04; 514/300

(58) Field of Classification Search ............ 514/253.04, 514/300
See application file for complete search history.

(56) References Cited

U.S. PATENT DOCUMENTS

| 5,019,586 | A | 5/1991 | Oxford et al. |
| 5,051,412 | A | 9/1991 | Macor |
| 5,338,849 | A | 8/1994 | Festal et al. |
| 5,563,150 | A | 10/1996 | Curtis et al. |
| 5,643,734 | A | 7/1997 | Henderson |
| 5,681,959 | A | 10/1997 | Bishop et al. |
| 6,335,342 | B1 | 1/2002 | Longo et al. |
| 6,589,950 | B1 | 7/2003 | Collingwood et al. |
| 6,699,883 | B1 | 3/2004 | Doemling et al. |
| 2002/0119982 | A1 | 8/2002 | Wang et al. |
| 2004/0019052 | A1 | 1/2004 | Garland et al. |
| 2007/0043068 | A1 | 2/2007 | Arnold et al. |

FOREIGN PATENT DOCUMENTS

| DE | 10053122 A1 | 5/2001 |
| DE | 1995915 A1 | 8/2001 |
| WO | WO-96-32391 A1 | 10/1996 |
| WO | WO-00-43393 A1 | 7/2000 |
| WO | WO-00-71537 A1 | 11/2000 |
| WO | WO-02-051837 A2 | 7/2002 |
| WO | WO-02-051837 A3 | 7/2002 |
| WO | WO-03-002563 A1 | 1/2003 |
| WO | WO-03-024969 A1 | 3/2003 |
| WO | WO-03-028724 A1 | 4/2003 |
| WO | WO-03-045949 A1 | 6/2003 |
| WO | WO-03-068221 A1 | 8/2003 |
| WO | WO-03-068773 A1 | 8/2003 |
| WO | WO-03-082868 A1 | 10/2003 |
| WO | WO-03-082869 A1 | 10/2003 |
| WO | WO-2004-014368 A1 | 2/2004 |
| WO | WO-2004-024895 A2 | 3/2004 |
| WO | WO-2004-032874 | 4/2004 |
| WO | WO-2004-078756 A2 | 9/2004 |
| WO | WO-2004-078756 A3 | 9/2004 |
| WO | WO-2004-078757 A2 | 9/2004 |
| WO | WO-2004-078757 A3 | 9/2004 |
| WO | WO-2004-101565 A2 | 11/2004 |
| WO | WO-2004-101565 A3 | 11/2004 |
| WO | WO-2005-062795 A2 | 7/2005 |
| WO | WO-2005-062795 A3 | 7/2005 |
| WO | WO-2005-085244 A1 | 9/2005 |
| WO | WO-2005-095400 A1 | 10/2005 |
| WO | WO-2006-015123 A | 2/2006 |
| WO | WO-03-087816 A1 | 10/2006 |
| WO | WO-2006-124863 A2 | 11/2006 |
| WO | WO-2007-106236 A2 | 9/2007 |
| WO | WO-2007-106236 A3 | 9/2007 |

OTHER PUBLICATIONS

PCT/US05/26792 Search Report dated Nov. 28, 2005.
PCT/US07/002123 Search Report dated Dec. 21, 2007.
Adamczyk et al., "Synthesis of 3,7-dihydroimidazol[1,2a]pyrazine-3-ones and their chemiluminescent properties," Tetrahedron 59:8129-8143 (2003).
Altschul et al., "Gapped BLAST and PSI-BLAST: a new generation of protein database search programs," Nucl. Acids Res. 24:3389-3402 (1997).
Arduengo et al., "Adducts of Carbenes with Group II and XII Metallocenes," Organometallics 17:3375-3382 (1998).
Arduengo et al., "Low-Coordinate Carbene Complexes of Nickel(0)and Platinum(0)†," J. Am. Chem. Soc. 116:4391-4394 (1994).
Bach et al., "Synthesis of 2'-Substituted 4-Bromo-2,4'-bithiazoles by Regioselective Cross-Coupling Reactions," J. Org. Chem. 67:5789-5795 (2002).
Berge et al., "Pharmaceutical Salts," J. Pharma. Sci. 66:1-19 (1977).
Blaney, J.M. and Dixon, J.S., "A good ligand is hard to find: Automated docking methods," Perspectivesin Drug Discovery and Design 1:301-319 (1993).
Bolm et al., "Iron-Catalyzed Reactions in Organic Synthesis," Chem. Rev. 104:6217-6254 (2004).

(Continued)

*Primary Examiner*—D. Margaret Seaman
*Assistant Examiner*—Nizal S Chandrakumar
(74) *Attorney, Agent, or Firm*—Wilson Sonsini Goorich & Rosati

(57) ABSTRACT

The present invention provides novel pyrrolo-pyridine kinase modulators and methods of using the novel pyrrolo-pyridine kinase modulators to treat diseases mediated by kinase activity.

32 Claims, 1 Drawing Sheet

OTHER PUBLICATIONS

Boudier et al., "New Applications of Polyfunctional Organometallic Compounds in Organic Synthesis," Angew. Chem. Int. Ed. 39: 4414-4435 (2000).

Brooks et al., "CHARMM: A program for macromolecular energy, minimization, and dynamics calculations," J. Comp. Chem. 4:187-217 (1983).

Charifson et al., "Consensus Scoring: A Method for Obtaining Improved Hit Rates from Docking Databases of Three-Dimensional Structures into Proteins," J. Med. Chem. 42:5100-5109 (1999).

Crabtree, S. et al., "Facile and Gentle Method for Quantitative Lysis of *Escherichia coli* and *Salmonella typhimurium*," J. Bacteriol. 158(1):354-356 (1984).

Deininger, M. et al., "The development of imatinib as a therapeutic agent for chronic myeloid leukemia," Blood 105(7):2640-2653 (2005).

Feldman et al. "Novel Small Molecule Inhibitors of 3-Phosphoinositide-Dependent Kinase-1 (PDK1)," JBC Papers in Press, Published Mar. 16, 2005 Manuscript M501367200.

Furstner et al., "Iron-Catalyzed Cross-Coupling Reactions," J. A. Chem. Soc. 124:13856-13863 (2002).

Goodsell & Olsen, "Automated Docking of Substrates to Proteins by Simulated Annealing," Proteins: Structure, Function and Genetics 8:195-202 (1990).

Harrington et al., "VX-680, a potent and selective small-molecule inhibitor of the Aurora kinases, suppresses tumor growth in vivo," Nature Medicine Advance Online Publication Feb. 22, 2004, pp. 1-6.

Hartwig, Acc. "Carbon-Heteroatom Bond-Forming Reductive Eliminations of Amines, Ethers, and Sulfides," Chem. Res. 31:852-860 (1998).

Ishiyama et al., "Paladium (0)-Catalyzed Cross-Coupling Reaction of Alkoxydiboron with Haloarenes: A Direct Procedure for Arylvoboronic Esters," J. Org. Chem. 60:7508-7510 (1995).

Ji et al., "Selective Amination of Polyhalopyridines Catalyzed by a Palladium-Xantphos Complex," Org. Lett. 5:4611-4614 (2003).

Jones et al., "Molecular Recognition of Receptor Sites using a Genetic Algorithm with a Description of Desolvation," J. Mol. Biol. 245:43-53 (1995).

Kuntz et al., "A Geometric Approach to Macromolecule-Ligand Interactions," J. Mol. Biol. 161:269-288 (1982).

Ley et al., "Modern Synthetic Methods for Copper-Mediated C(aryl)-O, C(aryl)-N, and C(aryl)-S Bond Formation," Angew Chem. 115:5400-5449 (2003).

Littke et al., "Palladium-Catalyzed Coupling Reactions of Aryl Chlorides," Angew. Chem. 41:4176-4211 (2002).

Maryanoff et al., "The Wittig Olefination Reaction and Modifications Involving Phosphoryl-Stabilized Carbanions. Stereochemistry, Mechanism, and Selected Synthetic Aspects," Chem. Rev. 89:863-927 (1989).

Matsui, T. et al., "Expression of Unphosphorylated Form of Human Double-Stranded RNA-Activated Protein Kinase in *Escherichia coli*," Biochem. Biophys. Res. Commun. 284:798-807 (2001).

Meng et al., "Automated Docking with Grid-Based Energy Evaluation," J. Comp. Chem. 13:505-524 (1992).

Molander et al., "Palladium-Catalyzed Suzuki-Miyaura Cross-Coupling Reactions of Potassium Aryl-and Heteroarylatrifluoroborates," J. Org. Chem. 68:4302-4314 (2003).

Molander et al., "*B*-Alkyl Suzuki-Miyaura Cross-Coupling Reactions with Air-Stable Potassium Alkyltrifluoroborates," J. Org. Chem. 68:5534-5539 (2003).

Mongin et al., "Advances in the directed metallation of azines and diazines (pyridines, pyrmimidines, pyrazines, pyrizadines, quinolines, benzodiazines and carbolines). Part 1: Metallation of pyridines, quinolines and carbolines," Tetrahedron 57:4059-4090 (2001).

Nahm et al., "N-Methoxy-N-Methylamides as Effective Acylating Agents," Tetrahedron Lett. 22(39):3815-3818 (1981).

Navarro et al., "Cross-Coupling and Dehalogenation Reactions Catalyzed by (N-Heterocyclic carbene)Pd(allyl)C1 Complexes," J. Org. Chem. 69:3173-3180 (2004).

Rarey et al., "A Fast Flexible Docking Method using an Incremental Construction Algorithm," J. Mol. Biol. 261:470-489 (1996).

Sakamoto et al., "Condensed Heteroaromatic Ring Systems. XXII.[1] Simple and General Synthesis of 1*H*-Pyrrolo-Pyridines," Heterocycles 34(12): 2379-84 (1992).

Sapountzis et al., "A New General Preparation of Polyfunctional Diarylamines by the Addition of Functionalized Arylmagnesium Compounds to Nitroarenes," J. Am. Chem. Soc. 124:9390-9391 (2002).

Thompson et al. "DbClustal: rapid and reliable global multiple alignments of protein sequences detected by database searches," Nucl. Acids Res. 28:2919-2926 (2000).

Travis, J., "Proteins and Organic Solvents Make an Eye-Opening Mix," Science 262:1374 (1993).

Turck et al., Advances in the directed metallation of azines and diazines (pyridines, pyrimidines, pyrazines, pyridazines, quinolines, benzodiazines and carbolines). Part 2. Metallation of pyrimidines, pyrazines, pyridazines and benzodiazines,) Tetrahedron 57:4489-4905 (2001).

Vilar et al., "Monoligated Palladium Species as Catalysts in Cross-Coupling Reactions," Angew. Chem. 117:366-374 (2005).

Weiner et al., "A New Force Field for Molecular Mechanical Simulation of Nucleic Acids and Proteins," J. Am. Chem. Soc. 106:765-784 (1984).

Wolfe et al., "Rational Development of Practical Catalysts for Aromatic Carbon—Nitrogen Bond Formation," Acc. Chem. Res. 31:805-818 (1998).

Zhang et al., "A Simple Statistical Parameter for Use in Evaluation and Validation of High Throughput Screening Assays," J. Biomol. Screening 4(2):67-73 (1999).

PCT/US08/65150 Search Report dated Aug. 21, 2008.

PCT/US08/59964 Search Report dated Nov. 18, 2008.

U.S. Appl. No. 10/139,775, filed May 3, 2002 (Klinger).

Figure 1

```
MLEICLKLVGCKSKKGLSSSSSCYLEEALQRPVASDFEPQGLSEAARWNS
1                                                 50
KENLLAGPSENDPNLFVALYDFVASGDNTLSITKGEKLRVLGYNHNGEWC
51                                                100
EAQTKNGQGWVPSNYITPVNSLEKHSWYHGPVSRNAAEYLLSSGINGSFL
101                                               150
VRESESSPGQRSISLRYEGRVYHYRINTASDGKLYVSSESRFNTLAELVH
151                                               200
HHSTVADGLITTLHYPAPKRNKPTVYGVSPNYDKWEMERTDITMKHKLGG
201                                               250
GQYGEVYEGVWKKYSLTVAVKTLKEDTMEVEEFLKEAAVMKEIKHPNLVQ
251                                               300
LLGVCTREPPFYIITEFMTYGNLLDYLRECNRQEVNAVVLLYMATQISSA
301                                               350
MEYLEKKNFIHRDLAARNCLVGENHLVKVADFGLSRLMTGDTYTAHAGAK
351                                               400
FPIKWTAPESLAYNKFSIKSDVWAFGVLLWEIATYGMSPYPGIDLSQVYE
401                                               450
LLEKDYRMERPEGCPEKVYELMRACWQWNPSDRPSFAEIHQAFETMFQES
451                                               500
SISDEVEKELGKQGVRGAVSTLLQAPELPTKTRTSRRAAEHRDTTDVPEM
501                                               550
PHSKGQGESDPLDHEPAVSPLLPRKERGPPEGGLNEDERLLPKDKKTNLF
551                                               600
SALIKKKKKTAPTPPKRSSSFREMDGQPERRGAGEEEGRDISNGALAFTP
601                                               650
LDTADPAKSPKPSNGAGVPNGALRESGGSGFRSPHLWKKSSTLTSSRLAT
651                                               700
GEEEGGGSSSKRFLRSCSASCVPHGAKDTEWRSVTLPRDLQSTGRQFDSS
701                                               750
TFGGHKSEKPALPRKRAGENRSDQVTRGTVTPPPRLVKKNEEAADEVFKD
751                                               800
IMESSPGSSPPNLTPKPLRRQVTVAPASGLPHKEEAEKGSALGTPAAAEP
801                                               850
VTPTSKAGSGAPGGTSKGPAEESRVRRHKHSSESPGRDKGKLSRLKPAPP
851                                               900
PPPAASAGKAGGKPSQSPSQEAAGEAVLGAKTKATSLVDAVNSDAAKPSQ
901                                               950
PGEGLKKPVLPATPKPQSAKPSGTPISPAPVPSTLPSASSALAGDQPSST
951                                              1000
AFIPLISTRVSLRKTRQPPERIASGAITKGVVLDSTEALCLAISRNSEQM
1001                                             1050
ASHSAVLEAGKNLYTFCVSYVDSIQQMRNKFAFREAINKLENNLRELQIC
1051                                             1100
PATAGSGPAATQDFSKLLSSVKEISDIVQR
1101                          1130
``` ic reticulopathies, psoriasis, and arthritis.

PYRROLO-PYRIDINE KINASE MODULATORS

CROSS-REFERENCES TO RELATED APPLICATIONS

This application is a divisional of patent application of U.S. patent application Ser. No. 11/192,341 filed Jul. 27, 2005, now U.S. Pat. No. 7,361,763, which claims priority under 35 U.S.C. § 119(e) to U.S. Provisional Patent Application No. 60/591,888, filed Jul. 27, 2004, U.S. Provisional Patent Application No. 60/591,887, filed Jul. 27, 2004, and U.S. Provisional Patent Application No. 60/683,510, filed May 19, 2005. The disclosures of these applications are incorporated herein by reference in their entirety.

BACKGROUND OF THE INVENTION

Mammalian protein kinases are important regulators of cellular functions. Because dysfunctions in protein kinase activity have been associated with several diseases and disorders, protein kinases are targets for drug development.

The tyrosine kinase receptor, FMS-like tyrosine kinase 3 (FLT3), is implicated in cancers, including leukemia, such as acute myeloid leukemia (AML), acute lymphoblastic leukemia (ALL), and myelodysplasia. About one-quarter to one-third of AML patients have FLT3 mutations that lead to constitutive activation of the kinase and downstream signaling pathways. Although in normal humans, FLT3 is expressed mainly by normal myeloid and lymphoid progenitor cells, FLT3 is expressed in the leukemic cells of 70-80% of patients with AML and ALL. Inhibitors that target FLT3 have been reported to be toxic to leukemic cells expressing mutated and/or constitutively-active FLT3. Thus, there is a need to develop potent FLT3 inhibitors that may be used to treat diseases and disorders such as leukemia.

The Abelson non-receptor tyrosine kinase (c-Abl) is involved in signal transduction, via phosphorylation of its substrate proteins. In the cell, c-Abl shuttles between the cytoplasm and nucleus, and its activity is normally tightly regulated through a number of diverse mechanisms. Abl has been implicated in the control of growth-factor and integrin signaling, cell cycle, cell differentiation and neurogenesis, apoptosis, cell adhesion, cytoskeletal structure, and response to DNA damage and oxidative stress.

The c-Abl protein contains approximately 1150 amino-acid residues, organized into a N-terminal cap region, an SH3 and an SH2 domain, a tyrosine kinase domain, a nuclear localization sequence, a DNA-binding domain, and an actin-binding domain.

Chronic myelogenous leukemia (CML) is associated with the Philadelphia chromosomal translocation, between chromosomes 9 and 22. This translocation generates an aberrant fusion between the bcr gene and the gene encoding c-Abl. The resultant Bcr-Abl fusion protein has constitutively active tyrosine-kinase activity. The elevated kinase activity is reported to be the primary causative factor of CML, and is responsible for cellular transformation, loss of growth-factor dependence, and cell proliferation.

The 2-phenylaminopyrimidine compound imatinib (also referred to as STI-571, CGP 57148, or Gleevec) has been identified as a specific and potent inhibitor of Bcr-Abl, as well as two other tyrosine kinases, c-kit and platelet-derived growth factor receptor. Imatinib blocks the tyrosine-kinase activity of these proteins. Imatinib has been reported to be an effective therapeutic agent for the treatment of all stages of CML. However, the majority of patients with advanced-stage or blast crisis CML suffer a relapse despite continued imatinib therapy, due to the development of resistance to the drug. Frequently, the molecular basis for this resistance is the emergence of imatinib-resistant variants of the kinase domain of Bcr-Abl. The most commonly observed underlying amino-acid substitutions include Glu255Lys, Thr315Ile, Tyr293Phe, and Met351Thr.

MET was first identified as a transforming DNA rearrangement (TPR-MET) in a human osteosarcoma cell line that had been treated with N-methyl-N'-nitro-nitrosoguanidine (Cooper et al. 1984). The MET receptor tyrosine kinase (also known as hepatocyte growth factor receptor, HGFR, MET or c-Met) and its ligand hepatocyte growth factor ("HGF") have numerous biological activities including the stimulation of proliferation, survival, differentiation and morphogenesis, branching tubulogenesis, cell motility and invasive growth. Pathologically, MET has been implicated in the growth, invasion and metastasis of many different forms of cancer including kidney cancer, lung cancer, ovarian cancer, liver cancer and breast cancer. Somatic, activating mutations in MET have been found in human carcinoma metastases and in sporadic cancers such as papillary renal cell carcinoma. The evidence is growing that MET is one of the long-sought oncogenes controlling progression to metastasis and therefore a very interesting target. In addition to cancer there is evidence that MET inhibition may have value in the treatment of various indications including: Listeria invasion, Osteolysis associated with multiple myeloma, Malaria infection, diabetic retinopathies, psoriasis, and arthritis.

The tyrosine kinase RON is the receptor for the macrophage stimulating protein and belongs to the MET family of receptor tyrosine kinases. Like MET, RON is implicated in growth, invasion and metastasis of several different forms of cancer including gastric cancer and bladder cancer.

The Aurora family of serine/theronine kinases is essential for mitotic progression. Expression and activity of the Arurora kinases are tightly regulated during the cell cycle. A variety of proteins having roles in cell division have been identified as Aurora kinase substrates. Based on the known function of the Aurora kinases, inhibition of their activity is believed to disrupt the cell cycle and block proliferation and therefore tumor cell viability. Harrington et al., *Nature Medicine*, advanced publication online (2004).

3-Phosphoinositide-dependent kinase 1 (PDK1) is a Ser/Thr protein kinase that can phosphorylate and activate a number of kinases in the AGC kinase super family, including Akt/PKB, protein kinase C (PKC), PKC-related kinases (PRK1 and PRK2), p70 ribobsomal S6-kinase (S6K1), and serum and glucocorticoid-regulated kinase (SGK). The first identified PDK1 substrate is the proto-oncogene Akt. Numerous studies have found a high level of activated Akt in a large percentage (30-60%) of common tumor types, including melanoma and breast, lung, gastric, prostate, hematological and ovarian cancers. The PDK1/Akt signaling pathway thus represents an attractive target for the development of small molecule inhibitors that may be useful in the treatment of cancer. Feldman et al., *JBC* Papers in Press. Published on Mar. 16, 2005 as Manuscript M501367200.

Because kinases have been implicated in numerous diseases and conditions, such as cancer, there is a need to develop new and potent protein kinase modulators that can be used for treatment. The present invention fulfills these and other needs in the art. Although certain protein kinases are specifically named herein, the present invention is not limited to modulators of these kinases, and, includes, within its scope, modulators of related protein kinases, and modulators of homologous proteins.

BRIEF SUMMARY OF THE INVENTION

It has been discovered that, surprisingly, pyrrolo-pyridine compounds of the present invention may be used to modulate kinase activity and to treat diseases mediated by kinase activity. These novel pyrrolo-pyridine kinase modulators are described in detail below. In addition, inhibitory activities of selected compounds are disclosed herein.

In one aspect, the present invention provides a pyrrolo-pyridine kinase modulator (also referred to herein as a "compound of the present invention") having the formula:

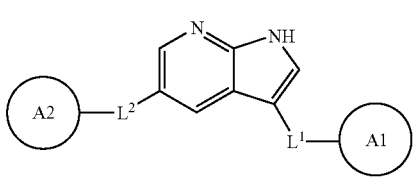

In Formula (I), $L^1$ and $L^2$ are independently a bond, —S(O)$_n$—, —O—, —NH—, substituted or unsubstituted $C_1$-$C_5$ alkylene, or substituted or unsubstituted 2 to 5 membered heteroalkylene. The symbol n represents an integer from 0 to 2.

$A^1$ and $A^2$ are independently substituted or unsubstituted cycloalkyl, substituted or unsubstituted heterocycloalkyl, substituted or unsubstituted aryl, or substituted or unsubstituted heteroaryl.

In another aspect, the present invention provides methods of modulating protein kinase activity using the pyrrolo-pyridine kinase modulators of the present invention. The method includes contacting said kinase with a pyrrolo-pyridine kinase modulator of the present invention.

In another aspect, the present invention provides methods of treating a disease mediated by kinase activity (kinase-mediated disease or disorder) in a subject (e.g. mammals, such as humans) in need of such treatment. The method includes administering to the subject an effective amount of a pyrrolo-pyridine kinase modulator of the present invention.

In another aspect, the present invention provides a pharmaceutical composition including a pyrrolo-pyridine kinase modulator in admixture with a pharmaceutically acceptable excipient.

BRIEF DESCRIPTION OF THE DRAWINGS

FIG. 1 (SEQ ID NO: 23) shows the wild-type ABL numbering according to ABL exon Ia.

DETAILED DESCRIPTION OF THE INVENTION

Definitions

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —CH$_2$CH$_2$CH$_2$CH$_2$—, —CH$_2$CH═CHCH$_2$—, —CH$_2$C≡CCH$_2$—, —CH$_2$CH$_2$CH(CH$_2$CH$_2$CH$_3$)CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" referrers to a carbon or heteroatom.

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical. Preferred substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R") =NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxo, and fluoro ($C_1$-$C_4$)alkyl, in a number ranging from zero to the total number of open valences on aromatic ring system; and where R', R", R'" and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties:
(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, and heteroaryl, substituted with at least one substituent selected from:
  (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)— or (S)— or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)— and (S)—, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

The symbol $\sim\!\!\sim\!\!\sim$ denotes the point of attachment of a moiety to the remainder of the molecule.

Pyrrolo-Pyridine Kinase Modulators

In one aspect, the present invention provides a pyrrolo-pyridine kinase modulator (also referred to herein as a "compound of the present invention") having the formula:

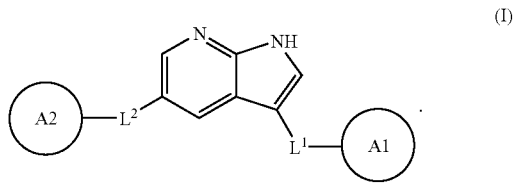

(I)

In Formula (I), $L^1$ and $L^2$ are independently a bond, —S(O)$_n$—, —O—, —NH—, substituted or unsubstituted $C_1$-$C_5$ alkylene, or substituted or unsubstituted 2 to 5 membered heteroalkylene. The symbol n represents an integer from 0 to 2.

$A^1$ and $A^2$ are independently substituted or unsubstituted cycloalkyl, substituted or unsubstituted heterocycloalkyl, substituted or unsubstituted aryl, or substituted or unsubstituted heteroaryl.

In some embodiments, $L^1$ and $L^2$ are independently a bond, —S(O)$_n$—, —O—, —NH—, unsubstituted $C_1$-$C_5$ alkylene, or unsubstituted 2 to 5 membered heteroalkylene. In other embodiments $L^1$ and/or $L^2$ is a bond.

$A^1$ and $A^2$ may independently be substituted or unsubstituted aryl, or substituted or unsubstituted heteroaryl. $A^1$ and $A^2$ may also independently be substituted or unsubstituted aryl, or 6-membered substituted or unsubstituted heteroaryl.

In some embodiments, $A^1$ is a substituted or unsubstituted aryl (e.g. a 6-membered substituted or unsubstituted aryl such as phenyl) or 6-membered substituted or unsubstituted heteroaryl. $A^1$ may also be substituted phenyl or 6-membered substituted heteroaryl. In some embodiments, $A^1$ is substituted or unsubstituted phenyl, substituted or unsubstituted pyridinyl, substituted or unsubstituted pyrimidinyl, substituted or unsubstituted benzodioxolyl, substituted or unsubstituted benzodioxanyl, substituted or unsubstituted benzimidazolyl, or substituted or unsubstituted indolyl.

$A^2$ may be a substituted aryl or substituted heteroaryl. In some embodiments, $A^2$ is a substituted phenyl, substituted thiopenyl, substituted pyridinyl, substituted pyrrolyl, substituted triazolyl, substituted pyrimidinyl, substituted pyrazinyl, or substituted imidazolyl.

In some embodiments, $A^1$ and $A^2$ are independently selected from substituted or unsubstituted phenyl, substituted or unsubstituted hydantoinyl, substituted or unsubstituted dioxolanyl, substituted or unsubstituted benzodioxolyl, substituted or unsubstituted dioxanyl, substituted or unsubstituted trioxanyl, substituted or unsubstituted tetrahydrothienyl, substituted or unsubstituted tetrahydrofuranyl, substituted or unsubstituted tetrahydrothiophenyl, substituted or unsubstituted tetrahydropyranyl, substituted or unsubstituted tetrahydrothiopyranyl, substituted or unsubstituted pyrrolidinyl, substituted or unsubstituted morpholino, substituted or unsubstituted piperidinyl, substituted or unsubstituted piperazinyl, substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyridyl, substituted or unsubstituted pyrazyl, substituted or unsubstituted pyrimidyl, substituted or unsubstituted pyridazinyl, substituted or unsubstituted thiazolyl, substituted or unsubstituted isothioazolyl, substituted or unsubstituted triazolyl, substituted or unsubstituted thienyl, substituted or unsubstituted triazinyl, substituted or unsubstituted thiadiazolyl, or substituted or unsubstituted tetrazolyl.

In some embodiments, $A^1$ is substituted with at least one $R^{19}$ group, wherein each $R^{19}$ group is optionally different. Each $R^{19}$ may be independently selected from halogen, $-OR^5$, $-NR^6R^7$, $-C(Z)R^8$, $-S(O)_wR^9$, $-CN$, $-NO_2$, $-CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, at least two $R^{19}$ groups are combined to form a substituted or unsubstituted ring with the atoms to which they are attached. As used herein, the term "substituted or unsubstituted ring" refers to a substituted or unsubstituted cycloalkyl, substituted or unsubstituted heterocycloalkyl, substituted or unsubstituted heteroaryl, or substituted or unsubstituted aryl. In other embodiments, $R^{19}$ is independently halogen (e.g. fluorine or chlorine), $-NR^6R^7$, $OR^5$, or substituted or unsubstituted alkyl.

In some embodiments, $A^2$ is substituted with at least one $R^{20}$ group and/or one $R^1$ group, wherein each $R^{20}$ group is optionally different. $R^1$ and each $R^{20}$ may be independently selected from halogen, $-OR^5$, $-NR^6R^7$, $-C(Z)R^8$, $-S(O)_wR^9$, $-CN$, $-NO_2$, $-CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, at least two $R^{20}$ groups or an $R^{20}$ and $R^1$ group are combined to form a substituted or unsubstituted ring with the atoms to which they are attached. In some embodiments, $R^{20}$ is independently halogen, $-NR^6R^7$, $-OR^5$, or substituted or unsubstituted alkyl.

Z represents Z is $N(R^{23})$, S, or O, and w represents an integer from 0 to 2. $R^{23}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{23}$ is hydrogen, substituted or unsubstituted alkyl, or substituted or unsubstituted heteroalkyl. $R^{23}$ may also be hydrogen, or substituted or unsubstituted $C_1$-$C_5$ alkyl. In some embodiments, $R^{23}$ is hydrogen or unsubstituted $C_1$-$C_5$ alkyl.

$R^5$ is independently hydrogen, $-CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ and $R^7$ are independently hydrogen, $-C(O)R^{10}$, $-S(O)_2R^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{10}$ and $R^{11}$ are independently hydrogen, $-NR^{12}R^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{12}$ and $R^{13}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^8$ is independently hydrogen, $-NR^{14}R^{15}$, $-OR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{14}$, $R^{15}$, and $R^{16}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, $R^{14}$ and $R^{15}$ are independently substituted or unsubstituted alkyl, substituted or unsubstituted heteroalkyl, or are combined with the nitrogen to which they are attached to form substituted or unsubstituted piperidinyl, or substituted or unsubstituted piperazinyl, substituted or unsubstituted pyrrolidinyl, or substituted or unsubstituted morpholino. In some embodiments, $R^{14}$ and/or $R^{15}$ are substituted with a group having the formula $-(CH_2)_t-NR^{21}R^{22}$. The symbol t represents an integer from 0 to 10. In some embodiments, t represents an integer from 0 to 6. $R^{21}$ and $R^{22}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{21}$ and $R^{22}$ are optionally combined with the nitrogen to which they are attached to form a substituted or unsubstituted heterocycloalkyl, or substituted or unsubstituted 5-membered heteroaryl.

In some embodiments, $R^{21}$ and $R^{22}$ are combined with the nitrogen to which they are attached to form a substituted or unsubstituted piperazinyl. In other embodiments, $R^{21}$ and $R^{22}$ are independently hydrogen, substituted or unsubstituted alkyl, or substituted or unsubstituted aminoalkyl.

$R^9$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein if w is 2, then $R^9$ may optionally be $-NR^{17}R^{18}$.

$R^{17}$ and $R^{18}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, $R^6$ and $R^7$, $R^{12}$ and $R^{13}$, $R^{14}$ and $R^{15}$, and/or $R^{17}$ and $R^{18}$ are, independently, may be joined with the nitrogen to which they are attached to form substituted or unsubstituted heterocycloalkyl, or substituted or unsubstituted 5-membered heteroaryl.

In some embodiments, $R^1$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and/or $R^{23}$ are independently selected from hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted aryl, or substituted or unsubstituted heteroaryl. In other embodiments, $R^1$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and/or $R^{23}$ are independently selected from hydrogen, substituted or unsubstituted $C_1$-$C_{10}$ alkyl, substituted or unsubstituted 2 to 20 membered heteroalkyl, substituted or unsubstituted $C_3$-$C_6$ cycloalkyl, substituted or unsubstituted 3 to 6 membered heterocycloalkyl, substituted or unsubstituted aryl, or substituted or unsubstituted heteroaryl.

Where $R^1$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and/or $R^{23}$ is a ring or are joined together to form a ring (e.g. cycloalkyl, heterocycloalkyl, aryl, or heteroaryl), the ring may be independently selected from substituted or unsubstituted phenyl, substituted or unsubstituted hydantoinyl, substituted or unsubstituted dioxolanyl, substituted or unsubstituted benzodioxolyl, substituted or unsubstituted dioxanyl, substituted or unsubstituted trioxanyl, substituted or unsubstituted tetrahydrothienyl, substituted or unsubstituted tetrahydrofuranyl, substituted or unsubstituted tetrahydrothiophenyl, substituted or unsubstituted tetrahydropyranyl, substituted or unsubstituted tetrahydrothiopyranyl, substituted or unsubstituted pyrrolidinyl, substituted or unsubstituted morpholino, substituted or unsubstituted piperidinyl, substituted or unsubstituted piperazinyl, substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyridyl, substituted or unsubstituted pyrazyl, substituted or unsubstituted pyrimidyl, substituted or unsubstituted pyridazinyl, substituted or unsubstituted thiazolyl, substituted or unsubstituted isothioazolyl, substituted or unsubstituted triazolyl, substituted or unsubstituted thienyl, substituted or unsubstituted triazinyl, substituted or unsubstituted thiadiazolyl, or substituted or unsubstituted tetrazolyl. One of skill will recognize that the normal rules of valency apply. Therefore, where two groups are joined together with a nitrogen to which they are attached to form a ring, the ring will typically be a substituted or unsubstituted heterocycloalkyl or 5 membered heteroaryl.

One of skill in the art will immediately recognize that the compounds of the present invention may include more than one $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and/or $R^{23}$ group. Where more than one $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and/or $R^{23}$ group is present, each $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and/or $R^{23}$ group is optionally different.

In some embodiments, $A^1$ is substituted with a halogen, $-OR^5$, or unsubstituted $C_1$-$C_{10}$ alkyl. In some embodiments, $A^1$ is substituted with at least one $-OR^5$. In some related embodiments, $R^5$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In other related embodiments, $R^5$ is hydrogen or unsubstituted $C_1$-$C_{10}$ alkyl (e.g. $A^1$ is substituted with $-O-CH_3$).

In some embodiments, $A^2$ is substituted with at least one $-C(Z)R^8$ group. In some related embodiments, Z is O and $R^8$ is $-NR^{14}R^{15}$. In some related embodiments, $R^{14}$ and $R^{15}$ are independently hydrogen, substituted or unsubstituted alkyl, substituted or unsubstituted heteroalkyl, or are joined together to form a substituted or unsubstituted heterocycloalkyl or 5-membered heteroaryl (e.g. piperidinyl or piperazinyl). In some embodiments, $R^{14}$ and/or $R^{15}$ are substituted with a group having the formula $-(CH_2)_t-NR^{21}R^{22}$. The symbol t, $R^{21}$ and $R^{22}$ are as described above.

In some embodiments, $A^1$ has the formula:

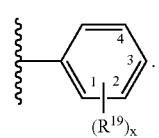

(II)

In Formula (II), x is an integer from 1 to 5.

As described above, each $R^{19}$ is independently halogen, $-OR^5$, $-NR^6R^7$, $-C(Z)R^8$, $-S(O)_wR^9$, $-CN$, $-NO_2$, $-CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, two $R^{19}$ groups are optionally combined to form a substituted or unsubstituted ring with the carbons to which they are attached. $R^5$, $R^6$, $R^7$, $R^8$, and $R^9$ are as defined above in the discussion of Formula (I).

In some embodiments, $R^{19}$ is attached at position 1 and/or position 2. An $R^{19}$ attached at position 1 may be combined with an $R^{19}$ attached at position 2 to form a substituted or unsubstituted ring (fused to $A^1$). In some embodiments, an $R^{19}$ attached at position 2 is combined with an $R^{19}$ attached at position 3 to form a substituted or unsubstituted ring (fused to $A^1$). Examples of rings formed by the combination of two $R^{19}$ groups are discussed above. In some embodiments, the ring formed is a substituted or unsubstituted heterocycloalkyl or substituted or unsubstituted heteroaryl.

In some embodiments, x is 1 and $R^{19}$ is attached at position 2. In other embodiments, x is 1 and $R^{19}$ is attached at position 1. Alternatively, x is an integer from 2 to 5 and at least one $R^{19}$ is attached at position 1. In other embodiments, x is an integer from 2 to 5 and at least one $R^{19}$ is attached at position 2.

Examples of $R^5$, $R^6$, and $R^7$ groups are discussed above. In some embodiments, if $R^{19}$ is $-OR^5$, or $-NR^6R^7$, then $R^5$, $R^6$, and $R^7$ are independently hydrogen, substituted or unsubstituted alkyl, or substituted or unsubstituted heteroalkyl. In other embodiments, $R^5$, $R^6$, and $R^7$ are hydrogen or substituted or unsubstituted $C_1$-$C_5$ alkyl. In other embodiments, $R^5$, $R^6$, and $R^7$ are hydrogen or unsubstituted $C_1$-$C_5$ alkyl.

In some embodiments, $A^1$ has the formula:

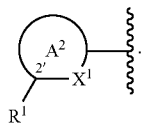

(III)

In Formula (III), $X^1$ is —C($R^2$)=, —C($R^2$)($R^3$)—, —N=, —N($R^4$)—, —S—, or —O—. Thus, $A^2$ substituted or unsubstituted cycloalkyl, substituted or unsubstituted heterocycloalkyl, substituted or unsubstituted aryl, or substituted or unsubstituted substituted heteroaryl. In Formula (III), where $A^2$ is unsubstituted, $A^1$ has no further substituents other than $R^1$ (and hydrogen). In Formula (III), where $A^2$ is substituted, $A^1$ is substituted with substituents in addition to $R^1$ (e.g. with one or more $R^{20}$ groups).

In some embodiments, $A^2$ is substituted or unsubstituted phenyl, substituted or unsubstituted thiopenyl, substituted or unsubstituted pyridinyl, substituted or unsubstituted pyrrolyl, substituted or unsubstituted triazolyl, substituted or unsubstituted pyrimidinyl, substituted or unsubstituted pyrazinyl, or substituted or unsubstituted imidazolyl.

$R^1$ is halogen, —$OR^5$, —$NR^6R^7$, —C(Z)$R^8$, —S(O)$_w$$R^9$, —CN, —$NO_2$, —$CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ and $R^3$ are independently hydrogen, halogen, —$OR^5$, —$NR^6R^7$, —C(Z)$R^8$, —S(O)$_w$$R^9$, —CN, —$NO_2$, —$CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is hydrogen, —C(O)$R^8$, —S(O)$_2$$R^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$, $R^6$, $R^7$, $R^8$, $R^9$, $R^{11}$, Z, and w are as described above in the discussion of Formula (I).

Thus, in some embodiments, the compound of the present invention has the formula:

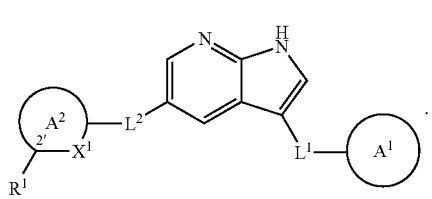

(IV)

In Formula (IV), $R^1$, $A^2$, and $X^1$ are as described above in Formula (III) and $L^2$, $L^3$ and $A^1$ are as described in Formulae (I) and (II). Thus, in some embodiments, $A^1$ is a 6-membered substituted or unsubstituted aryl or 6-membered substituted or unsubstituted heteroaryl.

In some embodiments, $A^2$ has the formula:

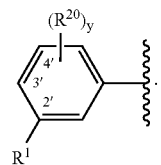

(V)

In Formula (IV), y is an integer from 0 to 4. $R^1$ is as described above in Formula (III). $R^{20}$ is as described above in the discussion of Formula (I).

As described above, each $R^{20}$ is independently halogen, —$OR^5$, —$NR^6R^7$, —C(Z)$R^8$, —S(O)$_w$$R^9$, —CN, —$NO_2$, —$CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, two $R^{20}$ groups are combined to form a substituted or unsubstituted ring with the carbons to which they are attached. In other embodiments, one $R^{20}$ and $R^1$ are combined to form a substituted or unsubstituted ring with the carbons to which they are attached.

Examples of $R^5$, $R^6$, and $R^7$ groups are discussed above. In some embodiments, if $R^{20}$ is —$OR^5$, or —$NR^6R^7$, then $R^5$, $R^6$, and $R^7$ are independently hydrogen, substituted or unsubstituted alkyl, or substituted or unsubstituted heteroaryl. In other embodiments, $R^5$, $R^6$, and $R^7$ are hydrogen or substituted or unsubstituted $C_1$-$C_5$ alkyl. In other embodiments, $R^5$, $R^6$, and $R^7$ are hydrogen or unsubstituted $C_1$-$C_5$ alkyl.

As also described above, $R^5$, $R^6$, and $R^7$ may independently be hydrogen, or substituted or unsubstituted alkyl. $R^5$, $R^6$, and $R^7$ may also independently be hydrogen, or substituted or unsubstituted $C_1$-$C_{20}$ alkyl. $R^5$, $R^6$, and $R^7$ may also be independently hydrogen, or unsubstituted $C_1$-$C_{20}$ alkyl.

In some embodiments, y is 1 and $R^{20}$ is attached at position 3'. In other embodiments, y is 2, and $R^{20}$ is attached at position 3' and position 4'. In other embodiments, an $R^{20}$ attached at position 3' is combined with an $R^{20}$ attached at position 4' to form a substituted or unsubstituted ring. In other embodiments, an $R^{20}$ attached at position 3' is combined with $R^1$ to form a substituted or unsubstituted ring.

In other embodiments, $A^2$ has the formula:

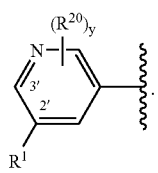

(VI)

In Formula (VI), y is an integer from 0 to 3. $R^1$ is as described above in Formula (III). $R^{20}$ is as described above in the discussion of Formula (I). In some embodiments, one $R^{20}$ and $R^1$ are optionally combined to form a substituted or unsubstituted ring with the carbons to which they are attached. In other embodiments, two $R^{20}$ groups are optionally combined to form a substituted or unsubstituted ring with the carbons to which they are attached.

In some embodiments, y is 1 and $R^{20}$ is attached at position 3'. In other embodiments, an $R^{20}$ attached at position 3' is combined with $R^1$ to form a substituted or unsubstituted ring.

In some embodiments of the compounds of Formulae (I)-(VI), $L^1$ and/or $L^2$ is a bond.

In some embodiments of the compounds of Formulae (I)-(VI), $R^1$ is —C(Z)$R^8$. The symbol Z may simply be O. $R^8$ may be —NR$^{14}$R$^{15}$. $R^{14}$ and $R^{15}$ are as described above. In some related embodiments, y is 0. Thus, $R^{14}$ and $R^{15}$ may independently be substituted or unsubstituted alkyl, substituted or unsubstituted heteroalkyl, or are combined with the nitrogen to which they are attached to form substituted or unsubstituted piperidinyl, or substituted or unsubstituted piperazinyl, substituted or unsubstituted pyrrolidinyl, or substituted or unsubstituted morpholino. $R^{14}$ and $R^{15}$ may also be combined with the nitrogen to which they are attached to form a substituted or unsubstituted piperidinyl, or substituted or unsubstituted piperazinyl. $R^{14}$ and $R^{15}$ may also be combined with the nitrogen to which they are attached to form a piperazinyl substituted with a substituted or unsubstituted alkyl or substituted or unsubstituted heteroalkyl.

$R^{14}$ and/or $R^{15}$ may be substituted with a substituent having the formula —(CH$_2$)$_t$—NR$^{21}$R$^{22}$. For example, where $R^{14}$ and $R^{15}$ are combined to form a heterocycloalkyl (e.g. piperazinyl or piperidinyl), the heterocycloalkyl may be substituted with a —(CH$_2$)$_t$—NR$^{21}$R$^{22}$. The symbol t, $R^{21}$ and $R^{22}$ are as described above.

In some embodiments, $A^1$ has the formula of Formula (II) and $A^2$ has the formula of Formula (III), (V) or (VI). In some related embodiments, $L^1$ and/or $L^2$ is a bond.

In some embodiments of the compounds of Formulae (V) and/or (VI), $R^{20}$ is —C(Z)$R^8$, Z is O, and $R^8$ is —NR$^{14}$R$^{15}$. $R^{15}$ and $R^1$ are combined to form a substituted or unsubstituted heterocycloalkyl, or heteroaryl with the carbon to which $R^1$ is attached and the nitrogen to which $R^{15}$ is attached.

In other embodiments, of the compounds of Formulae (V) and/or (VI), $R^1$ is —C(Z)$R^8$, Z is O, and $R^8$ is —NR$^{14}$R$^{15}$. $R^{15}$ and $R^{20}$ are combined to form a substituted or unsubstituted heterocycloalkyl, or heteroaryl with the carbon to which $R^{20}$ is attached and the nitrogen to which $R^{15}$ is attached.

In some embodiments, $R^5$, $R^6$, and $R^7$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ and $R^7$ may be joined with nitrogen to which they are attached to form substituted or unsubstituted heterocycloalkyl, or substituted or unsubstituted 5-membered heteroaryl. In other embodiments, $R^5$, $R^6$, and $R^7$ are independently hydrogen, or substituted or unsubstituted alkyl. $R^5$, $R^6$, and $R^7$ may also independently be hydrogen, or substituted or unsubstituted $C_1$-$C_{20}$ alkyl. In other embodiments, $R^5$, $R^6$, and $R^7$ are independently hydrogen, or unsubstituted $C_1$-$C_{20}$ alkyl.

In some embodiments, $A^1$ has the formula of Formula (II) and $A^2$ has the formula of Formulae (V) or (VI). In some related embodiments, $L^1$ and/or $L^2$ is a bond. In other related embodiments, x is 1 and y is 0. In other related embodiments, $R^{19}$ is attached at position 1. In other related embodiments, $R^{19}$ is attached at position 2. In other related embodiments, x is 2, y is 0, and $R^{19}$ is attached at positions 1 and 4. In other related embodiments, x is 2, y is 0, and $R^{19}$ is attached at positions 1 and 5. In other related embodiments, x is 1, y is 1, $R^{20}$ is attached at position 3', and $R^{19}$ is attached at position 1. In other related embodiments, x is 1, y is 2, $R^{20}$ is attached at positions 3' and 4', and $R^{19}$ is attached at position 1. In other related embodiments, x is 2, y is 0, and one $R^{19}$ is attached at position 2.

In some embodiments, the compound of the present invention has the formula:

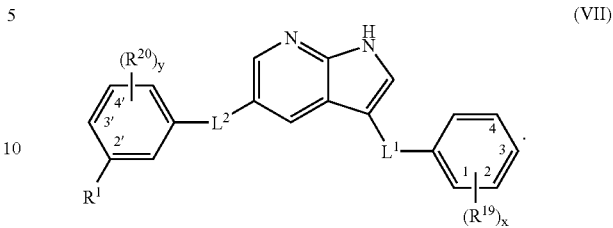

(VII)

In Formula (VII), $L^1$, $L^2$, $R^1$, $R^{19}$, $R^{20}$, x, and y are as defined above in Formulae (I), (II), and (V). In some embodiments, $L^1$ and/or $L^2$ is a bond. In some embodiments, x is 1 and y is 0. In other embodiments, $R^{19}$ is attached at position 1 and/or position 2. $R^1$ may be —C(Z)$R^8$ (defined above). In some related embodiments, Z is O and $R^8$ is —NR$^{14}$R$^{15}$ (defined above). $R^{19}$ may be —OR$^5$ (defined above).

In some embodiments, the compound of the present invention has the formula:

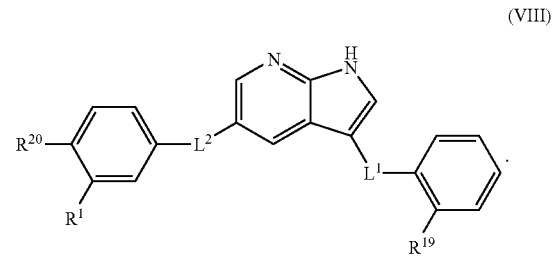

(VIII)

In Formula (VIII), $L^1$, $L^2$, $R^1$, $R^{19}$, and $R^{20}$ are as defined above in the Formulae (I), (II), and (V). In some embodiments, $L^1$ and/or $L^2$ is a bond. $R^1$ may be —C(Z)$R^8$ (defined above). In some related embodiments, Z is O and $R^8$ is —NR$^{14}$R$^{15}$ (defined above). $R^{19}$ may be —OR$^5$ (defined above). In some embodiments, $R^{20}$ is halogen, —OR$^5$, or —NR$^6$R$^7$ (defined above).

In some embodiments, the compound of the present invention has the formula:

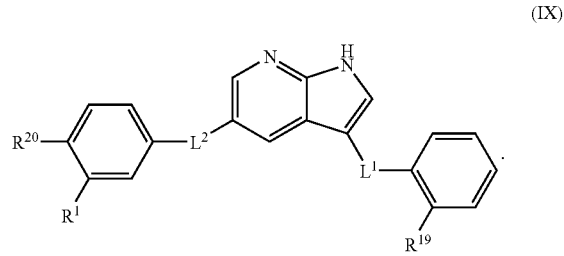

(IX)

In Formula (IX), $L^1$, $L^2$, $R^1$, $R^{19}$, and $R^{20}$ are as defined above in the Formulae (I), (II), and (V). In some embodiments, $L^1$ and/or $L^2$ is a bond. $R^1$ may be —C(Z)$R^8$ (defined above). In some related embodiments, Z is O and $R^8$ is —NR$^{14}$R$^{15}$ (defined above). $R^{19}$ may be —OR$^5$ (defined above).

In some embodiments, the compound of the present invention has the formula:

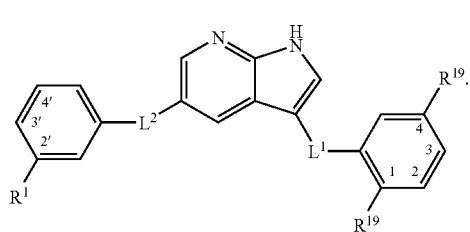

(X)

In Formula (X), $L^1$, $L^2$, $R^1$, and $R^{19}$ are as defined above in the Formulae (I), (II), and (V). $R^1$ may be —C(Z)$R^8$ (defined above). In some related embodiments, Z is O and $R^8$ is —$NR^{14}R^{15}$ (defined above). In some embodiments, $L^1$ and/or $L^2$ is a bond. $R^{19}$ attached at the 1 position may be —$OR^5$. $R^{19}$ attached at the 4 position may be halogen.

In some embodiments, the compound of the present invention has the formula:

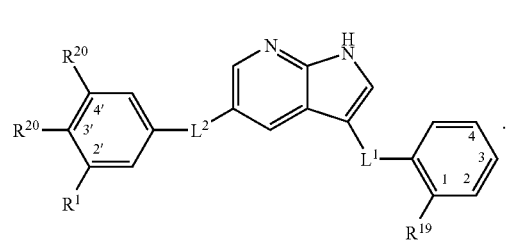

(XI)

In Formula (XI), $L^1$, $L^2$, $R^1$, $R^{19}$, and $R^{20}$ are as defined above in the Formulae (I), (II), and (V). In some embodiments, $L^1$ and/or $L^2$ is a bond. $R^1$ may be —C(Z)$R^8$ (defined above). In some related embodiments, Z is O and $R^8$ is —$NR^{14}R^{15}$ (defined above). $R^{19}$ may be —$OR^5$ (defined above). $R^{20}$ attached at the 3' position may be —$OR^5$. $R^{20}$ attached at the 4' position may be halogen or substituted or unsubstituted alkyl (such as $C_1$-$C_5$ alkyl).

In some embodiments, the compound of the present invention has the formula:

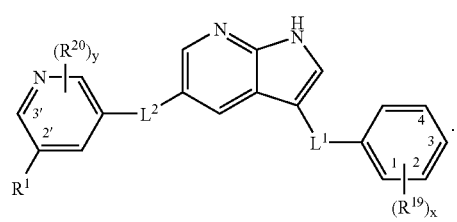

(XII)

In Formula (XII), $L^1$, $L^2$, $R^1$, $R^{19}$, $R^{20}$, x, and y are as defined above in the Formulae (I), (II), and (VI). In some embodiments, $L^1$ and/or $L^2$ is a bond. In some embodiments, x is 1 and y is 0. In other embodiments, $R^{19}$ is attached at position 1 and/or position 2. $R^1$ may be —C(Z)$R^8$ (defined above). In some related embodiments, Z is O and $R^8$ is —$NR^{14}R^{15}$ (defined above). $R^{19}$ may be —$OR^5$.

In some embodiments, the compound of the present invention has the formula:

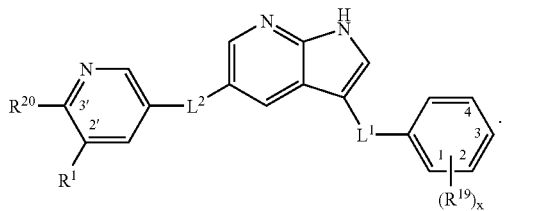

(XIII)

In Formula (XIII), $L^1$, $L^2$, $R^1$, $R^{19}$, $R^{20}$, and x are as defined above in the Formulae (I), (II), and (VI). In some embodiments, $L^1$ and/or $L^2$ is a bond. In some embodiments, x is 1. $R^1$ may be —C(Z)$R^8$ (defined above). $R^{19}$ may be —$OR^5$ (defined above). In some related embodiments, Z is O and $R^8$ is $NR^{14}R^{15}$ (defined above). $R^{20}$ may be halogen, or substituted or unsubstituted alkyl (such as $C_1$-$C_5$ alkyl). $R^{20}$ may be —$OR^5$.

In some embodiments, the compound of the present invention has the formula:

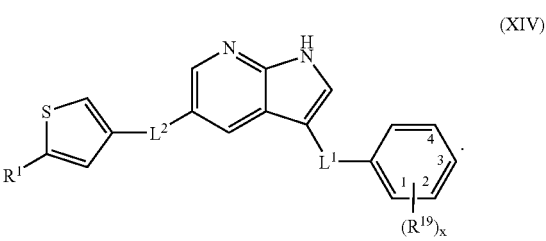

(XIV)

In Formula (XIV), $L^1$, $L^2$, $R^1$, $R^{19}$, and x are as defined above in the Formulae (I) and (II). In some embodiments, $L^1$ and/or $L^2$ is a bond. x is 1. $R^1$ may be —C(Z)$R^8$ (defined above). $R^{19}$ may be —$OR^5$ (defined above). In some related embodiments, Z is O and $R^8$ is $NR^{14}R^{15}$ (defined above).

In some embodiments, the compound of the present invention has the formula:

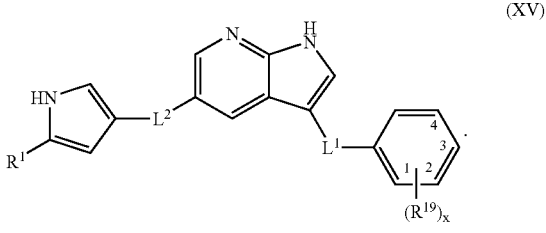

(XV)

In Formula (XV), $L^1$, $L^2$, $R^1$, $R^{19}$, and x are as defined above in the Formulae (I) and (II). In some embodiments, $L^1$ and/or $L^2$ is a bond. x is 1. $R^1$ may be —C(Z)$R^8$ (defined above). $R^{19}$ may be —$OR^5$ (defined above). In some related embodiments, Z is O and $R^8$ is $NR^{14}R^{15}$ (defined above).

In some embodiments, each substituted group described above in the compounds of Formulae (I)-(XV) is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, and/or substituted heteroalkylene, described above in the compounds of Formulae (I)-(XV) are substituted with at least one substituent group. In other embodiments, at least one or all of these groups are substituted with at least one size-limited substituent group. Alternatively, at least one or all of these groups are substituted with at least one lower substituent group.

In other embodiments of the compounds of Formulae (I)-(XV), each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, each substituted or unsubstituted heterocycloalkyl is a substituted or unsubstituted 4 to 8 membered heterocycloalkyl, each substituted or unsubstituted alkylene is a substituted or unsubstituted $C_1$-$C_{20}$ alkylene, and/or each substituted or unsubstituted heteroalkylene is a substituted or unsubstituted 2 to 20 membered heteroalkylene.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted alkylene is a substituted or unsubstituted $C_1$-$C_8$ alkylene, and/or each substituted or unsubstituted heteroalkylene is a substituted or unsubstituted 2 to 8 membered heteroalkylene.

In another embodiment, the compounds of the present invention include the compounds of any one of Tables 1-39, or any one of the methods 1-61. In other embodiments, the compounds of the present invention include the compounds of any one of Tables 2-39, or any one of the methods 2-61.

Exemplary Syntheses

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate how, in principle, to gain access to the compounds claimed under this invention and to give details on certain of the diverse methods available for use in assembling the compounds of the invention. However, the discussion is not intended to define or limit the scope of reactions or reaction sequences that are useful in preparing the compounds of the present invention. The compounds of this invention may be made by the procedures and techniques disclosed in the Examples section below, as well as by known organic synthesis techniques. In Schemes 1, 2 and 3, $L^1$ and $L^2$ are as defined above. $R^1$ in Schemes 1, 2 and 3 correspond to $A^1$ as defined above. $R^2$ in Schemes 1, 2 and 3 correspond to $A^2$ as defined above.

The complete synthesis of certain compounds of the present invention is outlined in Scheme 1. Many of these compounds can be synthesized conveniently from commercially available 2-amino-nicotinic acid. Starting from 2-aminonicotinic acid, bromination in the 5-position to 1 (X=Br) can be achieved by various methods well known in the chemical literature, such as, but not limited to reactions using elemental bromine or N-bromosuccinimide (step a in Scheme 1).

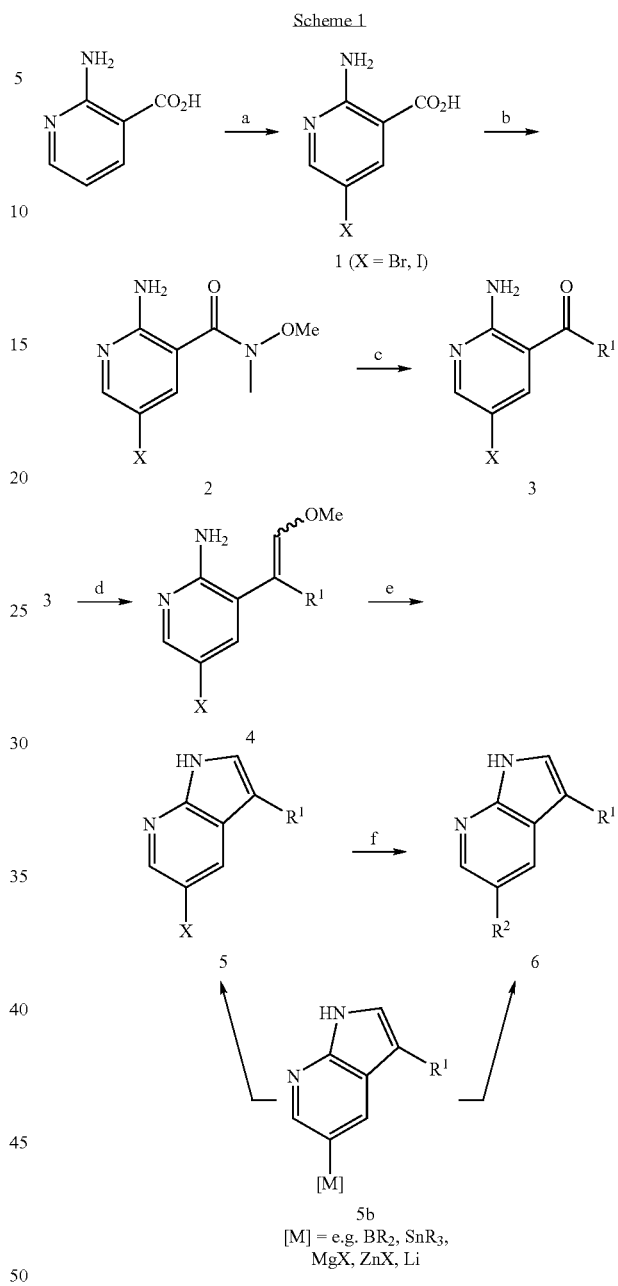

Synthesis of a ketone intermediate of general formula 3 (X=Br) can be achieved by treating the corresponding WEINREB-amide 2 or its hydrochloride salt with a suitable organometallic species, for example, using an organomagnesium or organolithium compound [step c in Scheme 1]. (for examples of the use of N-methoxy-N-methylamides (WEINREB amides) in ketone synthesis, see S. Nam, S. M. Weinreb—*Tetrahedron Lett.* 1981, 22, 3815.) The WEINREB-amide 2 (X=Br) is accessible by condensation of the parent acid 1 (X=Br, $X^2$=CH) with N,O-dimethylhydroxylamine using standard methods for amide-formation, either by prior activation of the acid or in situ or via a direct condensation. Methods and reagents for both transformations are described in the chemical literature and well known to someone skilled in the art [step b in Scheme 1]. For example, amide formation is achieved by direct methods using suitable coupling reagents such as, but not limited to, PyBOP, HBTU or HATU.

The organometallic reagents required for the introduction of a ketone residue $R^1$ in 3 (X=Br) [step c in Scheme 1] can be obtained either commercially or synthesized by various methods described in the literature, such as, but not limited to the Grignard-reaction of organic chlorides, bromides, or iodides, with magnesium (cf. J. March—*Advanced Organic Chemistry,* 3rd ed., John Wiley & Sons, 1992), metal-halogen exchange reactions of organic bromides or iodides using suitable organolithium or organomagnesium compounds such as, but not limited to, n-butyllithium, tert-butyllithium or isopropylmagnesium chloride or bromide (e.g. J. Clayden—*Organolithiums: Selectivity for Synthesis,* Pergamon, 2002; A. Boudier, L. O. Bromm, M. Lotz, P. Knochel—*Angew. Chem Int. Ed.* (2000) 39, 4414.) or deprotonation of sufficiently acidic compounds, such as for example pyrimidines, pyrazines, 2-chloro- or 2-fluoropyridines using a suitable base, such as for example lithium N,N-diisopropylamide or lithium 2,2,6,6-tetramethylpiperidide (cf. J. Clayden—*Organolithiums: Selectivity for Synthesis, Pergamon,* 2002; A. Turck, N. Plé, F. Mongin, G. Quéguiner—*Tetrahedron* (2001) 57,4489; F. Mongin, G. Quéguiner—*Tetrahedron* (2001) 57,4059). The aforementioned group $R^1$ can be substituted with one or more functional groups, in which acidic protons such as, for example, the hydrogen atoms attached to nitrogen or oxygen may, as needed, be protected by a suitable protecting group by methods well known in the chemical literature (cf. T. W. Greene, P. G. M. Wuts—*Protective Groups in Organic Synthesis,* 3rd ed., John Wiley & Sons, 1999). Such functional groups will allow for the elaboration of the products obtained in such fashion to various compounds claimed under this invention by generally well known methods.

Olefination of the resulting ketones 3 (X=Br) [step d in Scheme 1] can be achieved by several methods known to those skilled in the art but is most conveniently carried out via a WITTIG-reaction (cf. B. E. Maryanoff, A. B. Reitz—*Chem. Rev.* (1989) 89, 863) using an ylide generated from commercially available methoxymethyltriphenylphosphonium chloride and a suitable base, for example, but not limited to, a strong organometallic base such as, but not limited to, a non-nucleophilic amide such as the lithium, sodium or potassium salt of bis(trimethylsilyl)amine. Such olefinations can also be conveniently carried out without purification of the respective ketone 3 (X=Br), using the crude material obtained from the reaction of the WEINREB amide 2 (X=Br) with an organometallic reagent as described above.

Subsequent cyclization of the resulting olefin 4 (X=Br), [step e in Scheme 1] which can be utilized in either the E- or Z-form or a mixture of these both forms, can be achieved under general acid catalysis conditions using strong inorganic or organic acids, such as, but not limited to sulfuric acid, perchloric acid, hydrochloric acid, trifluoromethanesulfonic acid or trifluoroacetic acid in suitable solvents such as, but not limited to THF, dioxane, diethyl ether, dimethoxyethane, diglyme, dichloromethane, dichloroethane or chloroform, water, methanol, or ethanol, or mixtures thereof. A similar cyclization has been described by Sakamoto et al., *Heterocycles* (1992), 34(12), 2379-84. There the authors describe the conversion of 2-nitro-3-(2-ethoxyvinyl)pyridine to the parent pyrrolo[2,3-b]pyridine. Formation of the vinyl group is achieved via a STILLE-coupling of the 3-bromo analog with tributyl-2-ethoxyvinylstannane.

Introduction of aromatic, olefin, alkyne, or an aliphatic substituents at the 5-position of bromide 5 to afford compounds of the general formula 6 (X=Br) [stepf in Scheme 1] can be achieved via standard halogen cross-coupling methodologies (cf. F. Diederich, P. J. Stang (eds.)—*Metal-catalyzed Cross-coupling Reactions,* Wiley-VCH, 1998; J. Tsuji—*Palladium Reagents and Catalysts,* John Wiley & Sons, 1995). Couplings of the bromide 5 (X=Br) with suitable reagents such as, but not limited to, boronic acids and boronates, organoboranes, trifluoroborate salts (e.g. G. A. Molander, G.-S. Yun, M. Ribagorda, B. Biolatto—*J. Org. Chem.* (2003) 68, 5534; G. A. Molander, B. Biolatto—*J. Org. Chem.* (2003) 68, 4302.), organostannanes, organozinc compounds, organomagnesium compounds, olefins or terminal alkynes, either purchased or obtained via protocols well known in the chemical literature, are carried out in the presence of a suitable transition metal catalyst, for example, but not limited to, suitable palladium compounds, either in the presence of ligands such as, but not limited to, phosphines, diphosphines or arsines or without and, as necessary, organic or inorganic bases, such as tertiary or secondary amines, alkaline carbonates, bicarbonates or phosphates and, as needed, other additives that are known in the chemical literature to assist or accelerate such transformations, such as lithium chloride, copper halides or silver salts. These cross coupling reactions are carried out in suitable solvents such as, but not limited to, THF, dioxane, dimethoxyethane, diglyme, dichloromethane, dichloroethane, acetonitrile, DMF, N-methylpyrrolidone, ethanol, or water, or mixtures of these at temperatures ranging from 25° C. to 200° C. using either no heating, conventional heating or microwave irradiation.

This methodology may be extended to the incorporation of non-carbon based nucleophiles such as, but not limited to alcohols, thiols, primary or secondary amines, heterocyclic rings containing hydrogen attached to a nitrogen atom, that may or may not contain groups which are known in the chemical literature to be suitable protecting groups (examples of such groups can be found in T. W. Greene, P. G. M. Wuts—*Protective Groups in Organic Synthesis,* 3rd ed., John Wiley & Sons, 1999) of alcohols, thiols or amines by methods well known in the chemical literature such as, by way of example, those mentioned in S. V. Ley, A. W. Thomas—*Angew. Chem.* (2003) 115, 5558; J. P. Wolfe, S. Wagaw, J.-F. Marcoux, S. L. Buchwald—*Acc. Chem. Res.* (1998) 31, 805 and J. F. Hartwig—*Acc. Chem. Res.* (1998) 31, 852. The compounds obtained by such methods can be further elaborated by methods well known in the chemical literature to other compounds claimed under this invention.

In one embodiment of the invention, a halide 5 (X=Br) is treated with a boronic acid in the presence of a suitable palladium catalyst, for example, but not limited to tetrakis (triphenylphosphino)alladium(0), dichlorbis(triphenylphosphino)palladium(II) or dichloro[1,1'-bis(diphenylphosphino) ferrocene]palladium(II), and a suitable base (e.g. sodium carbonate, cesium carbonate or cesium fluoride) in aqueous solvent mixtures such as, acetonitrile/water or dimethoxyethane/water at temperatures between 110° C. and 200° C. either using conventional heating or microwave irradiation.

In some cases it may be advantageous to achieve crosscouplings to carbon or non-carbon atoms such as all those mentioned above, by first converting a halide 5 into an organometallic derivative 5b such as a boronic acid or ester, trifluoroborate salt, organomagnesium, organozinc, or organotin compound. Such compounds are accessible by means of substituting the bromide moiety with an appropriate metal or metalloid in which case any functional group present in derivative 5, most notably the ring nitrogen in position 1 of the pyrrolo[2,3-b]pyridine, may be protected by a suitable protecting group (examples of such groups can be found in T. W. Greene, P. G. M. Wuts—*Protective Groups in Organic Synthesis,* 3rd ed., John Wiley & Sons, 1999). Introduction of such metals or metalloids can be achieved in a number of ways, such as via reductive metallation using metals such alkaline or alkaline earth metals or activated forms of such metals such as lithium, magnesium or lithium naphthalide or via a metal-halogen exchange reactions using suitable organolithium or organomagnesium compounds (e.g. n-butyllithium, tert-butyllithium or iso-propylmagnesium chloride or bromide) and, as needed, subsequent transmetalation reactions of the organometallic intermediate with a suitable soluble and reactive metal compound (e.g. magnesium chloride, magnesium bromide, tri-n-butyltin chloride, trimethyltin chloride, trimethyl borate, triethyl borate, tri-iso-propyl borate, zinc triflate or zinc chloride). Introduction of a boronic acid pinacol ester may be conveniently achieved by reacting derivative 5 directly with bis(pinacolato)diboron in the presence of dichloro[1,1'-bis(diphenylphos-phino)-ferrocene]palladium(II) and suitable bases (e.g. potassium or sodium acetate) in solvents such as DMSO, DMF, DMA or N-methylpyrrolidone at temperatures ranging from 80-160° C. either using conventional heating or microwave irradiation (literature precedent for similar transformations can be found in T. Ishiyama, M. Murata, N. Miyaura—*J. Org. Chem.* (1995) 60, 7508.). Methods for conversion of the boronic acid pinacol ester obtained by this method into other boronic acid derivatives such as boronic acids, boronates, or trifluoroborate salts are well described in the chemical literature.

Cross-couplings of metallated derivatives 5b with suitable reagents such as aromatic, heteroaromatic or olefinic chlorides, bromides, iodides, triflates or acyl halides either purchased or obtained via protocols well known in the chemical literature, are carried out in the presence of a suitable transition metal catalyst (e.g. suitable palladium compounds, either in the presence of ligands such as phosphines, diphosphines or arsines or without and, as necessary, organic or inorganic bases, such as tertiary or secondary amines, alkaline carbonates, bicarbonates or phosphates and, as needed, other additives that are known in the chemical literature to assist or accelerate such transformations, such as copper halides or silver salts). These cross coupling reactions are carried out in suitable solvents (e.g. THF, dioxane, dimethoxyethane, diglyme, dichloromethane, dichloroethane, acetonitrile, DMF, N-methylpyrrolidone, or mixtures of these) at temperatures ranging from 25° C. to 200° C. using either no heating, conventional heating or microwave irradiation. The compounds obtained by such methods, particularly those containing suitable functional groups (e.g. carboxylic acids or esters, nitriles, amines, aldehydes or olefins) can be further elaborated by methods well known in the chemical literature to other compounds claimed under this invention.

More reactive organic nucleophiles such as organometallic compounds 5b containing alkaline, or alkaline earth or certain transition metals (e.g. organolithium, organomagnesium or organozinc compounds) can also be coupled to a range of other electrophilic coupling partners such as activated olefins (MICHAEL-acceptors), aldehydes, nitriles, aromatic nitro compounds (see for example I. Sapountzis, P. Knochel—*J. Am. Chem. Soc.* (2002) 124, 9390.), carboxylic acid derivatives, carbon dioxide, organic disulfides or organic halides. Such couplings can be achieved using either no catalyst or a suitable transition metal catalyst, such as a suitable copper, cobalt or iron compound in suitable solvents (e.g. ether, THF, dioxane, dimethoxyethane, or diglyme, or mixtures of these) at temperatures ranging from –100° C. to 100° C. either in the presence of other additives that are known in the chemical literature to assist or accelerate such transformations, such as, for example, lithium halides, amines or diamines or their derivatives, or without. As will be apparent to someone with skill in the art, the compounds obtained by such methods, particularly such compounds containing suitable functional groups, such as carboxylic acids or esters, nitriles, amines, aldehydes or olefins, can be further elaborated by methods well known in the chemical literature to other compounds claimed under this invention.

3,5-disubstituted pyrrolo[2,3-b]pyridines can also be accessed via another method outlined in Scheme 2 (see also WO 2004/032874). Iodination of 2-amino-5-bromopyridine can be achieved by reacting it with iodine and sodium periodate in a suitable solvent such as DMF, DMA or N-methylpyrrolidone at elevated temperatures of 100-200° C. to afford intermediate 31. This intermediate 31 can be acylated under standard conditions, such as reacting it with acetyl chloride in a suitable solvent such as pyridine at 25-100° C. Coupling of bromide 32 with ethynyltrimethylsilane to afford alkyne 33 can be achieved via standard halogen cross-coupling methodologies (cf. F. Diederich, P. J. Stang (eds.), *Metal-catalyzed Cross-coupling Reactions*, Wiley-VCH, 1998; J. Tsuji, *Palladium Reagents and Catalysts*, John Wiley & Sons, 1995) such as using suitable palladium compounds, such as dichlorobis(triphenylphosphino)palladium(ii) or dichloro[1,1'-bis(diphenylphosphino)ferrocene]palladium (II) as a catalyst in the presence of copper(I)-salts, such as cuprous iodide in the presence of organic bases, such as triethyl amine, in suitable solvents, such as dichloromethane at temperatures of 25° C. or above. Cyclization of the resulting alkynylpyridine 33 can be most conveniently achieved by exposure to soluble fluorides, such as tetrabutylammonium fluoride, in suitable solvents such as THF or dioxane at temperatures of 25-110° C. to afford 5-bromo-pyrrolo[2,3-b]pyridine (34).

Scheme 2

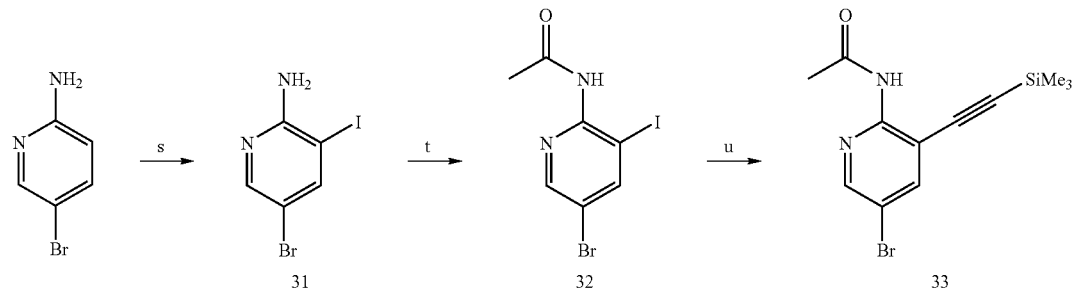

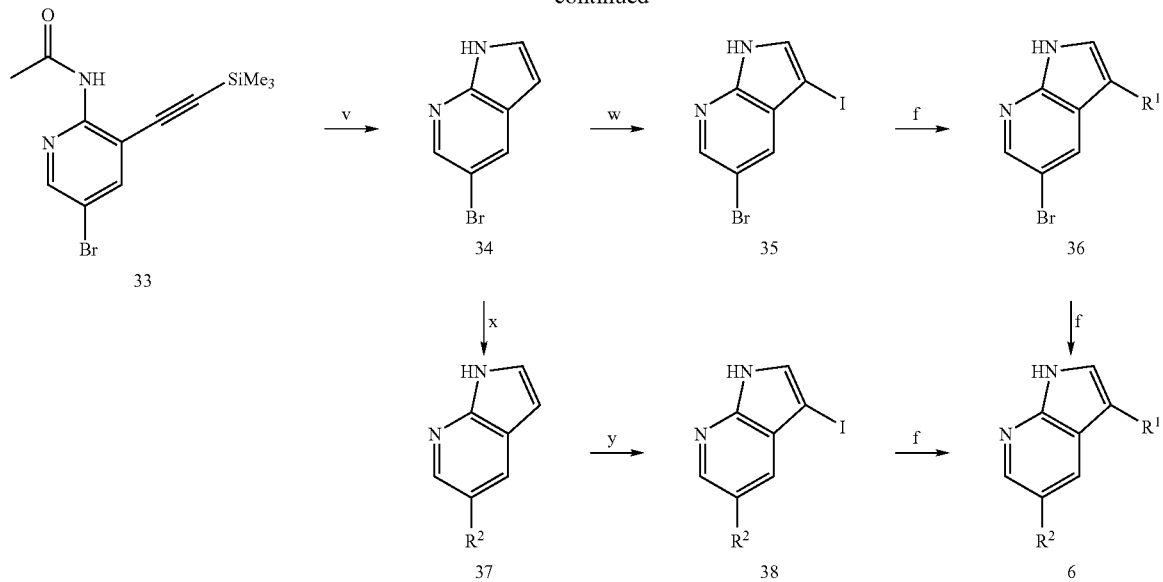

Elaboration of halides 34, 35 or 38 can be readily accomplished by generally well known methods. For example, metal catalyzed cross coupling reactions may be employed using various known transition metal compounds (e.g. compounds derived from palladium, iron or nickel). Examples of such transformations can be found in the following references: Diederich, F., Stang, P. J.—*Metal-catalyzed Cross-coupling Reactions*, Wiley-VCH, 1998; Beller, M., *Transition Metals for Organic Synthesis*, Wiley-VCH, 1998; Tsuji, J., *Palladium Reagents and Catalysts*, Wiley-VCH, 1$^{st}$. & 2$^{nd}$ ed.s, 1995, 2004; Fuerstner, A., et al., *J. Am. Chem. Soc.* (2002) 124, 13856; and Bolm, C., et al., *Chem Rev.* (2004) 104, 6217. Other useful methods involve the conversion of a bromine or iodine substituent into a metal or metalloid substituent (e.g. organoboron, organolithium, organotin, organosilicon, organozinc, organocopper or organomagnesium compound) using generally well known methods (e.g. metal halogen exchange and, as appropriate or required, subsequent transmetallation using soluble and reactive compounds of boron, magnesium, zinc, tin, silicon or copper; for representative examples of such methodology see: Schlosser, M., *Organometallics in Synthesis*, 2nd. ed., Wiley-VCH, 2002.). Organometallic derivatives obtained in such fashion may itself be of use in transition metal catalyzed coupling reactions with aromatic or olefinic halides or triflates, or, if sufficiently reactive, be reacted directly with suitable electrophiles, such as, for example, certain organic halides, MICHAEL-acceptors, oxiranes, aziridines, aldehydes, acyl halides, or nitriles.

Selective functionalization at either the 3- or 5-position may require different strategies depending on the nature of the transformations utilized to introduce functionalities at either position, especially the sequence of functionalization at either position. Thus, it may be advantageous or necessary to achieve functionalization at the 3-position prior to functionalization of the 5-position in some cases while the opposite approach may be required in other cases, depending on the nature of the specific groups to be introduced, the methods required to accomplish such transformations, or the inherent selectivity of the methods utilized. For example, some reactants, such as for example some boronic acids or their esters that are electron deficient (i.e. contain one or more electron withdrawing substituents or that represent derivatives of certain heterocyclic systems) and/or contain one or more substituents ortho to the boron-carbon bond may require the use of highly active palladium catalysts (such as, for example, those mentioned in Vilar, R., Christman, U. *Angew. Chem.* (2005)117, 370; Littke, A. F., Fu, G.—*Angew. Chem.* (2002) 114, 4350.) and more forcing conditions, such as for example higher temperatures and/or longer reaction times. Such conditions may not be conducive to achieving appreciable selectivities in reactions of 5-bromo-3-iodo-1H-pyrrolo[3,4-b]pyridine. Hence, in such cases, it will be advantageous to avoid selectivity issues altogether by sequential substitution of bromine in 5-bromo-1H-pyrrolo[3,4-b]pyridine, iodination at the 3-position and subsequent introduction of the second substituent at position 3 utilizing the methods detailed above. Generally speaking, whenever substitution of the halogen atom at either position may require conditions that involve highly reactive catalysts or reagents under conditions that generally do not favor high levels of selectivity between the two halogen atoms present in 5-bromo-3-iodo-1H-pyrrolo[3,4-b]pyridine it will be advantageous to resort to this sequential approach.

It will also be appreciated that protection of reactive groups within $R^1$ and/or $R^2$ as well as the pyrrolo[3,4-b]pyridine scaffold, (e.g. the proton at position 1), with a suitable protecting group may be advantageous or required. For example it was found to be advantageous in some cross-coupling reactions to protect the nitrogen at position 1 of the 1H-pyrrolo[3,4-b]pyridine scaffold by introduction of, for example, a 4-toluoylsulfonyl, tri-iso-propylsilyl or tetrahydro-1H-pyranyl group at that position. Introduction and removal of these protecting groups could be conveniently accomplished by methods well known in the chemical literature. As will be apparent to someone with skill in the art, the compounds obtained by any of the aforementioned methods may contain functional groups, either free or protected, that can be further elaborated by generally well known methods.

A more detailed description of the utilization of cross-coupling procedures in the synthesis of the compounds claimed under this invention is illustrated in Scheme 3: $X^1$ and $X^2$ are selected from, but not limited to, halogen, boronic acid or ester, trifluoroborate salt, organomagnesium, organozinc, or organotin. With respect to the introduction of individual residues $L^1R^1$ or $L^2R^2$ such transformations, as outlined above, can be achieved via standard halogen cross-coupling methodologies.

transition metal catalyzed transformations are well precedented in the chemical literature: see for example Ji, J., et al.—*Org. Lett* (2003) 5, 4611; Bach, T. et al.—*J. Org. Chem* (2002) 67, 5789, Adamczyk, M. et.al.—*Tetrahedron* (2003) 59, 8129.

This methodology may be extended to the incorporation of non-carbon based nucleophiles (e.g. alcohols, thiols, primary or secondary amines) that may optionally contain suitable protecting groups of alcohols, thiols or amines. Examples of Scheme 3

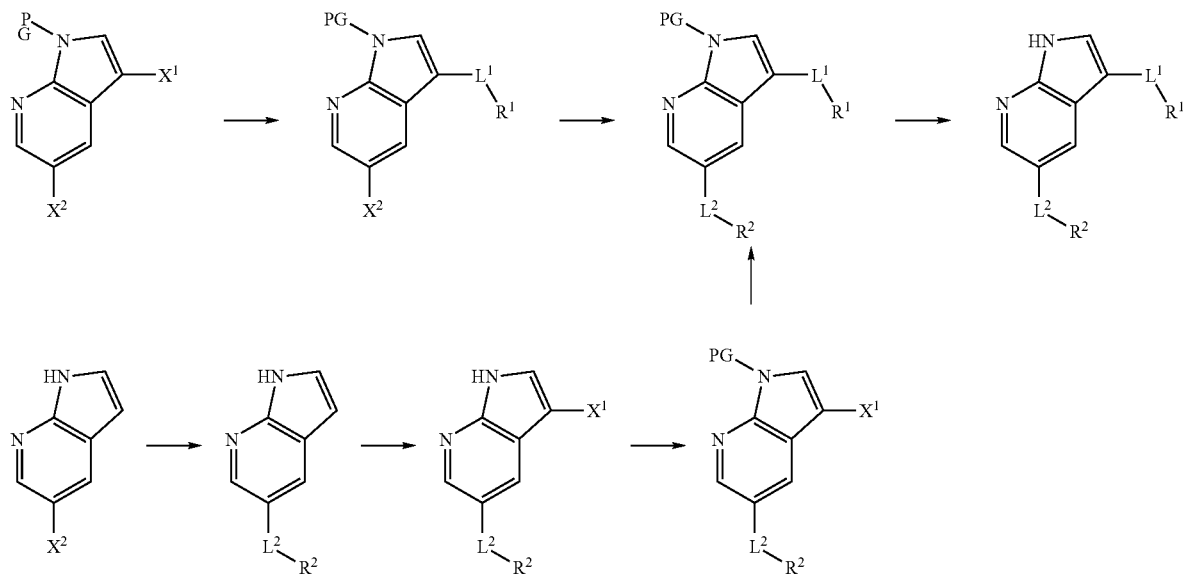

Couplings of the corresponding bromide or iodide ($X^1$, $X^2$=Br, I) with suitable reagents such as boronic acids and boronates, organoboranes, organostannanes, organozinc compounds, organomagnesium compounds, olefins or terminal alkynes (either purchased or obtained via generally well known protocols) can be carried out in the presence of a suitable transition metal catalyst (e.g. palladium compounds). The coupling may optionally be performed in the presence of ligands such as, but not limited to, phosphines, diphosphines, ARDUENGO-type heterocyclic carbenes (cf A. J. Arduengo III et al.—*Organometallics* (1998) 17, 3375; A. J. Arduengo III et al.—*J. Am. Chem. Soc.* (1994) 116, 4391) or arsines. Organic or inorganic bases (e.g. tertiary or secondary amines, alkaline carbonates, bicarbonates, fluorides or phosphates) and/or other well known additives (e.g. lithium chloride, copper halides or silver salts) may be utilized to effect, assist or accelerate such transformations.

These cross coupling reactions may be carried out in suitable solvents such as THF, dioxane, dimethoxyethane, diglyme, dichloromethane, dichloroethane, acetonitrile, DMF, N-methylpyrrolidone, water, or mixtures of thereof at temperatures ranging from 25° C. to 200° C. using. The temperature may optionally be maintained with heating, conventional heating or microwave irradiation. In the case of the 3-iodo-5-bromo-1H-pyrrolo[3,4-b]pyridine, the selective or preferential substitution of the iodo substituent over the bromo substituent is possible under generally less forcing conditions, such as lower temperature and shorter reaction times using a suitable transition metal catalyst. Selective functionalizations of di- or oligohalogen compounds by means of such groups can be found in Greene, T., et al., *Protective Groups in Organic Synthesis*, 3rd ed., John Wiley & Sons, 1999. Exemplary methods of such utilization of non-carbon nucleophiles in related cross-coupling reactions may be found in Ley, S., et al., *Angew. Chem.* (2003) 115, 5558; Wolfe, J., et al., *Acc. Chem. Res.* (1998) 31, 805; Hartwig, *Acc. Chem. Res.* (1998) 31, 852; Navarro, O., et al., *J. Org. Chem.* (2004) 69, 3173, Ji, J., et al., *Org. Lett* (2003) 5, 4611. The skilled artisan will recognize that the compounds obtained by such methods can be further elaborated by generally well known methods to obtain other compounds of the present invention.

In some cases it may be advantageous to achieve cross-couplings to carbon or non-carbon atoms by first converting the respective halogen derivative into the corresponding organometallic derivative (e.g., a boronic acid or ester, trifluoroborate salt, organomagnesium, organozinc or organotin compound). Such compounds are accessible by means of substituting the halide moiety with an appropriate metal or metalloid. Any functional groups present (e.g. the ring nitrogen in position 1 of the pyrrolo[3,4-b]pyridine), may need to be protected by a suitable protecting group ("PG", c.f. Greene, T., et al., *Protective Groups in Organic Synthesis*, 3rd ed., John Wiley & Sons, 1999).

Introduction of such metals or metalloids can be achieved by generally well-known methods, such as metallation using metals or a metal-halogen exchange reaction. Useful metals for metallation include alkaline or alkaline earth metals or activated forms of such metals. Suitable reagents for use in metal-halogen exchange reactions include organolithium or organomagnesium compounds (e.g. n-butyllithium, tert-butyllithium or iso-propylmagnesium chloride or bromide). Subsequent transmetalation reactions of the organometallic intermediate may be performed as needed with a suitable soluble and reactive metal compound such as magnesium chloride, magnesium bromide, tri-n-butyltin chloride, trimethyltin chloride, trimethyl borate, triethyl borate, tri-isopropyl borate, zinc triflate or zinc chloride. Introduction of a boronic acid pinacol ester can be conveniently achieved by reacting the halogen derivative directly with bis(pinacolato) diboron in the presence of dichloro[1,1'-bis(diphenylphosphino)ferrocene]palladium(II) and suitable bases (e.g. potassium or sodium acetate) in solvents such as DMSO, DMF, DMA or N-methylpyrrolidone at temperatures ranging from 80-160° C. Conventional heating or microwave irradiation may be employed to maintain the appropriate temperature (for literature precedent of similar transformations, see Ishiyama, T. et al.—*J. Org. Chem.* (1995) 60, 7508.).

Methods for conversion of the boronic acid pinacol ester obtained by this method into other boronic acid derivatives such as boronic acids, boronates, or trifluoroborate salts are generally well known. As will be apparent to the skilled artisan, such organometallic derivatives may be utilized in cross-coupling reactions similar to those described above in the case of halogen containing derivatives of pyrrolo[3,4-b] pyridine. Such couplings can be effected utilizing suitable coupling partners, such as aromatic, heteroaromatic halides or olefinic reagents under conditions identical or evidently similar and/or related to the methods described above.

Other methods may utilize the reactivity of organometallic derivatives generated from halogen containing derivatives of pyrrolo[3,4-b]pyridine by any of the methods described above. For example, derivatives containing alkaline or alkaline earth metals (e.g. organolithium, organomagnesium or organozinc compounds) may be employed in direct couplings to a range of other electrophilic coupling partners such as, for example, activated olefins (MICHAEL-acceptors), aldehydes, nitriles, aromatic nitro compounds, carboxylic acid derivatives, oxiranes, aziridines, organic disulfides or organic halides. Such transformations are generally well known in the art (for reactions with aromatic nitro compounds, see for example Sapountzis, I., et al., *J. Am. Chem. Soc.* (2002) 124, 9390.).

Protecting Groups

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

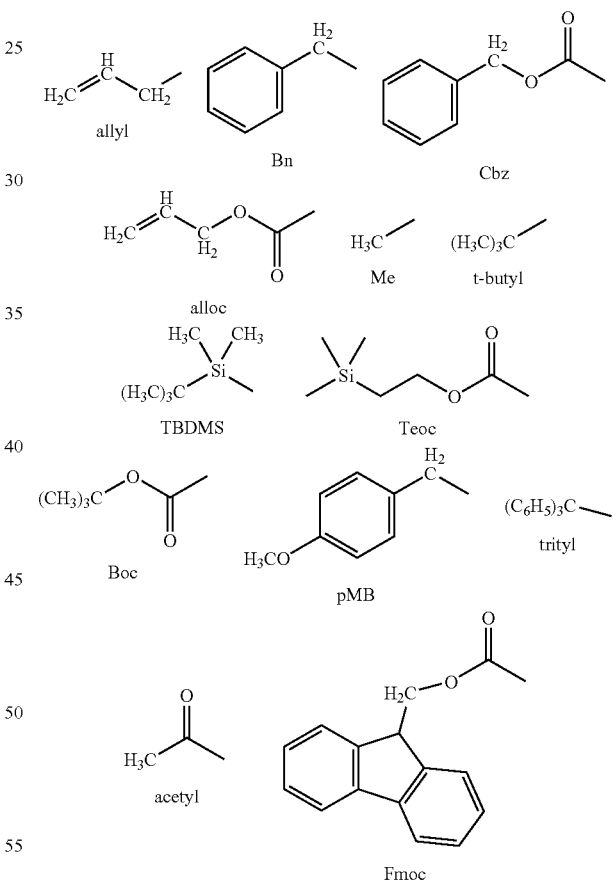

Methods of Inhibiting Kinases

In another aspect, the present invention provides methods of modulating protein kinase activity using the pyrrolo-pyridine kinase modulators of the present invention. The term "modulating kinase activity," as used herein, means that the activity of the protein kinase is increased or decreased when contacted with a pyrrolo-pyridine kinase modulator of the present invention relative to the activity in the absence of the pyrrolo-pyridine kinase modulator. Therefore, the present invention provides a method of modulating protein kinase activity by contacting the protein kinase with a pyrrolo-pyridine kinase modulator of the present invention (e.g. the compounds of any one of Formulae (I)-(XV)). In some embodiments, the compound of Formula (IV) is contacted with the protein kinase.

In some embodiments, the pyrrolo-pyridine kinase modulator inhibits kinase activity. The term "inhibit," as used herein in reference to kinase activity, means that the kinase activity is decreased when contacted with a pyrrolo-pyridine kinase modulator relative to the activity in the absence of the pyrrolo-pyridine kinase modulator. Therefore, the present invention further provides a method of inhibiting protein kinase activity by contacting the protein kinase with a pyrrolo-pyridine kinase modulator of the present invention.

In certain embodiments, the protein kinase is a protein tyrosine kinase. A protein tyrosine kinase, as used herein, refers to an enzyme that catalyzes the phosphorylation of tyrosine residues in proteins with a phosphate donors (e.g. a nucleotide phosphate donor such as ATP). Protein tyrosine kinases include, for example, Abelson tyrosine kinases ("Abl") (e.g. c-Abl and v-Abl), Ron receptor tyrosine kinases ("RON"), Met receptor tyrosine kinases ("MET"), Fms-like tyrosine kinases ("FLT") (e.g. FLT3), src-family tyrosine kinases (e.g. lyn, CSK), and p21-activated kinase-4 ("PAK"), FLT3, aurora kinases, B-lymphoid tyrosine kinases ("Blk"), cyclin-dependent kinases ("CDK") (e.g. CDK1 and CDK5), src-family related protein tyrosine kinases (e.g. Fyn kinase), glycogen synthase kinases ("GSK") (e.g. GSK3α and GSK3β), lymphocyte protein tyrosine kinases ("Lck"), ribosomal S6 kinases (e.g. Rsk1, Rsk2, and Rsk3), sperm tyrosine kinases (e.g. Yes), and subtypes and homologs thereof exhibiting tyrosine kinase activity. In certain embodiments, the protein tyrosine kinase is Abl, RON, MET, PAK, or FLT3. In other embodiments, the protein tyrosine kinase is a FLT3 or Abl family member.

In another embodiment, the kinase is a mutant kinase, such as a mutant Bcr-Abl kinase, FLT3 kinase or aurora kinases. Useful mutant Bcr-Abl kinases include those having at least one of the following clinically isolated mutations: M244V, L248V, G250E, G250A, Q252H, Q252R, Y253F, Y253H, E255K, E255V, D276G, F311L, T315I, T315N, T315A, F317V, F317L, M343T, M351T, E355G, F359A, F359V, V379I, F382L, L387M, H396P, H396R, S417Y, E459K and F486S. In some embodiments, the mutant Abl kinase has a T315I mutation. The numbering system denoting the position of the amino acid mutation above is the well known wild-type ABL numbering according to ABL exon Ia. See Deininger, M., et al., *Blood* 105(7), 2640 (2005). The numbering system is reproduced in FIG. 1. In some embodiments, the mutant Bcr-Abl kinase includes at least one of the mutations listed above and has at least 80%, 85%, 90%, 95%, 96%, 97%, 98%, 99%, or 100% sequence identity to the sequence of FIG. 1. In some embodiments, the mutant Bcr-Abl kinase includes at least one of the mutations listed above, has a sequence identity to FIG. 1 as discussed above, and includes at least 50, 100, 150, 200, 250, 300, 350, 400, 450, 500, 550, 600, 650, 700, 750, 800, 850, 900, 950, 1000, 1050, or 1100 amino acids.

In some embodiments, the kinase is selected from Abelson tyrosine kinase, Ron receptor tyrosine kinase, Met receptor tyrosine kinase, Fms-like tyrosine kinase-3, Aurora kinases, p21-activated kinase-4, and 3-phosphoinositide-dependent kinase-1. In some embodiments, the compound of Formula (I) is contacted with the kinase.

In another embodiment, the kinase is a mutant kinase, such as mutant Bcr-abl kinase, FLT3 kinase or aurora kinases. Useful Bcr-Abl mutant kinases include those having at least one of the following clinically isolated mutations: M244V, L248V, G250E, G250A, Q252H, Q252R, Y253F, Y253H, E255K, E255V, D276G, F311L, T315I, T315N, T315A, F317V, F317L, M343T, M351T, E355G, F359A, F359V, V379I, F382L, L387M, H396P, H396R, S417Y, E459K and F486S. In some embodiments, the mutant Abl kinase has a T315I mutation. The numbering system denoting the position of the amino acid mutation above is the well known wild-type ABL numbering according to ABL exon Ia. See Deininger, M., et al., *Blood* 105(7), 2640 (2005). The numbering system is reproduced in FIG. 1. In some embodiments, the mutant Bcr-Abl kinase includes at least one of the mutations listed above and has at least 80%, 85%, 90%, 95%, 96%, 97%, 98%, 99%, or 100% sequence identity to the sequence of FIG. 1 (SEQ ID NO: 23). In some embodiments, the mutant Bcr-Abl kinase includes at least one of the mutations listed above, has a sequence identity to FIG. 1 as discussed above, and includes at least 50, 100, 150, 200, 250, 300, 350, 400, 450, 500, 550, 600, 650, 700, 750, 800, 850, 900, 950, 1000, 1050, or 1100 amino acids.

Homology may also be determined by comparing the active site binding pocket of the enzyme with the active site binding pockets of a known kinase. For example, in homologous enzymes, at least 50%, 60%, 70%, 80%, or 90% of the amino acids of the molecule or homolog have amino acid structural coordinates of a domain comparable in size to the kinase domain that have a root mean square deviation of the alpha carbon atoms of up to about 1.5 Å, about 1.25 Å, about 1 Å, about 0.75 Å, about 0.5 Å, and or about 0.25 Å.

The compounds and compositions of the present invention are useful for inhibiting kinase activity and also for inhibiting other enzymes that bind ATP. They are thus useful for the treatment of diseases and disorders that may be alleviated by inhibiting such ATP-binding enzyme activity. Methods of determining such ATP binding enzymes include those known to those of skill in the art, those discussed herein relating to selecting homologous enzymes, and by the use of the database PROSITE, where enzymes containing signatures, sequence patterns, motifs, or profiles of protein families or domains may be identified.

The compounds of the present invention, and their derivatives, may also be used as kinase-binding agents. As binding agents, such compounds and derivatives may be bound to a stable resin as a tethered substrate for affinity chromatography applications. The compounds of this invention, and their derivatives, may also be modified (e.g., radiolabelled or affinity labeled, etc.) in order to utilize them in the investigation of enzyme or polypeptide characterization, structure, and/or function.

In an exemplary embodiment, the pyrrolo-pyridine kinase modulator of the present invention is a kinase inhibitor. In some embodiments, the kinase inhibitor has an $IC_{50}$ of inhibition constant ($K_i$) of less than 1 micromolar. In another embodiment, the kinase inhibitor has an $IC_{50}$ or inhibition constant ($K_i$) of less than 500 micromolar. In another embodiment, the kinase inhibitor has an $IC_{50}$ or $K_i$ of less than 10 micromolar. In another embodiment, the kinase inhibitor has an $IC_{50}$ or $K_i$ of less than 1 micromolar. In another embodiment, the kinase inhibitor has an $IC_{50}$ or $K_i$ of less than 500 nanomolar. In another embodiment, the kinase inhibitor has an $IC_{50}$ or $K_i$ of less than 10 nanomolar. In another embodiment, the kinase inhibitor has an $IC_{50}$ or $K_i$ of less than 1 nanomolar.

Methods of Treatment

In another aspect, the present invention provides methods of treating a disease mediated by kinase activity (kinase-mediated disease or disorder) in a subject (e.g. mammals, such as humans) in need of such treatment. By "kinase-mediated" or "kinase-associated" diseases is meant diseases in which the disease or symptom can be alleviated by inhibiting kinase activity (e.g. where the kinase is involved in signaling, mediation, modulation, or regulation of the disease process). By "diseases" is meant diseases, or disease symptoms. The method includes administering to the subject an effective amount of a pyrrolo-pyridine kinase modulator of the present invention (e.g. the compounds of any one of Formulae (I)-(XV)).

Examples of kinase associated diseases include cancer (e.g. leukemia, tumors, and metastases), allergy, asthma, obesity, inflammation (e.g. inflammatory diseases such as inflammatory airways disease), hematological disorders, obstructive airways disease, asthma, autoimmune diseases, metabolic diseases, infection (e.g. bacterial, viral, yeast, fungal), CNS diseases, brain tumors, degenerative neural diseases, cardiovascular diseases, and diseases associated with angiogenesis, neovascularization, and vasculogenesis. In an exemplary embodiment, the compounds are useful for treating cancer, including leukemia, and other diseases or disorders involving abnormal cell proliferation, such as myeloproliferative disorders. In some embodiments, the compound of Formula (I) is administered to the subject.

More specific examples of cancers treated with the compounds of the present invention include breast cancer, lung cancer, melanoma, colorectal cancer, bladder cancer, ovarian cancer, prostate cancer, renal cancer, squamous cell cancer, glioblastoma, pancreatic cancer, Kaposi's sarcoma, multiple myeloma, and leukemia (e.g. myeloid, chronic myeloid, acute lymphoblastic, chronic lymphoblastic, Hodgkins, and other leukemias and hematological cancers).

Other specific examples of diseases or disorders for which treatment by the compounds or compositions of the invention are useful for treatment or prevention include, but are not limited to transplant rejection (for example, kidney, liver, heart, lung, islet cells, pancreas, bone marrow, cornea, small bowel, skin allografts or xenografts and other transplants), graft vs. host disease, osteoarthritis, rheumatoid arthritis, multiple sclerosis, diabetes, diabetic retinopathy, inflammatory bowel disease (for example, Crohn's disease, ulcerative colitis, and other bowel diseases), renal disease, cachexia, septic shock, lupus, myasthenia gravis, psoriasis, dermatitis, eczema, seborrhea, Alzheimer's disease, Parkinson's disease, stem cell protection during chemotherapy, ex vivo selection or ex vivo purging for autologous or allogeneic bone marrow transplantation, ocular disease, retinopathies (for example, macular degeneration, diabetic retinopathy, and other retinopathies), corneal disease, glaucoma, infections (for example bacterial, viral, or fungal), heart disease, including, but not limited to, restenosis.

Assays

The compounds of the present invention may be easily assayed to determine their ability to modulate protein kinases, bind protein kinases, and/or prevent cell growth or proliferation. Some examples of useful assays are presented below.

Kinase Inhibition and Binding Assays

Inhibition of various kinases is measured by methods known to those of ordinary skill in the art, such as the various methods presented herein, and those discussed in the Upstate Kinase Profiler Assay Protocols June 2003 publication.

For example, where in vitro assays are performed, the kinase is typically diluted to the appropriate concentration to form a kinase solution. A kinase substrate and phosphate donor, such as ATP, is added to the kinase solution. The kinase is allowed to transfer a phosphate to the kinase substrate to form a phosphorylated substrate. The formation of a phosphorylated substrate may be detected directly by any appropriate means, such as radioactivity (e.g. [$\gamma$-$^{32}$P-ATP]), or the use of detectable secondary antibodies (e.g. ELISA). Alternatively, the formation of a phosphorylated substrate may be detected using any appropriate technique, such as the detection of ATP concentration (e.g. Kinase-Glo® assay system (Promega)). Kinase inhibitors are identified by detecting the formation of a phosphorylated substrate in the presence and absence of a test compound (see Examples section below).

The ability of the compound to inhibit a kinase in a cell may also be assayed using methods well known in the art. For example, cells containing a kinase may be contacted with an activating agent (such as a growth factor) that activates the kinase. The amount of intracellular phosphorylated substrate formed in the absence and the presence of the test compound may be determined by lysing the cells and detecting the presence phosphorylated substrate by any appropriate method (e.g. ELISA). Where the amount of phosphorylated substrate produced in the presence of the test compound is decreased relative to the amount produced in the absence of the test compound, kinase inhibition is indicated. More detailed cellular kinase assays are discussed in the Examples section below.

To measure the binding of a compound to a kinase, any method known to those of ordinary skill in the art may be used. For example, a test kit manufactured by Discoverx (Fremont, Calif.), ED-Staurosporine NSIP™ Enzyme Binding Assay Kit (see U.S. Pat. No. 5,643,734) may be used. Kinase activity may also be assayed as in U.S. Pat. No. 6,589,950, issued Jul. 8, 2003.

Suitable kinase inhibitors may be selected from the compounds of the invention through protein crystallographic screening, as disclosed in, for example Antonysamy, et al., PCT Publication No. WO03087816A1, which is incorporate herein by reference in its entirety for all purposes.

The compounds of the present invention may be computationally screened to assay and visualize their ability to bind to and/or inhibit various kinases. The structure may be computationally screened with a plurality of compounds of the present invention to determine their ability to bind to a kinase at various sites. Such compounds can be used as targets or leads in medicinal chemistry efforts to identify, for example, inhibitors of potential therapeutic importance (Travis, *Science*, 262:1374, 1993). The three dimensional structures of such compounds may be superimposed on a three dimensional representation of kinases or an active site or binding pocket thereof to assess whether the compound fits spatially into the representation and hence the protein. In this screening, the quality of fit of such entities or compounds to the binding pocket may be judged either by shape complementarity or by estimated interaction energy (Meng, et al., *J. Comp. Chem.* 13:505-24, 1992).

The screening of compounds of the present invention that bind to and/or modulate kinases (e.g. inhibit or activate kinases) according to this invention generally involves consideration of two factors. First, the compound must be capable of physically and structurally associating, either covalently or non-covalently with kinases. For example, covalent interactions may be important for designing irreversible or suicide inhibitors of a protein. Non-covalent molecular interactions important in the association of kinases with the compound include hydrogen bonding, ionic interactions, van der Waals, and hydrophobic interactions. Second, the compound must be able to assume a conformation and orientation in relation to the binding pocket, that allows it to associate with kinases. Although certain portions of the compound will not directly participate in this association with kinases, those portions may still influence the overall conformation of the molecule and may have a significant impact on potency. Conformational requirements include the overall three-dimensional structure and orientation of the chemical group or compound in relation to all or a portion of the binding pocket, or the spacing between functional groups of a compound comprising several chemical groups that directly interact with kinases.

Docking programs described herein, such as, for example, DOCK, or GOLD, are used to identify compounds that bind to the active site and/or binding pocket. Compounds may be screened against more than one binding pocket of the protein structure, or more than one set of coordinates for the same protein, taking into account different molecular dynamic conformations of the protein. Consensus scoring may then be used to identify the compounds that are the best fit for the protein (Charifson, P. S. et al., *J. Med. Chem.* 42: 5100-9 (1999)). Data obtained from more than one protein molecule structure may also be scored according to the methods described in Klingler et al., U.S. Utility Application, filed May 3, 2002, entitled "Computer Systems and Methods for Virtual Screening of Compounds." Compounds having the best fit are then obtained from the producer of the chemical library, or synthesized, and used in binding assays and bioassays.

Computer modeling techniques may be used to assess the potential modulating or binding effect of a chemical compound on kinases. If computer modeling indicates a strong interaction, the molecule may then be synthesized and tested for its ability to bind to kinases and affect (by inhibiting or activating) its activity.

Modulating or other binding compounds of kinases may be computationally evaluated by means of a series of steps in which chemical groups or fragments are screened and selected for their ability to associate with the individual binding pockets or other areas of kinases. This process may begin by visual inspection of, for example, the active site on the computer screen based on the kinases coordinates. Selected fragments or chemical groups may then be positioned in a variety of orientations, or docked, within an individual binding pocket of kinases (Blaney, J. M. and Dixon, J. S., *Perspectives in Drug Discovery and Design,* 1:301, 1993). Manual docking may be accomplished using software such as Insight II (Accelrys, San Diego, Calif.) MOE (Chemical Computing Group, Inc., Montreal, Quebec, Canada); and SYBYL (Tripos, Inc., St. Louis, Mo., 1992), followed by energy minimization and/or molecular dynamics with standard molecular mechanics force fields, such as CHARMM (Brooks, et al., *J. Comp. Chem.* 4:187-217, 1983), AMBER (Weiner, et al., *J. Am. Chem. Soc.* 106: 765-84, 1984) and $C^2$ MMFF (Merck Molecular Force Field; Accelrys, San Diego, Calif.). More automated docking may be accomplished by using programs such as DOCK (Kuntz et al., *J. Mol. Biol.,* 161:269-88, 1982; DOCK is available from University of California, San Francisco, Calif.); AUTODOCK (Goodsell & Olsen, Proteins: Structure, Function, and Genetics 8:195-202, 1990; AUTODOCK is available from Scripps Research Institute, La Jolla, Calif.); GOLD (Cambridge Crystallographic Data Centre (CCDC); Jones et al., *J. Mol. Biol.* 245: 43-53, 1995); and FLEXX (Tripos, St. Louis, Mo.; Rarey, M., et al., *J. Mol. Biol.* 261:470-89, 1996). Other appropriate programs are described in, for example, Halperin, et al.

During selection of compounds by the above methods, the efficiency with which that compound may bind to kinases may be tested and optimized by computational evaluation. For example, a compound that has been designed or selected to function as a kinases inhibitor may occupy a volume not overlapping the volume occupied by the active site residues when the native substrate is bound, however, those of ordinary skill in the art will recognize that there is some flexibility, allowing for rearrangement of the main chains and the side chains. In addition, one of ordinary skill may design compounds that could exploit protein rearrangement upon binding, such as, for example, resulting in an induced fit. An effective kinase inhibitor may demonstrate a relatively small difference in energy between its bound and free states (i.e., it must have a small deformation energy of binding and/or low conformational strain upon binding). Thus, the most efficient kinase inhibitors should, for example, be designed with a deformation energy of binding of not greater than 10 kcal/mol, not greater than 7 kcal/mol, not greater than 5 kcal/mol, or not greater than 2 kcal/mol. Kinase inhibitors may interact with the protein in more than one conformation that is similar in overall binding energy. In those cases, the deformation energy of binding is taken to be the difference between the energy of the free compound and the average energy of the conformations observed when the inhibitor binds to the enzyme.

Specific computer software is available in the art to evaluate compound deformation energy and electrostatic interaction. Examples of programs designed for such uses include: Gaussian 94, revision C (Frisch, Gaussian, Inc., Pittsburgh, Pa. (C1995); AMBER, version 7. (Kollman, University of California at San Francisco, ®2002); QUANTA/CHARMM (Accelrys, Inc., San Diego, Calf., ®1995); Insight II/Discover (Accelrys, Inc., San Diego, Calif., ®1995); DelPhi (Accelrys, Inc., San Diego, Calif., ®1995); and AMSOL (University of Minnesota) (Quantum Chemistry Program Exchange, Indiana University). These programs may be implemented, for instance, using a computer workstation, as are well known in the art, for example, a LINUX, SGI or Sun workstation. Other hardware systems and software packages will be known to those skilled in the art.

Those of ordinary skill in the art may express kinase protein using methods known in the art, and the methods disclosed herein. The native and mutated kinase polypeptides described herein may be chemically synthesized in whole or part using techniques that are well known in the art (see, e.g., Creighton, Proteins: Structures and Molecular Principles, W.H. Freeman & Co., NY, 1983).

Gene expression systems may be used for the synthesis of native and mutated polypeptides. Expression vectors containing the native or mutated polypeptide coding sequence and appropriate transcriptional/translational control signals, that are known to those skilled in the art may be constructed. These methods include in vitro recombinant DNA techniques, synthetic techniques and in vivo recombination/genetic recombination. See, for example, the techniques described in Sambrook et al., Molecular Cloning: A Laboratory Manual, Cold Spring Harbor Laboratory, NY, 2001, and Ausubel et al., Current Protocols in Molecular Biology, Greene Publishing Associates and Wiley Interscience, NY, 1989.

Host-expression vector systems may be used to express kinase. These include, but are not limited to, microorganisms such as bacteria transformed with recombinant bacteriophage DNA, plasmid DNA or cosmid DNA expression vectors containing the coding sequence; yeast transformed with recombinant yeast expression vectors containing the coding sequence; insect cell systems infected with recombinant virus expression vectors (e.g., baculovirus) containing the coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence; or animal cell systems. The protein may also be expressed in human gene therapy systems, including, for example, expressing the protein to augment the amount of the protein in an individual, or to express an engineered therapeutic protein. The expression elements of these systems vary in their strength and specificities.

Specifically designed vectors allow the shuttling of DNA between hosts such as bacteria-yeast or bacteria-animal cells. An appropriately constructed expression vector may contain: an origin of replication for autonomous replication in host cells, one or more selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency.

The expression vector may also comprise various elements that affect transcription and translation, including, for example, constitutive and inducible promoters. These elements are often host and/or vector dependent. For example, when cloning in bacterial systems, inducible promoters such as the T7 promoter, pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, mammalian promoters (e.g., metallothionein promoter) or mammalian viral promoters, (e.g., adenovirus late promoter; vaccinia virus 7.5K promoter; SV40 promoter; bovine papilloma virus promoter; and Epstein-Barr virus promoter) may be used.

Various methods may be used to introduce the vector into host cells, for example, transformation, transfection, infection, protoplast fusion, and electroporation. The expression vector-containing cells are clonally propagated and individually analyzed to determine whether they produce the appropriate polypeptides. Various selection methods, including, for example, antibiotic resistance, may be used to identify host cells that have been transformed. Identification of polypeptide expressing host cell clones may be done by several means, including but not limited to immunological reactivity with anti-kinase antibodies, and the presence of host cell-associated activity.

Expression of cDNA may also be performed using in vitro produced synthetic mRNA. Synthetic mRNA can be efficiently translated in various cell-free systems, including but not limited to wheat germ extracts and reticulocyte extracts, as well as efficiently translated in cell-based systems, including, but not limited, to microinjection into frog oocytes.

To determine the cDNA sequence(s) that yields optimal levels of activity and/or protein, modified cDNA molecules are constructed. A non-limiting example of a modified cDNA is where the codon usage in the cDNA has been optimized for the host cell in which the cDNA will be expressed. Host cells are transformed with the cDNA molecules and the levels of kinase RNA and/or protein are measured.

Levels of kinase protein in host cells are quantitated by a variety of methods such as immunoaffinity and/or ligand affinity techniques, kinase-specific affinity beads or specific antibodies are used to isolate $^{35}$S-methionine labeled or unlabeled protein. Labeled or unlabeled protein is analyzed by SDS-PAGE. Unlabeled protein is detected by Western blotting, ELISA or RIA employing specific antibodies.

Following expression of kinase in a recombinant host cell, polypeptides may be recovered to provide the protein in active form. Several purification procedures are available and suitable for use. Recombinant kinase may be purified from cell lysates or from conditioned culture media, by various combinations of, or individual application of, fractionation, or chromatography steps that are known in the art.

In addition, recombinant kinase can be separated from other cellular proteins by use of an immuno-affinity column made with monoclonal or polyclonal antibodies specific for full length nascent protein or polypeptide fragments thereof. Other affinity based purification techniques known in the art may also be used.

Alternatively, the polypeptides may be recovered from a host cell in an unfolded, inactive form, e.g., from inclusion bodies of bacteria. Proteins recovered in this form may be solubilized using a denaturant, e.g., guanidinium hydrochloride, and then refolded into an active form using methods known to those skilled in the art, such as dialysis.

Cell Growth Assays

A variety of cell growth assays are known in the art and are useful in identifying pyrrolo-pyridine compounds (i.e. "test compounds") capable of inhibiting (e.g. reducing) cell growth and/or proliferation.

For example, a variety of cells are known to require specific kinases for growth and/or proliferation. The ability of such a cell to grow in the presence of a test compound may be assessed and compared to the growth in the absence of the test compound thereby identifying the anti-proliferative properties of the test compound. One common method of this type is to measure the degree of incorporation of label, such as tritiated thymidine, into the DNA of dividing cells. Alternatively, inhibition of cell proliferation may be assayed by determining the total metabolic activity of cells with a surrogate marker that correlates with cell number. Cells may be treated with a metabolic indicator in the presence and absence of the test compound. Viable cells metabolize the metabolic indicator thereby forming a detectable metabolic product. Where detectable metabolic product levels are decreased in the presence of the test compound relative to the absence of the test compound, inhibition of cell growth and/or proliferation is indicated. Exemplary metabolic indicators include, for example tetrazolium salts and AlamorBlue® (see Examples section below).

Pharmaceutical Compositions and Administration

In another aspect, the present invention provides a pharmaceutical composition including a pyrrolo-pyridine kinase modulator in admixture with a pharmaceutically acceptable excipient. One of skill in the art will recognize that the pharmaceutical compositions include the pharmaceutically acceptable salts of the pyrrolo-pyridine kinase modulators described above.

In therapeutic and/or diagnostic applications, the compounds of the invention can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A most preferable dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intrasynovial, intra-hepatic, intralesional, intracranial, intraperitoneal, intranasal, or intraocular injections or other modes of delivery.

For injection, the agents of the invention may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a subject (e.g. patient) to be treated.

For nasal or inhalation delivery, the agents of the invention may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this invention. For example, chemotherapeutic agents or other anti-proliferative agents may be combined with the inhibitors of this invention to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the inhibitors of this invention may also be combined with include, without limitation, antiinflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

The present invention is not to be limited in scope by the exemplified embodiments, which are intended as illustrations of single aspects of the invention. Indeed, various modifications of the invention in addition to those described herein will become apparent to those having skill in the art from the foregoing description. Such modifications are intended to fall within the scope of the invention. Moreover, any one or more features of any embodiment of the invention may be combined with any one or more other features of any other embodiment of the invention, without departing from the scope of the invention. For example, the pyrrolo-pyridine kinase modulators described in the Pyrrolo-pyridine Kinase Modulators section are equally applicable to the methods of treatment and methods of inhibiting kinases described herein. References cited throughout this application are examples of the level of skill in the art and are hereby incorporated by reference herein in their entirety for all purposes, whether previously specifically incorporated or not.

EXAMPLES

The following examples are offered to illustrate, but not to limit the claimed invention. The preparation of embodiments of the present invention is described in the following examples. Those of ordinary skill in the art will understand that the chemical reactions and synthesis methods provided may be modified to prepare many of the other compounds of the present invention. Where compounds of the present invention have not been exemplified, those of ordinary skill in the art will recognize that these compounds may be prepared by modifying synthesis methods presented herein, and by using synthesis methods known in the art. The compounds with assay results given are marked with AE.

Synthesis of Compounds:

Method 1:

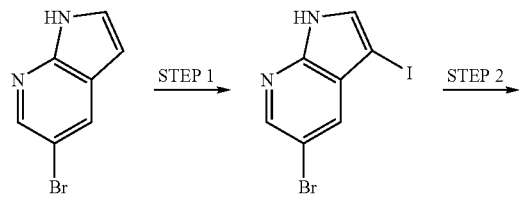

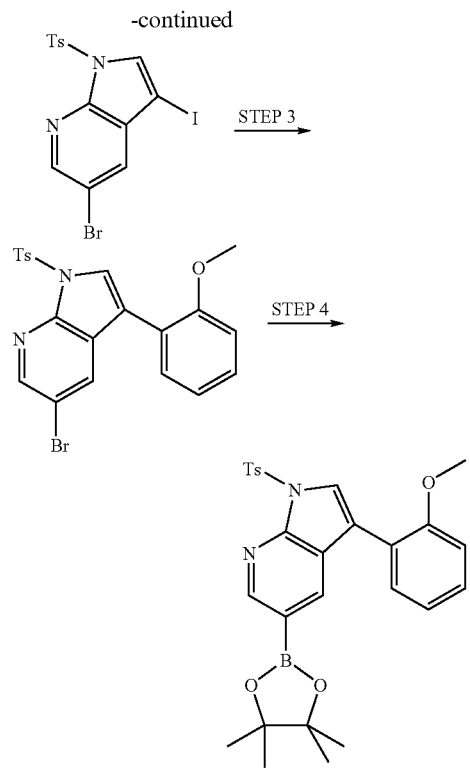

Step 1: Synthesis of 5-bromo-3-iodo-1H-pyrrolo[2,3-b]pyridine

Into a 500 mL round bottomed flask were added 5-bromo-1H-pyrrolo[2,3-b]pyridine (10.11 g, 51.3 mmol) and 250 ml acetone. N-iodosuccinimide (NIS, 12.7 g, 56.4 mmol) was added, and the reaction mixture was stirred at room temperature for 1 hour. The precipitate was collected and washed with cold acetone to afford 12.2 g (74%) of the title compound as a tan powder. $^1$H-NMR (500 MHz, d$_6$-DMSO) δ=12.35 (br.s, 1H), 8.29 (d, J=2.0 Hz, 1H), 7.84 (d, J=2.0 Hz 1H), 7.79 (s, 1H); MS: m/z 322.8/324.8 [MH$^+$].

Step 2: Synthesis of 5-Bromo-3-iodo-1-(toluene-4-sulfonyl)-1H-pyrrolo[2,3-b]pyridine Into a 250 mL round bottomed flask were added 5-bromo-3-iodo-1H-pyrrolo[2,3-b]pyridine (8.00 g, 40.6 mmol) and 120 mL dry THF. The solution was cooled in an ice bath at 0° C. and NaH (2.40 g, 60.0 mmol) was added in three portions. After 20 min, p-toluenesulfonyl chloride (8.70 g, 45.63 mmol) was added, and the reaction mixture was allowed to warm to rt over 30 min. The reaction mixture was concentrated and hexanes was added to obtain a precipitate, which was collected and washed with ice cold 2M NaOH. The crude product was recrystallized from EtOAc/hexanes to afford 17.8 g (92%) of the title compound as a light tan powder. $^1$H-NMR (500 MHz, d$_6$-DMSO) δ 8.49 (d, J=2.5 Hz, 1H), 8.21 (s, 1H), 7.99 (d, J=2.0 Hz, 1H), 7.98 (d, J=8.5 Hz, 2H), 7.42 (d, J=8.5 Hz, 2H), 2.32 (s, 3H); MS: m/z 476.8/478.8 [MH$^+$].

Step 3: Synthesis of 5-Bromo-3-(2-methoxy-phenyl)-1-(toluene-4-sulfonyl)-1H-pyrrolo[2,3-b]pyridine Into a 500 mL round bottomed flask were added 5-Bromo-3-iodo-1-(toluene-4-sulfonyl)-1H-pyrrolo[2,3-b]pyridine (11.80 g, 20.96 mmol), 2-methoxyphenyl boronic acid (3.76 g, 24.74 mmol), dichlorobis(triphenylphosphine)palladium (II) (0.756 g, 1.08 mmol), acetonitrile (100 mL) and 100 mL of 2M $Na_2CO_3$ (aq). The flask was fitted with a reflux condenser and heated at 60° C. with rapid stirring under $N_2$ for 8 h. The reaction mixture was filtered to obtain a grey-tan precipitate, which was dissolved in EtOAc and washed with water followed by brine. Concentration of this solution afforded 7.70 g (80%) of the title compound as a tan powder. $^1$H-NMR (500 MHz, $d_6$-DMSO) δ 8.50 (d, J=2.0 Hz, 1H), 8.14 (d, J=2.5 Hz, 1H), 8.07 (s, 1H), 8.03 (d, J=8.0 Hz, 2H), 7.54 (dd, J=1.5, 7.5 Hz, 1H), 7.43 (d, J=8.0 Hz, 2H), 7.39 (m, 1H), 7.15 (d, J=7.5 Hz, 1H), 7.05 (t, J=7.0 Hz, 1H), 3.80 (s, 3H), 2.34 (s, 3H); MS: m/z 456.9/458.9 [MH$^+$].

Step 4: Synthesis of 3-(2-Methoxy-phenyl)-5-(4,4,5,5-tetramethyl-[1,3,2]dioxaborolan-2-yl)-1-(toluene-4-sulfonyl)-1H-pyrrolo[2,3-b]pyridine Into a 5 mL Personal Chemistry microwave reaction vial were added 5-Bromo-3-(2-methoxy-phenyl)-1-(toluene-4-sulfonyl)-1H-pyrrolo[2,3-b]pyridine (0.102 g, 0.220 mmol), Bis(pinacolato)diboron (0.123 g, 0.483 mmol), 1,1'-bis(diphenylphosphino)ferrocenepalladium(II)-dichloride dichloromethane adduct (9.1 mg, 0.01 mmol) and anhydrous sodium acetate (55 mg, 0.67 mmol) and anhydrous DMF (1 mL). The resulting mixture was irradiated in a Personal Chemistry Optimizer at 140° C. for 60 min and then diluted with EtOAc and extracted 4× with water. The organic phase was treated with brine, dried ($Na_2SO_4$), filtered and concentrated. The crude product was purified by flash silica gel chromatography using a gradient of ethyl acetate in hexanes to afford 90.9 mg (81%) of the title compound a white powder. $^1$H-NMR (500 MHz, $CDCl_3$) δ 8.79 (d, J=1.0 Hz, 1H), 8.32 (d, J=1.0 Hz, 1H), 8.11 (d, J=5.5 Hz, 2H), 7.94 (d, J=3.0 Hz, 1H), 7.50 (m, 1H), 7.35 (t, J=7.5 Hz, 1H), 7.25 (d, J=7.5 Hz, 2H), 7.05 (t, J=7.2 Hz, 1H), 7.01 (d, J=7.2 Hz, 1H), 3.85 (s, 3H), 2.35 (s, 3H), 1.31 (s, 12H); MS: m/z 505.1 [MH$^+$].

Other compounds prepared by Method 1:

TABLE 1

| Structure |
| --- |
| 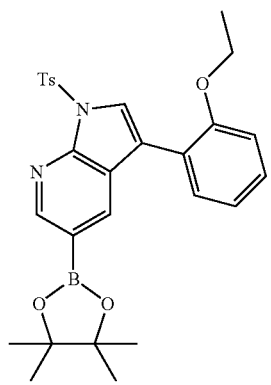<br>MS: m/z 519 [MH$^+$]. |
| 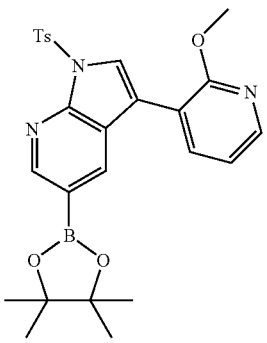<br>MS: m/z 506 [MH$^+$]. |
| 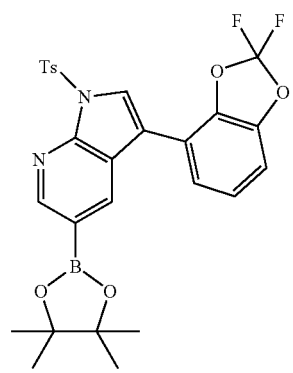<br>MS: m/z 555 [MH$^+$]. |
| 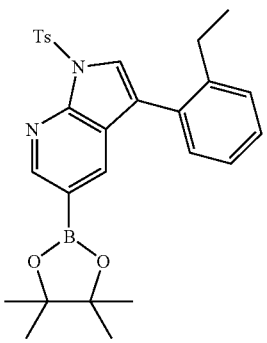<br>MS: m/z 503 [MH$^+$]. |
| 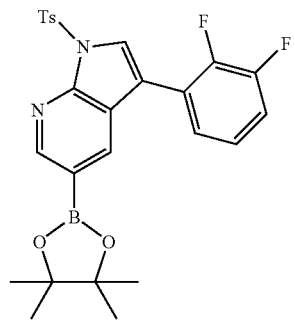<br>MS: m/z 511 [MH$^+$]. |

TABLE 1-continued
Structure
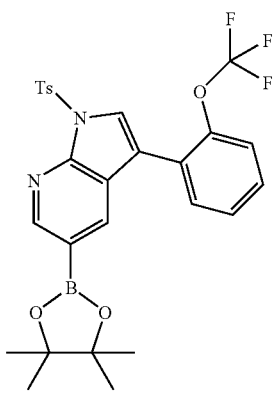
MS: m/z 559 [MH+].
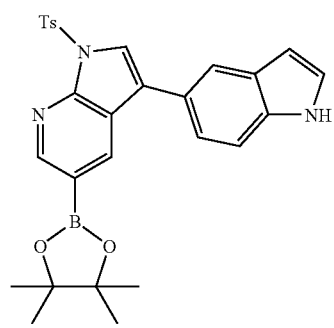
MS: m/z 514 [MH+].
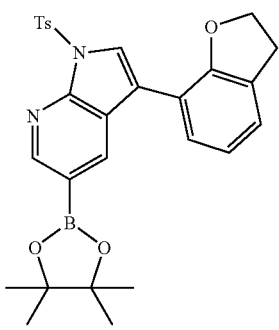
MS: m/z 517 [MH+].
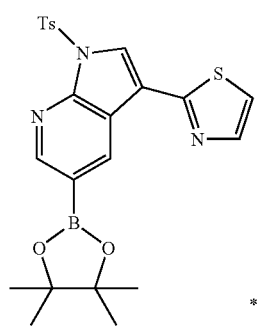
MS: m/z 505 [MH+].
TABLE 1-continued
Structure
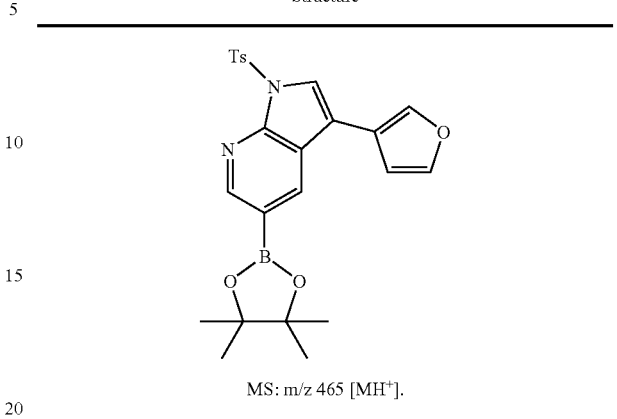
MS: m/z 465 [MH+].
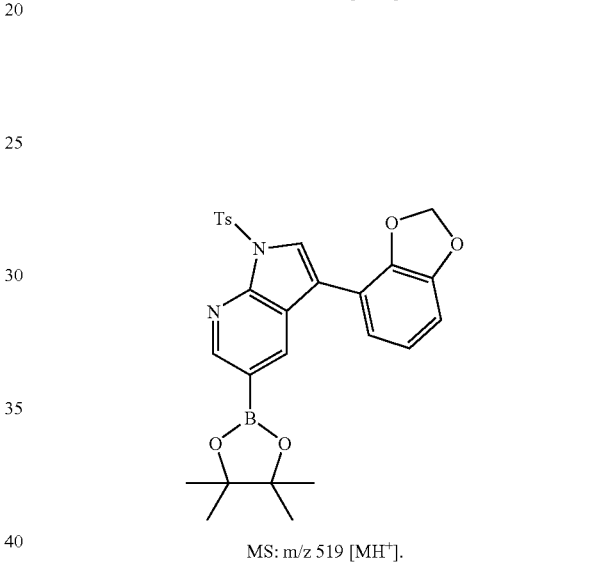
MS: m/z 519 [MH+].
* See Method 23 on synthesis of 2-(5-(pyridine-3-yl)-1H-pyrrolo[2,3-b]pyridine-3-yl)thiazole.
Method 2:
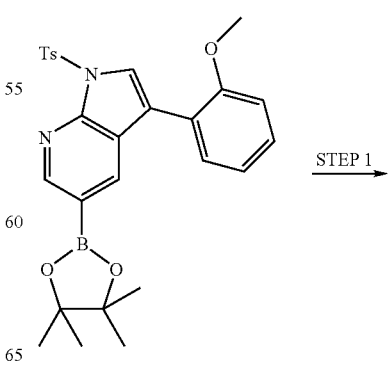
STEP 1

-continued

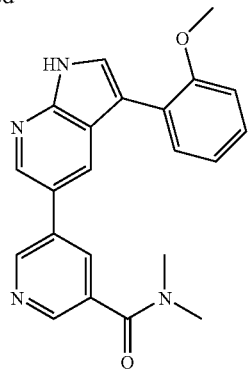

Step 1: Synthesis of 5-[3-(2-Methoxy-phenyl)-1H-pyrrolo[2,3-b]pyridin-5-yl]-N,N-dimethyl-nicotinamide Into a 5 mL Personal Chemistry microwave reaction vial were added 3-(2-Methoxy-phenyl)-5-(4,4,5,5-tetramethyl-[1,3,2]dioxaborolan-2-yl)-1-(toluene-4-sulfonyl)-1H-pyrrolo[2,3-b]pyridine (0.136 g, 0.270 mmol), 5-Bromo-N,N-dimethyl-nicotinamide (0.0756 g, 0.332 mmol; preparation described below), 1,1'-bis(diphenylphosphino)ferrocenepalladium(II)-dichloride dichloromethane adduct (16.2 mg, 0.01 mmol), acetonitrile (2 mL) and saturated aqueous $NaHCO_3$ (2 mL). The vial was sealed, purged with $N_2$, and irradiated in a Personal Chemistry Optimizer at 90° C. for 15 min. The layers were separated, and the aqueous phase was extracted 3× with EtOAc. The combined organic phase was treated with brine, dried ($Na_2SO_4$), filtered and concentrated. The crude product was dissolved in 3:1 MeOH/acetone (4 mL total) and treated with 500 µL of 50% w/w KOH(aq) for 1 h. Glacial Acetic acid was added to obtain pH 7, then the reaction mixture was concentrated. The residue was partitioned between EtOAc and water, then the layers were separated, and the organic phase was washed 2× with water. The organic phase was treated with brine, dried ($Na_2SO_4$), filtered and concentrated. Purification by flash silica gel chromatography using a gradient of ethyl acetate (containing 10% MeOH) and hexanes afforded the title compound as a tan powder (57 mg, 57%). $^1$H-NMR (500 MHz, $d_6$-DMSO) δ=11.96 (br. s, 1H), 8.95 (d, J=2.5 Hz, 1H), 8.56 (d, J=2.0 Hz, 1H), 8.52 (d, J=2.0 Hz, 1H), 8.24 (d, J=2.0 Hz, 1H), 8.13 (t, J=2.0 Hz, 1H), 7.72 (d, J=3.0 Hz, 1H), 7.59(dd, J=2.0, 5.5 Hz, 1H), 7.25 (dd, J=1, 7.5 Hz, 1H), 7.08 (d, J=7.5 Hz, 1H), 6.99 (t, J=7.5 Hz, 1H), 3.76 (s, 3H), 2.97 (s, 3H), 2.92 (s, 3H); MS: m/z 373.1 [MH$^+$].

Preparation of intermediate: 5-Bromo-N,N-dimethyl-nicotinamide: Into a 100 mL round bottomed flask were added 5-bromonicotinoyl chloride (0.531 g, 2.41 mmol) and anhydrous pyridine (5 mL). A 2M solution of dimethylamine in THF (5 mL, 10.0 mmol) was added dropwise, and the reaction mixture was stirred at rt under $N_2$ for 6 h after which it was concentrated under vacuum. The crude residue was partitioned between EtOAc and water. The layers were separated, and the organic phase was washed 3× with water, then treated with brine, dried ($Na_2SO_4$), filtered and concentrated to afford 5-Bromo-N,N-dimethyl-nicotinamide as a brown oil (0.4951 g, 89%). MS: m/z 229/231 [MH$^+$].

Other compounds prepared by Method 2 (Either silica gel chromatography or mass triggered reverse phase HPLC or both may be used for the purification of the following compounds):

TABLE 2

Structure

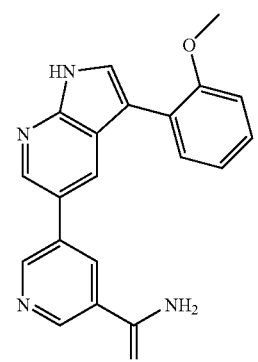

MS: m/z 345[MH$^+$]

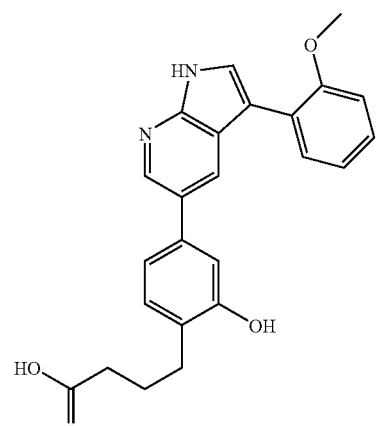

MS: m/z 403[MH$^+$]

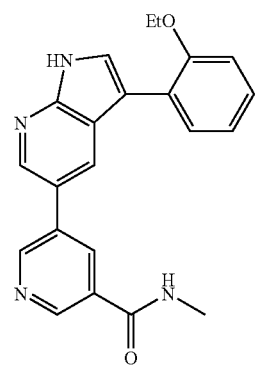

AE17

MS: m/z 373.1(M + H$^+$)

TABLE 2-continued
Structure
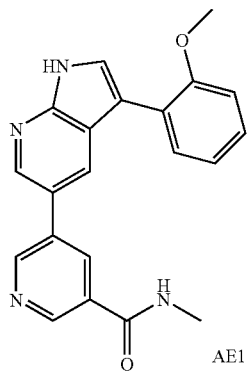
MS: m/z 359[MH+]
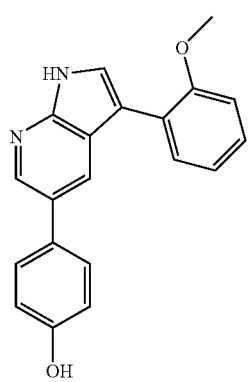
MS: m/z 317[MH+]
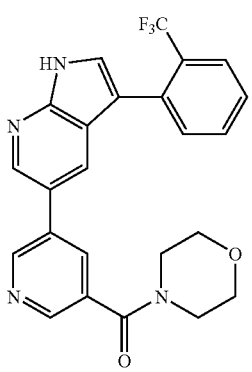
MS: m/z 453.1(M + H+)
TABLE 2-continued
Structure
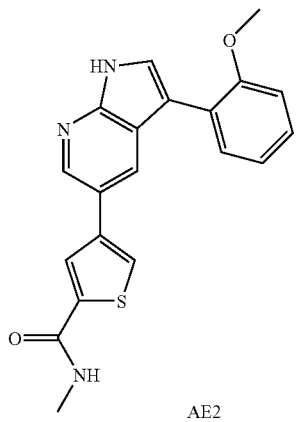
MS: m/z 364[MH+]
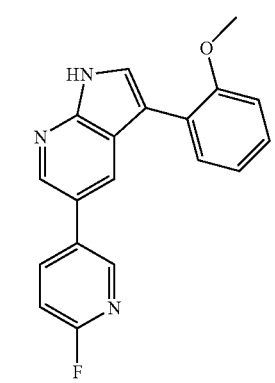
MS: m/z 320[MH+]
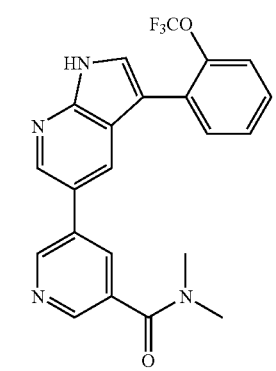
MS: m/z 427.1(M + H+)

TABLE 2-continued
Structure
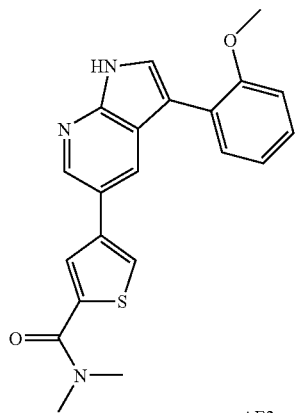
AE3
MS: m/z 378[MH+]
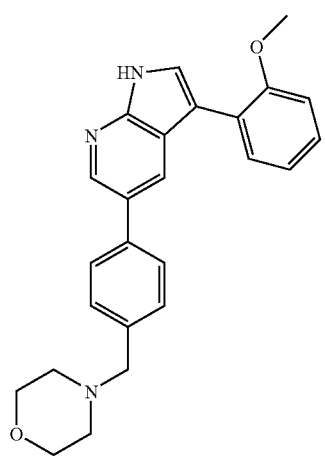
MS: m/z 400[MH+]
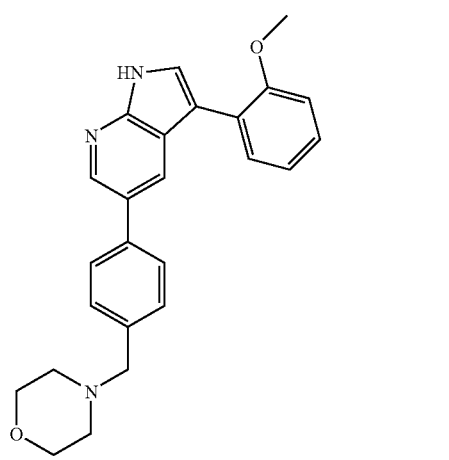
MS: m/z 413.1(M + H)+
TABLE 2-continued
Structure
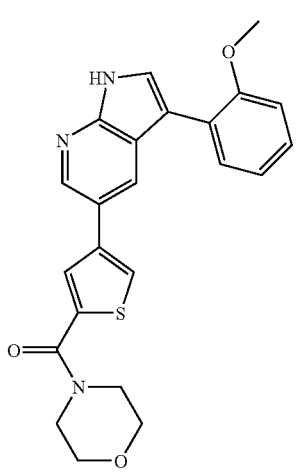
MS: m/z 420[MH+]
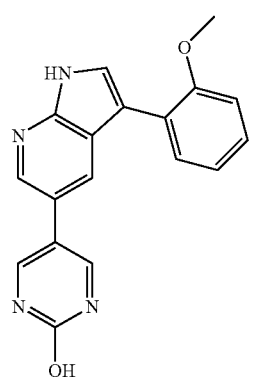
MS: m/z 319[MH+]
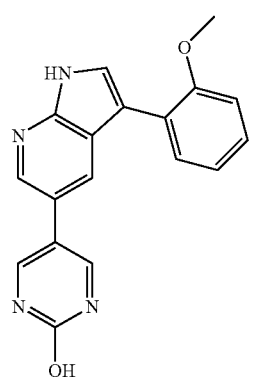
MS: m/z 469.1(M + H+)

TABLE 2-continued
| Structure |
|---|
| 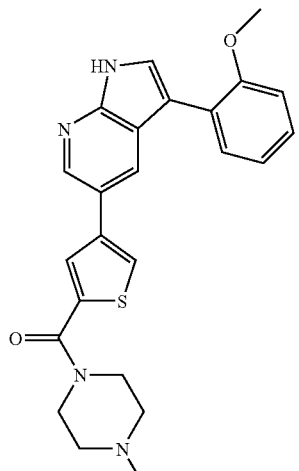<br>AE4<br>MS: m/z 433[MH⁺] |
| 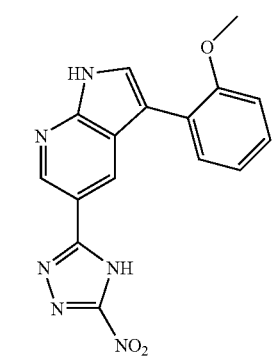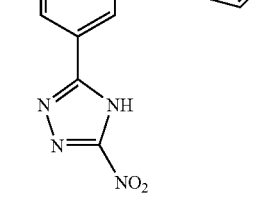<br>MS: m/z 337[MH⁺] |
| 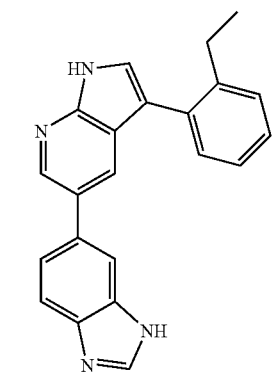<br>MS: m/z 339[MH⁺] |
TABLE 2-continued
| Structure |
|---|
| 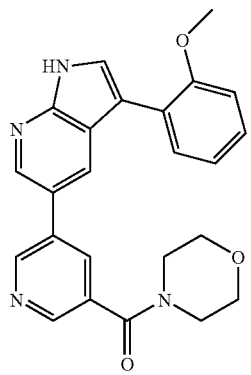<br>MS: m/z 415[MH⁺] |
| 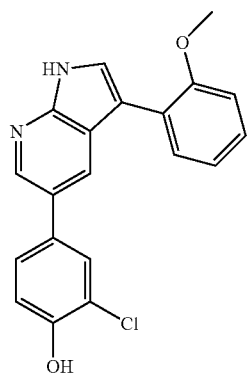<br>MS: m/z 351[MH⁺] |
| 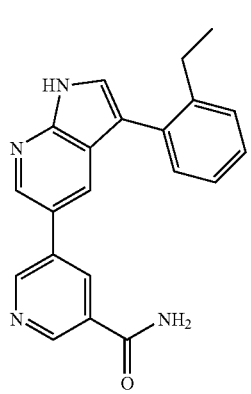<br>MS: m/z 343[MH⁺] |

TABLE 2-continued
Structure
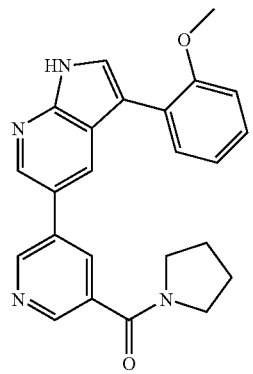
MS: m/z 399[MH+]
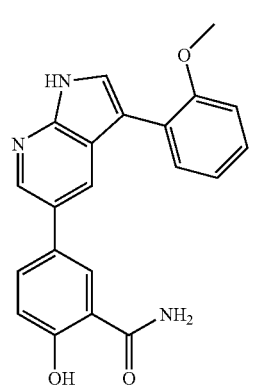
MS: m/z 360[MH+]
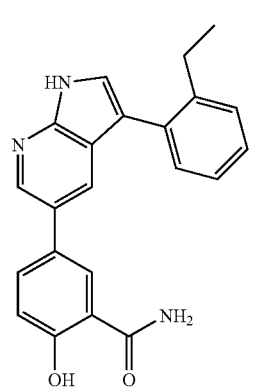
MS: m/z 358[MH+]
TABLE 2-continued
Structure
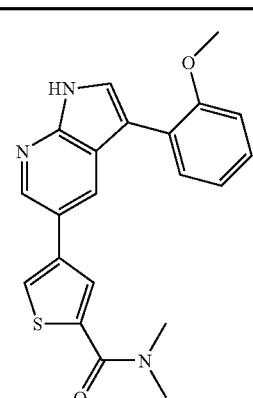
MS: m/z 378[MH+]
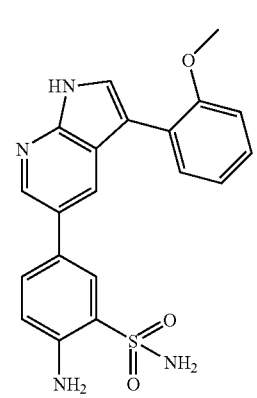
MS: m/z 395[MH+]
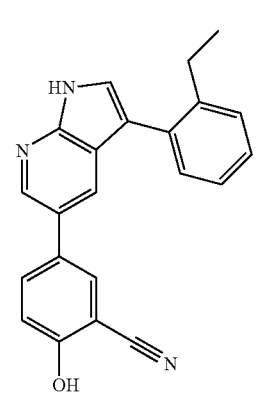
MS: m/z 340[MH+]

TABLE 2-continued
Structure
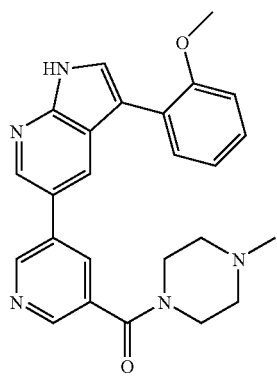
MS: m/z 428[MH⁺]
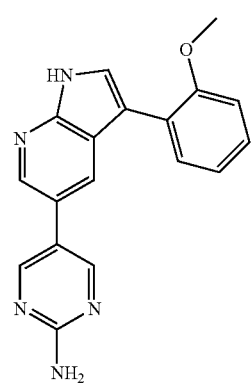
MS: m/z 318[MH⁺]
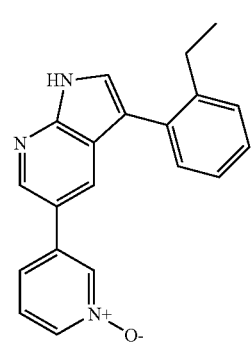
MS: m/z 316[MH⁺]
TABLE 2-continued
Structure
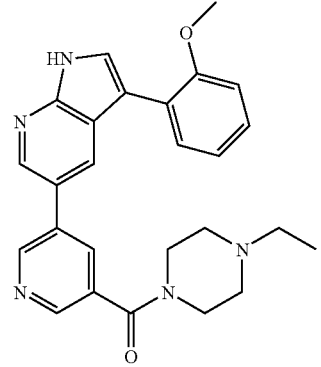
MS: m/z 442[MH⁺]
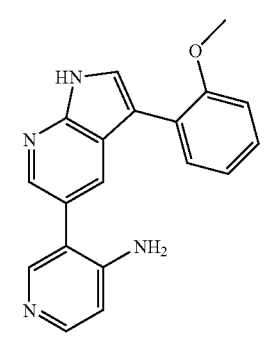
MS: m/z 317[MH⁺]
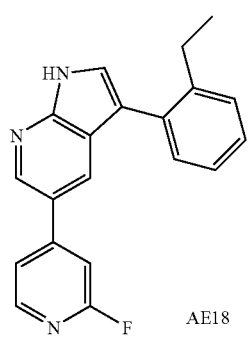
AE18
MS: m/z 318[MH⁺]
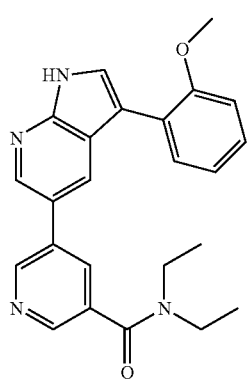
MS: m/z 401[MH⁺]

TABLE 2-continued
| Structure |
|---|
| 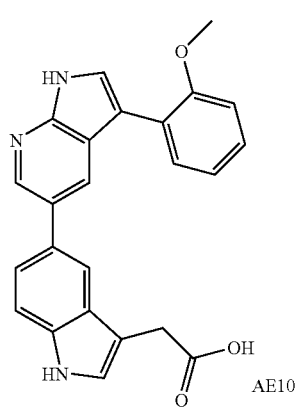 AE10<br>MS: m/z 398[MH⁺] |
| 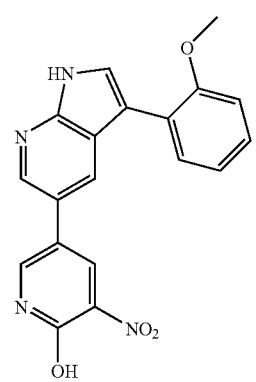<br>MS: m/z 363[MH⁺] |
| 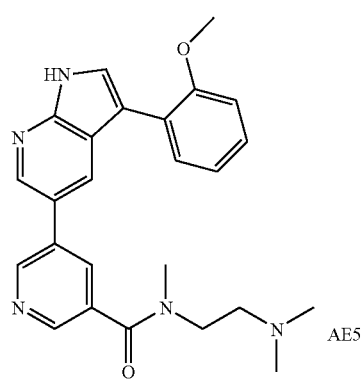 AE5<br>MS: m/z 430[MH⁺] |
TABLE 2-continued
| Structure |
|---|
| 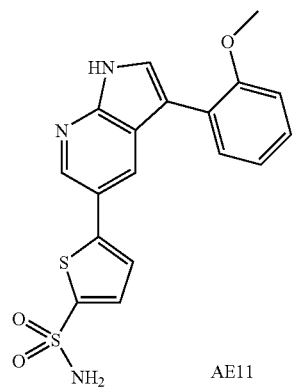 AE11<br>MS: m/z 386[MH⁺] |
| 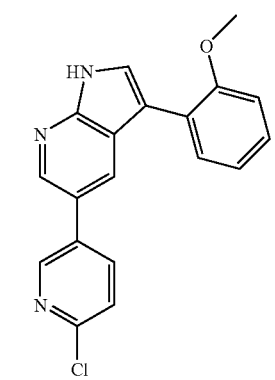<br>MS: m/z 336[MH⁺] |
| 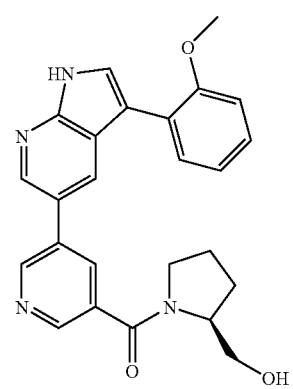<br>MS: m/z 429[MH⁺] |

TABLE 2-continued
Structure
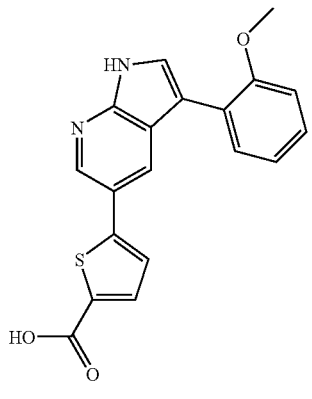
MS: m/z 351[MH+]
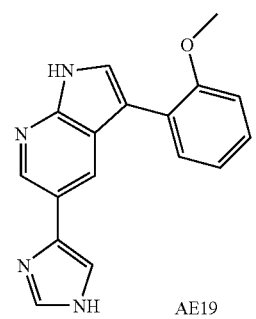
AE19
MS: m/z 291[MH+]
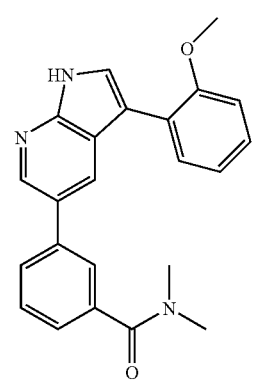
MS: m/z 372[MH+]
TABLE 2-continued
Structure
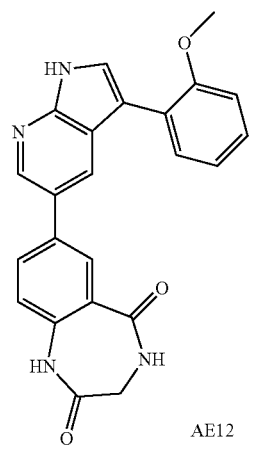
AE12
MS: m/z 399[MH+]
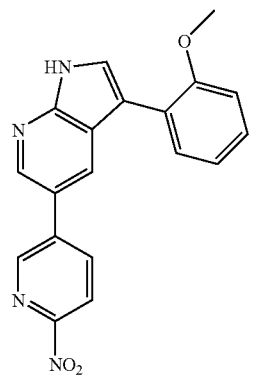
MS: m/z 347[MH+]
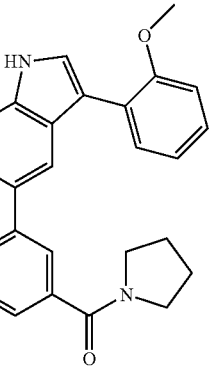
MS: m/z 398[MH+]

TABLE 2-continued
Structure
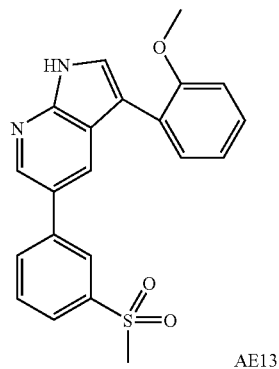
AE13
MS: m/z 379[MH+]
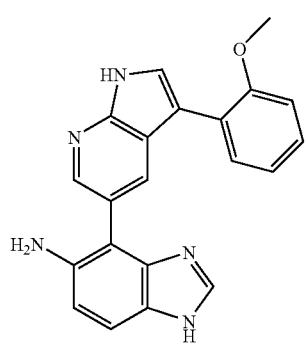
MS: m/z 356[MH+]
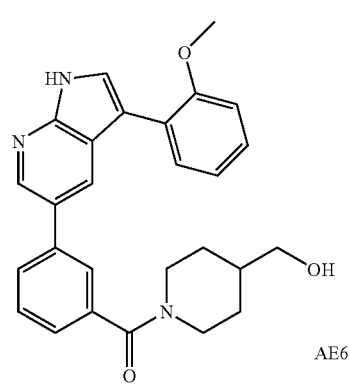
AE6
MS: m/z 442[MH+]
TABLE 2-continued
Structure
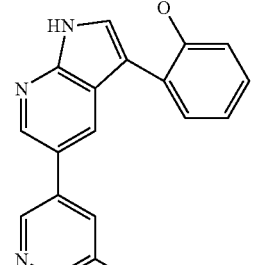
MS: m/z 318[MH+]
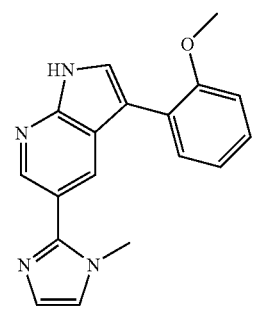
MS: m/z 305[MH+]
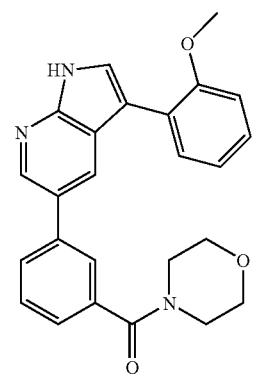
MS: m/z 414[MH+]
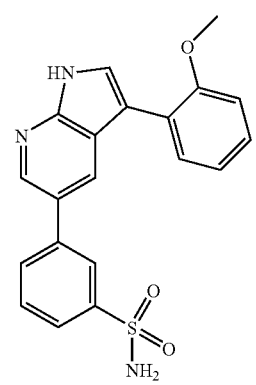
MS: m/z 380[MH+]

TABLE 2-continued
Structure
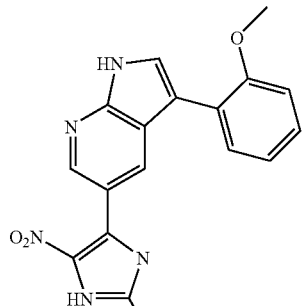
MS: m/z 350[MH+]
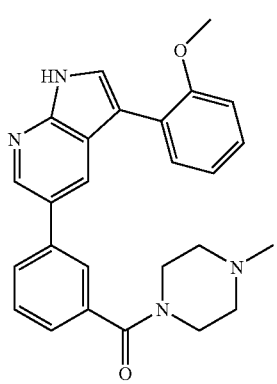
MS: m/z 427[MH+]
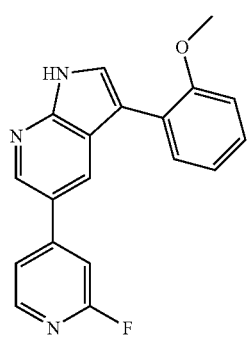
MS: m/z 320[MH
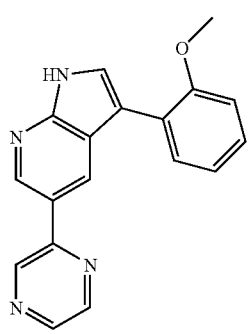
MS: m/z 303[MH+]
TABLE 2-continued
Structure
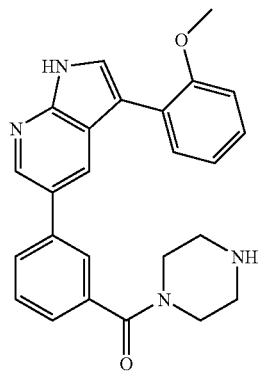
MS: m/z 413[MH+]
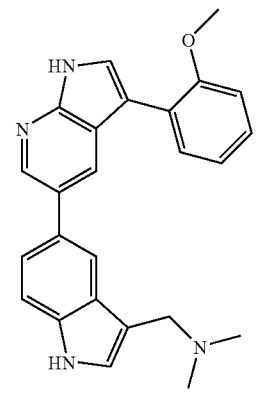
MS: m/z 397[MH+]
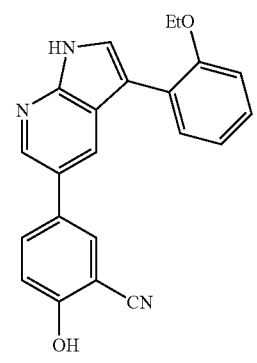
MS: m/z 356[MH+].

TABLE 2-continued
Structure
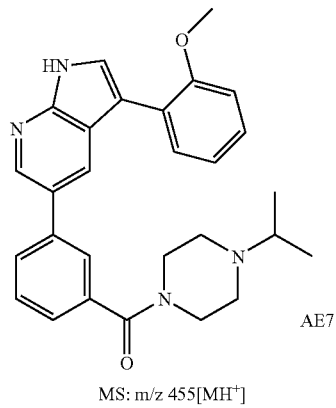
MS: m/z 455[MH+]
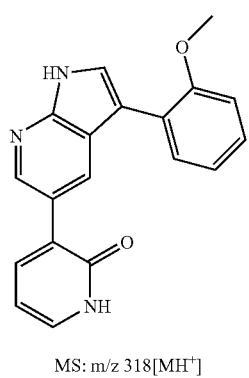
MS: m/z 318[MH+]
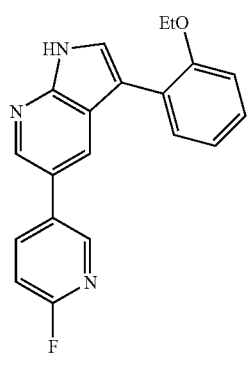
MS: m/z 334[MH+].
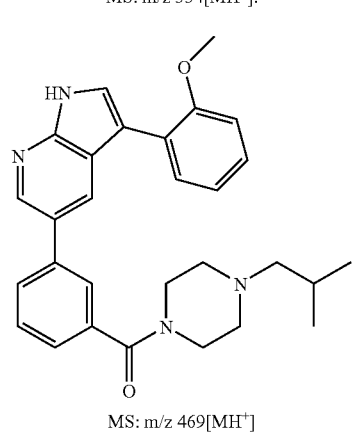
MS: m/z 469[MH+]
TABLE 2-continued
Structure
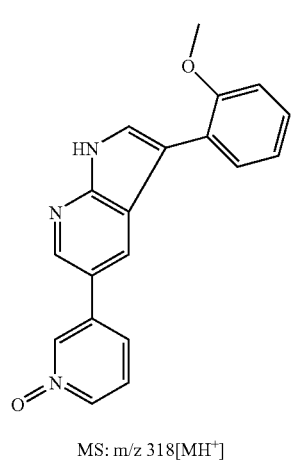
MS: m/z 318[MH+]
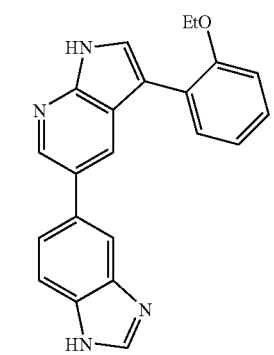
MS: m/z 335[MH+].
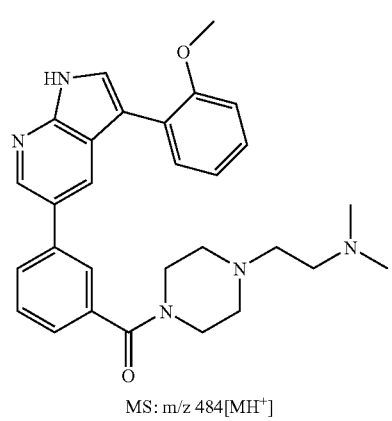
MS: m/z 484[MH+]

TABLE 2-continued
Structure
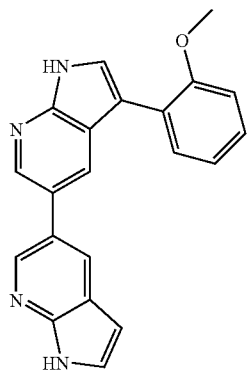
MS: m/z 341[MH+]
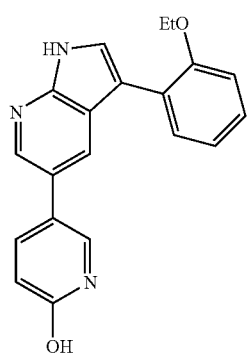
MS: m/z 332[MH+].
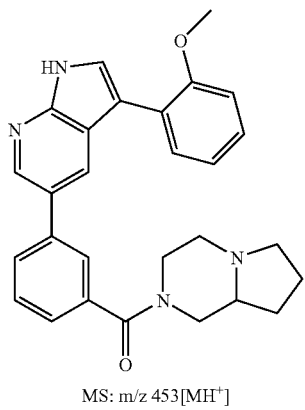
MS: m/z 453[MH+]
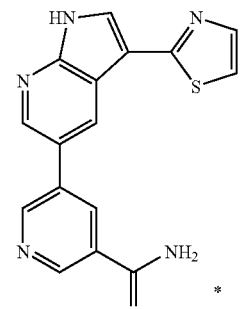
MS: m/z 321.8(M + H+)
TABLE 2-continued
Structure
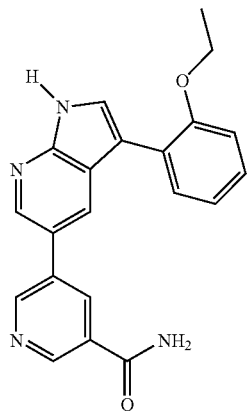
MS: m/z 359[MH+].
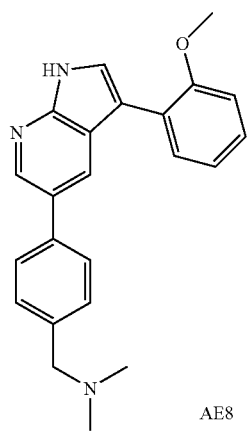
AE8
MS: m/z 358[MH+]
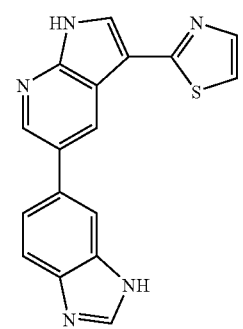
MS: m/z 318.0(M + H+)

TABLE 2-continued
Structure
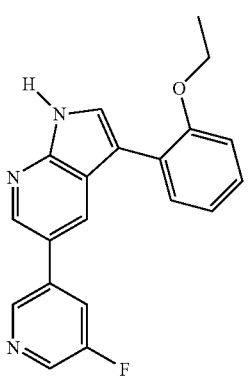
MS: m/z 334[MH+].
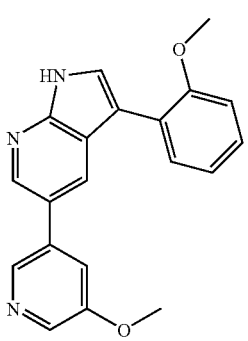
MS: m/z 332[MH⁺]
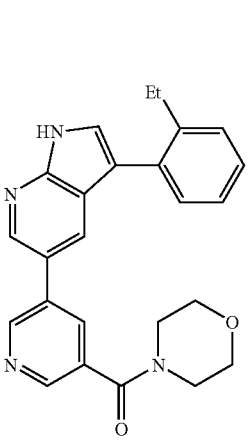
MS: m/z 413.1(M + H⁺
TABLE 2-continued
Structure
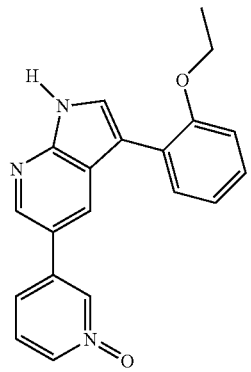
MS: m/z 332[MH+].
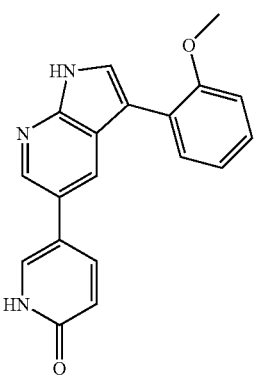
MS: m/z 318[MH⁺]
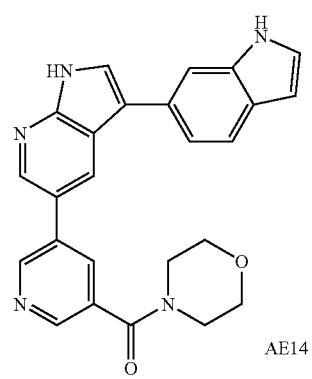
AE14
MS: m/z 424.1(M + H⁺)

TABLE 2-continued
Structure
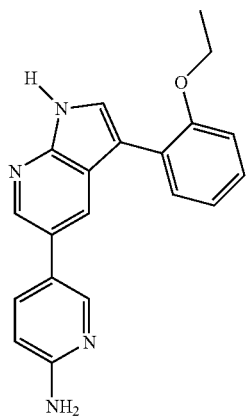
MS: m/z 331[MH+].
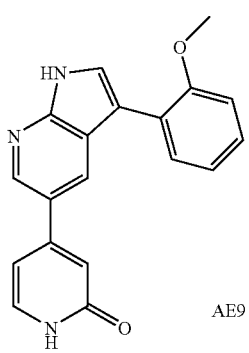
AE9
MS: m/z 318[MH+]
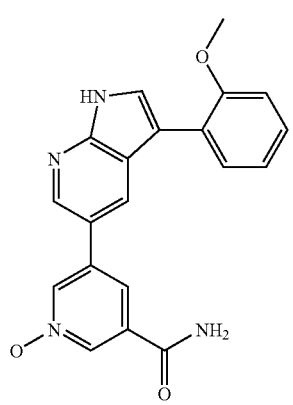
MS: m/z 361.1(M + H+)
TABLE 2-continued
Structure
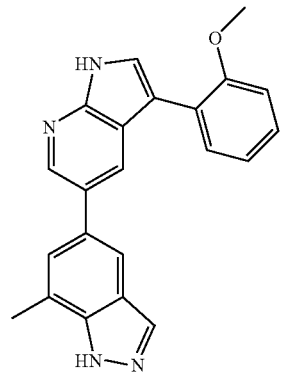
MS: m/z 355[MH+].
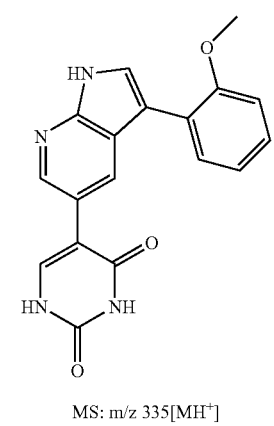
MS: m/z 335[MH+]
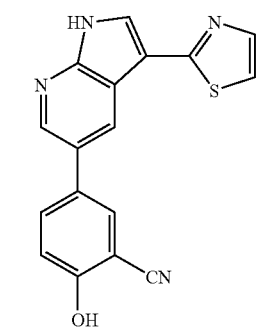
MS: m/z 318.0(M + H+)*
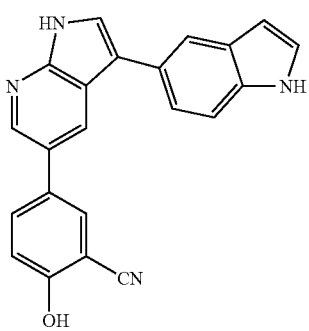
AE20
MS: m/z 351[MH+].

TABLE 2-continued
Structure
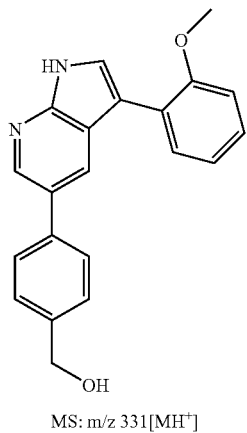
MS: m/z 331[MH⁺]
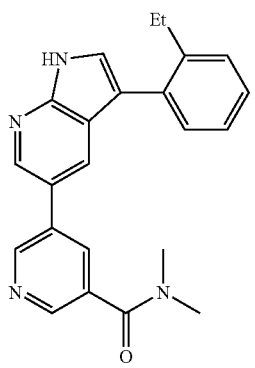
AE15
MS: m/z 371.1(M + H⁺)
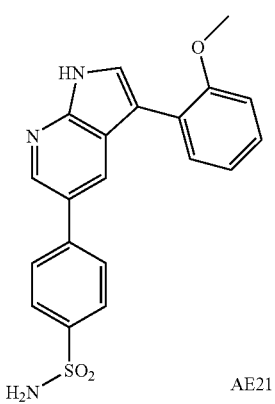
AE21
MS: m/z 380[MH+].
TABLE 2-continued
Structure
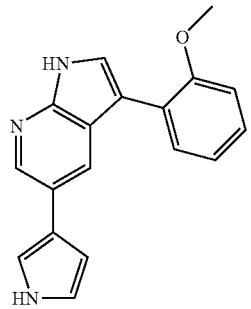
MS: m/z 290[MH⁺]
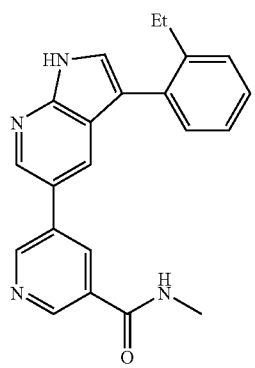
MS: m/z 357.1(M + H⁺)
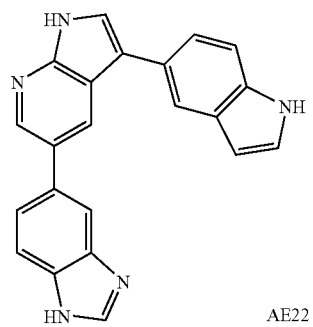
AE22
MS: m/z 350[MH⁺].
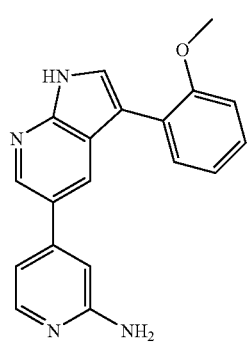
MS: m/z 317[MH⁺]

TABLE 2-continued

Structure

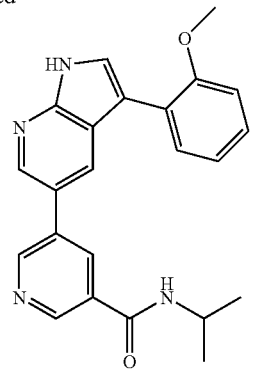

AE16
MS: m/z 387.1(M + H⁺)

*Suzuki coupling was carried out at 140° C. in microwave for 30 min, and no base treatment was need for the removal of the Ts group.

Method 3:

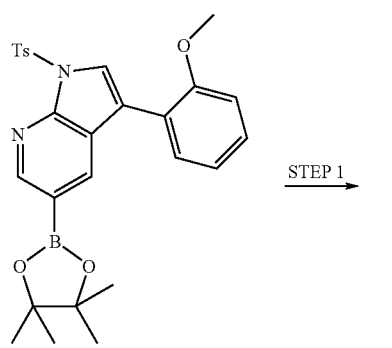

STEP 1

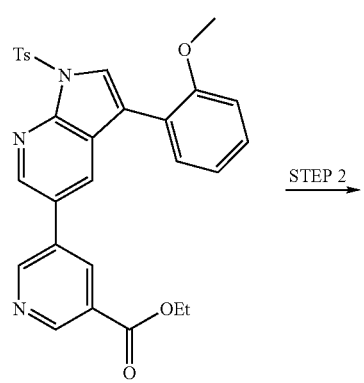

STEP 2

Step 1: Synthesis of 5-[3-(2-Methoxy-phenyl)-1-(toluene-4-sulfonyl)-1H-pyrrolo[2,3-b]pyridin-5-yl]-nicotinic acid ethyl ester Into a 20 mL Personal Chemistry microwave reaction vial were added 3-(2-Methoxy-phenyl)-5-(4,4,5,5-tetramethyl-[1,3,2]dioxaborolan-2-yl)-1-(toluene-4-sulfonyl)-1H-pyrrolo[2,3-b]pyridine (0.995 g, 2.18 mmol), 5-Bromo-nicotinic acid ethyl ester (0.645 g, 2.33 mmol), 1,1'-bis(diphenylphosphino)ferrocenepalladium(II)-dichloride dichloromethane adduct (95.5 mg, 0.117 mmol), acetonitrile (10 mL) and saturated aqueous NaHCO₃ (10 mL). The vial was sealed, purged with N₂, and irradiated in a Personal Chemistry Optimizer at 90° C. for 15 min. The layers were separated, and the aqueous phase was extracted 3× with EtOAc. The combined organic phase was treated with brine, dried (Na₂SO₄), filtered and concentrated. Purification by flash silica gel chromatography using a gradient of ethyl acetate and hexanes afforded 5-[3-(2-Methoxy-phenyl)-1-(toluene-4-sulfonyl)-1H-pyrrolo [2,3-b]pyridin-5-yl]-nicotinic acid ethyl ester as a white powder (0.794 g, 69%). MS: m/z 528.1 [MHz⁺].

Step 2: Synthesis of N-Isopropyl-5-[3-(2-methoxy-phenyl)-1H-pyrrolo[2,3-b]pyridin-5-yl]-nicotinamide Into a 5 mL screw-cap vial were added 5-[3-(2-Methoxy-phenyl)-1-(toluene-4-sulfonyl)-1H-pyrrolo[2,3-b]pyridin-5-yl]-nicotinic acid ethyl ester (50.2 mg, 0.095 mmol) and isopropylamine (500 µL). The vial was sealed and placed in heated block at 100° C. for 48 h. The reaction solution was concentrated and the residue was dissolved in 1:1 MeOH/acetone (2 mL total) and treated with 100 µL of 50% w/w KOH(aq) for 1 h. Glacial Acetic acid was added to obtain pH 7, then the reaction mixture was concentrated. The residue was partitioned between EtOAc and water, then the layers were separated, and the organic phase was washed 2× with water. The organic phase was treated with brine, dried (Na₂SO₄), filtered and concentrated. Purification by flash silica gel chromatography using a gradient of ethyl acetate (containing 10% MeOH) and hexanes afforded the title compound as a white powder (13 mg, 35%). ¹H-NMR (500 MHz, d₆-DMSO) δ=11.96 (br. s, 1H), 9.05 (d, J=2.5 Hz, 1H), 8.94 (d, J=2.0 Hz, 1H), 8.64 (d, J=2.0 Hz, 1H), 8.51 (d, J=8.0 Hz, 1H), 8.46 (d, J=2.0 Hz, 1H), 8.30 (d, J=2.0 Hz, 1H), 7.76 (s, 1H), 7.61 (d, J=5.5 Hz, 1H), 7.29 (dd, J=2, 7.5 Hz, 1H), 7.12 (d, J=7.5 1H), 7.04 (d, J=7.5 Hz, 1H), 4.11 (m, 1H), 3.84 (s, 3H), 1.17 (s, 6H); MS: m/z 387.1 [MH⁺].

Other compounds prepared by Method 3:
TABLE 3
| Structure |
|---|
| 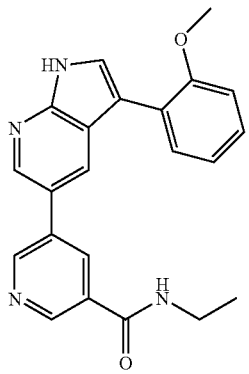<br>MS: m/z 373[MH$^+$] |
| 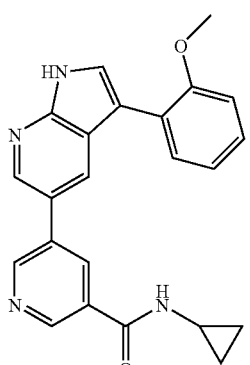<br>MS: m/z 385[MH$^+$] |
| 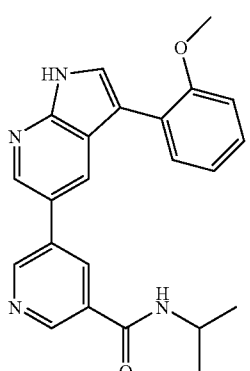<br>MS: m/z 387[MH$^+$] |
TABLE 3-continued
| Structure |
|---|
| 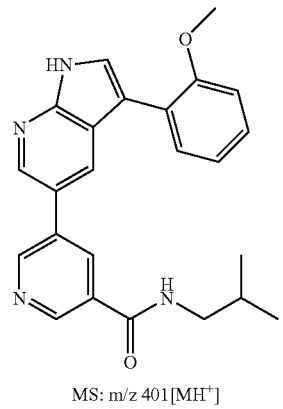<br>MS: m/z 401[MH$^+$] |
| 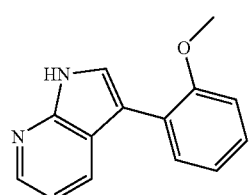<br>MS: m/z 416[MH$^+$] |
Method 4:
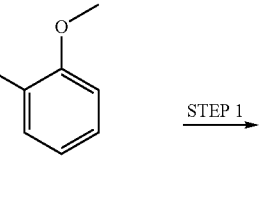 STEP 1 →
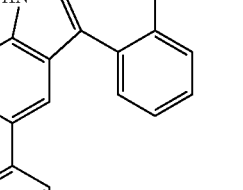 STEP 2 →

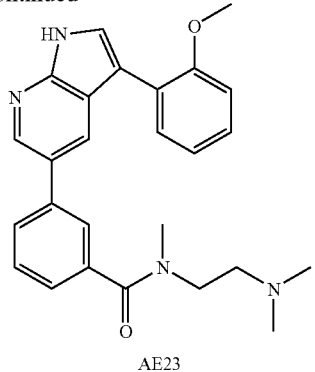

AE23

Step 1: Synthesis of 3-[3-(2-methoxy-phenyl)-1H-pyrrolo[2,3-b]pyridin-5-yl]-benzoic acid To a solution of 5-bromo-3-(2-methoxy-phenyl)-1-(toluene-4-sulfonyl)-1H-pyrrolo[2,3-b]pyridine (1.01 g, 2.21 mmol) in a 1:1 acetonitrile/saturated aqueous NaHCO$_3$ solution (20 mL total) was added (3-tert-butoxycarbonylphenyl) boronic acid (0.54 g, 2.43 mmol) and [1,1'-bis(diphenylphosphino)ferrocene]dichloropalladium (II), complex with dichloromethane (1:1) (0.90 g, 0.11 mmol) in a microwave vial. The vial was capped, flushed with N$_2$, evacuated under vacuum, and subsequently heated in a microwave at 90° C. for 1800 seconds. The material was diluted with ethyl acetate and the organic layer was washed with H$_2$O then dried over Na$_2$SO$_4$. The solution was adsorbed onto silica gel and purified by flash chromatography with a gradient of ethyl acetate and hexanes, affording 3-[3-(2-methoxy-phenyl)-1-(toluene-4-sulfonyl)-1H-pyrrolo [2,3-b]pyridine-5-yl]-benzoic acid tert-butyl ester as a white solid (1.07 g, 87% yield). $^1$H NMR (500 MHz, CDCl$_3$) δ 8.68 (s, 1H), 8.17 (br s, 3H), 8.09 (s, 1H), 7.99 (m, 2H), 7.71 (d, J=6.5 Hz, 1H), 7.50 (m, 2H), 7.34 (t, J=8.0 Hz, 1H), 7.32 (d, J=6.5 Hz, 2H), 7.06 (m, 2H), 3.88 (s, 3H), 2.39 (s, 3H), 1.60 (s, 9H). MS: m/e 555.1 (M +H$^+$).

To 3-[3-(2-methoxy-phenyl)-1-(toluene-4-sulfonyl)-1H-pyrrolo[2,3-b]pyridine-5-yl]-benzoic acid tert-butyl ester (1.07 g, 1.82 mmol) in a 1:1 MeOH/acetone solution (40 mL total) was added 4 mL of a 50% KOH (aq) solution. The reaction mixture was stirred for 20 hours at ambient temperature. Glacial acetic acid was added dropwise until the solution had a pH=6. The product was extracted into ethyl acetate and dried over Na$_2$SO$_4$. The material was adsorbed onto silica gel and purified by flash chromatography in an ethyl acetate and hexane gradient, affording 3-[3-(2-methoxy-phenyl)-1H-pyrrolo[2,3-b]pyridin-5-yl]-benzoic acid tert-butyl ester as a colorless oil that started to crystallize into a white solid (1.97 g, quantitative yield). $^1$H NMR (500 MHz, CDCl$_3$) δ 11.34 (s, 1H), 8.50 (s, 2H), 8.21 (s, 1H), 8.05 (d, J=8.0 Hz, 1H), 7.75 (m, 2H), 7.55 (m, 2H), 7.40 (t, J=6.0 Hz, 1H), 7.10 (m, 2H), 3.88 (s, 3H), 1.25 (s, 9H). MS: m/e 401.1 (M+H$^+$).

To a solution of 3-[3-(2-methoxy-phenyl)-1H-pyrrolo[2,3-b]pyridin-5-yl]-benzoic acid tert-butyl ester (1.97 g, 4.92 mmol) in acetic acid (4 mL) was added dropwise a premixed solution of hydrogen bromide (33% wt in acetic acid) (889 uL, 4.92 mmol) and mercaptoacetic acid (444 uL, 6.39 mmol). The sides of the flask were rinsed with additional acetic acid (3 mL) and the reaction solution was stirred at ambient temperature for 10 minutes whereupon the product began to precipitate out of solution. The reaction was stirred for an additional hour at ambient temperature. The precipitate was filtered and rinsed well with acetic acid and diethyl ether, affording the title compound as a bright yellow solid (448 mg, 67% yield). $^1$H NMR (500 MHz, d$_6$-DMSO) δ 12.03 (br s, 1H), 8.58 (s, 1H), 8.21 (d, 2H), 7.99 (d, 1H), 7.94 (d, 1H), 7.76 (d, 1H), 7.61 (m, 2H), 7.31 (t, 1H), 7.14 (d, 1H), 7.06 (t, 1H), 3.83 (s, 3H). MS: m/e 345.1 (M+H$^+$).

Step 2: N-(2-Dimethylamino-ethyl)-3-[3-(2-methoxy-phenyl)-1H-pyrrolo [2,3-b]pyridin-5-yl]-N-methyl-benzamide To a solution of 3-[3-(2-methoxy-phenyl)-1H-pyrrolo[2,3-b]pyridin-5-yl]-benzoic acid (21 mg, 0.06 mmol) in anhydrous DMF (1 mL) was added HATU (23 mg, 0.06 mmol) and N,N,N'-trimethylethylenediamine (7.9 µL, 0.06 mmol). The reaction solution was stirred 16 hours at ambient temperature then diluted with DMSO (1 mL), filtered through a 0.45 um syringe filter, and purified by reverse phase chromatography in a mobile phase of H$_2$O and acetonitrile (with 0.1% formic acid as the modifier). Clean fractions were combined and lyophilized, affording the title compound as a white powder (14.0 mg, 54% yield). $^1$H NMR (500 MHz, CD$_3$OD) δ 8.51 (d, J=2.0 Hz, 1H), 8.29 (d, J=2.0 Hz, 1H), 7.83 (br s, 1H), 7.81 (bs, 1H), 7.69 (s, 1H), 7.60 (m, 2H), 7.49 (m, 1H), 7.32 (t, J=7.5 Hz, 1H), 7.13 (d, 8.5 Hz, 1H), 7.07 (t, J=6.5 Hz, 1H), 3.90 (t, J=6.0 Hz, 2H), 3.86 (s, 3H), 3.33 (s, 3H), 3.17 (s, 3H), 2.91 (s, 3H), 2.80 (br s, 2H). MS: m/e 429.1 (M+H$^+$).

Other compounds prepared by Method 4:

TABLE 4

| Structure |
|---|
| <br>MS: m/z 415[MH$^+$] |
| <br>MS: m/z 490[MH$^+$] |

TABLE 4-continued
Structure
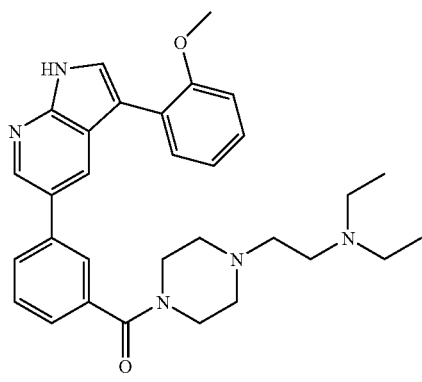
MS: m/z 512[MH+]
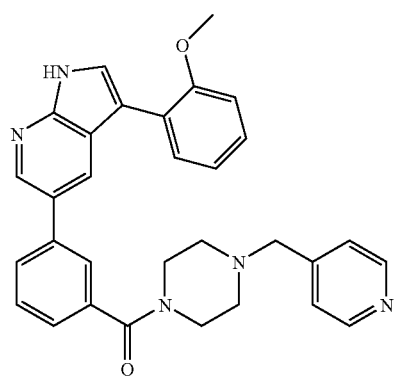
MS: m/z 504[MH+]
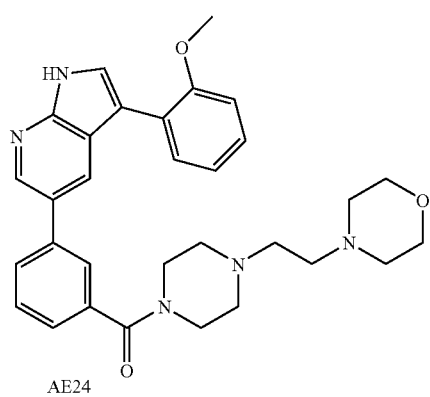
AE24
MS: m/z 526[MH+]
TABLE 4-continued
Structure
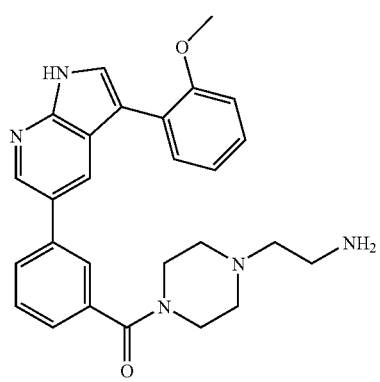
MS: m/z 456[MH+]
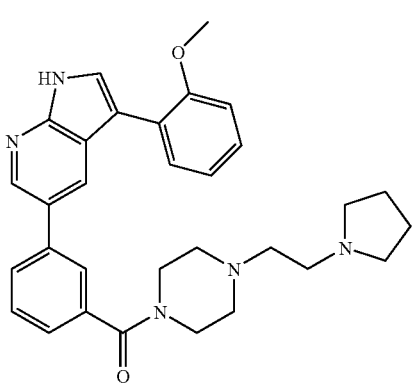
MS: m/z 510[MH+]
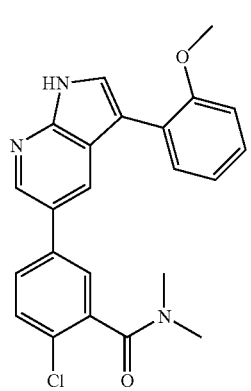
MS: m/z 406[MH+]

TABLE 4-continued
Structure
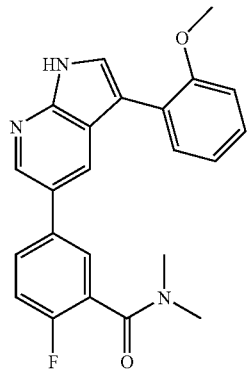
MS: m/z 390[MH+]
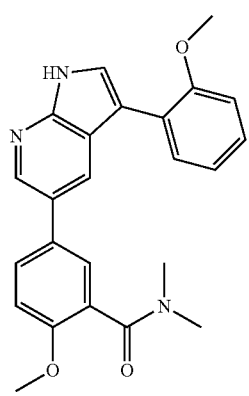
MS: m/z 402[MH+]
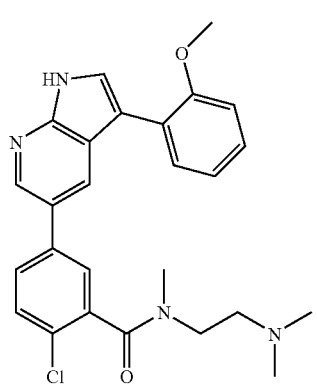
MS: m/z 463[MH+]
TABLE 4-continued
Structure
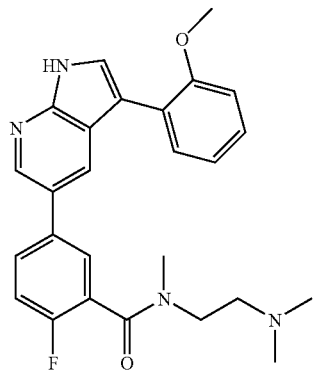
MS: m/z 447[MH+]
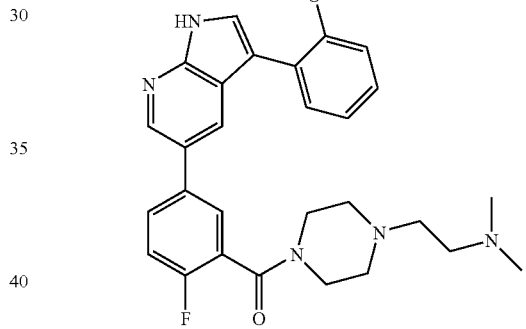
MS: m/z 502[MH+]
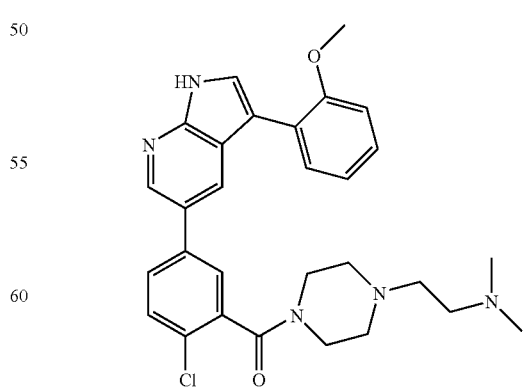
MS: m/z 518[MH+]

TABLE 4-continued

Structure

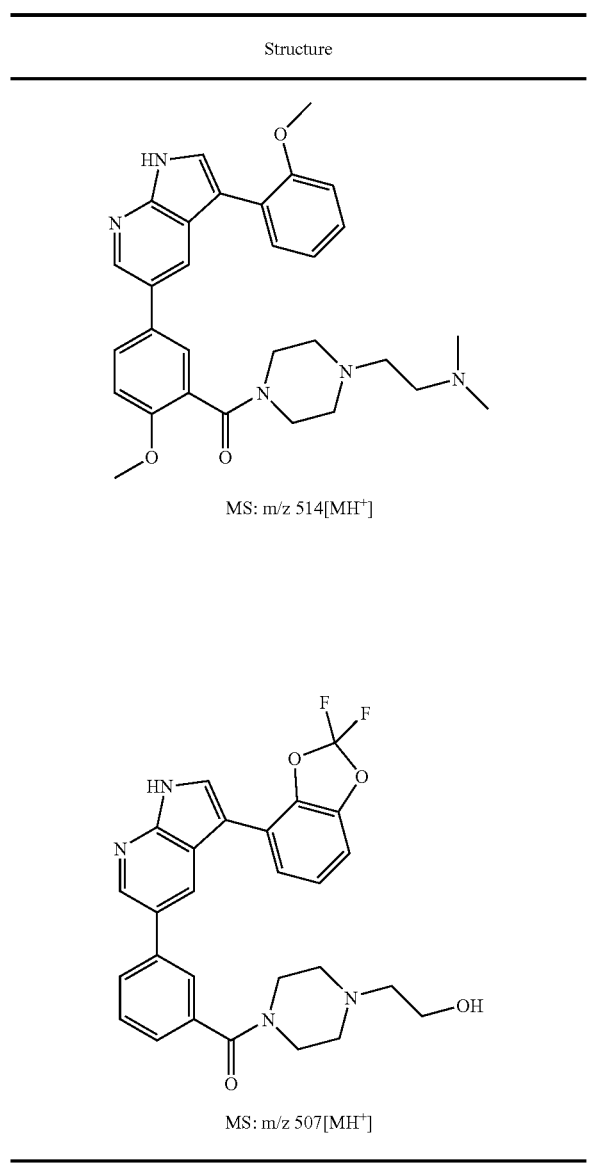

MS: m/z 514[MH⁺]

MS: m/z 507[MH⁺]

Method 5:

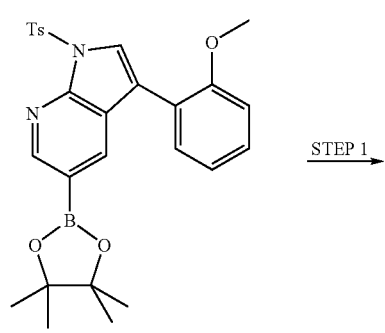

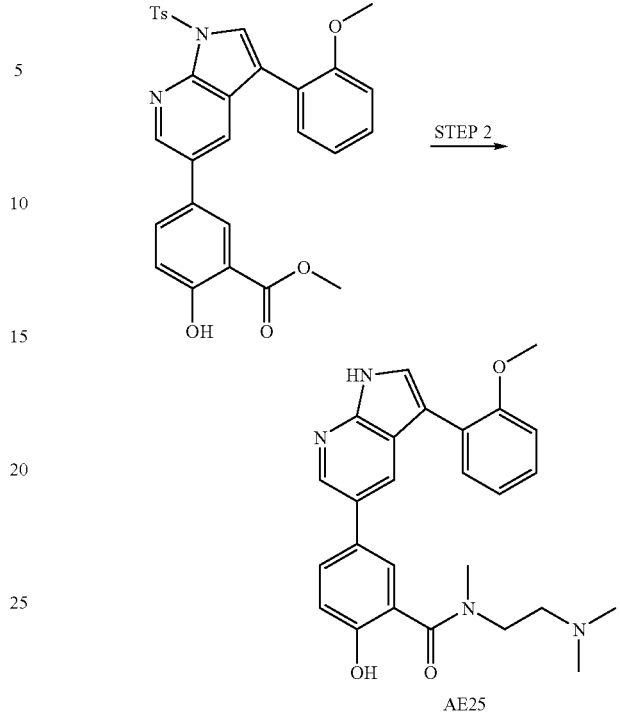

Step 1: Synthesis of 2-Hydroxy-5-[3-(2-methoxy-phenyl)-1-(toluene-4-sulfonyl)-1H-pyrrolo[2,3-b]pyridin-5-yl]-benzoic acid methyl ester To a solution of 3-(2-methoxy-phenyl)-5-(4,4,5,5-tetramethyl-[1,3,2]dioxaborolan-2-yl)-1-(toluene-4-sulfonyl)-1H-pyrrolo[2,3-b]pyridine (502 mg, 1.00 mmol) in 1.5 mL saturated aqueous NaHCO₃ and 5.0 mL acetonitrile was added methyl 5-bromosalicylate (253 mg, 1.10 mmol) and [1,1'-bis(diphenylphosphino)ferrocene]dichloropalladium (II), complex with dichloromethane (1:1) (41 mg, 0.05 mmol) in a microwave vial. The vial was capped, flushed with N₂, evacuated under vacuum, and subsequently heated in a microwave at 90° C. for 300 seconds. The material was diluted with ethyl acetate and the organic layer was washed with saturated NaHCO₃ (aq) and brine then dried over Na₂SO₄. The material was filtered then adsorbed onto silica gel and purified by flash chromatography with a gradient of ethyl acetate and hexane, affording the title compound as a hydroscopic white solid (480 mg, 91% yield). $^1$H NMR (500 MHz, CD₃OD) δ 8.55 (d, J=2.0 Hz, 1H), 8.06 (m, 4H), 7.96 (s, 1H), 7.77 (dd, J=2.5, 6.0 Hz, 1H), 7.52 (dd, J=2.0, 6.0 Hz, 1H), 7.40 (m, 3H), 7.16 (d, J=8.5 Hz, 1H), 7.08 (m, 2H), 3.98 (s, 3H), 3.87 (s, 3H), 2.39 (s, 3H). MS: m/z 529.1 (M+H⁺).

Step 2: Synthesis of N-(2-Dimethylamino-ethyl)-2-hydroxy-5-[3-(2-methoxy-phenyl)-1H-pyrrolo[2,3-b]pyridin-5-yl]-N-methyl-benzamide To a solution of 2-hydroxy-5-[3-(2-methoxy-phenyl)-1-(toluene-4-sulfonyl)-1H-pyrrolo[2,3-b]pyridin-5-yl]-benzoic acid methyl ester (52 mg, 0.10 mmol) in pyridine (0.5 mL) was added an excess of N,N,N'-trimethylethylenediamine (0.5 mL). The reaction was stirred for 16 hours at 100° C. in a scintillation vial. There appeared to be ~50% product formation and ~50% hydrolysis of the methyl ester to the carboxylic acid. PS-carbodiimide resin (244 mg, 0.29 mmol, 1.21 mmol/g load capacity) and DMF (1 mL) were added to the reaction solution and heating was continued for 16 hours at 70° C. The resin was filtered off and rinsed well with THF and MeOH. The filtrate was concentrated down to a yellow oil and then redissolved in a 1:1 MeOH/acetone solution (4 mL total). The solution was treated with 200 uL of a 50% KOH (aq) solution and stirred at ambient temperature for 3 hours. Glacial acetic acid was added dropwise until the pH=7. The product was extracted into ethyl acetate, whereupon the organic layer was washed with $H_2O$, dried over $Na_2SO_4$, filtered, and concentrated under vacuum. The material was dissolved in MeOH and filtered through a 0.45 μm syringe filter. The solution was purified by reverse phase chromatography using a gradient of $H_2O$ and acetonitrile (with 0.1% formic acid as a modifier). Clean fractions were lyophilized, affording the title compound as a white powder (5.2 mg, 12% yield). $^1$H NMR (500 MHz, $d_6$-DMSO) δ 11.80 (d, J=2.5 Hz, 1H), 8.49 (s, 1H), 8.19 (s, 1H), 8.10 (s, 1H), 7.74 (d, J=2.5 Hz, 1H), 7.63 (dd, J=2.0, 6.0 Hz, 1H), 7.51 (d, J=8.5 Hz, 1H), 7.43 (s, 1H), 7.33 (m, 1H), 7.17 (d, J=8.5 Hz, 1H), 7.09 (t, J=6.5 Hz, 1H), 7.01 (d, J=9.0 Hz, 1H), 3.85 (s, 3H), 3.01 (br s, 3H), 2.90 (br s, 2H), 2.59 (m, 2H), 2.36 (br s, 3H), 2.00 (br s, 3H). MS: m/z 445.1 (M+H$^+$).

Other compounds prepared by method 5:

TABLE 5

Structure

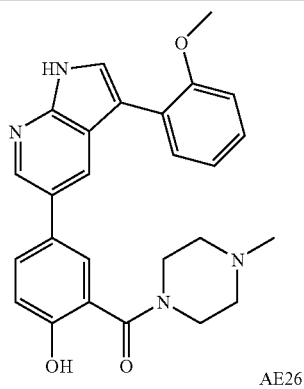

AE26

MS: m/z 443[MH$^+$]

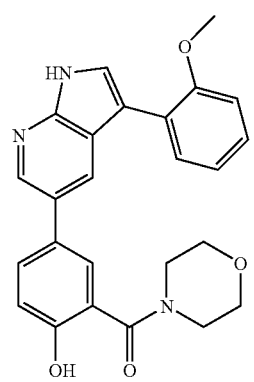

MS: m/z 430[MH$^+$]

TABLE 5-continued

Structure

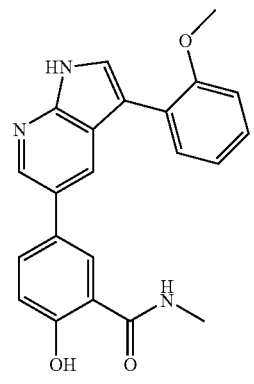

MS: m/z 374[MH$^+$]

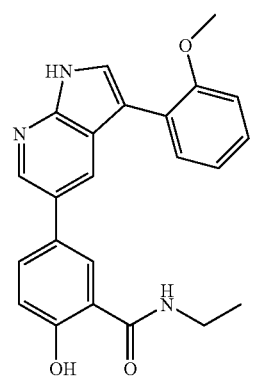

MS: m/z 388[MH$^+$]

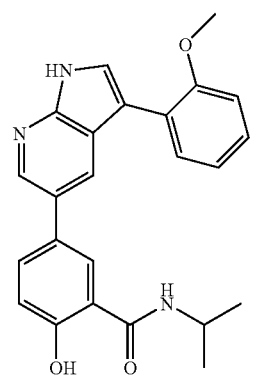

MS: m/z 402[MH$^+$]

TABLE 5-continued
Structure
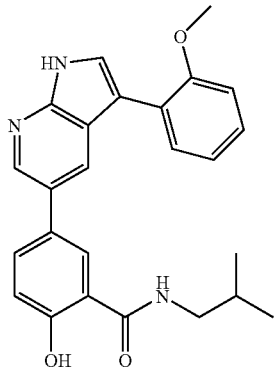
MS: m/z 416[MH+]
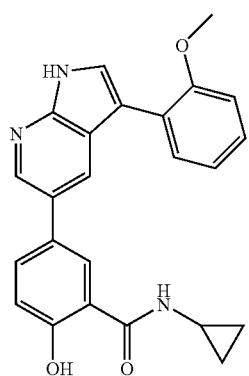
MS: m/z 400[MH+]
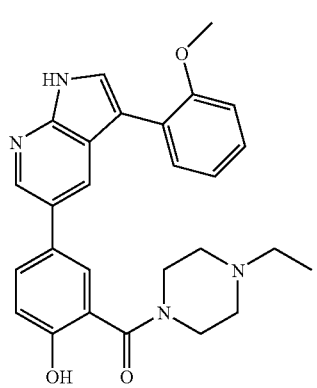
MS: m/z 457[MH+]
TABLE 5-continued
Structure
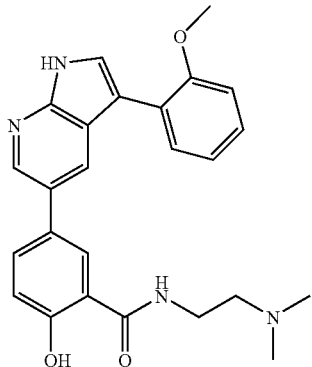
MS: m/z 431[MH+]
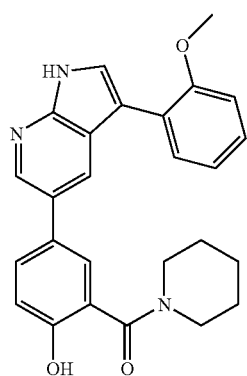
MS: m/z 428[MH+]
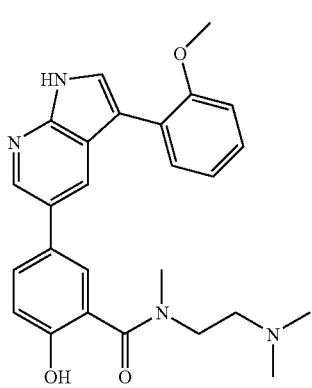
MS: m/z 445[MH+]

TABLE 5-continued
Structure
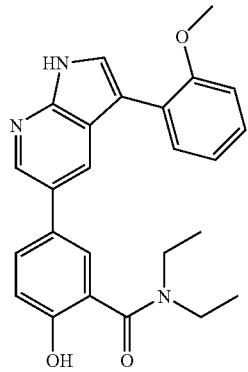
MS: m/z 416[MH+]
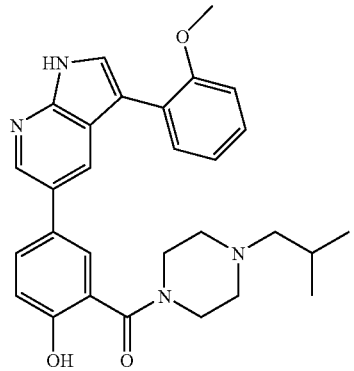
MS: m/z 485[MH+]
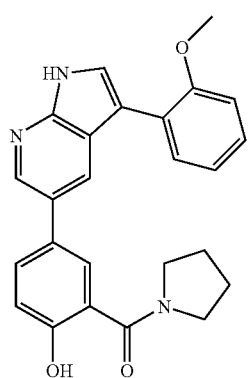
MS: m/z 414[MH+]
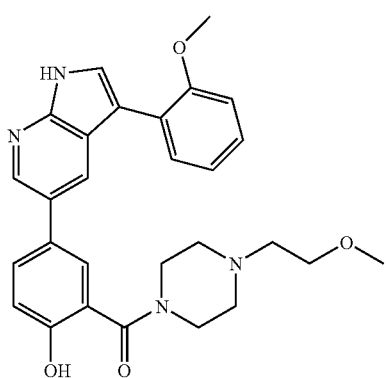
MS: m/z 487[MH+]
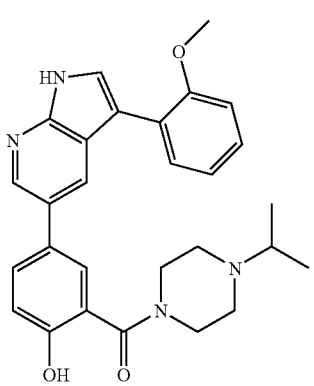
MS: m/z 471[MH+]
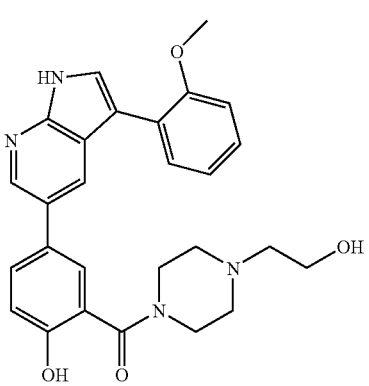
MS: m/z 473[MH+]

TABLE 5-continued
| Structure |
|---|
| 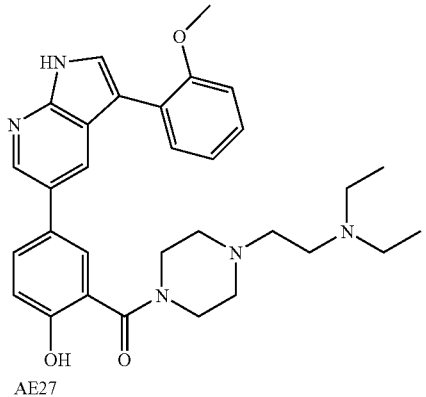<br>AE27<br>MS: m/z 528[MH⁺] |
| 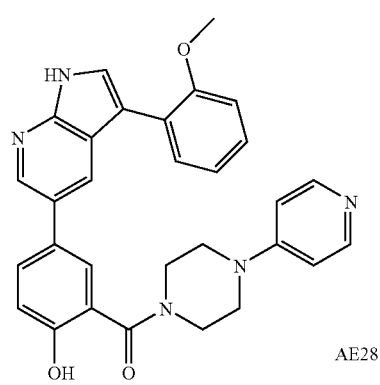<br>AE28<br>MS: m/z 506[MH⁺] |
| 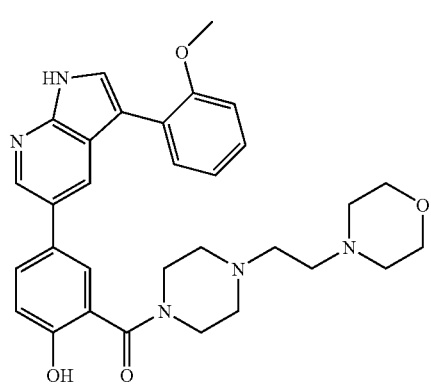<br>MS: m/z 542[MH⁺] |
TABLE 5-continued
| Structure |
|---|
| 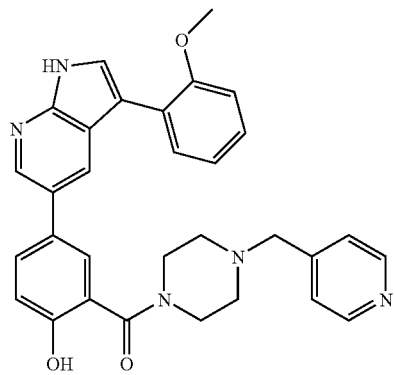<br>MS: m/z 520[MH⁺] |
| 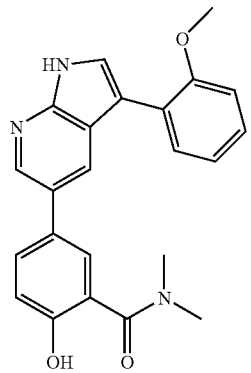<br>MS: m/z 388[MH⁺] |
| 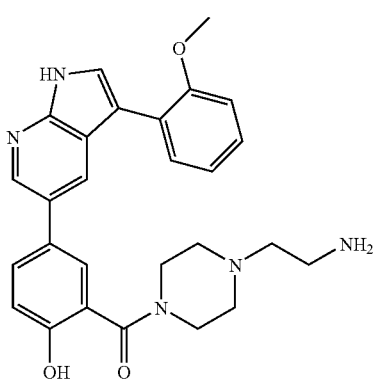<br>MS: m/z 472[MH⁺] |

TABLE 5-continued
Structure
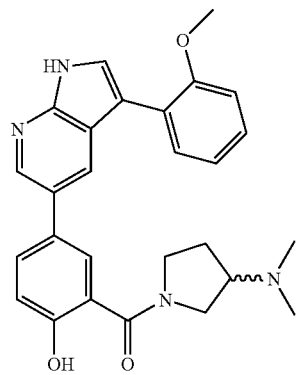
MS: m/z 457[MH+]
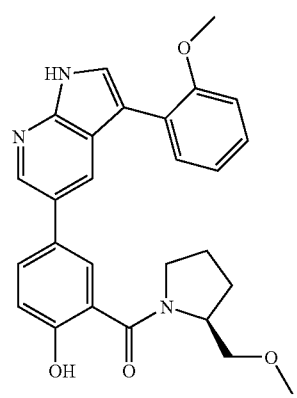
MS: m/z 458[MH+]
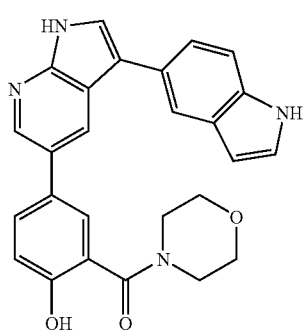
MS: m/z 439[MH+]
TABLE 5-continued
Structure
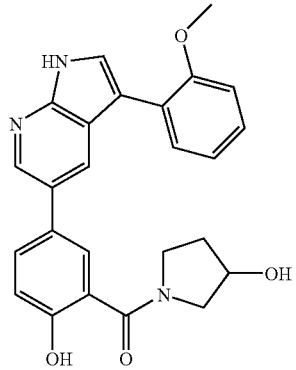
MS: m/z 430[MH+]
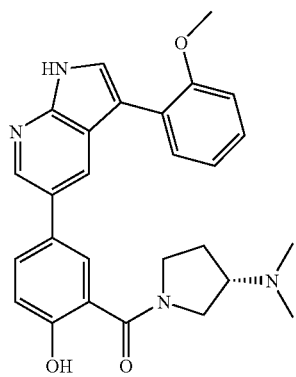
MS: m/z 457[MH+]
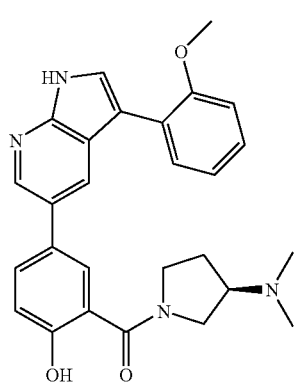
MS: m/z 457[MH+]

TABLE 5-continued
Structure
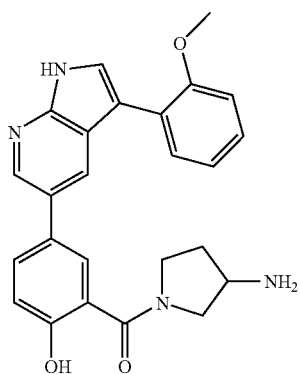
MS: m/z 429[MH+]
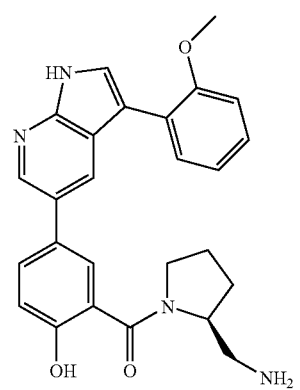
MS: m/z 443[MH+]
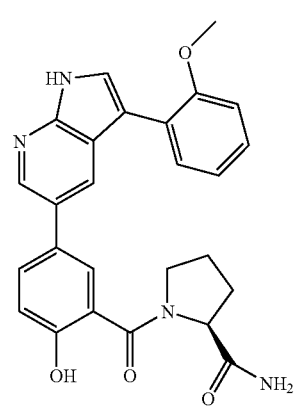
MS: m/z 457[MH+]
TABLE 5-continued
Structure
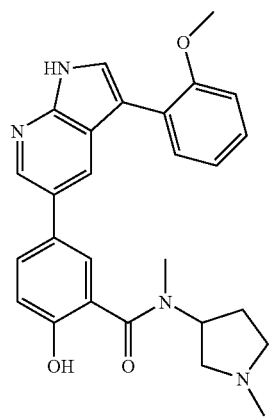
MS: m/z 457[MH+]
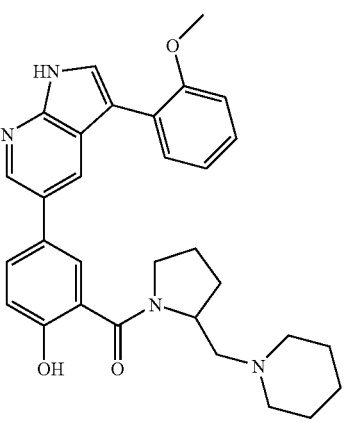
MS: m/z 511[MH+]
Method 6:
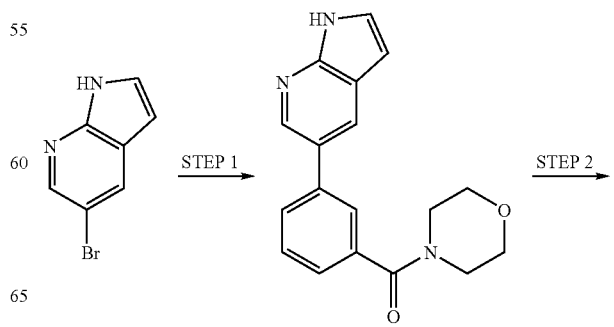

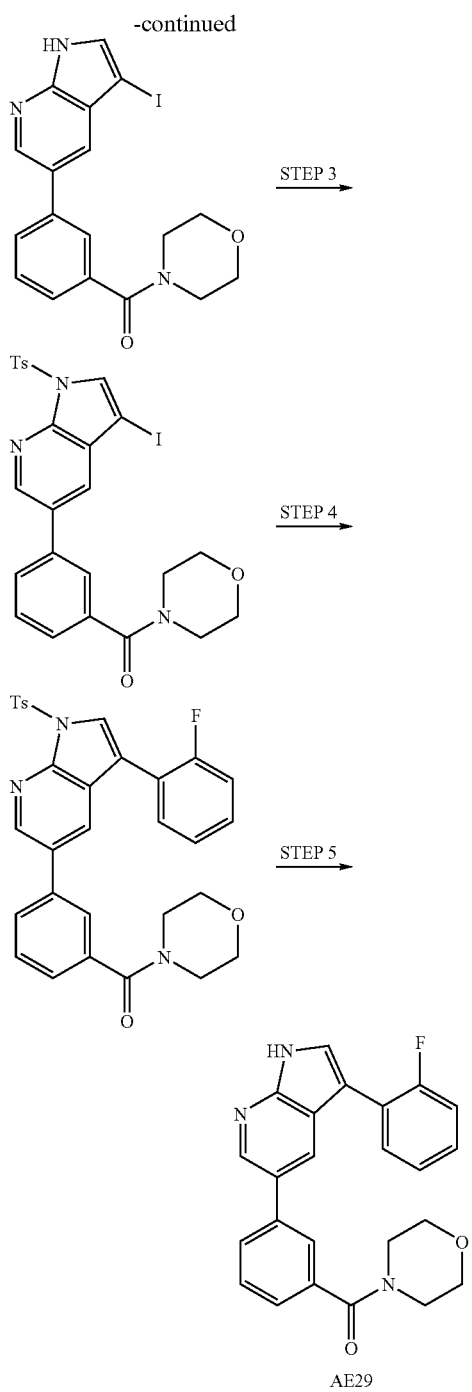

Step 1: Synthesis of (3-(1H-pyrrolo[2,3-b]pyridin-5-yl)phenyl)(morpholino) methanone A mixture of 5-bromo-1H-pyrrolo[2,3-b]pyridine (3 g, 15 mmol), 3-(morpholine-4-carbonyl)phenylboronic acid (4 g, 18 mmol), sodium bicarbonate (4 g, 46 mmol), and tetrakis (triphenylphosphine)palladium(0) in dioxane/water (100 mL/20 mL) was stirred at 110° C. for 15 hours. The mixture was then poured into ice water and extracted with ethyl acetate (3×). The organic layers were combined, dried over sodium sulfate, filtered and concentrated to dryness. Silica gel chromatography of the crude product afforded (3-(1H-pyrrolo[2,3-b]pyridin-5-yl)phenyl)(morpholino)methanone (3.86 g, 84% yield) as yellow solids. MS: m/z 308.1 (M+H$^+$).

Step 2: Synthesis of (3-(3-iodo-1H-pyrrolo[2,3-b]pyridin-5-yl)phenyl)(morpholino)methanone To a solution of (3-(1H-pyrrolo[2,3-b]pyridin-5-yl)phenyl)(morpholino)methanone (550 mg, 1.79 mmol) in acetone (10 mL) was added NIS (604 mg, 2.68 mmol) and the mixture was stirred at room temperature for 20 minutes. Acetone was removed by reduced pressure and the crude product was purified by silica gel chromatography to afforded (3-(3-iodo-1H-pyrrolo[2,3-b]pyridin-5-yl)phenyl)(morpholino)methanone (600 mg, 77% yield). MS: m/z 434.2 (M+H$^+$).

Step 3: Synthesis of (3-(3-iodo-1-tosyl-1H-pyrrolo[2,3-b]pyridin-5-yl)phenyl)(morpholino)methanone A mixture of (3-(3-iodo-1H-pyrrolo[2,3-b]pyridin-5-yl)phenyl)(morpholino)methanone (600 mg, 1.38 mmol), p-toluenesulfonyl chloride (528 mg, 2.77 mmol), potassium hydroxide (50% w/v in water, 0.387 mL, 3.45 mmol) and tetrabutylammonium hydroxide (40% w/v in water, 0.448 mL, 0.69 mmol) in toluene (5 mL) was stirred at room temperature for 15 hours. Water was added to the mixture and the aqueous mixture was extracted by ethyl acetate (3×). The organic layers were combined, dried over sodium sulfate, filtered and concentrated to dryness. Silica gel chromatography of the crude product afforded (3-(3-iodo-1-tosyl-1H-pyrrolo[2,3-b]pyridin-5-yl)phenyl)(morpholino)methanone (600 mg, 74% yield) as yellow solids. MS: m/z 588.1 (M+H$^+$).

Step 4: Synthesis of (3-(3-(2-fluorophenyl)-1-tosyl-1H-pyrrolo[2,3-b]pyridin-5-yl)phenyl)(morpholino)methanone A mixture of (3-(3-iodo-1-tosyl-1H-pyrrolo[2,3-b]pyridin-5-yl)phenyl)(morpholino)methanone (40 mg, 0.068 mmol), 2-fluorophenylboronic acid (18 mg, 0.128 mmol), [1,1'-Bis(diphenylphosphino)ferrocene]dichloropalladium (II) complex with dichloromethane (3.9 mg, 0.005 mmol) and sodium carbonate (2M aqueous solution, 0.102 mL, 0.204 mmol) in acetonitrile (1 mL) was heated in a Personal microwave at 90° C. for 30 min. The resulting mixture was diluted with water and extracted with ethyl acetate. The organic layers were combined, dried over sodium sulfate, filtered and concentrated to dryness to afford crude (3-(3-(2-fluorophenyl)-1-tosyl-1H-pyrrolo[2,3-b]pyridin-5-yl)phenyl)(morpholino)methanone, which was used in step 5 without further purification.

Step 5: Synthesis of (3-(3-(2-fluorophenyl)-1H-pyrrolo[2,3-b]pyridin-5-yl)phenyl)(morpholino)methanone Crude (3-(3-(2-fluorophenyl)-1-tosyl-1H-pyrrolo[2,3-b]pyridin-5-yl)phenyl)(morpholino)methanone from last step was dissolved in methanol (1 mL) and potassium hydroxide (50% w/v, 0.038 mL, 0.136 mmol) was added to the solution. The resulting mixture was stirred at room temperature for 30 minutes before being diluted with water and extracted with ethyl acetate. The organic layers were combined, dried over sodium sulfate, filtered and concentrated to dryness. The crude product was then dissolved in DMSO and purified by mass triggered reverse phase HPLC to afford pure (3-(3-(2- fluorophenyl)-1H-pyrrolo[2,3-b]pyridin-5-yl)phenyl)(morpholino)methanone (5.6 mg, 21% yield from (3-(3-iodo-1-tosyl-1H-pyrrolo [2,3-b]pyridin-5-yl)phenyl)(morpholino)methanone) as light brown syrup. $^1$H NMR (500 MHz, DMSO-d6) δ 3.60 (m, br, 8H), 7.33 (m, 3H), 7.39 (m, 1H), 7.55 (t, J=7.5 Hz, 1H), 7.74 (m, 1H), 7.84 (m, 3H), 8.28 (m, 1H), 8.61 (d, J=2.5 Hz, 1H), 12.17 (s, 1H). MS: m/z 402.1 (M+H$^+$).

Other compounds prepared by Method 6:

TABLE 6

| Structure |
| --- |
| MS: m/z 428.1(M + H$^+$). |
| MS: m/z 427.1(M + H$^+$). |
| MS: m/z 448.1(M + H$^+$). |

TABLE 6-continued

| Structure |
| --- |
| MS: m/z 444.1(M + H$^+$). |
| MS: m/z 432.1(M + H$^+$). |
| MS: m/z 428.1(M + H$^+$). AE31 |

TABLE 6-continued
Structure
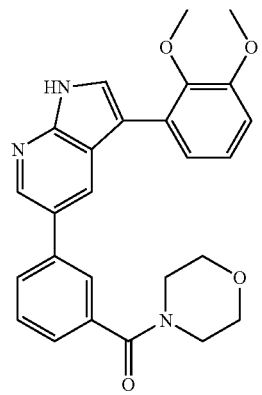
MS: m/z 444.1(M + H+).
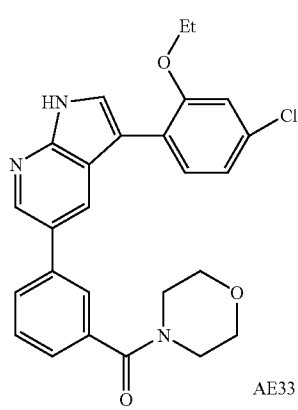
AE33
MS: m/z 462.1(M + H+).
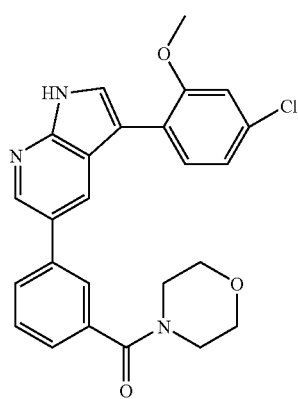
MS: m/z 448.1(M + H+).
TABLE 6-continued
Structure
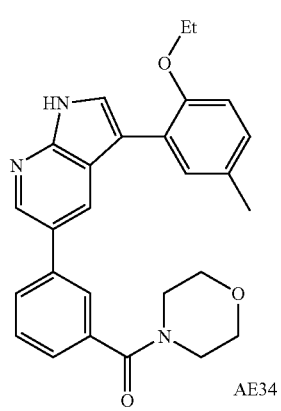
AE34
MS: m/z 442.2(M + H+).
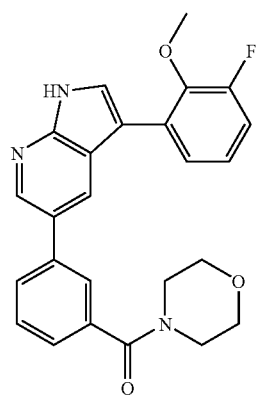
MS: m/z 432.1(M + H+).
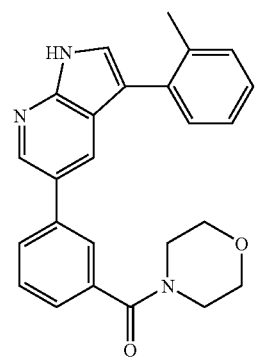
MS: m/z 398.1(M + H+).

TABLE 6-continued
Structure
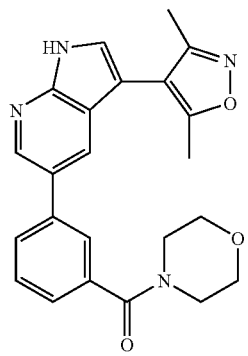
MS: m/z 403.1(M + H+).
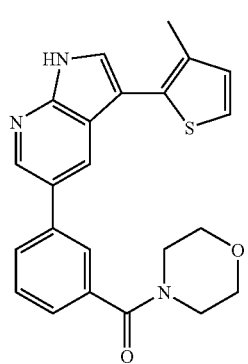
MS: m/z 404.1(M + H+).
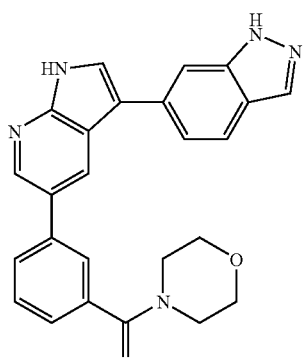
MS: m/z 424.1(M + H+).
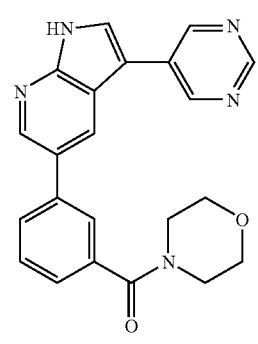
MS: m/z 386.1(M + H+).
TABLE 6-continued
Structure
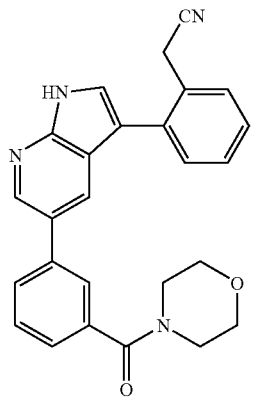
AE36
MS: m/z 423.1(M + H+).
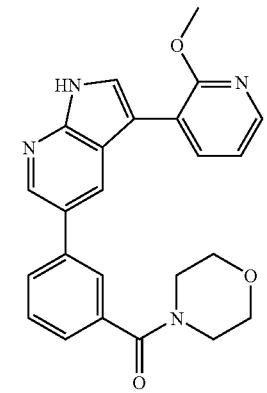
MS: m/z 415.1(M + H+).
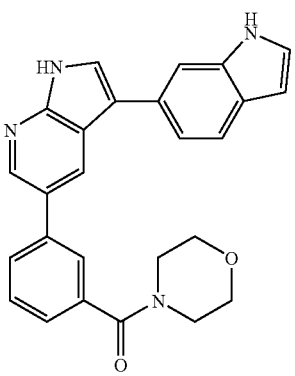
MS: m/z 423.1(M + H+).

TABLE 6-continued
Structure
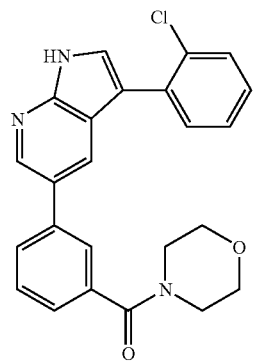
MS: m/z 418.1(M + H⁺).
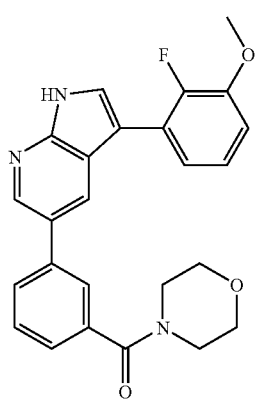
MS: m/z 432.1(M + H⁺).
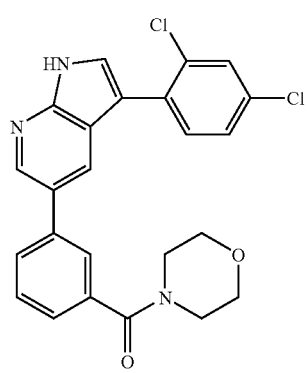
MS: m/z 452.0(M + H⁺).
TABLE 6-continued
Structure
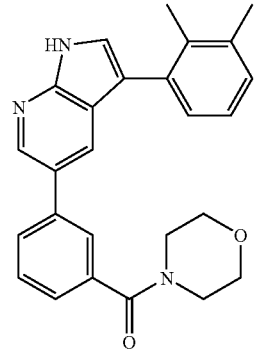
MS: m/z 412.1(M + H⁺).
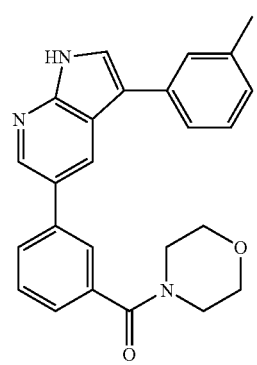
MS: m/z 398.1(M + H⁺).
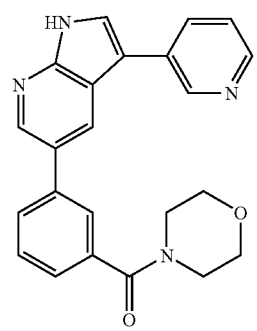
MS: m/z 385.1(M + H⁺).
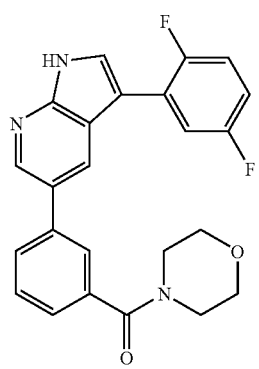
MS: m/z 420.0(M + H⁺).

TABLE 6-continued

Structure

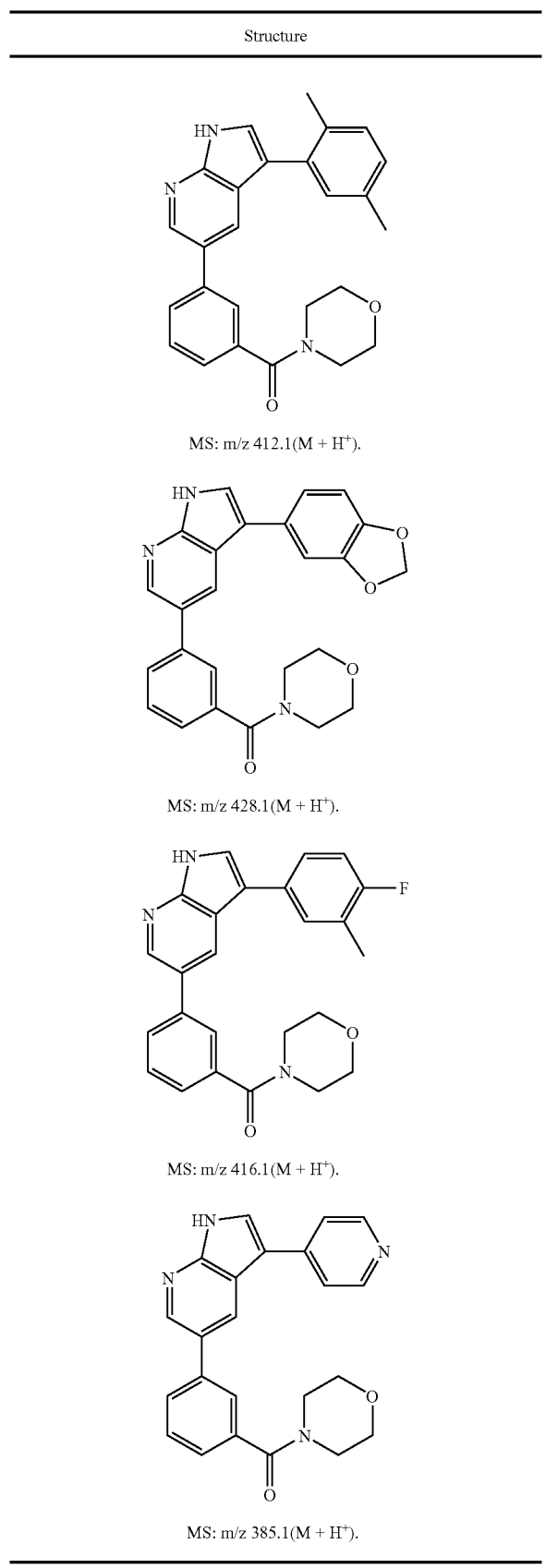

MS: m/z 412.1(M + H⁺).

MS: m/z 428.1(M + H⁺).

MS: m/z 416.1(M + H⁺).

MS: m/z 385.1(M + H⁺).

Method 7:

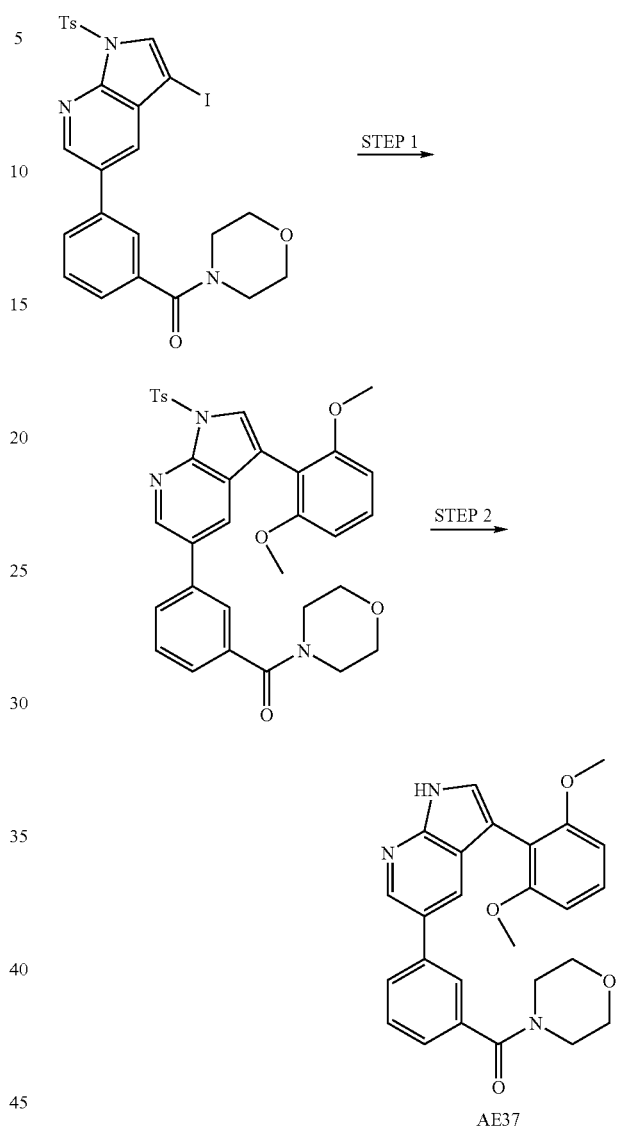

AE37

Step 1: Synthesis of (3-(3-(2,6-dimethoxyphenyl)-1-tosyl-1H-pyrrolo [2,3-b]pyridin-5-yl)phenyl)(morpholino)methanone A mixture of (3-(3-iodo-1-tosyl-1H-pyrrolo[2,3-b]pyridin-5-yl)phenyl)(morpholino)methanone (40 mg, 0.068 mmol), 2,6-dimethoxyphenylboronic acid (18.6 mg, 0.102 mmol), tetrakis(triphenylphosphine)palladium(0) (3.9 mg, 0.0034 mmol) and sodium carbonate (2M aqueous solution, 0.102 mL, 0.204 mmol) in acetonitrile (1 mL) was heated in a Personal microwave at 120° C. for 30 minutes. The resulting mixture was diluted with water and extracted with ethyl acetate. The organic layers were combined, dried over sodium sulfate, filtered and concentrated to dryness to afford crude (3-(3-(2,6-dimethoxyphenyl)-1-tosyl-1H-pyrrolo[2,3-b]pyridin-5-yl)phenyl)(morpholino)methanone, which was used in step 2 without further purification.

Step 2: Synthesis of (3-(3-(2,6-dimethoxyphenyl)-1H-pyrrolo[2,3-b]pyridin-5-yl)phenyl)(morpholino)methanone.

Methanol (1 mL) was added to crude (3-(3-(2,6-dimethoxyphenyl)-1-tosyl-1H-pyrrolo[2,3-b]pyridin-5-yl)phenyl)(morpholino)methanone from step 1 and potassium hydroxide (50% w/v, 0.038 mL, 0.34 mmol) was added to the resulting solution. The mixture was stirred for 30 minutes at room temperature before being diluted with water and extracted with ethyl acetate. The organic layers were combined, dried over sodium sulfate, filtered and concentrated to dryness. Silica gel chromatography afforded (3-(3-(2,6-dimethoxyphenyl)-1H-pyrrolo [2,3-b]pyridin-5-yl)phenyl)(morpholino)methanone (7) (31% yield from (3-(3-iodo-1-tosyl-1H-pyrrolo [2,3-b]pyridin-5-yl)phenyl)(morpholino)methanone) as light yellow solids. $^1$H NMR (500 MHz, CD$_3$OD) δ 3.65 (m, br, 8H), 3.75 (s, 6H), 6.77 (d, J=8.5 Hz, 2H), 7.31 (t, J=8.5 Hz, 1H), 7.39 (m, 1H), 7.46 (s, 1H), 7.55 (t, J=7.5 Hz, 1H), 7.67 (m, 1H), 7.74 (m, 1H), 7.91 (d, J=2.0 Hz, 1H), 8.45 (d, J=2.0 Hz, 1H). MS: m/z 444.1 (M+H$^+$).

Other compounds prepared by Method 7:

TABLE 7

| Structure |
|---|
| MS: m/z 448.1(M + H$^+$). |
| MS: m/z 432.1(M + H$^+$). |

Method 8:

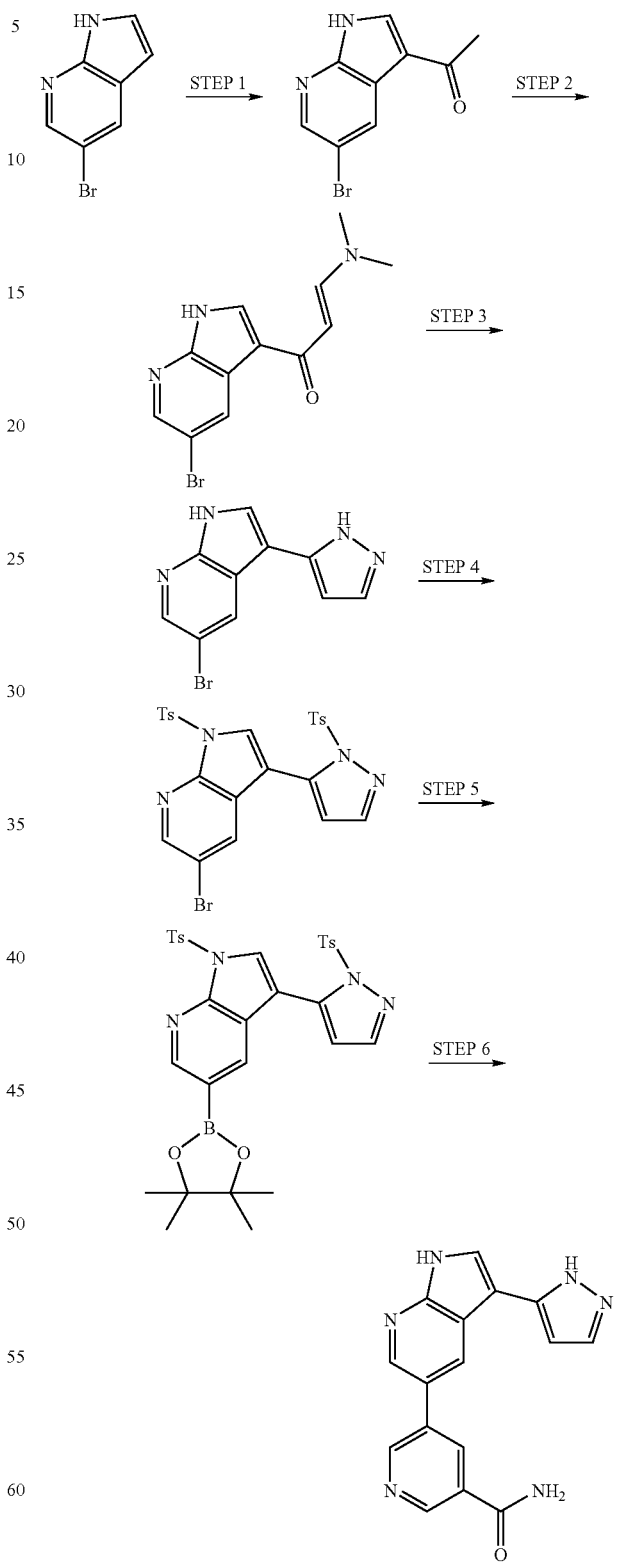

Step 1: Synthesis of 1-(5-bromo-1H-pyrrolo[2,3-b]pyridin-3-yl)-ethanone

To a stirring solution of aluminum chloride (6.77 g, 50.75 mmol) suspended in anhydrous $CH_2Cl_2$ (100 mL) under $N_2$ was added 5-bromo-1H-pyrrolo[2,3-b]pyridine (2.00 g, 10.15 mmol). The reaction solution was stirred for 1 hour at ambient temperature whereupon acetyl chloride (3.61 mL, 50.75 mmol) was added dropwise and the resulting solution was stirred for 5 more hours. The reaction was cooled to 0° C. in an ice bath and quenched carefully by addition of MeOH until the solution became clear. The reaction was concentrated under vacuum. $H_2O$ was added and 1 N NaOH was added dropwise until the pH=4. The product was extracted into ethyl acetate and the organic layer was washed with a saturated solution of sodium potassium tartrate to remove any remaining aluminum salts. The organic layer was dried over $Na_2SO_4$ and concentrated under vacuum. The material was redissolved in ethyl acetate and filtered through a bed of silica gel. The filtrate was concentrated to afford the title compound as an orange solid (2.25 g, 93% yield). $^1$H NMR (500 MHz, $d_6$-DMSO) δ 12.70 (br s, 1H), 8.56 (d, J=2.5 Hz, 1H), 8.55 (s, 1H), 8.40 (d, J=2.5 Hz, 1H), 2.46 (s, 3H). MS: m/z 238.9/240.9 (M+H$^+$).

Step 2: Synthesis of 1-(5-bromo-1H-pyrrolo[2,3-b]pyridin-3-yl)-3-dimethylamino-propenone To 1-(5-bromo-1H-pyrrolo[2,3-b]pyridin-3-yl)-ethanone (2.25 g, 9.41 mmol) was added tert-butoxybis(dimethylamino)methane (5.83 mL, 28.23 mmol) (neat) and refluxed in an oil bath at 100° C. for 6.5 hours. The reaction was cooled and titrated with diethyl ether. The solid was filtered and dried under vacuum to afford the title compound as an orange powder (1.93 g, 70% yield). $^1$H NMR (500 MHz, $d_6$-DMSO) δ 8.67 (d, J=2.5 Hz, 1H), 8.37 (s, 1H), 8.31 (d, J=2.0 Hz, 1H), 7.57 (d, J=12.5 Hz, 1H), 5.78 (d, J=12.0 Hz, 1H), 2.49 (s, 6H).

Step 3: Synthesis of 5-bromo-3-(2H-pyrazol-3-yl)-1H-pyrrolo[2,3-b]pyridine

To a solution of 1-(5-bromo-1H-pyrrolo[2,3-b]pyridin-3-yl)-3-dimethylamino-propenone (1.93 g, 6.54 mmol) in ethanol (5 mL) in a microwave vial was added anhydrous hydrazine (247 uL, 7.85 mmol). The reaction mixture was heated in a microwave at 80° C. for 2.5 hours. The reaction mixture was concentrated under vacuum to afford the title compound as a reddish brown powder (1.50 g, 87% yield). $^1$H NMR (500 MHz, $d_6$-DMSO) δ 12.71 (s, 1H), 11.97 (s, 1H), 8.62 (s, 1H), 8.30 (s, 1H), 7.94 (s, 1H), 7.75 (s, 1H), 6.65 (s, 1H). MS: m/z 263.0 (M+H$^+$).

Step 4: Synthesis of 5-bromo-1-(toluene-4-sulfonyl)-3-[2-(toluene-4-sulfonyl)-2H-pyrazol-3-yl]-1H-pyrrolo[2,3-b]pyridine To a solution of 5-bromo-3-(2H-pyrazol-3-yl)-1H-pyrrolo[2,3-b]pyridine (1.51 g, 5.75 mmol) in toluene (5 mL) was added tetrabutylammonium hydroxide (40% wt in $H_2O$, 285 uL) and a 50% KOH (aq) solution (5.7 mL). The reaction mixture was stirred for 20 minutes at ambient temperature and para-toluenesulfonylchloride (2.17 g, 11.50 mmol) was added. The reaction was stirred at ambient temperature for 2.5 hours. The product was extracted into ethyl acetate and the organic layer was washed with $H_2O$ then dried over $Na_2SO_4$. The material was concentrated under vacuum and adsorbed onto silica gel. Purification by flash chromatography on silica gel with a gradient of ethyl acetate and hexane afforded the title compound as a yellow solid (1.73 g, 53% yield). $^1$H NMR (500 MHz, $d_6$-DMSO) δ 8.68 (s, 1H), 8.57 (d, J=2.5 Hz, 1H), 8.54 (d, J=2.5 Hz, 1H), 8.49 (d, J=2.5 Hz, 1H), 7.96 (d, J=9 Hz, 2H), 7.92 (d, J=8.5 Hz, 2H), 7.47 (d, J=8.5 Hz, 2H), 7.41 (d, J=8 Hz, 2H), 7.29 (d, J=3 Hz, 1H), 2.36 (s, 3H), 2.32 (s, 3H). MS: m/z 570.9/571.9 (M+H$^+$).

Step 5: Synthesis of 5-(4,4,5,5-tetramethyl-[1,3,2]dioxaborolan-2-yl)-1-(toluene-4-sulfonyl)-3-[2-(toluene-4-sulfonyl)-2H-pyrazol-3-yl]-1H-pyrrolo[2,3-b]pyridine To a solution of 5-bromo-1-(toluene-4-sulfonyl)-3-[2-(toluene-4-sulfonyl)-2H-pyrazol-3-yl]-1H-pyrrolo[2,3-b]pyridine (1.73 g, 3.02 mmol) in DMF (7 mL) in a microwave vial was added bis(pinacolato)diboron (1.54 g, 6.04 mmol), [1,1'-bis(diphenylphosphino)ferrocene]dichloropalladium (II), complex with dichloromethane (1:1) (86 mg, 0.11 mmol), and sodium acetate (0.74 g, 9.06 mmol). The vial was capped, flushed with $N_2$, evacuated under vacuum, and heated in a microwave at 140° C. for 3600 seconds. The product was extracted into ethyl acetate, washed with $H_2O$, dried over $Na_2SO_4$, filtered, and adsorbed onto silica gel. The crude material was purified immediately by flash chromatography using a gradient of ethyl acetate and hexane. The purification afforded the title compound as a white solid (0.72 g, 39% yield). $^1$H NMR (500 MHz, $CDCl_3$) δ 8.81 (s, 1H), 8.73 (s, 1H), 8.16 (m, 1H), 8.07 (d, J=8.0 Hz, 2H), 8.04 (m, 2H), 7.038 (d, J=8.0 Hz, 2H), 7.24 (d, J=8.0 Hz, 2H), 6.67 (m, 1H), 2.41 (d, J=6.5 Hz, 3H), 2.36 (d, J=5.5 Hz, 3H), 1.39 (s, 12H). MS: m/z 619.1 (M+H$^+$).

Step 6: Synthesis of 5-[3-(2H-pyrazol-3-yl)-1H-pyrrolo[2,3-b]pyridin-5-yl]-nicotinamide To a solution of 5-(4,4,5,5-tetramethyl-[1,3,2]dioxaborolan-2-yl)-1-(toluene-4-sulfonyl)-3-[2-(toluene-4-sulfonyl)-2H-pyrazol-3-yl]-1H-pyrrolo [2,3-b]pyridine (56 mg, 0.09 mmol) in a 1:1 acetonitrile/saturated aqueous $NaHCO_3$ solution (2 mL total) in a microwave vial was added 5-bromonicotinamide (20 mg, 0.10 mmol) and [1,1'-bis(diphenylphosphino)ferrocene]dichloropalladium (II), complex with dichloromethane (1:1) (3.7 mg, 0.004 mmol). The vial was capped, flushed with $N_2$, evacuated under vacuum, and heated in a microwave at 90° C. for 1800 seconds. The product was extracted into ethyl acetate and the organic layer was dried over $Na_2SO_4$. The solution was filtered and concentrated under vacuum. The residue was redissolved in a 1:1 MeOH/acetone solution (2 mL total) and treated with 200 uL of 50% KOH (aq) solution and stirred at ambient temperature for 1 hour. Citric acid (1 M) was added dropwise until pH=7 and the product was extracted into ethyl acetate. The organic layer was dried over $Na_2SO_4$, filtered, and adsorbed onto silica gel. The material was purified by flash chromatography using a gradient of ethyl acetate (containing 10% MeOH) and hexane then concentrated under vacuum. The residue was titrated with diethyl ether to afford the title compound as a beige solid (0.8 mg, 3% yield). $^1$H NMR (500 MHz, $d_6$-DMSO) δ 12.67 (s, 1H), 11.87 (s, 1H), 8.95 (s, 1H), 8.62 (s, 1H), 8.50 (s, 1H), 8.25 (s, 1H), 7.89 (s, 1H), 7.63 (s, 1H), 7.41 (d, J=7.5 Hz, 1H), 7.05 (d, J=7.5 Hz, 1H). MS: m/z 305.0 (M +H$^+$).

Other compounds prepared by Method 8:
TABLE 8
Structure
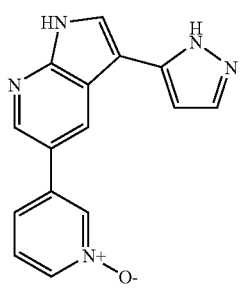
MS: m/z 278.1(M + H⁺).
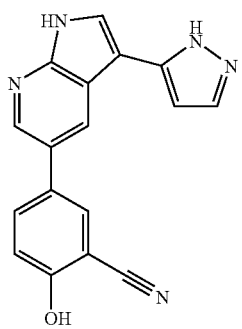
AE38
MS: m/z 302.0(M + H⁺).
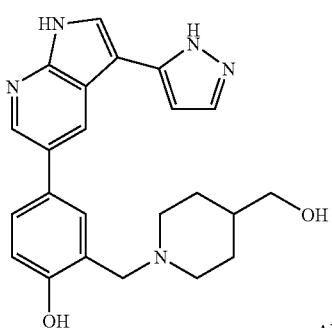
AE39
MS: m/z 403.9(M + H⁺).
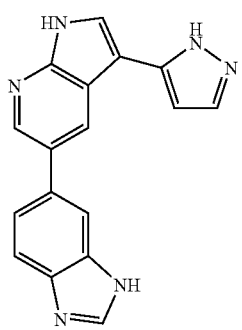
MS: m/z 301.1(M + H⁺).
TABLE 8-continued
Structure
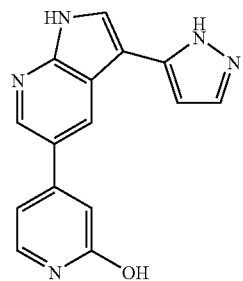
MS: m/z 278.1(M + H⁺).
Method 9:
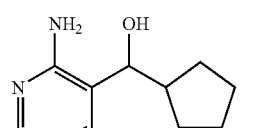
STEP 1
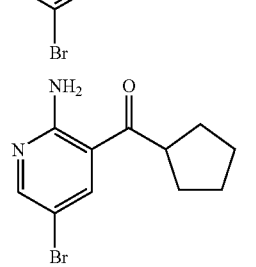
STEP 2
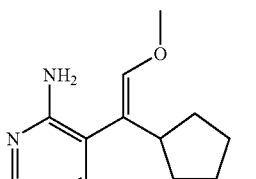
STEP 3
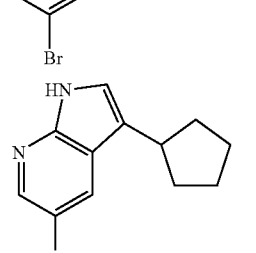
STEP 4
STEP 5

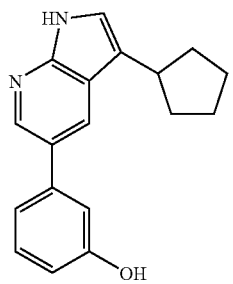

Step 1: Synthesis of (2-amino-5-bromo-phenyl)-cyclopentyl-methanol

To a solution of 2-Amino-5-bromo-pyridine-3-carbaldehyde (632 mg, 3.14 mmol) in anhydrous THF (20 mL) was methylmagnesium bromide 3M in diethyl ether (6.06 mL, 34.8 mmol) is added at −50° C. The reaction mixture was warmed to room temperature and stirred overnight. Saturated aqueous ammonium chloride was added to the mixture (15 mL), the organic layer separated and the aqueous phase extracted with EtOAc (3×20 mL). Organic layers were dried over sodium sulfate, filtered and concentrated. The crude residue was purified by flash silica chromatography with a gradient of ethyl acetate in hexanes. (2-Amino-5-bromo-phenyl)-cyclopentyl-methanol (425.9 mg, 50% yield) was obtained as a yellow powder. MS: m/z 271/273[MH+].

Step 2: Synthesis of (2-amino-5-bromo-pyridin-3-yl)-cyclopentyl-methanone

A mixture of (2-Amino-5-bromo-phenyl)-cyclopentyl-methanol (425.9 mg, 1.57 mmol) and manganese(IV) oxide (2.73 g, 31.4 mmol) in dichloroethane (12 mL) was heated at 50° C. for 20 hrs. The mixture was filtered over a pad of celite, the filtrate was then evaporated down to give (2-Amino-5-bromo-pyridin-3-yl)-cyclopentyl-methanone (363.2 mg, 86% yield) as a yellow powder. MS: m/z 269/271 [MH+].

Step 3: Synthesis of 5-bromo-3-(1-cyclopentyl-2-methoxy-vinyl)-pyridin-2-ylamine To a suspension of methoxymethyltriphenylphosphonium chloride (2.03 g, 5.92 mmol) in THF (8 mL) cooled to 0° C., potassium(bistrimethylsilyl)amide was added (1.26 g, 6.32 mmol). The mixture was stirred at 0° C. for 30 minutes, and 2-amino-5-bromo-pyridin-3-yl)-cyclopentyl-methanone (363.2 mg, 1.35 mmol) in 5 mL of THF was added. The reaction mixture was stirred at room temperature overnight. The solution was filtered over a pad of silica gel, the filtrate was then evaporated, and the residue was purified on flash chromatography with a gradient of EtOAc in hexanes to give 5-bromo-3-(1-cyclopentyl-2-methoxy-vinyl)-pyridin-2-ylamine (116.9 mg, 29% yield) as a white solid. MS: m/z 297/299 [MH+].

Step 4: Synthesis of 5-bromo-3-cyclopentyl-1H-pyrrolo[2,3-b]pyridine

A mixture of 5-bromo-3-(1-cyclopentyl-2-methoxy-vinyl)-pyridin-2-ylamine (116.9 mg, 0.39 mmol) and perchloric acid (0.11 mL) in dioxane (1 mL) was heated at 80° C. for 2 hrs. Solvents were evaporated and the residue was washed with a solution of 2M sodium carbonate (5 mL). A precipitate was formed and filtered off. It was washed with water and dried to afford the product 5-bromo-3-cyclopentyl-1H-pyrrolo[2,3-b]pyridine (69.8 mg, 67% yield) as a brown solid. MS: m/z 265/266 [MH+].

Step 5: Synthesis of 3-(3-cyclopentyl-1H-pyrrolo[2,3-b]pyridin-5-yl)-phenol

A mixture of 5-bromo-3-cyclopentyl-1H-pyrrolo[2,3-b]pyridine (31.8 mg, 0.12 mmol), 3-hodroxyphenylboronic acid (33.1 mg, 0.24 mmol) and 4.2 mg (5 mol %) of dichlorobis(triphenylphosphino)palladium(II) were placed in a vial and 0.8 ml of acetonitrile and 0.8 ml of a 2M aqueous solution of sodium carbonate were added and the mixture irradiated in a Personal Chemistry® microwave reactor to 150° C. for 900 seconds. The resulting mixture was distributed between 15 mL of a saturated aqueous solution of sodium bicarbonate and 30 mL of dichloromethane. The organic phase was dried over sodium sulfate and evaporated. The crude was purified via silica gel chromatography using a gradient of ethyl acetate in hexanes to give 3-(3-Cyclopentyl-1H-pyrrolo[2,3-b]pyridin-5-yl)-phenol (4.5 mg, 14% yield) as off white powder. $^1$H NMR (500 MHz, CD3OD) δ 8.36 (s, 1H), 8.14 (d, 2 Hz, 1H), 7.29 (t, 8 Hz, 1H), 7.19 (s, 1H), 7.10 (d, 7 Hz, 1H), 7.06 (s, 1H), 6.79 (dd, 2 Hz, 8 Hz, 1H), 2.1 (m, 2H), 1.94 (m, 2H), 1.8 (m, 4H), 1.37 (m, 1H). MS: m/z 279.1 [MH+].

Method 10:

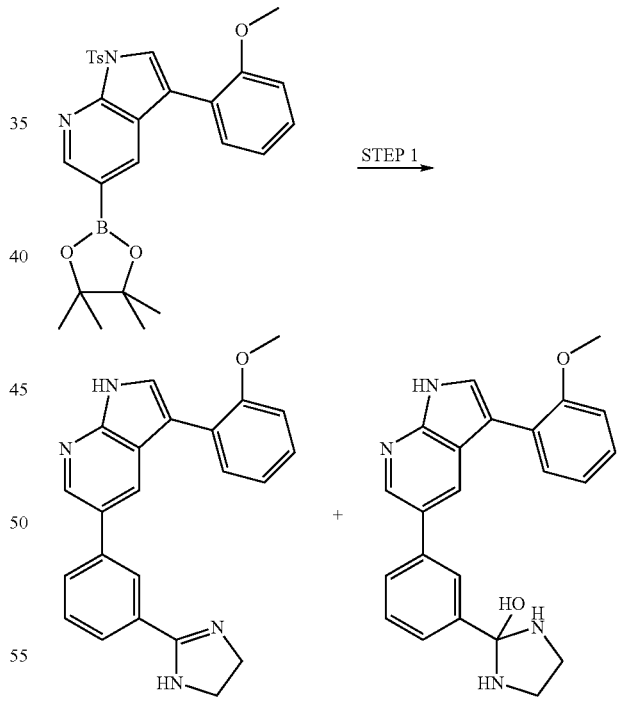

Step 1: Synthesis of 5-[3-(4,5-dihydro-1H-imidazol-2-yl)-phenyl]-3-(2-methoxy-phenyl)-1H-pyrrolo[2,3-b]pyridine (723-zl-26a) and 2-{3-[3-(2-Methoxy-phenyl)-1H-pyrrolo[2,3-b]pyridin-5-yl]-phenyl}-imidazolidin-2-ol A mixture of the 3-(2-Methoxy-phenyl)-5-(4,4,5,5-tetramethyl-[1,3,2]dioxaborolan-2-yl)-1-(toluene-4-sulfonyl)-1H- pyrrolo[2,3-b]pyridine (43 mg, 0.085 mmol), 2-(3-Iodo-phenyl)-4,5-dihydro-1H-imidazole (34.7 mg, 0.128 mmol) and 1,1'-bis(diphenylphosphino)ferrocenepalladium(II)-dichloride dichlormethane adduct (3.1 mg, 4.2 µmol) in 0.8 ml acetonitrile/0.8 ml 2N sodium carbonate irradiated in a Personal Chemistry Optimizer at 135° C. for 20 minutes. The crude reaction mixture was distributed between dichloromethane and a saturated aqueous solution of sodium bicarbonate. The aqueous phase was then extracted with dichloromethane and the combined organic phases were dried over sodium sulfate, filtered and concentrated. The crude product was then purified by flash silica gel chromatography using a gradient of ethyl acetate in hexanes to afford 5-[3-(4,5-Dihydro-1H-imidazol-2-yl)-phenyl]-3-(2-methoxy-phenyl)-1H-pyrrolo[2,3-b]pyridine (11.2 mg, MS: MS: m/z 369.1 [MHz]) and 2-{3-[3-(2-Methoxy-phenyl)-1H-pyrrolo[2,3-b]pyridin-5-yl]-phenyl}-imidazolidin-2-ol (13.2 mg, m/z 387.1 [MH$^+$]), both as green solid.

Method 11:

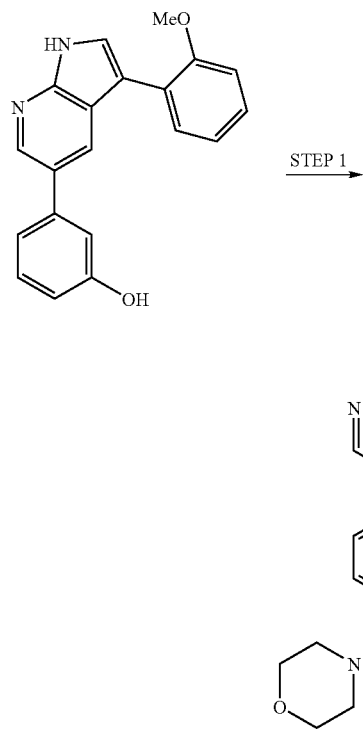

Step 1: Synthesis of 5-[3-(2-Methoxy-phenyl)-1H-pyrrolo[2,3-b]pyridin-5-yl]-2-morpholin-4-ylmethyl-phenol A mixture of 3-[3-(2-methoxy-phenyl)-1H-pyrrolo[2,3-b]pyridin-5-yl]-phenol (14.2 mg, 0.045 mmol), morpholine (5.87 µl, 0.067 mmol) and paraformaldehyde (2.7 mg, 0.09 mmol) in 400 µl of methanol/toluene (3:7) was stirred at 60° C. for 1 hour, then 90° C. for 3 hours. The resulting light brown residue was purified by flash silica gel chromatography using a gradient of ethyl acetate in hexanes to afford 5-[3-(2-methoxy-phenyl)-1H-pyrrolo[2,3-b]pyridin-5-yl]-2-morpholin-4-ylmethyl-phenol (11.7 mg, 63% yield) as white solid. $^1$H NMR (500 MHz, CD3OD) δ 8.44 (d, 1.5 Hz, 1H), 8.22 (d, 1.5 Hz, 1H), 7.65 (s, 1H), 7.56 (dd, 1.5 Hz, 7 Hz, 1H), 7.37 (d, 8 Hz, 1H), 7.32 (dt, 2 Hz, 7.8 Hz, 1H), 7.19 (dd, 2 Hz, 8 Hz, 1H), 7.17 (d, 1.5 Hz, 1H), 7.14 (d, 8 Hz, 1H), 7.06 (dt, 1 Hz, 7 Hz, 1H), 4.18 (s, 2H), 3.87 (s, 3H), 3.85 (br s, 4H), 3.09 (br s, 4H). MS: m/z 416.1 [MH$^+$].

Other compounds prepared by Method 11:

TABLE 9

| Structure |
|---|
| MS: m/z 457[MH$^+$]. |
| MS: m/z 431[MH$^+$]. |
| MS: m/z 444[MH$^+$]. |

TABLE 9-continued
Structure
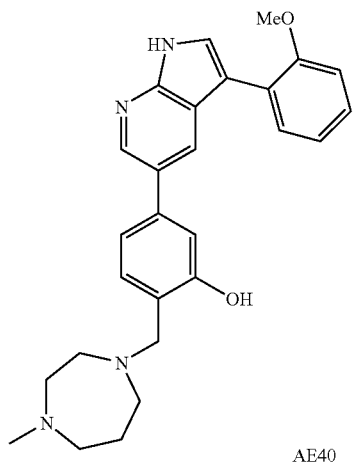
AE40
MS: m/z 443[MH+].
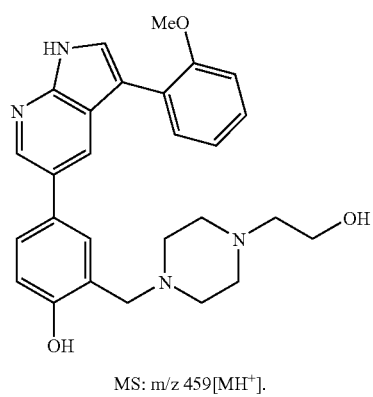
MS: m/z 459[MH+].
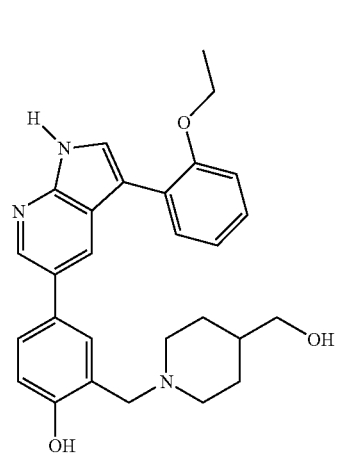
MS: m/z 458[MH+].
TABLE 9-continued
Structure
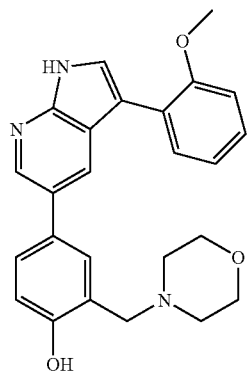
MS: m/z 416[MH+].
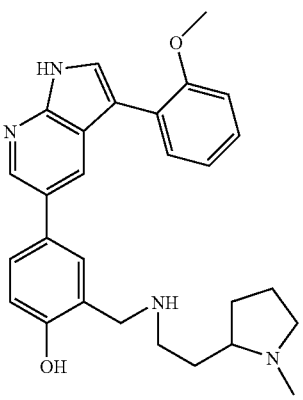
MS: m/z 457[MH+].
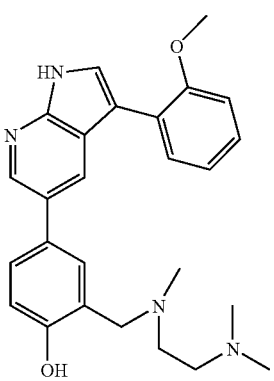
MS: m/z 431[MH+].

TABLE 9-continued

Structure

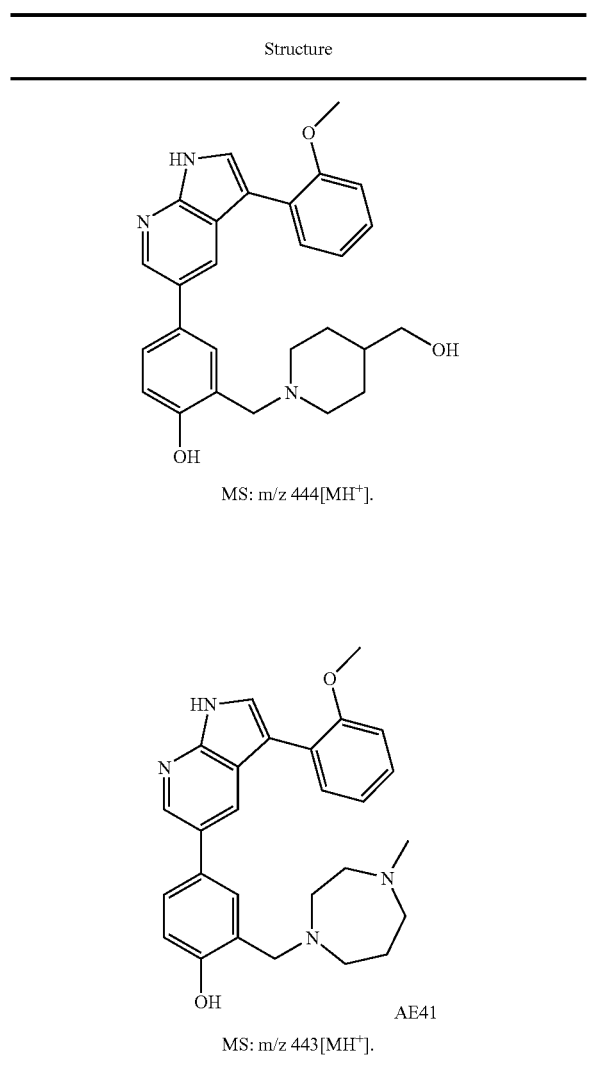

MS: m/z 444[MH+].

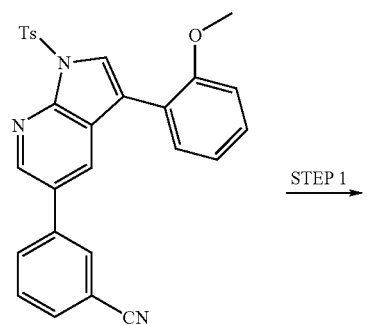

AE41

MS: m/z 443[MH+].

Method 12:

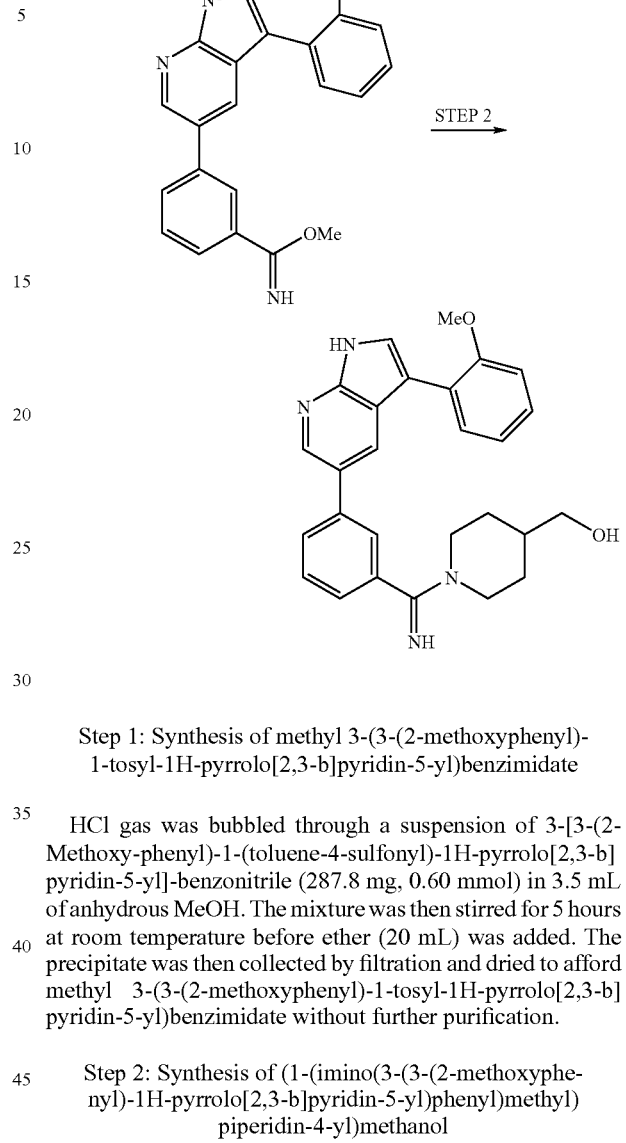

Step 1: Synthesis of methyl 3-(3-(2-methoxyphenyl)-1-tosyl-1H-pyrrolo[2,3-b]pyridin-5-yl)benzimidate HCl gas was bubbled through a suspension of 3-[3-(2-Methoxy-phenyl)-1-(toluene-4-sulfonyl)-1H-pyrrolo[2,3-b]pyridin-5-yl]-benzonitrile (287.8 mg, 0.60 mmol) in 3.5 mL of anhydrous MeOH. The mixture was then stirred for 5 hours at room temperature before ether (20 mL) was added. The precipitate was then collected by filtration and dried to afford methyl 3-(3-(2-methoxyphenyl)-1-tosyl-1H-pyrrolo[2,3-b]pyridin-5-yl)benzimidate without further purification.

Step 2: Synthesis of (1-(imino(3-(3-(2-methoxyphenyl)-1H-pyrrolo[2,3-b]pyridin-5-yl)phenyl)methyl)piperidin-4-yl)methanol The imidate precipitate was then dissolved in MeOH to a total volume of 15.0 mL, it was then divided into 15 equal portions (ca. 0.04 mmol each) for reaction with 15 different amines. To this imidate solution was added the 4-hydroxymethylpiperidine (9.9 mg, 0.086 mmol, 2 eq) and triethylamine (60 μl, 0.43 mmol, 10 eq.), the mixture was stirred at room temperature for 2 days. At the end of 2 days, NaOH (20 mg, 0.5 mmol) in 100 μl water was added to each reaction mixture to hydrolyze the sulfonamide. The reaction was done 0° C. overnight. After removing the solvents, the crude product was purified on reverse phase HPLC to give 5.0 mg of [4-(imino-{3-[3-(2-methoxy-phenyl)-1H-pyrrolo[2,3-b]pyridin-5-yl]-phenyl}-methyl)-cyclohexyl]-methanol as a white solid. $^1$H-NMR (500 MHz, CD3OD) δ 8.54 (d, 2 Hz, 1H), 8.33 (d, 2.5 Hz, 1H), 8.00 (dt, 1.5 Hz, 9 Hz, 1H), 7.91 (br s, 1H), 7.35 (t, 7.8 Hz, 1H), 7.70 (s, 1H), 7.58 (m, 2H), 7.32 (dt, 1 Hz, 8.3 Hz, 1H), 7.12 (dd, 1 Hz, 8 Hz, 1H), 7.07 (dt, 1 Hz, 7.3 Hz, 1H), 3.86 (s, 3H), 3.48 (d, 6.5 Hz, 2H), 3.38 (m, 4H), 1.78 (m, 1H), 1.42 (m, 4H). MS: m/z 441.1 [MH+].

Other compounds prepared by Method 12:
TABLE 10
Structure
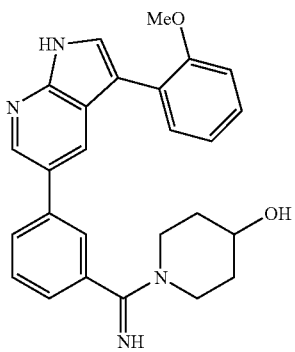
MS: m/z 427.1 [MH+].
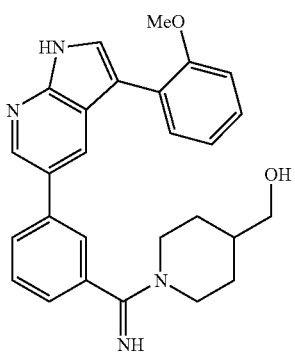
MS: m/z 441.1 [MH+].
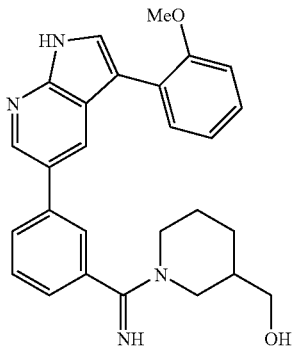
MS: m/z 441.2 [MH+].
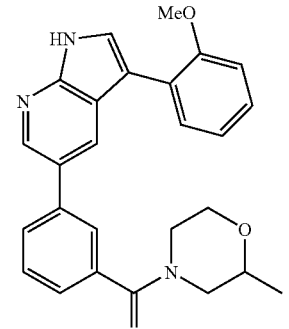
MS: m/z 427.1 [MH+].
TABLE 10-continued
Structure
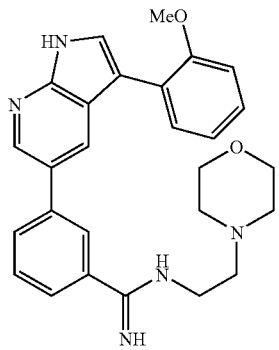
MS: m/z 456.2 [MH+].
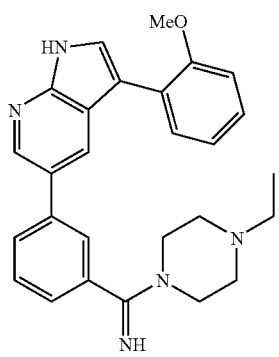
MS: m/z 440.2 [MH+].
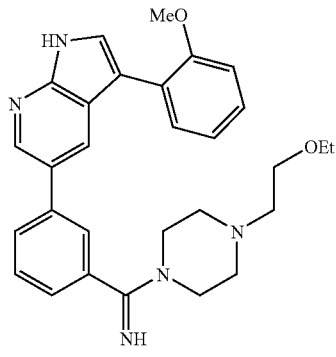
MS: m/z 484.2 [MH+].
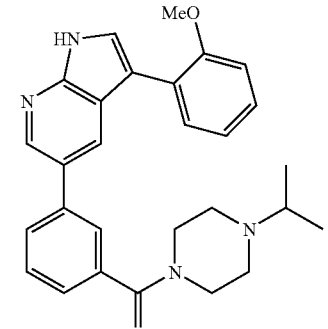
MS: m/z 454.2 [MH+].

TABLE 10-continued

| Structure |
|---|
| (structure) MS: m/z 440.2 [MH+]. |
| (structure) MS: m/z 413.1 [MH+]. |
| (structure) MS: m/z 371.1 [MH+]. |
| (structure) MS: m/z 399.1 [MH+]. |

TABLE 10-continued

| Structure |
|---|
| (structure) MS: m/z 399.2 [MH+]. |
| (structure) MS: m/z 428.2 [MH+]. |
| (structure) MS: m/z 456.1 [MH+]. |
| (structure) AE42 MS: m/z 411.1 [MH+]. |

TABLE 10-continued

| Structure |
|---|
| 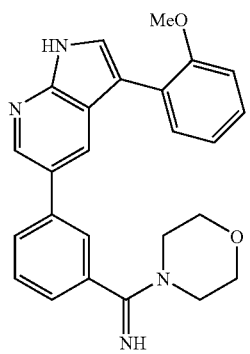<br>MS: m/z 413.1 [MH⁺]. |
| 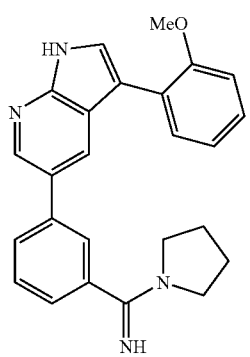<br>MS: m/z 397.2 [MH⁺]. |
| 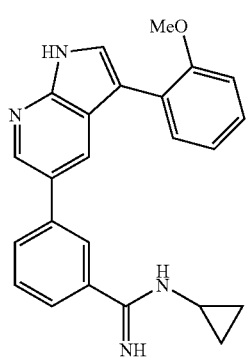<br>MS: m/z 383.1 [MH⁺]. |
| 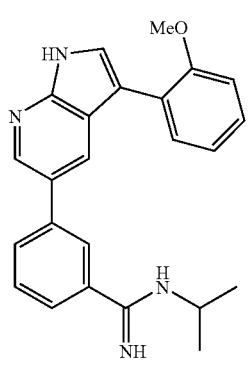<br>MS: m/z 385.2 [MH⁺]. |

TABLE 10-continued

| Structure |
|---|
| 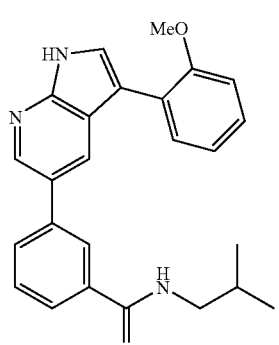<br>MS: m/z 399.2 [MH⁺]. |

Method 13:

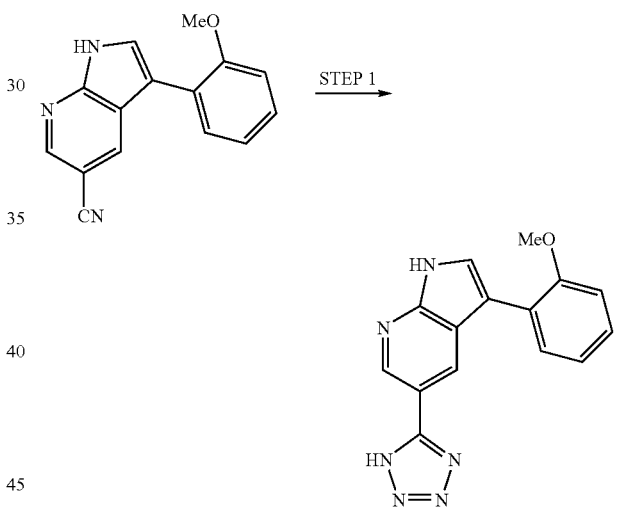

Step 1: Synthesis of 3-(2-Methoxy-phenyl)-5-(1H-tetrazol-5-yl)-1H-pyrrolo[2,3-b]pyridine A mixture of -(2-Methoxy-phenyl)-1H-pyrrolo[2,3-b]pyridine-5-carbonitrile (24.9 mg, 0.10 mmol), sodium azide (78 mg, 1.2 mmol) and ammonium chloride (64.2 mg, 1.2 mmol) were placed in a vial and 2 ml of DMF were added. The mixture was irradiated in a Personal Chemistry® microwave reactor at 150° C. for 900 sec, then 165° C. for 600 sec. The mixture was concentrated and purified via flash silica gel chromatography using a gradient of ethyl acetate in hexanes to give 3-(2-Methoxy-phenyl)-5-(1H-tetrazol-5-yl)-1H-pyrrolo[2,3-b]pyridine (28 mg, 95% yield) as a pale yellow solid. ¹H NMR (500 MHz, DMSO-d6) δ 11.95 (brs, 1H), 8.92 (d, 2 Hz, 1H), 8.59 (d, 2 Hz, 1H), 7.99 (br s, 1H), 7.74 (s, 1H), 7/59 (dd, 1.5 Hz, 7.5 Hz, 1H), 7.33 (t, 7.8 Hz, 1H), 7.16 (d, 8 Hz, 1H), 7.10 (t, 7.5 Hz, 1H), 3.84 (s, 3H). MS: m/z 293.1 [MH⁺].

Method 14:

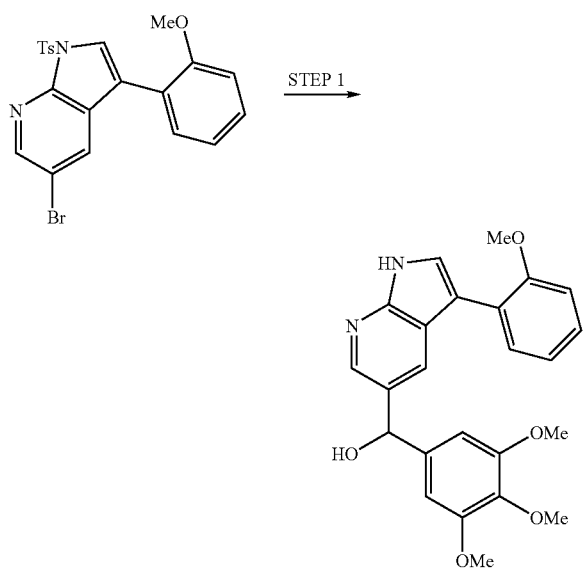

Step 1: Synthesis of [3-(2-Methoxy-phenyl)-1H-pyrrolo[2,3-b]pyridin-5-yl]-(3,4,5-trimethoxy-phenyl)-methanol A solution 1.5M n-BuLi in hexanes (160 µL, 0.24 mmol) was added to a solution of the 5-bromo-3-(2-methoxy-phenyl)-1-(toluene-4-sulfonyl)-1H-pyrrolo [2,3-b]pyridine (91.5 mg, 0.20 mmol) in 2 ml THF at −78° C. The mixture was stirred at −78° C. for 30 minutes before 3,4,5-trimethoxy-benzaldehyde (94.2 mg, 0.48 mmol) in 3 mL of THF was added. The mixture was stirred at −78° C. for 1 hour and then at 0° C. for 30 minutes, quenched with MeOH, and then concentrated. The crude residue was purified by silica gel chromatography using a gradient of ethyl acetate in hexanes to give [3-(2-Methoxy-phenyl)-1H-pyrrolo[2,3-b]pyridin-5-yl]-(3,4,5-trimethoxy-phenyl)-methanol (32 mg, 38% yield) as a white solid. MS: m/z 420.1 [MH$^+$].

Other compounds prepared by Method 14:

TABLE 11

| Structure |
|---|
| 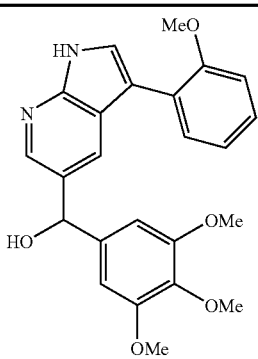 MS: m/z 421 [MH$^+$]. |

TABLE 11-continued

| Structure |
|---|
| 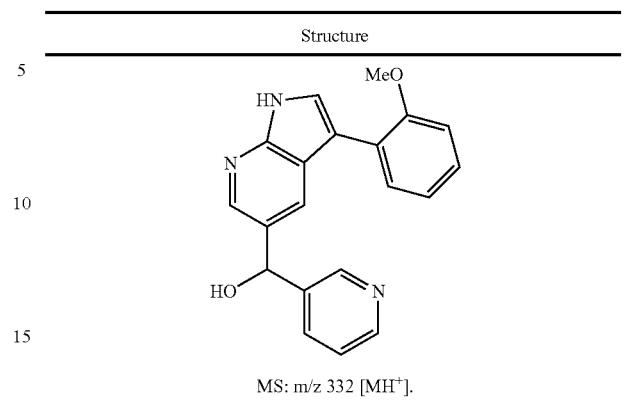 MS: m/z 332 [MH$^+$]. |

Method 15:

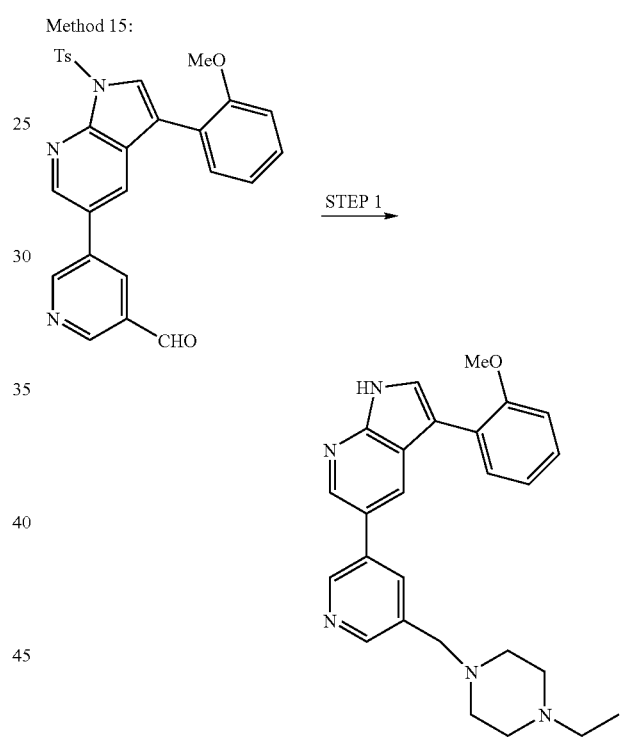

Step 1: Synthesis of [2-(4-{5-[3-(2-Methoxy-phenyl)-1H-pyrrolo[2,3-b]pyridin-5-yl]-pyridin-3-yl}-piperazin-1-yl)-ethyl]-dimethyl-amine To a solution of 5-[3-(2-Methoxy-phenyl)-1-(toluene-4-sulfonyl)-1H-pyrrolo[2,3-b]pyridin-5-yl]-pyridine-3-carbaldehyde (24 mg, 0.050 mmol) and dimethyl-(2-piperazin-1-yl-ethyl)-amine (10 µL, 0.065 mmol) in 1.5 ml dichloroethane was added 3 µL of AcOH. The mixture was stirred at room temperature for 30 minutes before sodium trioxyacetylborohydride (22 mg, 0.10 mmol) was added. The reaction mixture was stirred at room temperature for another 2 hours before being concentrated. The resulting residue was then dissolved in 2 ml of MeOH, to this was added 100 µL of 5N NaOH, the mixture was stirred at 60° C. for 2 hours. Solvents were removed and the residue was purified by flash silica gel chromatography using ethyl acetate and then a solvent mixture (NH₄OH/MeOH/CH₂Cl₂/EtOAc=0.05/1/4/4) to afford [2-(4-{5-[3-(2-Methoxy-phenyl)-1H-pyrrolo[2,3-b]pyridin-5-yl]-pyridin-3-yl}-piperazin-1-yl)-ethyl]-dimethyl-amine (4.70 mg, 20% yield) as a white solid. MS: m/z 471 [MH⁺].
Other compounds prepared by Method 15:
TABLE 12
Structure
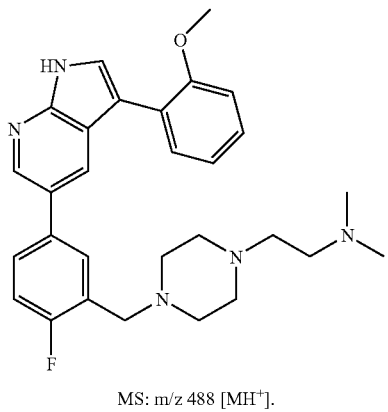
MS: m/z 488 [MH⁺].
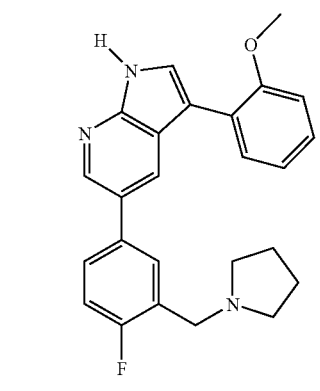
MS: m/z 402 [MH⁺].
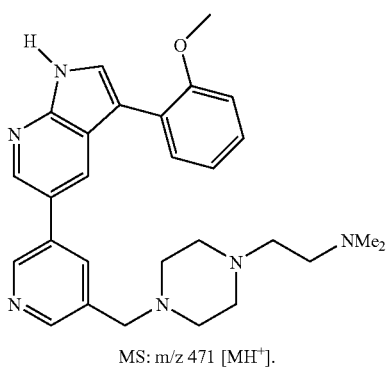
MS: m/z 471 [MH⁺].
TABLE 12-continued
Structure
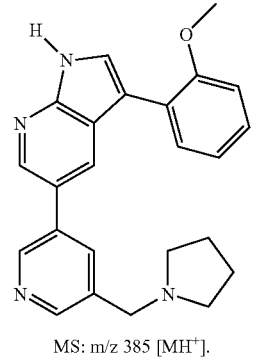
MS: m/z 385 [MH⁺].
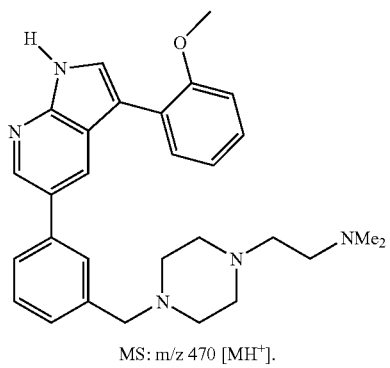
MS: m/z 470 [MH⁺].
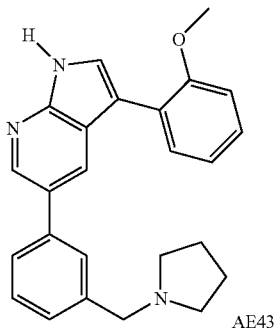
AE43
MS: m/z 384 [MH⁺].
Method 16:
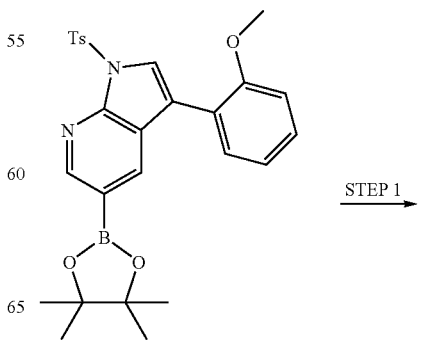
STEP 1

-continued

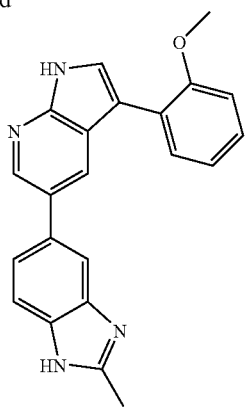

Step 1: Synthesis of 5-[3-(2-Methoxy-phenyl)-1H-pyrrolo[2,3-b]pyridin-5-yl]-2-methyl-1H-benzoimidazole To a solution of 5-(4,4,5,5-tetramethyl-[1,3,2]dioxaborolan-2-yl)-1-(toluene-4-sulfonyl)-3-[2-(toluene-4-sulfonyl)-2H-pyrazol-3-yl]-1H-pyrrolo [2,3-b]pyridine (50.4 mg, 0.10 mmol) in a 1:1 acetonitrile/saturated aqueous NaHCO₃ solution (2 mL total) in a microwave vial was added 5-bromo2-methyl-1H-benzoimidazole (46 mg, 0.22 mmol) and [1,1'-bis(diphenylphosphino)ferrocene]dichloropalladium (II), complex with dichloromethane (1:1) (3.7 mg, 0.004 mmol). The vial was capped, flushed with N₂, evacuated under vacuum, and stirred in a microwave at 155° C. for 1800 seconds. The product was extracted into ethyl acetate and the organic layer was dried over Na₂SO₄. The solution was filtered and concentrated under vacuum. The residue was purified by reverse-phase HPLC to afford 5-[3-(2-Methoxy-phenyl)-1H-pyrrolo[2,3-b]pyridin-5-yl]-2-methyl-1H-benzoimidazole as a beige solid (10.1 mg, 28% yield m/e 355 (M+H⁺).

Intermediate Synthesis:

Synthesis of
5-Bromo-2-isopropyl-1H-benzoimidazole

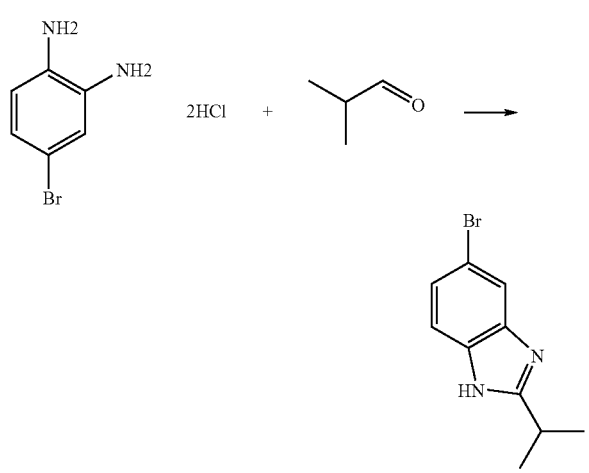

A mixture of 4-bromo-benzene-1,2-diamine di-HCl salts (1 g, 3.8 mmol) and isobutyraldehyde (0.71 mL, 7.7 mmol) in 10 mL of water was stirred at 100° C. for 15 hours. Solvents were removed to afford the crude 5-bromo-2-isopropyl-1H-benzoimidazole as a dark brown solid, which was used directly without further purification. MS: m/e 239.0/241.0 [MH⁺].

Synthesis of 5-Bromo-2-methyl-1H-benzoimidazole

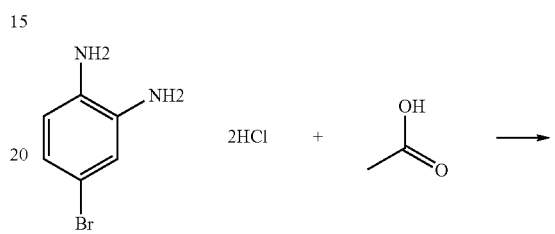

A mixture of 4-bromo-benzene-1,2-diamine di-HCl salts (2 g, 3.8 mmol) and acetic acid (0.87 mL, 15.2 mmol) in 10 mL of water was heated at 100° C. for 15 hrs. Solvents were removed, the crude 5-bromo-2-methyl-1H-benzoimidazole was obtained as a dark brown solid, which was used directly without further purification. MS: m/e 239.0/241.0 [MH⁺].

Other compounds prepared by Method 16:

TABLE 13

| Structure |
| --- |
| 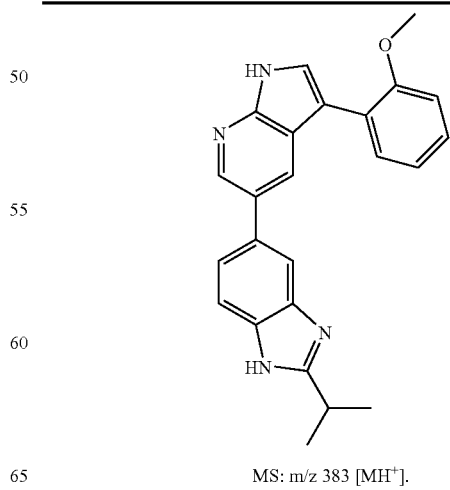<br>MS: m/z 383 [MH⁺]. |

TABLE 13-continued

Structure

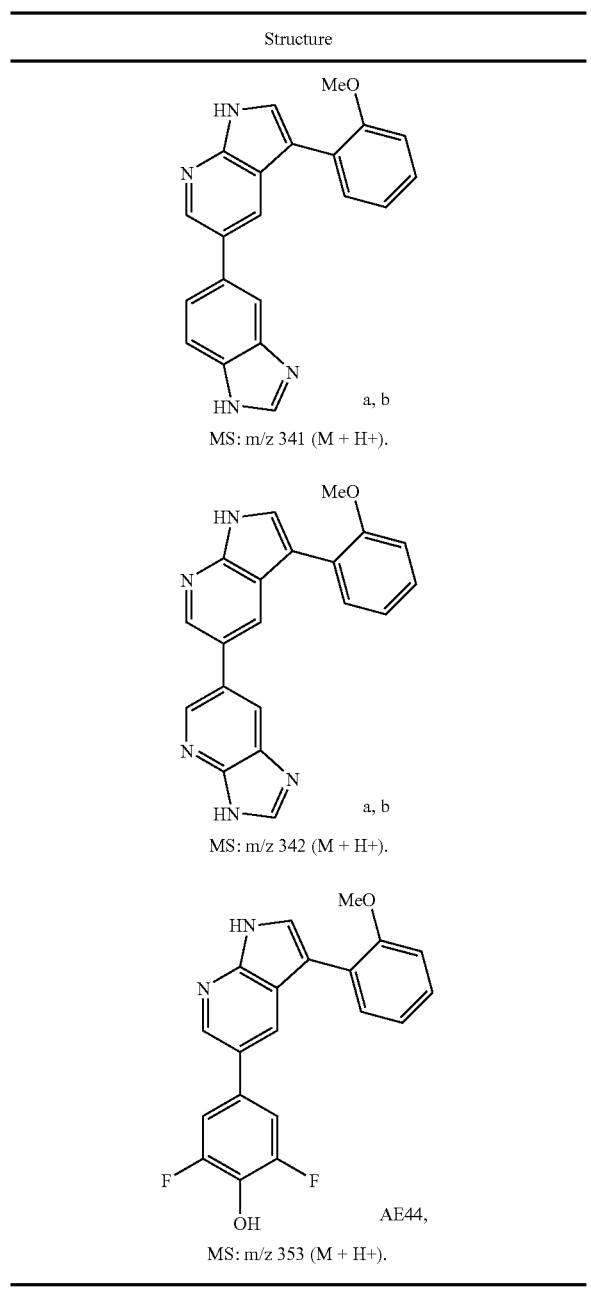

MS: m/z 341 (M + H+). a, b

MS: m/z 342 (M + H+). a, b

AE44, MS: m/z 353 (M + H+).

a Purification on silica gel with a gradient of methanol/dichloromethane
b Dichlorobis (triphenylphosphino)palladium (II) as catalyst Method 17:

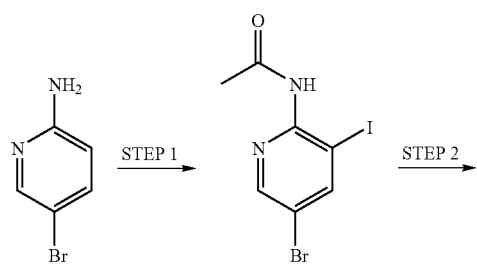

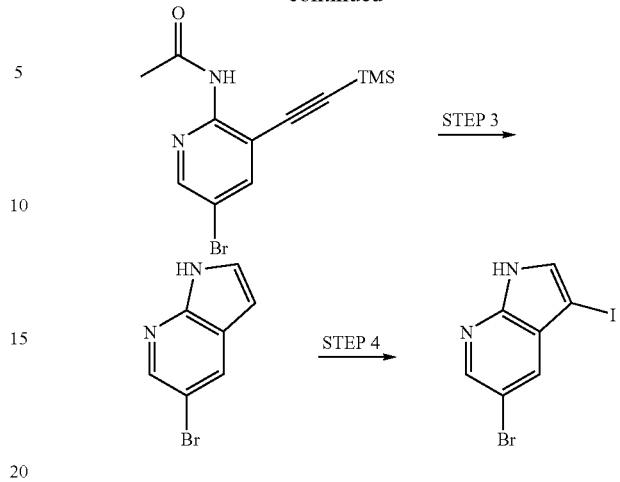

Step 1: Synthesis of N-(5-bromo-3-iodo-pyridin-2-yl)-acetamide

To a solution of 2-amino-5-bromopyridine (12.7 g, 73.4 mmol) in DMF (150 ml) was added iodine (14.9 g, 58.7 mmol) and sodium periodate (6.3 g, 29.4 mmol). The reaction mixture was stirred at 90° C. for 20 hours, then diluted with water and extracted with ethyl acetate. The combined organic extracts were washed twice with a 1 M aqueous solution of sodium thiosulfate, dried over anhydrous magnesium sulfate, and filtered over a pad of silica gel. Solvent was evaporated to give 16.5 g of a brown solid. The solid was dissolved in THF (150 ml) and cooled to 0° C. Pyridine (6.7 ml, 71.7 mmol) was added, followed by dropwise addition of acetyl chloride (5.1 ml, 71.7 mmol). The reaction mixture was stirred at room temperature for 20 hours then at 60° C. for 4 hours. Solvent was evaporated and the residue was partitioned between water (200 ml) and dichloromethane(250 ml). The aqueous layer was extracted three times with dichloromethane and the combined organic layers were dried over anhydrous magnesium sulfate and filtered off. Purification by flash chromotography on silica gel with a gradient of ethyl acetate/hexanes afforded the title compound as an orange solid (7.76 g, 41% yield). $^1$H NMR (DMSO-$d_6$): δ 10.17 (s, 1H), 8.55 (d, J=2.0 Hz, 1H), 8.54 (d, J=2.0 Hz, 1H), 2.01 (s, 3H); HPLC/MS m/z: 340.8, 342.8 [MH]$^+$. Diacetylated material was also isolated as a light orange solid (7.0 g, 33% yield). $^1$H NMR (DMSO-$d_6$): δ 8.78 (d, J=2.5 Hz, 1H), 8.74 (d, J=2.5 Hz, 1H), 2.17 (s, 6H); HPLC/MS m/z: 402.8, 404.8 [MNa]$^+$.

The diacetylated material (7 g, 18.27 mmol) was dissolved in dichloromethane (180 ml) and treated with PS-trisamine (26 g, 3.53 mmol/g loading, Argonaut Technologies) for 17 hours. The resin was filtered off, washed with, dichloromethane and the solvent was evaporated to give 5.95 g of the title compound, contaminated with 10% of 2-amino-3-iodo-5-bromopyridine.

Step 2: Synthesis of N-(5-bromo-3-trimethylsilanyl-ethynyl-pyridin-2-yl)-acetamide To a suspension of N-(5-bromo-3-iodo-pyridin-2-yl)-acetamide (6.42 g, 18.83 mmol) in dichloromethane (90 ml) was added triethyl amine (3.15 ml, 22.6 mmol), then the mixture was cooled to 0° C. and dichlorobis(triphenylphosphino)palladium (II) (66 mg, 0.094 mmol) and copper(i) iodide (36 mg, 0.188 mmol) were added sequentially. Finally trimethylsilylacetylene (2.93 ml, 20.71 mmol) was added dropwise, and the ice bath was removed. After stirring at room temperature for 17 hours, the crude mixture was directly adsorbed on silica gel. Purification by flash chromatography on silica gel with a gradient of ethyl acetate/hexane afforded the title compound as light yellow solid (4.75 g, 81% yield). $^1$H NMR (DMSO-$d_6$): δ 9.99 (s, 1H), 8.31 (d, J=2.5 Hz, 1H), 7.95 (d, J=2.5 Hz, 1H), 1.82 (s, 3H), 0.00 (s, 9H); HPLC/MS m/z: 311, 313 [MH]$^+$.

Step 3: Synthesis of 5-bromo-1H-pyrrolo[2,3-b]pyridine

To a solution of N-(5-bromo-3-trimethylsilanylethynyl-pyridin-2-yl)-acetamide (4.75 g, 15.26 mmol) in THF (90 ml) was added dropwise a 1 M solution of tetra-n-butyl ammonium fluoride in THF (30.5 ml, 30.5 mmol). After stirring at reflux for 15 hours, the reaction mixture was concentrated in vacuo and water was added. The aqueous layer was extracted three times with dichloromethane with, and the combined extracts were directly adsorbed on silica gel. Purification by flash chromotography on silica gel with a gradient of ethyl acetate/hexanes afforded 2.29 g of a beige solid. Recrystallization from ethyl acetate/hexanes provided the title compound as light beige flakes (1.33 g). Further purification of the filtrate on silica gel with a gradient of ethyl acetate/hexanes afforded more of the title compound as a crystalline powder (675 mg) for a combined yield of 2.01 g; 67% $^1$H NMR (DMSO-$d_6$): δ 11.89 (s, 1H), 8.24 (d, J=2.0 Hz, 1H), 8.17 (d, J=2.5 Hz, 1H), 7.53 (t, J=3.0 Hz, 1H), 6.42 (dd, J=1.0, 3.0 Hz, 1H); HPLC/MS m/z: 197 [MH]$^+$.

Step 4: Synthesis of 5-bromo-3-iodo-1H-pyrrolo[2,3-b]pyridine

To a solution of 5-bromo-1H-pyrrolo[2,3-b]pyridine (300 mg, 1.52 mmol) in acetone (10 ml) was added N-iodosuccinimide (377 mg, 1.67 mmol) in one portion. The reaction mixture was stirred at room temperature for 45 minutes. The resulting precipitate was filtered off, washed with a minimal amount of acetone, and dried in vacuo to give the title compound as a cream-colored solid (329 mg, 67% yield). $^1$H NMR (DMSO-$d_6$): δ 12.36 (s, 1H), 8.30 (d, J=2.0 Hz, 1H), 7.85 (d, J=2.0 Hz, 1H), 7.80 (d, J=2.5 Hz, 1H); HPLC/MS m/z: 323.

Method 18:

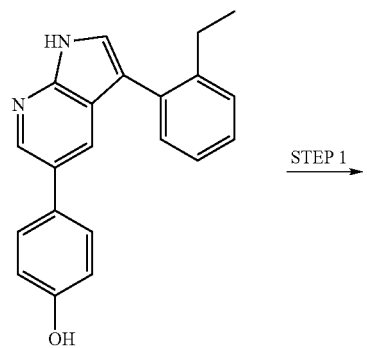

-continued

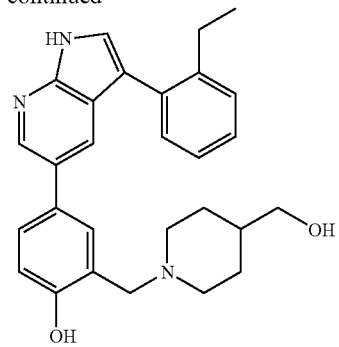

Step 1: Synthesis of 4-[3-(2-ethyl-phenyl)-1H-pyrrolo[2,3-b]pyridin-5-yl]-2-(4-hydroxy-methyl-piperidin-1-ylmethyl)-phenol 59.8 mg (0.19 mmol) of 4-[3-(2-ethyl-phenyl)-1H-pyrrolo[2,3-b]pyridin-5-yl]-phenol was dissolved in a mixture of 0.6 ml of methanol and 2.4 ml of toluene. 11.4 mg (0.38 mmol) of paraformaldehyde and 32.3 mg (0.28 mmol) of 4-piperidinemethanol were added and the mixture heated to 90° C. for 20 hours.

The mixture was distributed between ethyl acetate and a saturated aqueous solution of ammonium chloride. The aqueous layer was extracted three times with ethyl acetate and the combine organic layers were washed with brine, dried over sodium sulfate and evaporated. The crude was purified by mass-triggered reverse-phase HPLC to afford 2 mg (4 μmol, 2% yield) of 4-[3-(2-ethyl-phenyl)-1H-pyrrolo[2,3-b]pyridin-5-yl]-2-(4-hydroxymethyl-piperidin-1-ylmethyl)-phenol as a beige solid. $^1$H-NMR ($d_4$-methanol) δ: 8.50 (m, 1H), 8.45 (s, 1H), 7.90 (d, J=2 Hz, 1H), 7.52 (m, 2H), 7.41 (s, 1H), 7.38 (d, J=7.3 Hz, 1H), 7.32-7.34 (m, 2H), 7.26 (t, J=7.3 Hz, 1H), 6.96 (d, J=8.8 Hz, 1H), 4.17 (s, 2H), 3.44 (d, J=5.9 Hz, 2H), 3.38 (d, J=12.2 Hz, 2H), 2.80 (t, J=11.2 Hz, 2H), 2.68 (q, J=7.3 Hz, 2H), 1.91 (d, J=13.2 Hz, 2H), 1.46 (m, 2H), 1.08 (t, J=7.8 Hz, 3H). MS: m/z 442 [MH$^+$].

Method 19:

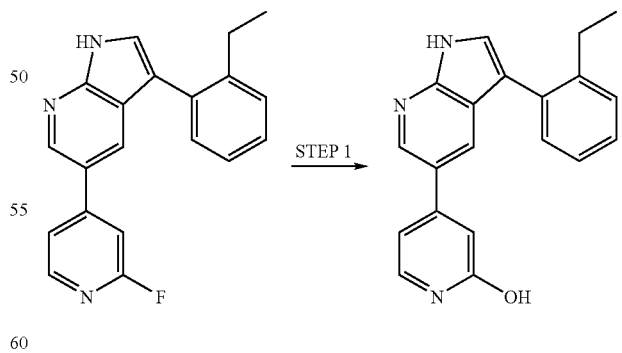

Synthesis of 4-[3-(2-ethyl-phenyl)-1H-pyrrolo [2,3-b]pyridin-5-yl]-pyridin-2-ol 26 mg (82 μmol) of 3-(2-ethyl-phenyl)-5-(2-fluoro-pyridin-4-yl)-1H-pyrrolo[2,3-b]pyridine was dissolved in a mixture of 3 ml of 1,4-dioxane, 1.5 Ll of water, and 0.5 mL of concentrated aqueous hydrochloric acid. The solution was stirred at room temperature for 16 hours and then at 100° C. for 3 hours.

Upon cooling the mixture was distributed between ethyl acetate and a saturated aqueous solution of sodium bicarbonate. The aqueous layer was extracted twice with ethyl acetate and the combined organic phases were subsequently washed with brine, dried over sodium sulfate and evaporated to afford 25 mg (79 µmol, 96% yield) of 4-[3-(2-ethyl-phenyl)-1H-pyrrolo[2,3-b]pyridin-5-yl]-pyridin-2-ol. $^1$H-NMR (d$_4$-methanol) δ: 8.52 (s, 1H), 7.97 (d, J=2 Hz, 1H), 7.44 (d, J=6.3 Hz, 1H), 7.40 (m, 1H), 7.32 (d, J=7.8 Hz, 1H), 7.25-7.28 (m, 2H), 7.18-7.22 (m, 1H), 6.69-6.71 (m, 2H), 2.59-2.63 (m, 2H), 1.02 (m, 3H). MS: m/z 316 [MH$^+$].

TABLE 14

| Structure |
|---|
| 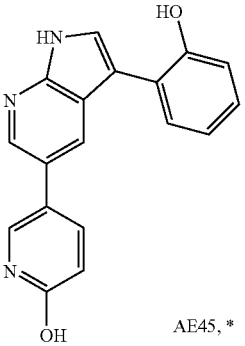 AE45, * <br> MS: m/z 304 [MH$^+$]. |

* 30% HBr was used instead of conc. HCl.

Method 20:

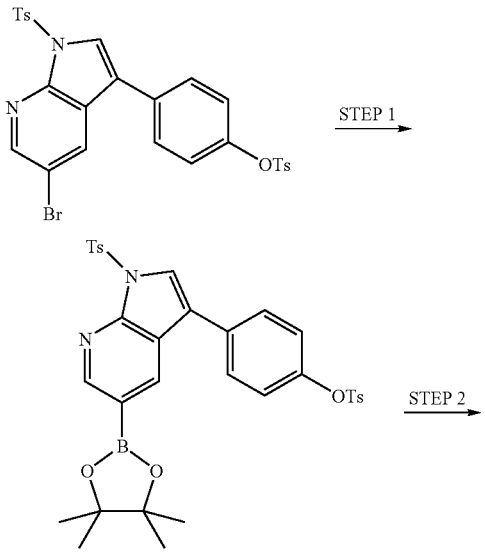

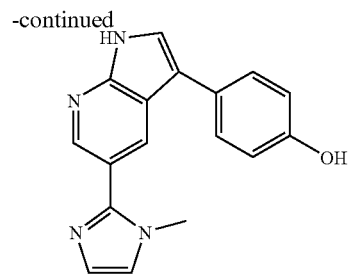

Step 1: Synthesis of toluene-4-sulfonic acid 4-[5-(4,4,5,5-tetramethyl-[1,3,2]dioxaborolan-2-yl)-1-(toluene-4-sulfonyl)-1H-pyrrolo [2,3-b]pyridine-3-yl]-phenyl ester 2.82 g (9.75 mmol) of 4-(5-bromo-1H-pyrrolo[2,3-b]pyridine-3-yl)-phenol and 3.10 g of para-toluenesulfonyl chloride were dispersed in 400 ml of toluene at 45° C. 45 ml of 50% aqueous solution of KOH and 1.5 ml of 40% aqueous solution of tetra-n-butylammonium hydroxide were added and the resulting mixture stirred vigorously at ambient temperature for 6 h. The resulting mixture was diluted with 100 ml of a saturated aqueous solution of sodium bromide, the phases separated and the aqueous layer extracted three times with toluene. The combined organic phases were washed with a 2 M aqueous solution of sodium hydroxide, dried over sodium sulfate and evaporated. The crude was crystallized from ethanol containing 10% v/v of toluene to afford 3.22 g (5.29 mmol, 55% yield) of toluene-4-sulfonic acid 4-[5-bromo-1-(toluene-4-sulfonyl)-1H-pyrrolo[2,3-b]pyridine-3-yl]-phenyl ester as ivory crystalline needles.

1.50 g (2.51 mmol) of this material, 1.30 mg of bis(pinacolato)diboron, 680 mg of anhydrous sodium acetate, and 100 mg of [1,1'-bis(diphenylphosphino)ferrocene]-palladium(II)-dichloride dichloromethane adduct were placed in Smith® vial and the vial was flushed with nitrogen. 15 ml of anhydrous DMF was added and the mixture irradiated in a Personal Chemistry microwave reactor to 130° C. for 1 h. The mixture was then evaporated at 65° C. under reduced pressure and the resulting residue distributed between ether and saturated aqueous sodium bromide solution. The aqueous layer was extracted three times with ether, the organic phases combined, dried over sodium sulfate and filtered over celite. The filtrate was evaporated and dried in vacuum.

The residue was re-dissolved in 150 ml of ether and the resulting suspension washed three times with 80 ml of a saturated aqueous sodium bromide solution, dried over sodium sulfate and evaporated. The residue was stirred with 200 ml of hexanes until a beige suspension was obtained. The insoluble residue was filtered off and dried in vacuo to afford 1.00 g (1.55 mmol, 62%) of toluene-4-sulfonic acid 4-[5-(4,4,5,5-tetramethyl-[1,3,2]dioxaborolan-2-yl)-1-(toluene-4-sulfonyl)-1H-pyrrolo[2,3-b]pyridine-3-yl]-phenyl ester as a beige powder. $^1$H-NMR (d$_4$-methanol): δ 9.19 (d, J=1.4 Hz, 1H), 8.95 (d, J=1.5 Hz, 1H), 8.57 (d, J=8.3 Hz, 2H), 8.57 (s, 1H), 8.26 (d, J=8.3 Hz, 2H), 8.16 (d, J=8.3 Hz, 2H), 7.96 (d, J=7.8 Hz, 2H), 7.88 (d, J=8.3 Hz, 2H), 7.64 (d, J=8.7 Hz, 2H), 2.99 (s, 3H), 2.89 (s, 3H), 1.89 (s, 12H).

Step 2: Synthesis of 4-[5-(1-methyl-1H-imidazol-2-yl)-1H-pyrrolo[2,3-b]pyridine-3-yl]-phenol 50 mg (80 µmol) of toluene-4-sulfonic acid 4-[5-(4,4,5,5-tetramethyl-[1,3,2]dioxaborolan-2-yl)-1-(toluene-4-sulfonyl)-1H-pyrrolo[2,3-b]pyridine-3-yl]-phenyl ester and 7 mg of [1,1'-bis(diphenylphosphino)ferrocene]palladium(II)-dichloride dichloromethane adduct were placed in a Smith® vial. 1 ml of acetonitrile, 1 ml of a 2 M aqueous solution of sodium carbonate and 16 μl of 2-bromo-1-methyl-1H-imidazole were added and the resulting mixture was irradiated in a Personal Chemistry microwave reactor to 165° C. for 20 min. The resulting mixture was diluted with 2 ml of DMSO and 1 ml of methanol and subsequently filtered over sodium sulfate and a 0.45 μm PTFE syringe filter. The filtrate is directly purified via mass-triggered reverse phase HPLC to afford 12 mg (41 μmol, 52% yield) of 4-[5-(1-methyl-1H-imidazol-2-yl)-1H-pyrrolo[2,3-b]pyridine-3-yl]-phenol as a colorless solid. $^1$H-NMR (d$_6$-DMSO): δ 11.97 (s, 1H), 9.40 (s, 1H), 8.53 (d, J=2.0 Hz, 1H), 8.40 (d, J=1.4 Hz, 1H), 8.14 (s, 1H), 7.77 (d, J=2.4 Hz, 1H), 7.54 (d, J=8.3 Hz, 2H), 7.30 (s, 1H), 7.02 (s, 1H), 6.86 (d, J=8.7 Hz, 2H), 3.78 (s, 3H); MS: m/z 291 [MH$^+$].

Other compounds prepared by Method 20:

TABLE 15

Structure

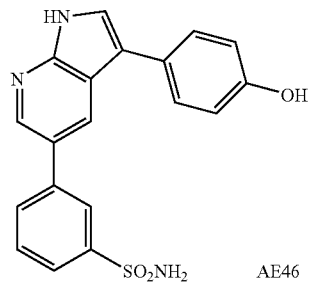

AE46

MS: m/z 366 [MH$^+$]

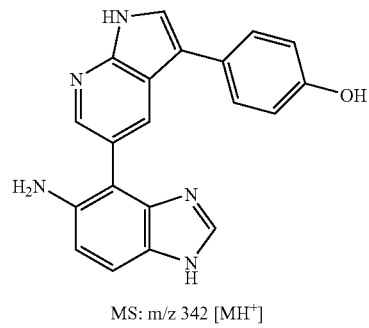

MS: m/z 342 [MH$^+$]

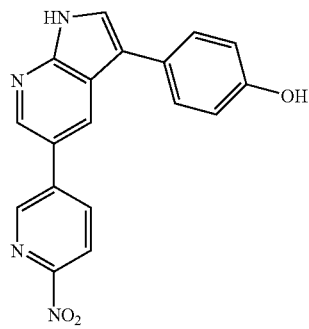

MS: m/z 333 [MH$^+$]

TABLE 15-continued

Structure

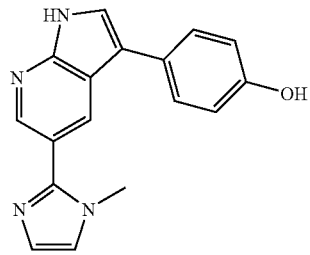

MS: m/z 291 [MH$^+$]

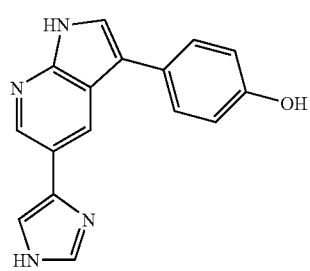

MS: m/z 277 [MH$^+$]

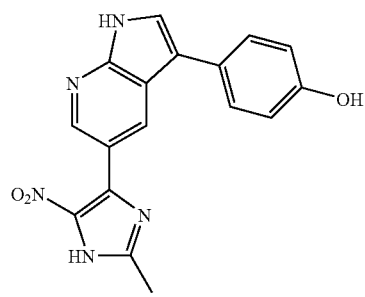

MS: m/z 336 [MH$^+$]

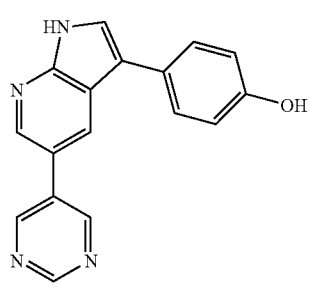

MS: m/z 289 [MH$^+$]

Method 21:

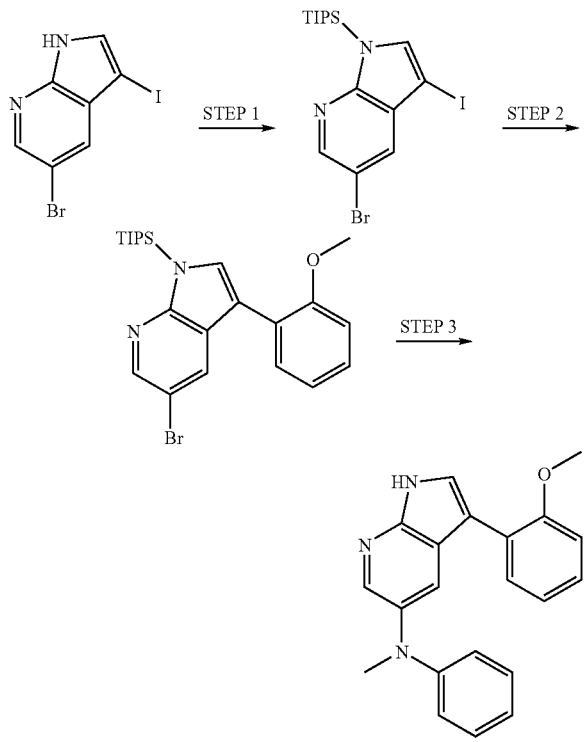

Step 1: Synthesis of 5-bromo-3-iodo-1-triisopropyl-silanyl-1H-pyrrolo[2,3-b]pyridine 2.30 g (11.67 mmol) of 5-bromo-3-iodo-1H-pyrrolo[2,3-b]pyridine was dissolved in 90 ml of anhydrous THF under nitrogen. An excess of sodium hydride was added at room temperature and subsequently 3 ml of tri-iso-propylsilyl chloride were added. The reaction mixture was allowed to stir at ambient temperature for 4 h.

The mixture was distributed between ethyl acetate and a saturated aqueous solution of ammonium chloride. The aqueous phase was extracted three times with ethyl acetate and the organic phases were combined, washed with brine, dried over sodium sulfate and evaporated. The crude material was purified by flash chromatorgraphy on silica gel using a gradient of ethyl acetate in hexanes to afford 3.493 g (7.235 mmol, 62% yield) of -bromo-3-iodo-1-triisopropylsilanyl-1H-pyrrolo[2,3-b]pyridine as a crystalline solid. $^1$H-NMR (d$_6$-DMSO): δ 8.34 (d, J=1.9 Hz, 1H), 7.88 (d, J=2.0 Hz, 1H), 7.72 (s, 1H), 1.86 (m, 3H), 1.05 (d, J=7.8 Hz, 18H).

Step 2: Synthesis of 5-bromo-3-(2-methoxy-phenyl)-1-triisopropylsilanyl-1H-pyrrolo[2,3-b]pyridine 1.01 g (2.10 mmol) of 5-bromo-3-iodo-1-triisopropylsilanyl-1H-pyrrolo[2,3-b]pyridine, 336 mg of 2-methoxyphenylboronic acid, and 75 mg of (1,1'-bis(diphenyl-phosphino)ferrocene)palladium(II)-dichloride dichloromethane adduct were placed in a Smith® vial and dissolved in a mixture of 15 ml of acetonitrile, 5 ml of toluene, and 7 ml of a saturated aqueous solution of sodium bicarbonate. The mixture was heated to 65° C. for 4 h and then cooled to room temperature. The crude was distributed between dichloromethane and water and the organic phase was dried over sodium sulfate and evaporated. The crude was then purified by flash chromatorgraphy on silica gel using a gradient of ethyl acetate in hexanes to afford 708 mg (1.53 mmol, 73%) of 5-bromo-3-(2-methoxy-phenyl)-1-triisopropylsilanyl-1H-pyrrolo[2,3-b]pyridine as a yellow oil (containing about 20% of residual starting material as an inseparable mixture). $^1$H-NMR (d$_6$-DMSO): δ 8.33 (d, J=2.4 Hz, 1H), 8.15 (d, J=2.0 Hz, 1H), 7.76 (s, 1H), 7.55 (dd, J=1.3 Hz, 7.3 Hz, 1H), 7.33 (ddd, J=1.9 Hz, 7.3 Hz, 1H), 7.15 (dd, J=1.0 Hz, 8.3 Hz 1H), 7.06 (dt, J=1.0 Hz, 7.3 Hz, 1H), 3.82 (s, 3H), 1.88 (m, 3H), 1.10 (d, 18H).

Step 3: Synthesis of [3-(2-methoxy-phenyl)-1H-pyrrolo[2,3-b]pyridine-5-yl]-methyl-phenyl-amine 30 mg of sodium-tert-butoxide and 12 mg of bis(tert-butylphosphino)palladium(0) were placed in a Smith® vial and the vial flushed with nitrogen. 100 mg (0.22 mmol) of 5-bromo-3-(2-methoxy-phenyl)-1-triisopropylsilanyl-1H-pyrrolo[2,3-b]pyridine in 1 ml of anhydrous 1,4-dioxane and 35 μl of N-methylaniline were added and the resulting mixture heated to 130° C. for 15 h. The reaction mixture was then cooled to ambient temperature and 0.4 ml of a 1 M solution of tetra-n-butylammonium fluoride in THF added. The mixture was stirred at room temperature for 2 h. 2 ml of methanol and amberlyst strongly acidic ion exchange resin loaded with sodium was added. After shaking at room temperature for 2 h the crude material is directly adsorbed onto silica gel and purified by flash chromatorgraphy on silica gel using a gradient of ethyl acetate in hexanes to afford 42 mg (0.14 mmol; 64% yield) of [3-(2-methoxy-phenyl)-1H-pyrrolo[2,3-b]pyridine-5-yl]-methyl-phenyl-amine as a brown residue. $^1$H-NMR(d$_6$-DMSO): δ 11.88 (s, 1H), 8.11 (d, J=2.5 Hz, 1H), 7.75 (d, J=2.4 Hz, 1H), 7.70 (d, J=2.5 Hz, 1H), 7.48 (dd, J=1.5 Hz, 7.3 Hz, 1H), 7.26 (ddd, J=1.5 Hz, 8.3 Hz, 1H), 7.16 (t, J=7.9 Hz, 2H), 7.08 (d, J=8.3 Hz, 1H), 7.00 (t(d), J=0.9 Hz, 8.3 Hz, 1H), 6.72-6.68 (m, 3H), 3.76 (s, 3H), 3.29 (s, 3H); MS: m/z 330 [MH$^+$].

Other examples prepared by Method 21:

TABLE 16

| Structure |
|---|
| <br>MS: m/z 316 [MH$^+$] |

TABLE 16-continued

Structure

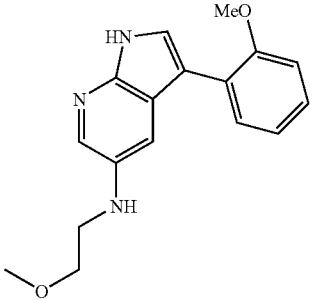

MS: m/z 298 [MH⁺]

Method 22:

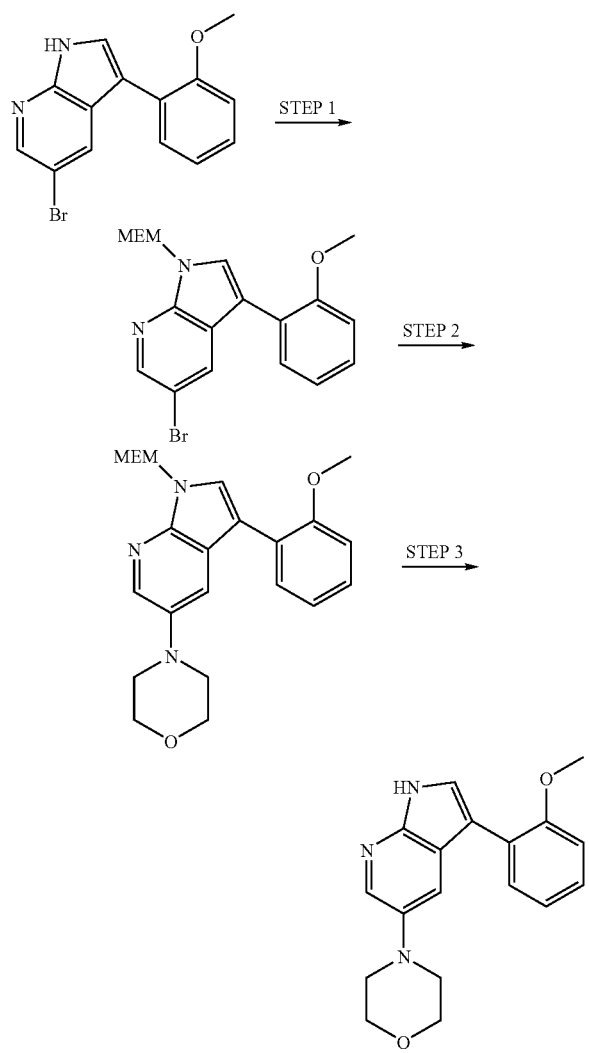

Step 1: Synthesis of 5-bromo-1-(2-methoxy-ethoxymethyl)-3-(2-methoxy-phenyl)-1H-pyrrolo[2,3-b]pyridine Under nitrogen 755 mg (2.49 mmol) of 5-bromo-3-(2-methoxy-phenyl)-1H-pyrrolo[2,3-b]pyridine was dissolved in 30 ml of anhydrous THF. 200 mg of sodium hydride were added and the resulting mixture was stirred at ambient temperature for 4 h. 0.5 ml of (2-methoxy-ethoxy)methyl chloride was added and the resulting mixture stirred at room temperature for 72 h. 0.75 ml of (2-methoxy-ethoxy)methyl chloride and an excess of sodium hydride were added and the reaction mixture allowed to stir at ambient temperature for am additional 4 h. 250 mg of tetra-n-butylammonium iodide were added and the reaction mixture stirred for 2 h at room temperature. The reaction was then quenched by addition of methanol and distributed between a saturated aqueous solution of ammonium chloride and dichloromethane. The aqueous phase was extracted with pyridinepethane and the combined organic phases dried over sodium sulfate and evaporated. The crude was then purified by chromatorgraphy on silica gel using a gradient of ethyl acetate in hexanes to afford 922 mg (2.36 mmol, 95% yield) of 5-bromo-1-(2-methoxy-ethoxymethyl)-3-(2-methoxy-phenyl)-1H-pyrrolo[2,3-b]pyridine as a yellow oil. $^1$H-NMR (d$_6$-DMSO): δ 8.40 (d, J=1.9 Hz, 1H), 8.17 (d, J=1.9 Hz, 1H), 7.97 (s, 1H), 7.52 (dd, J=1.3 Hz, 7.3 Hz, 1H), 7.34 (dd, J=1.4 Hz, 8.7 Hz, 1H), 7.15 (d, J=8.2 Hz 1H), 7.06 (t, J=7.3 Hz, 1H), 5.71 (s, 2H), 3.83 (s, 3H), 3.57 (m, 2H), 3.41 (m, 2H), 3.20 (s, 3H); MS: m/z 315, 317 [MH⁺-MeOC$_2$H$_4$O].

Step 2: Synthesis of 1-(2-methoxy-ethoxymethyl)-3-(2-methoxy-phenyl)-5-morpholin-4-yl-1H-pyrrolo[2,3-b]pyridine 180 mg (0.5 mmol) of 5-bromo-1-(2-methoxy-ethoxymethyl)-3-(2-methoxy-phenyl)-1H-pyrrolo[2,3-b]pyridine, 10 mg of bis(benzonitrile)palladium(II)-chloride, 11 mg of 2,5-bis-(2,6-di-iso-propylphenyl)imidazolium chloride, and 65 mg of potassium-tert-butoxide were placed in a Smith® vial. The vial was flushed with nitrogen and 3 ml of anhydrous 1,4-dioxane and 70 μl of morpholine were added. The resulting mixture was heated to 120° C. for 14 h. The mixture was cooled to room temperature, adsorbed onto silica gel, and purified by flash chromatorgraphy on silica gel using a gradient of ethyl acetate in hexanes to afford 65 mg (0.17 mmol, 33% yield) of 1-(2-methoxy-ethoxymethyl)-3-(2-methoxy-phenyl)-5-morpholin-4-yl-1H-pyrrolo[2,3-b]pyridine as a colorless oil. $^1$H-NMR (CDCl$_3$): δ 8.17 (d, J=2.8 Hz, 1H), 7.63 (s, 1H), 7.59 (d, J=2.5 Hz, 1H), 7.54 (dd, J=1.6 Hz, 7.4 Hz, 1H), 7.31 (ddd, J=1.6 Hz, 7.4 Hz, 9 Hz, 1H), 7.07 (ddd, J=1.1 Hz, 7.4 Hz, 7.4 Hz, 1H), 7.03 (d(m), J=8.3 Hz, 1H), 5.71 (s, 2H), 3.87 (s, 3H), 3.68 (m, 2H), 3.49 (m, 2H), 3.35 (s, 3H); MS: m/z 398 [MH⁺].

Step 3: Synthesis of 3-(2-methoxy-phenyl)-5-morpholin-4-yl-1H-pyrrolo[2,3-b]pyridine 65 mg (0.17 mmol) of 1-(2-methoxy-ethoxymethyl)-3-(2-methoxy-phenyl)-5-morpholin-4-yl-1H-pyrrolo[2,3-b]pyridine was dissolved in a mixture of 3 ml of ethanol and 2 ml of water. 500 μl of formic acid was added and the mixture heated to 65° C. for 16 h and then irradiated in the microwave to 150° C. for 40 min. The resulting mixture was neutralized by addition of sodium bicarbonate and water and the crude distributed between ethyl acetate and brine. The aqueous phase was extracted twice with ethyl acetate. The combined organic phases were dried over sodium sulfate and evaporated to afford 47 mg (0.15 mmol, 94% yield) of 3-(2-methoxy-phenyl)-5-morpholin-4-yl-1H-pyrrolo[2,3-b]pyridine. $^1$H-NMR (d$_6$-DMSO): δ 11.58 (s, 1H), 8.11 (d, J=2.5 Hz, 1H), 7.59 (d, J=2.4 Hz, 1H), 7.51 (dd, J=1.4 Hz, 7.3 Hz, 1H), 7.46 (s, 1H), 7.27 (ddd, J=1.5 Hz, 8.8 Hz, 1H), 7.11 (d, J=8.3 Hz, 1H), 7.02

(dd(d), J=1.5 Hz, 7.3 Hz, 1H), 3.82 (s, 3H), 3.77 (m, 4H), 3.07 (m, 4H); MS: m/z 310 [MH+].

Method 23:

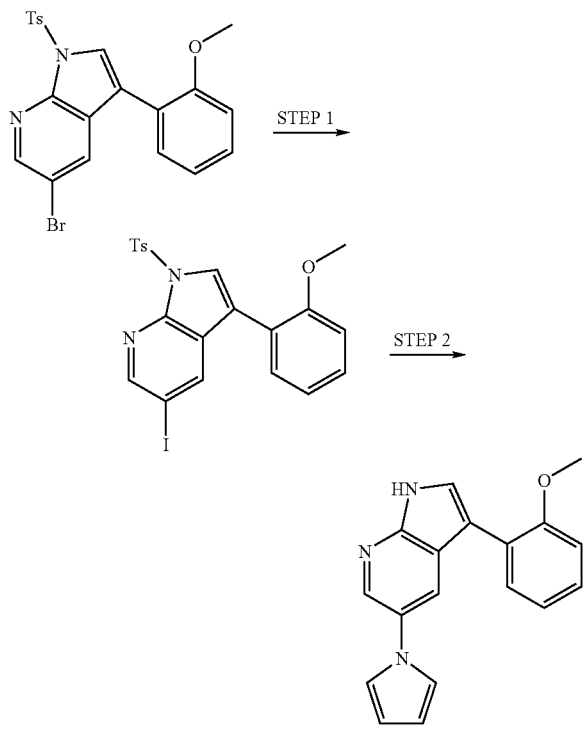

Step 1: Synthesis of 5-iodo-3-(2-methoxy-phenyl)-1-(toluene-4-sulfonyl)-1H-pyrrolo[2,3-b]pyridine 337.3 mg (0.74 mmol) of 5-bromo-3-(2-methoxy-phenyl)-1-(toluene-4-sulfonyl)-1H-pyrrolo[2,3-b]pyridine, 11.3 mg (59 µmol) of copper(I)-iodide, and 185 mg (1.24 mmol) of sodium iodide were placed in a Smith® vial and the vial flushed with nitrogen. 6 ml of anhydrous toluene and 14 µl (0.13 mmol) of N,N'-dimethylethylenediamine were added and the resulting suspension was heated to 120° C. for 16 h.

The mixture was cooled to room temperature and distributed between ethyl acetate and water. The aqueous layer was extracted three times with ethyl acetate. The combined organic phases were washed with brine, dried over sodium sulfate and evaporated. The crude was purified by flash chromatography on silica gel using a gradient of ethyl acetate in hexanes to afford 261 mg (0.52 mmol, 70% yield) of 5-iodo-3-(2-methoxy-phenyl)-1-(toluene-4-sulfonyl)-1H-pyrrolo[2,3-b]pyridine as a colorless solid.

Step 2: Synthesis of 3-(2-methoxy-phenyl)-5-pyrrol-1-yl-1H-pyrrolo[2,3-b]pyridine 40 mg (79 µmol) of 5-iodo-3-(2-methoxy-phenyl)-1-(toluene-4-sulfonyl)-1H-pyrrolo[2,3-b]pyridine, 30 mg (0.14 mmol) of anhydrous potassium phosphate and 1.2 mg (6 µmol) of copper(I)-iodide were placed in a Smith® vial. The vial was flushed with nitrogen and 1 ml of anhydrous toluene, 6.7 µl (95 µmol) of pyrrole, and 2 µl (10 µmol) of rac-trans-N,N'-dimethyl-1,2-cyclohexanediamine were added. The resulting suspension was heated to 120° C. for 22 h. 1.2 mg (6 µmol) of copper(I)-iodide and 2 µl (10 µmol) of rac-trans-N,N'-dimethyl-1,2-cyclohexanediamine were added and the reaction mixture heated for another 20 h.

The resulting mixture was distributed between water and ethyl acetate, the phases separated, and the aqueous layer extracted three times with ethyl acetate. The combined organic phases were washed with brine, dried over sodium sulfate and evaporated. The crude material was purified by flash chromatography on silica gel using a gradient of ethyl acetate in hexanes to afford 27.9 mg (63 µmol, 80% yield) of 3-(2-methoxy-phenyl)-1-(toluene-4-sulfonyl)-5-pyrrol-1-yl-1H-pyrrolo[2,3-b]pyridine as a beige solid.

The material was dissolved in ethanol and 400 µl of 50% aqueous potassium hydroxide solution added. The solution was heated in a Personal Chemistry Optimizer® microwave reactor to 165° C. for 20 min. The crude was distributed between water and ethyl acetate, the phases separated, and the aqueous layer extracted three times with ethyl acetate. The combined organic phases were washed with brine, dried over sodium sulfate and evaporated to afford 20 mg (70 µmol, 87% yield) of 3-(2-methoxy-phenyl)-5-pyrrol-1-yl-1H-pyrrolo[2,3-b]pyridine as a beige solid. $^1$H-NMR (d$_6$-CDCl$_3$): δ 10.48 (s) [1H], 8.49 (s) [1H], 8.09 (d) [1H], 7.73 (s) [1H], 7.56 (d) [1H], 7.34 (t) [1H], 7.05-7.10 (m) [4H], 7.40 (d) [2H], 3.81 (s) [3H]. MS: m/z 290 (88%) [MH+].

Method 24:

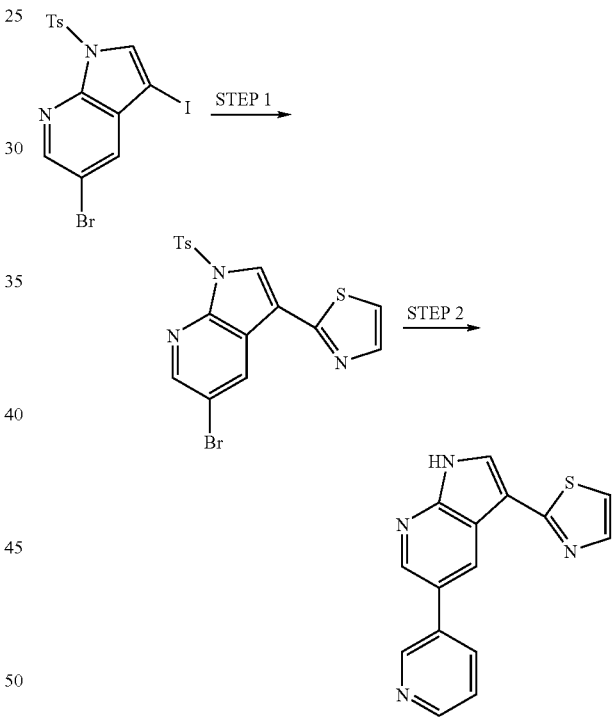

Step 1: Synthesis of 2-(5-bromo-1-tosyl-1H-pyrrolo[2,3-b]pyridine-3-yl)thiazole A mixture of 5-bromo-3-iodo-1-tosyl-1H-pyrrolo[2,3-b]pyridine (1.66 g, 3.48 mmol), 2-tributylstannanyl-thiozole (1.3 g, 1.21 mL, 3.48 mmol) and tetrakis(triphenylphosphine)palladium (0) (116 mg, 0.1 mmol) in anhydrous dioxane was stirred under reflux conditions under nitrogen atmosphere for 3 days. The reaction mixture was cooled to room temperature, treated with activated carbon and filtered over Celite. The filtrate was concentrated, purified by silica gel chromatography and recrystallized in ethyl acetate to afford a mixture of 2-(5-bromo-1-tosyl-1H-pyrrolo [2,3-b]pyridine-3-yl)thiazole (1.11 g, 73% yield). MS: m/z 434/436 (M+H+).

Step 2: Synthesis of 2-(5-(pyridine-3-yl)-1H-pyrrolo[2,3-b]pyridine-3-yl)thiazole A mixture of 2-(5-bromo-1-tosyl-1H-pyrrolo[2,3-b]pyridine-3-yl)thiazole (75 mg, 0.17 mmol), pyridine-3-ylboronic acid (27 mg, 0.22 mmol) 1,1'-bis(diphenylphosphino)ferrocenepalladium(II)-dichloride dichloromethane adduct (6.9 mg, 0.009 mmol), acetonitrile (1 mL) and saturated aqueous NaHCO$_3$ (1 mL) were stirred in a sealed microwave tube at 140° C. for 30 minutes. The mixture was then cooled to room temperature, diluted with ethyl acetate, washed with brine and concentrated to dryness. Silica gel chromatography afforded 2-(5-(pyridine-3-yl)-1H-pyrrolo[2,3-b]pyridine-3-yl)thiazole (36 mg, 76% yield) as a white solid. $^1$H NMR (500 MHz, DMSO-d6) δ 7.47 (m, 1H), 7.56 (d, J=3.5 Hz, 1H), 7.81 (d, J=3.5 Hz, 1H), 8.10 (m, 1H), 8.24 (s, 1H), 8.55 (dd, J=2.0, 5.0 Hz, 1H), 8.61 (d, J=2.5 Hz, 1H), (d, J=2.0 Hz, 1H), 8.89 (m, 1H), 12.37 (s, 1H). MS: m/z 279.0 (M+H$^+$)

Other compounds prepared by method 24:

TABLE 17

| Structure |
| --- |
| 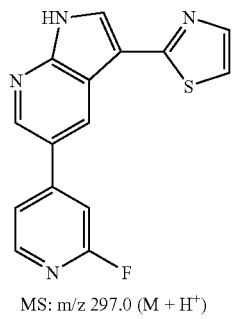<br>MS: m/z 297.0 (M + H$^+$) |
| 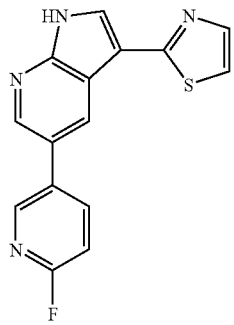<br>MS: m/z 297.0 (M + H$^+$) |
| 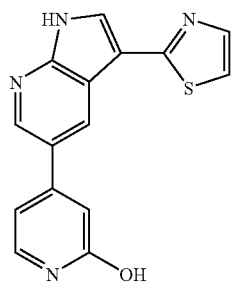<br>MS: m/z 295.0 (M + H$^+$) |

Method 25:

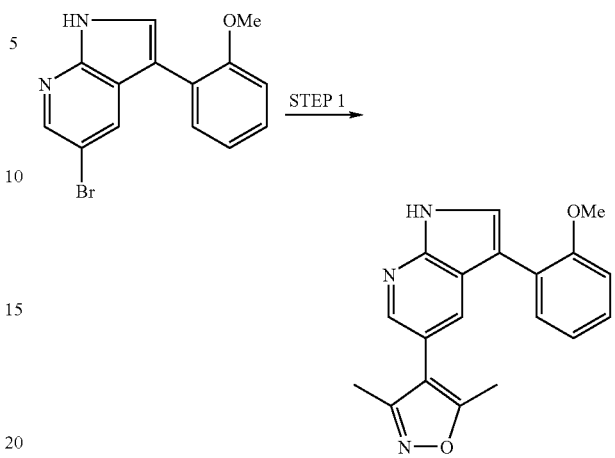

Step 1: Synthesis of 5-(3,5-dimethyl-isoxazol-4-yl)-3-(2-methoxy-phenyl)-1H-pyrrolo[2,3-b]pyridine To 5-bromo-3-(2-methoxy-phenyl)-1H-pyrrolo[2,3-b]pyridine (40 mg, 0.087 mmol), 3,5-dimethyl-isoxazole-4-boronic acid (16 mg, 0.114 mmol) and [1,1'-bis(diphenylphosphino)ferrocene]dichloropalladium (II), complex with dichloromethane (1:1) (4 mg, 0.0044 mmol) in a Smith process vial was added 0.6 mL of a 1:1 mixture of acetonitrile, and a 2 M solution of sodium carbonate in water. The reaction was run in a Personal Chemistry® microwave reactor at 165° C. for 1200 s. The reaction mixture was diluted with 1:1 methanol/dichloromethane, filtered, and the filtrate was adsorbed on silica gel. Purification on silica gel with a gradient of MeOH/CH2Cl2 afforded 5-(3,5-dimethyl-isoxazol-4-yl)-3-(2-methoxy-phenyl)-1H-pyrrolo[2,3-b]pyridine as beige crystals (20 mg, 71% yield). $^1$H NMR (500 MHz, DMSO-d6) δ 2.23 (s, 3H), 2.41 (s, 3H), 3.81 (s, 3H), 7.01 (dt, J=1.0, 7.0 Hz, 1H), 7.11 (dd, J=1.0, 8.0 Hz, 1H), 7.28 (dt, J=1.5, 7.0 Hz, 1H), 7.51 (dd, J=2.0, 8.0 Hz, 1H), 7.73 (d, J=3.0 Hz, 1H), 7.90 (d, J=1.5 Hz, 1H), 8.22 (d, J=2.0 Hz, 1H), 11.9 (s, 1H). MS: m/z 320 (M+H$^+$).

Other compounds prepared by method 25:

TABLE 18

| Structure |
| --- |
| 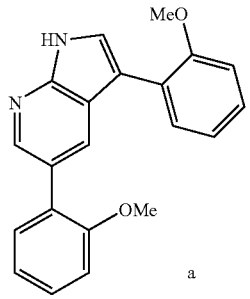<br>a<br>MS: m/z 331(M + H+). |

TABLE 18-continued

Structure

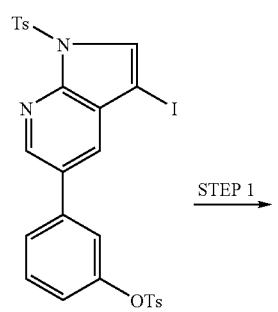

MS: m/z 253 (M + H+).

a Dichlorobis (triphenylphosphino)palladium (II) as catalyst
b Obtained from 1-(5-bromo-1H-pyrrolo[2,3-b]pyridine-3-yl)-ethanone Method 26:

AE47

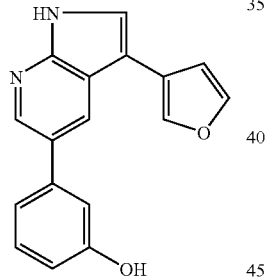

STEP 1 →

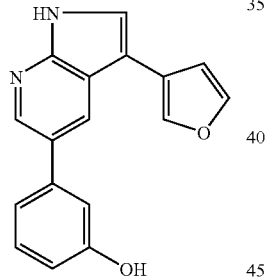

Step 1: Synthesis of 3-(3-furan-3-yl-1H-pyrrolo[2,3-b]pyridine-5-yl)-phenol

To toluene-4-sulfonic acid 3-[3-iodo-1-(toluene-4-sulfonyl)-1H-pyrrolo[2,3-b]pyridine-5-yl]-phenyl ester (50 mg, 0.077 mmol, prepared method 6), furan-3-boronic acid (11 mg, 0.1 mmol) and dichlorobis (triphenylphosphino)palladium (ii) (3 mg, 0.0046 mmol) in a Smith process vial was added 0.6 mL of a 1:1 mixture of acetonitrile, and a 2 M solution of sodium carbonate in water. The reaction was run in a Personal Chemistry® microwave reactor at 165° C. for 1200 s. The mixture was diluted with DMF (ca. 5 mL) and filtered with a syringe filter (0.45 micron). The filtrate was concentrated in vacuo and redissolved in DMSO. Purification by reverse phase chromatography using a gradient of $H_2O$ and acetonitrile (with 0.1% formic acid as a modifier) afforded 3-(3-furan-3-yl-1H-pyrrolo[2,3-b]pyridine-5-yl)-phenol as an off-white solid (6 mg, 56% yield). $^1$H NMR (500 MHz, DMSO-d6) δ 6.70 (dd, J=2.5, 8.0 Hz, 1H), 6.92 (d, J=2.0 Hz, 1H), 7.07 (t, J=2.0 Hz, 1H), 7.13 (d, J=8.0 Hz, 1H), 7.21 (t, J=8.0 Hz, 1H), 7.67 (t, J=1.5 Hz, 1H), 7.77 (d, J=2.5 Hz, 1H), 8.25 (d, J=2.0 Hz, 1H), 8.27 (s, 1H), 8.41 (d, J=2.0 Hz, 1H), 9.5 (broad s, 1H), 11.8 (s, 1H). MS: m/z 277 (M+H+).

Other compounds prepared by Method 26:

TABLE 19

Structure

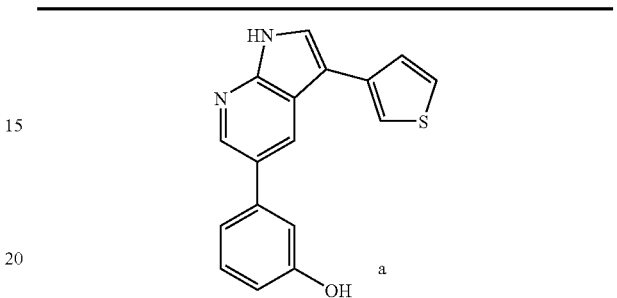

MS: m/z 293 (M + H+).

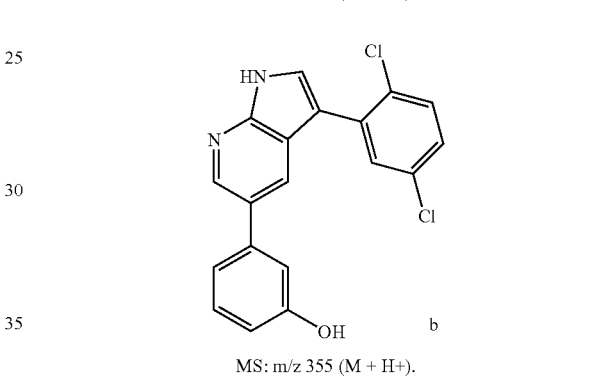

MS: m/z 355 (M + H+).

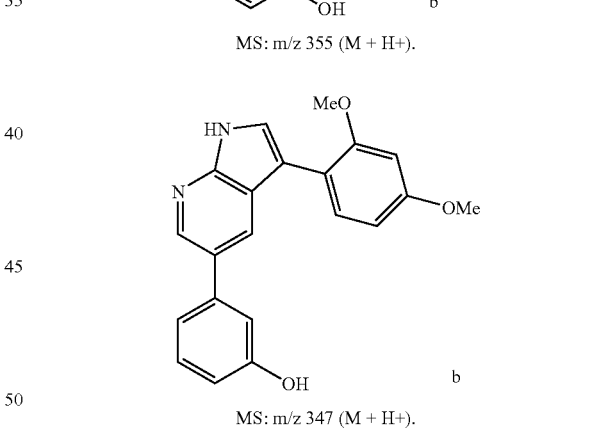

MS: m/z 347 (M + H+).

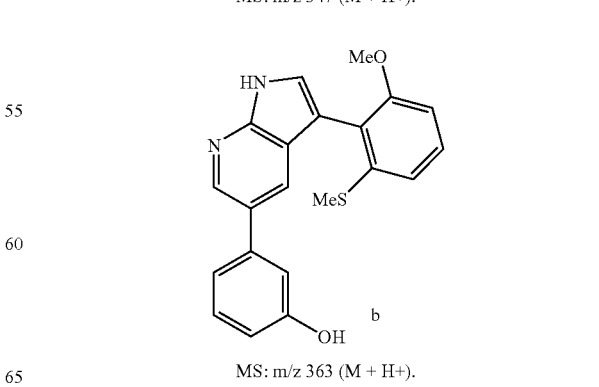

MS: m/z 363 (M + H+).

TABLE 19-continued
| Structure |
|---|
| 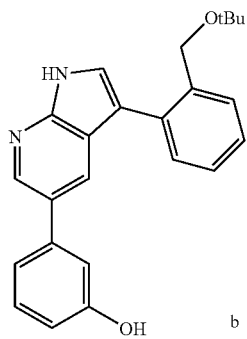<br>MS: m/z 373 (M + H+). b |
| 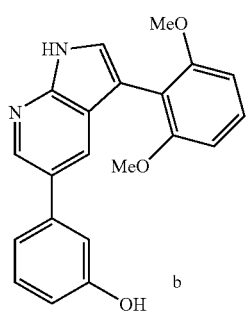<br>MS: m/z 347 (M + H+). b |
| 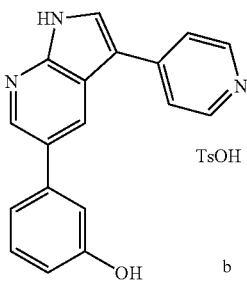<br>MS: m/z 288 (M + H+). b |
| 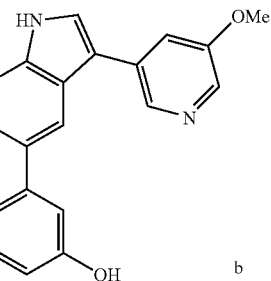<br>MS: m/z 318 (M + H+). b |
TABLE 19-continued
| Structure |
|---|
| 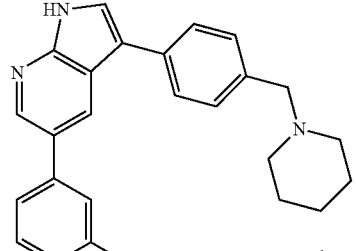<br>MS: m/z 347 (M + H+). b |
| 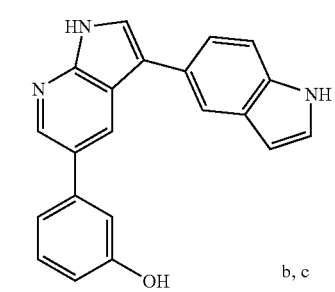<br>MS: m/z 386 (M + H+). b, c |
| 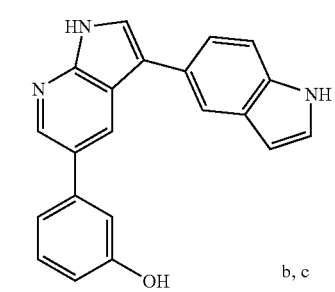<br>MS: m/z 326 (M + H+). b, c |
| 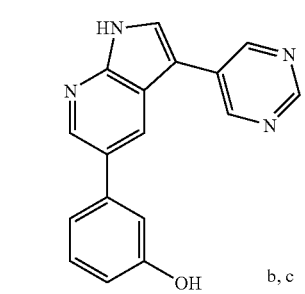<br>MS: m/z 289 (M + H+). b, c |

TABLE 19-continued
Structure
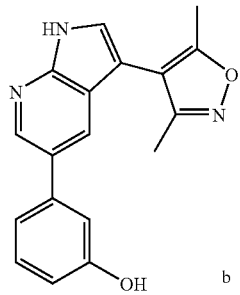
MS: m/z 306 (M + H+).          b
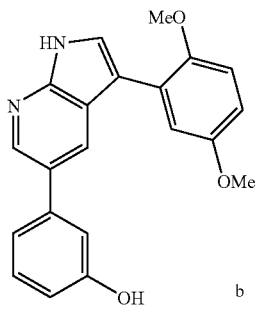
MS: m/z 347 (M + H+).          b
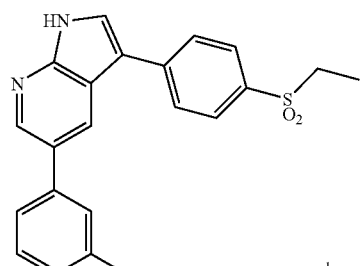
MS: m/z 379 (M + H+).          b
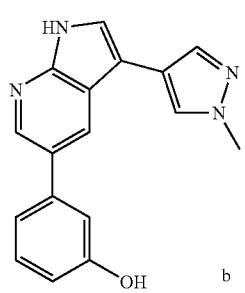
MS: m/z 291 (M + H+).          b
TABLE 19-continued
Structure
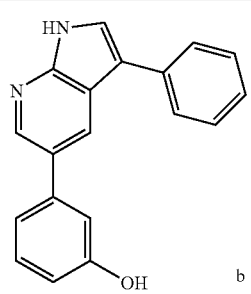
MS: m/z 287 (M + H+).          b
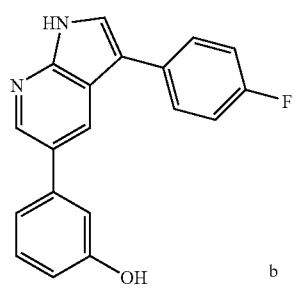
MS: m/z 305 (M + H+).          b
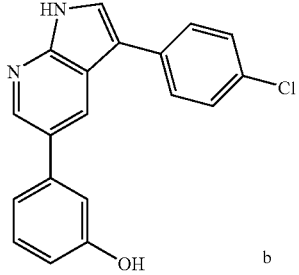
MS: m/z 321 (M + H+).          b
MS: m/z 301 (M + H+).

TABLE 19-continued
Structure
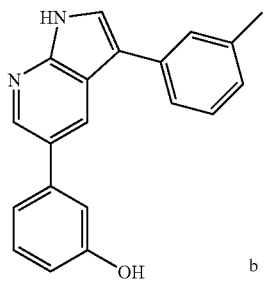
b
MS: m/z 301 (M + H+).
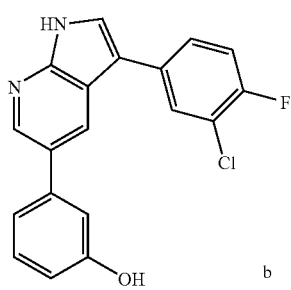
b
MS: m/z 339 (M + H+).
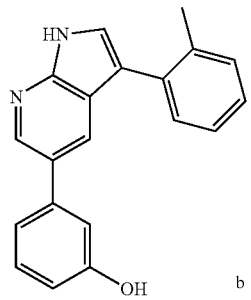
b
MS: m/z 301 (M + H+).
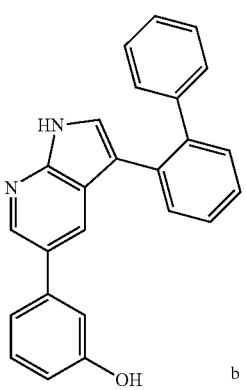
b
MS: m/z 363 (M + H+).
TABLE 19-continued
Structure
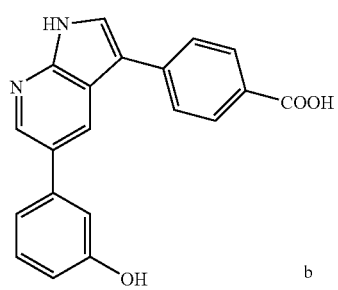
b
MS: m/z 331 (M + H+).
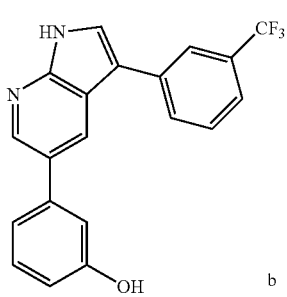
b
MS: m/z 355 (M + H+).
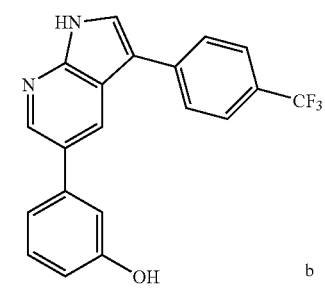
b
MS: m/z 355 (M + H+).
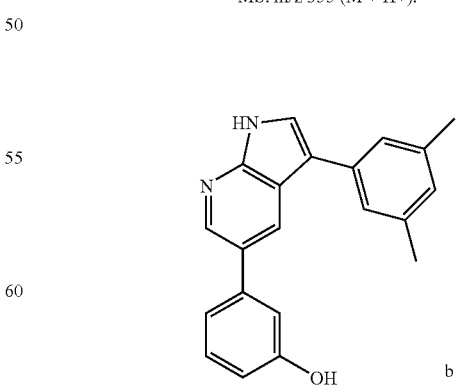
b
MS: m/z 315 (M + H+).

TABLE 19-continued
Structure
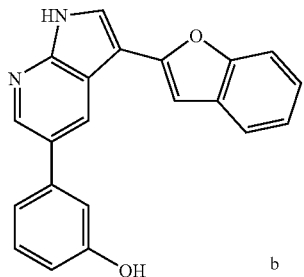
MS: m/z 327 (M + H+).   b
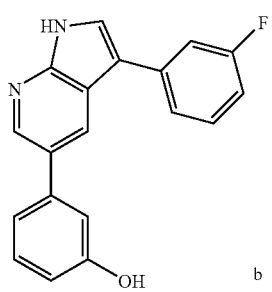
MS: m/z 305 (M + H+).   b
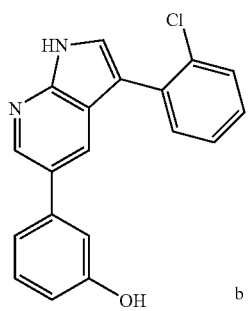
MS: m/z 321 (M + H+).   b
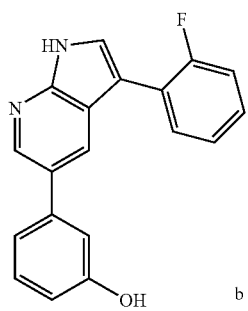
MS: m/z 305 (M + H+).   b
TABLE 19-continued
Structure
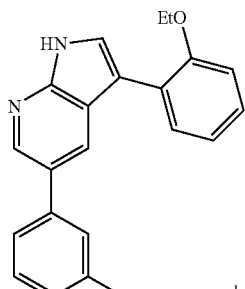
MS: m/z 331 (M + H+).   b
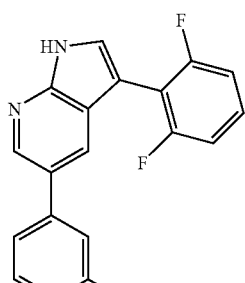
MS: m/z 323 (M + H+).   b
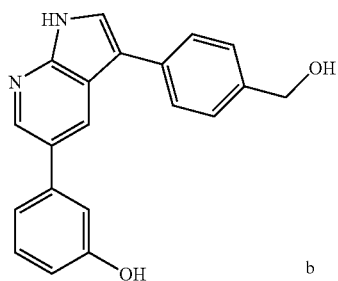
MS: m/z 317 (M + H+).   b
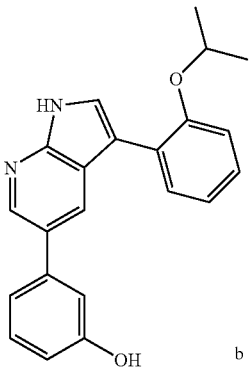
MS: m/z 345 (M + H+).   b TABLE 19-continued
| Structure | |
|---|---|
| 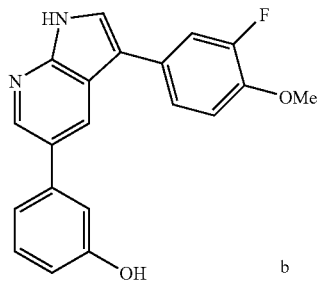 MS: m/z 335 (M + H+). | b |
| 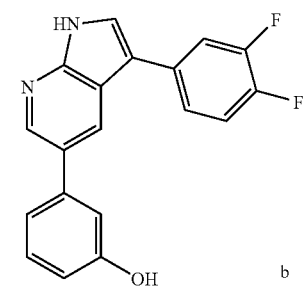 MS: m/z 323 (M + H+). | b |
| 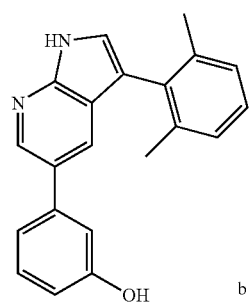 MS: m/z 315 (M + H+). | b |
| 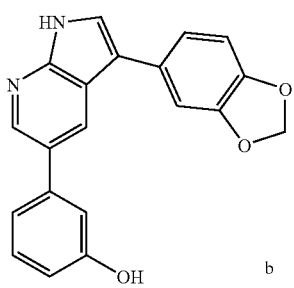 MS: m/z 331 (M + H+). | b |
TABLE 19-continued
| Structure | |
|---|---|
| 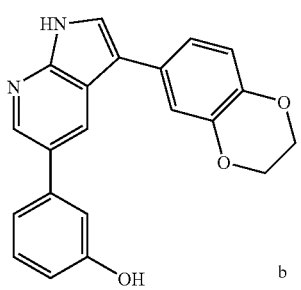 MS: m/z 345 (M + H+). | b |
| 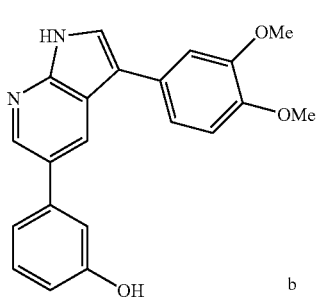 MS: m/z 347 (M + H+). | b |
| 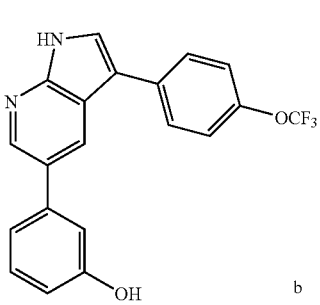 MS: m/z 371 (M + H+). | b |
| 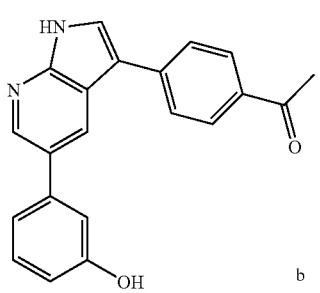 MS: m/z 329 (M + H+). | b |

TABLE 19-continued
Structure
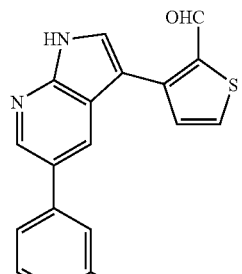
b
MS: m/z 321 (M + H+).
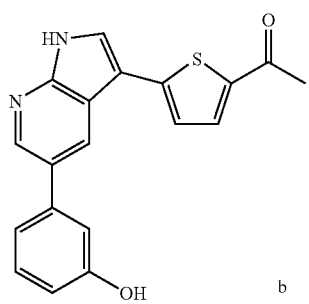
b
MS: m/z 335 (M + H+).
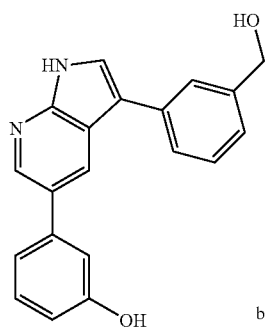
b
MS: m/z 317 (M + H+).
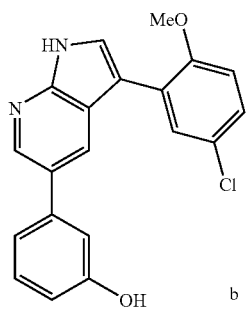
b
MS: m/z 351 (M + H+).
TABLE 19-continued
Structure
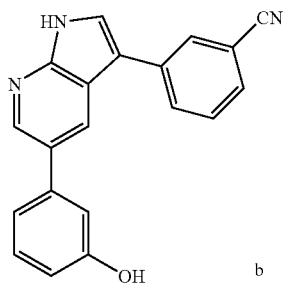
b
MS: m/z 312 (M + H+).
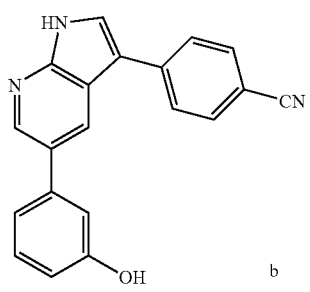
b
MS: m/z 312 (M + H+).
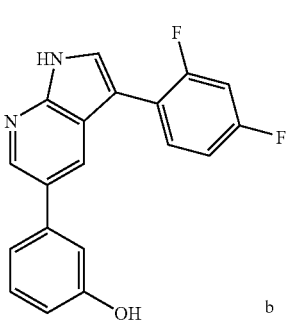
b
MS: m/z 323 (M + H+).
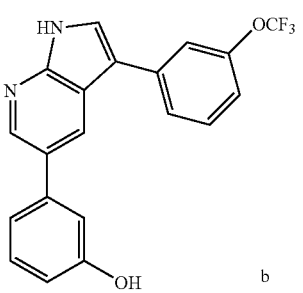
b
MS: m/z 371 (M + H+).

TABLE 19-continued
Structure
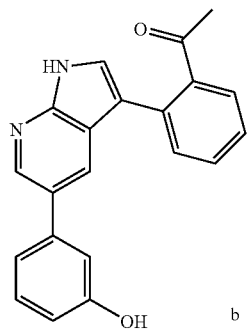
MS: m/z 329 (M + H+). b
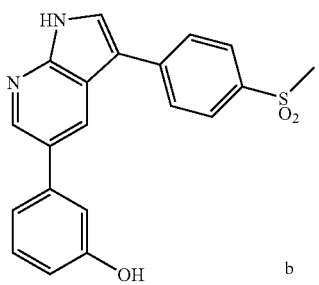
MS: m/z 365 (M + H+). b
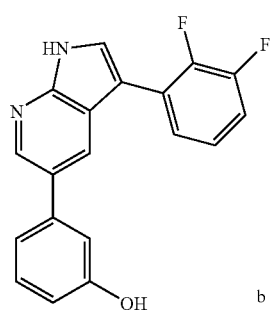
MS: m/z 323 (M + H+). b
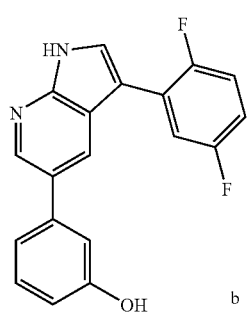
MS: m/z 323 (M + H+). b
TABLE 19-continued
Structure
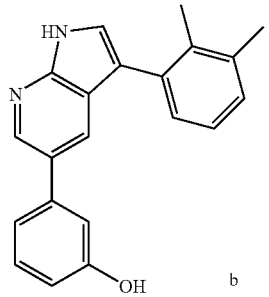
MS: m/z 315 (M + H+).
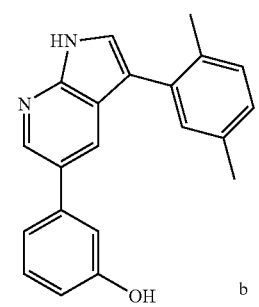
MS: m/z 315 (M + H+). b
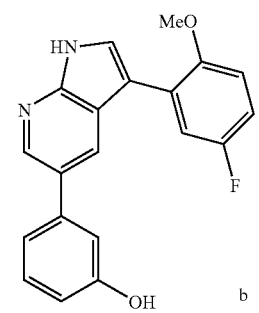
MS: m/z 335 (M + H+). b
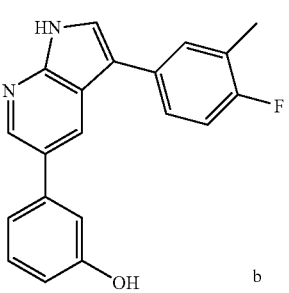
MS: m/z 319 (M + H+). b TABLE 19-continued
| Structure |
|---|
| 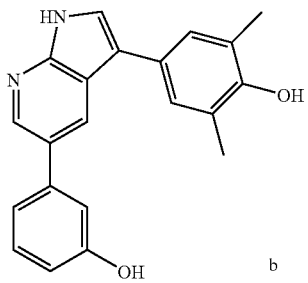 b<br>MS: m/z 331 (M + H+). |
| 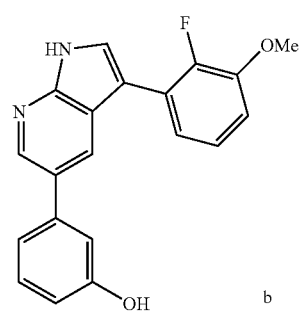 b<br>MS: m/z 335 (M + H+). |
| 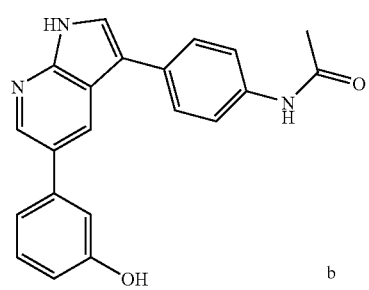 b<br>MS: m/z 344 (M + H+). |
| 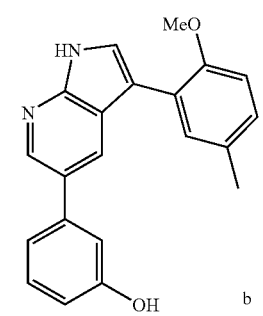 b<br>MS: m/z 331 (M + H+). |
TABLE 19-continued
| Structure |
|---|
| 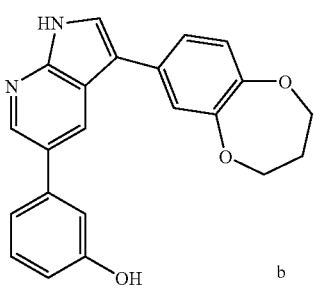 b<br>MS: m/z 359 (M + H+). |
| 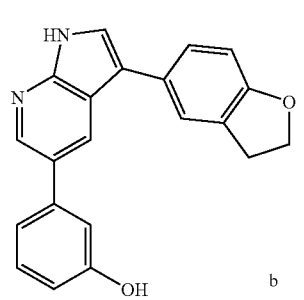 b<br>MS: m/z 329 (M + H+). |
| 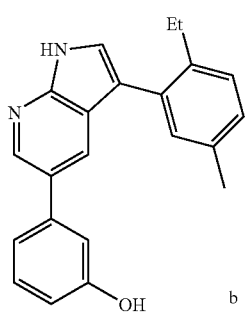 b<br>MS: m/z 315 (M + H+). |
| 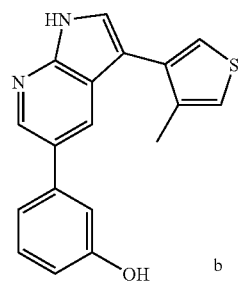 b<br>MS: m/z 307 (M + H+). |

TABLE 19-continued

Structure

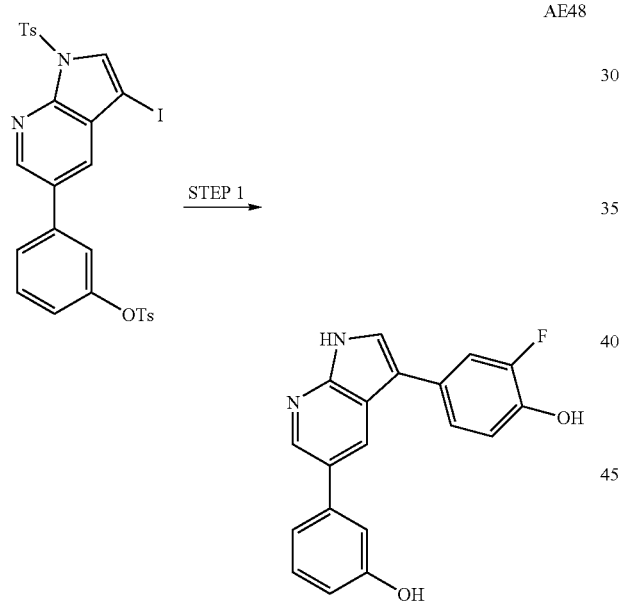

MS: m/z 345 (M + H+).  b a 10 wt % Pd/C as catalyst
b [1,1'-bis(diphenylphosphino)ferrocene]dichloropalladium (II), complex with dichloromethane (1:1) as catalyst
c Purification on silica gel with a gradient of methanol/dichloromethane Method 27:

AE48

STEP 1

Step 1: Synthesis of 3-[3-(3-fluoro-4-hydroxyphenyl)-3-yl-1H-pyrrolo[2,3-b]pyridine-5-yl)-phenol To toluene-4-sulfonic acid 3-[3-iodo-1-(toluene-4-sulfonyl)-1H-pyrrolo[2,3-b]pyridine-5-yl]-phenyl ester (50 mg, 0.077 mmol), 3-fluoro-4-benzyloxyphenyl boronic acid (24 mg, 0.1 mmol) and [1,1'-bis(diphenylphosphino)ferrocene] dichloropalladium (II), complex with dichloromethane (1:1) (3 mg, 0.0046 mmol) in a Smith process vial was added 0.6 mL of a 1:1 mixture of acetonitrile, and a 2 M solution of sodium carbonate in water. The reaction was run in a Personal Chemistry® microwave reactor at 165° C. for 1200 s. Water was added, followed by a saturated aqueous solution of NH4Cl to pH 6. Aqueous layer was extracted with EtOAc three times. The crude organics were concentrated and dissolved in 4 mL of (1:1) EtOH/aqueous KOH (50% wt). The mixture was stirred at 100° C. for 21 h, then diluted with water and acidified to pH 4 with aqueous 1N HCl. The resulting precipitate was filtered, washed with water, and dried in vacuum. The grey solid was suspended in 1N aqueous HCl (2 mL) and stirred at reflux for 17 h. 1N Aqueous NaOH was added to pH 4, the mixture was concentrated in vacuo and diluted with MeOH. Salts were filtered, and the filtrate was adsorbed on silica gel. Purification on silica gel with a gradient of methanol/dichloromethane afforded 3-[3-(3-fluoro-4-hydroxyphenyl)-3-yl-1H-pyrrolo[2,3-b]pyridine-5-yl)-phenol as a yellow solid (5 mg, 20% yield). $^1$H NMR (500 MHz, DMSO-d6) δ 6.75 (dd, J=2.5, 7.5 Hz, 1H), 7.03 (dd, J=9.0, 10.0 Hz, 1H), 7.09 (t, J=2.0 Hz, 1H), 7.16 (d, J=8.0 Hz, 1H), 7.27 (t, J=8.0 Hz, 1H), 7.41 (dd, J=1.5, 8.5 Hz, 1H), 7.51 (dd, J=1.5, 13.0 Hz, 1H), 7.82 (d, J=2.0 Hz, 1H), 8.30 (d, J=2.0 Hz, 1H), 8.47 (d, J=2.0 Hz, 1H), 9.54 (s, 1H), 9.80 (broad s, 1H), 11.9 (s, 1H). MS: m/e 321 (M+H$^+$).

Method 28:

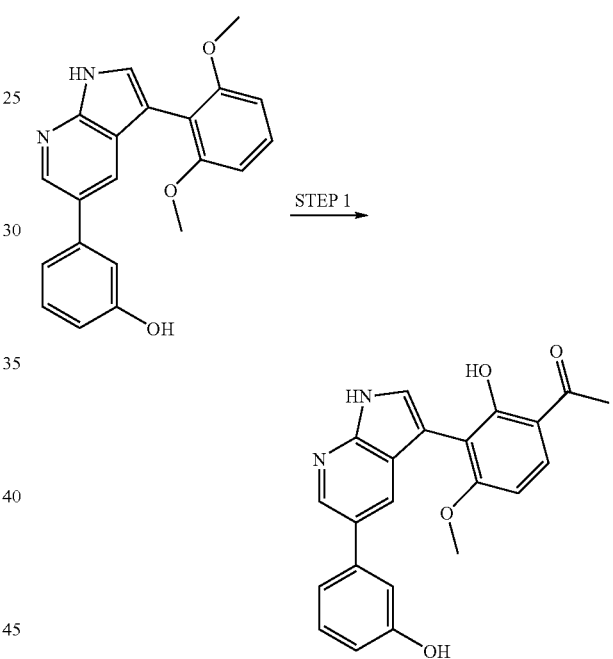

Step 1: Synthesis of 1-{2-hydroxy-3-[5-(3-hydroxyphenyl)-1H-pyrrolo[2,3-b]pyridine-3-yl]-4-methoxyphenyl}-ethanone To 3-[3-(2,6-dimethoxy-phenyl)-1H-pyrrolo[2,3-b]pyridine-5-yl]-phenol (12 mg, 0.0346 mmol) was added 0.5 mL of 33 wt % bromine in AcOH. The mixture was stirred at 70° C. for 6 h, then it was treated with 1.2 mL 50 wt % of aqueous KOH and it was further stirred at room temperature for 3 days, then at 80° C. for 3 hours. The mixture was acidified to pH4 with 1N aqueous HCl and extracted with EtOAc three times. The extracts were combined and adsorbed on silica gel. Purification on silica gel with a gradient of methanol/dichloromethane afforded 1-{2-hydroxy-3-[5-(3-hydroxy-phenyl)-1H-pyrrolo[2,3-b]pyridine-3-yl]-4-methoxy-phenyl}-ethanone as a white solid (2.6 mg, 20% yield). $^1$H NMR (500 MHz, DMSO-d6) δ 2.65 (s, 3H), 3.85 (s, 3H), 6.72 (dd, J=2.5, 8.5 Hz, 1H), 6.83 (d, J=8.5 Hz, 1H), 6.99 (t, J=2.0 Hz, 1H), 7.05 (d, J=8.0 Hz, 1H), 7.23 (t, J=8.0 Hz, 1H), 7.54 (d, J=2.5

Hz, 1H), 7.73 (d, J=2.0 Hz, 1H), 8.00 (d, J=9.0 Hz, 1H), 8.44 (d, J=2.0 Hz, 1H), 9.49 (s, 1H), 11.9 (s, 1H), 13.0 (s, 1H). MS: m/z 375 (M+H+).

Method 29:

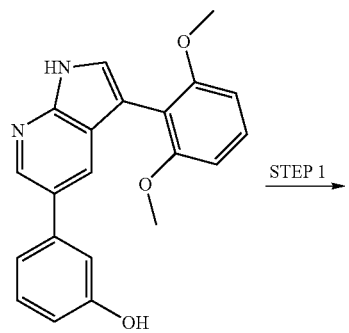

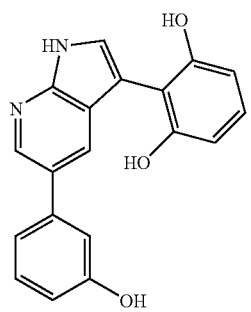

Step 1: Synthesis of 2-[5-(3-hydroxy-phenyl)-1H-pyrrolo[2,3-b]pyridine-3-yl]-benzene-1,3-diol To a suspension of 3-[3-(2,6-dimethoxy-phenyl)-1H-pyrrolo[2,3-b]pyridine-5-yl]-phenol (23 mg, 0.066 mmol) in dichloromethane (1 mL) at −78° C. was added 1 M boron tribromide solution in dichloromethane (0.23 mL, 0.23 mmol) dropwise. The reaction mixture was warmed up to room temperature over 4 h, then quenched with water and neutralized to pH8 with a saturated solution of aqueous sodium bicarbonate. The mixture was extracted with EtOAc three times and the extracts were combined and adsorbed on silica gel. Purification on silica gel with a gradient of methanol/dichloromethane afforded 2-[5-(3-hydroxy-phenyl)-1H-pyrrolo [2,3-b]pyridine-3-yl]-benzene-1,3-diol as a beige solid (17 mg, 81% yield). $^1$H NMR (500 MHz, DMSO-d6) δ 6.43 (d, J=8.0 Hz, 1H), 6.73 (dd, J=2.5, 7.5 Hz, 1H), 6.91 (t, J=8.0 Hz, 1H), 7.00 (t, J=2.0 Hz, 1H), 7.05 (d, J=8.0 Hz, 1H), 7.24 (t, J=8.0 Hz, 1H), 7.46 (d, J=2.5 Hz, 1H), 7.85 (d, J=2.0 Hz, 1H), 8.42 (d, J=2.0 Hz, 1H), 9.10 (broad s, 2H), 9.49 (broad s, 1H), 11.7 (s, 1H). MS: m/z 319 (M+H+).

Method 30:

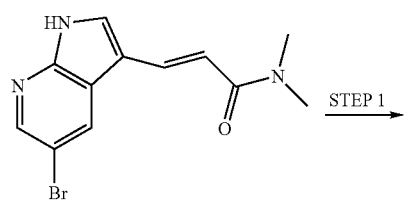

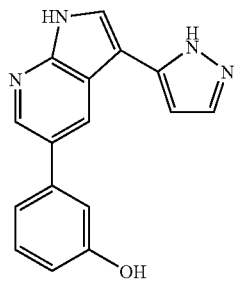

Step 1: Synthesis of 3-[3-(2H-pyrazol-3-yl)-1H-pyrrolo[2,3-b]pyridine-5-yl]-phenol To a suspension of 1-(5-bromo-1H-pyrrolo[2,3-b]pyridine-3-yl)-3-dimethylamino-propenone (30 mg, 0.102 mmol) in EtOH was added hydrazine (5 uL, 0.122 mmol). The reaction mixture was stirred at 80° C. for 3 h, then concentrated in vacuo. To the crude was added 3-hydroxyphenyl boronic acid (18 mg, 0.132 mmol) and dichlorobis(triphenylphosphino)palladium (II) (4 mg, 0.006 mmol), and 1 mL of a 1:1 mixture of acetonitrile, and a 2 M solution of sodium carbonate in water. The reaction was run in a Personal Chemistry® microwave reactor at 150° C. for 600 s. The reaction mixture was diluted with methanol (ca. 6 mL), filtered, and the filtrate was adsorbed on silica gel. Purification on silica gel with a gradient of MeOH/CH2Cl2 afforded a beige solid that was further purified by reverse phase chromatography using a gradient of H$_2$O and acetonitrile (with 0.1% formic acid as a modifier) to give 3-[3-(2H-pyrazol-3-yl)-1H-pyrrolo[2,3-b]pyridine-5-yl]-phenol as white solid (9.6 mg, 34% yield). $^1$H NMR (500 MHz, DMSO-d6) δ 6.61 (d, J=2.0 Hz, 1H), 6.71 (dd, J=2.5, 8.0 Hz, 1H), 7.03 (s, 1H), 7.08 (d, J=8.0 Hz, 1H), 7.22 (t, J=8.0 Hz, 1H), 7.65 (broad s, 1H), 7.84 (d, J=2.5 Hz, 1H), 8.43 (d, J=2.0 Hz, 1H), 8.53 (broad s, 1H), 9.51 (broad s, 1H), 11.8 (broad s, 1H). MS: m/z 277 (M+H+).

Other compounds prepared by method 30:

TABLE 20

| Structure |
| --- |
| 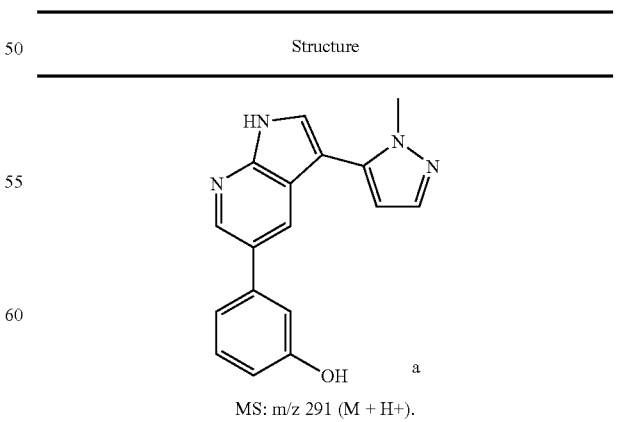<br>AE49<br>MS: m/z 291 (M + H+). a |

TABLE 20-continued

| Structure |
|---|
| 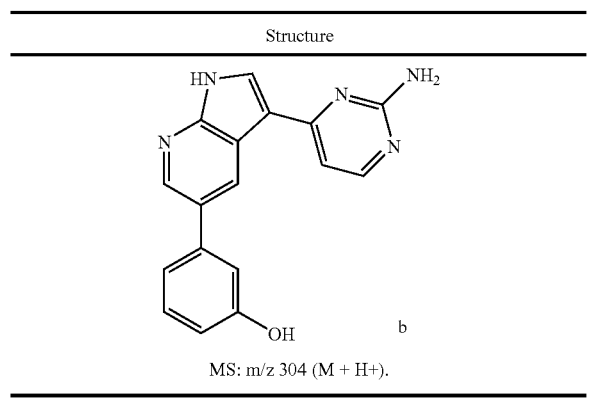 b |
| MS: m/z 304 (M + H+). | a From methylhydrazine
b From guanidine hydrochloride and sodium carbonate

Method 31:

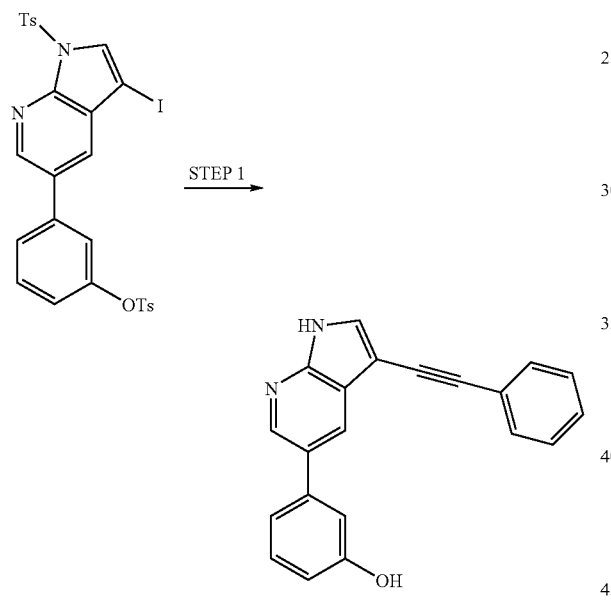

Step 1: Synthesis of 3-(3-phenylethynyl-1H-pyrrolo[2,3-b]pyridine-5-yl)-phenol

To a solution of toluene-4-sulfonic acid 3-[3-iodo-1-(toluene-4-sulfonyl)-1H-pyrrolo[2,3-b]pyridine-5-yl]-phenyl ester (60 mg, 0.093 mmol, prepared as exemplified in Method 6) in dichloromethane (0.5 mL) under nitrogen atmosphere was added successively triethylamine (16 uL, 0.112 mmol), copper (I) iodide (0.6 mg, 0.00315 mmol), dichlorobis (triphenylphosphino)palladium (II) (0.9 mg, 0.00128 mmol), and phenyl acetylene (11 uL, 0.102 mmol). The reaction mixture was stirred at room temperature for 16 h, then adsorbed directly on silica gel. Purification on silica gel with a gradient of MeOH/CH2Cl2 afforded 46 mg of an off-white solid that further suspended in 2 ml of EtOH and 2 mL of aqueous KOH (50 wt %). The reaction mixture was stirred at 80° C. for 4 h, then acidified to pH 4 with 1 N aqueous HCl. The milky solution was extracted with EtOAc three times, and the extracts were combined and adsorbed on silica gel. Purification on silica gel with a gradient of MeOH/CH2Cl2 afforded 3-(3-phenylethynyl-1H-pyrrolo[2,3-b]pyridine-5-yl)-phenol as a beige solid (12 mg, 41% yield). $^1$H NMR (500 MHz, DMSO-d6) δ 6.77 (dd, J=2.5, 7.5 Hz, 1H), 7.10 (t, J=2.0 Hz, 1H), 7.17 (d, J=6.0 Hz, 1H), 7.28 (t, J=8.0 Hz, 1H), 7.37-7.43 (m, 3H), 7.58 (d, J=7.0 Hz, 1H), 7.97 (s, 1H), 8.18 (d, J=2.5 Hz, 1H), 8.54 (d, J=2.5 Hz, 1H), 9.55 (s, 1H), 12.2 (broad s, 1H). MS: m/e 311 (M+H+).

Method 32:

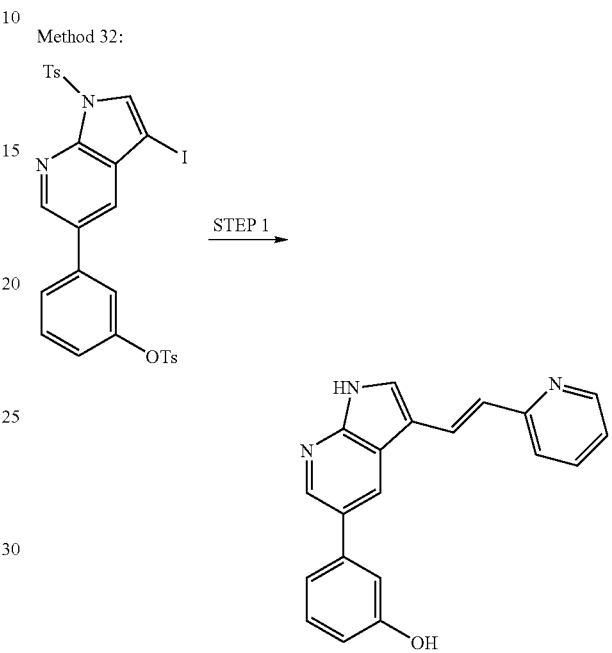

Step 1: Synthesis of 3-[3-(2-pyridin-2-yl-vinyl)-1H-pyrrolo[2,3-b]pyridine-5-yl]-phenol To toluene-4-sulfonic acid 3-[3-iodo-1-(toluene-4-sulfonyl)-1H-pyrrolo[2,3-b]pyridine-5-yl]-phenyl ester (50 mg, 0.077 mmol), tri-ortho-tolylphosphine (10 mg, 0.031 mmol), palladium (II) acetate (2 mg, 0.0077 mmol) was added DMF (0.5 mL), triethylamine (32 uL, 0.232 mmol), and 2-vinylpyridine (42 uL, 0.388 mmol). The vial was flushed with nitrogen, and the reaction was run in a Personal Chemistry® microwave reactor at 150° C. for 900 s. Water was added and the mixture was neutralized to pH 6 with 1 N aqueous HCl, then extracted with EtOAc three times. The extracts were combined and concentrated in vacuo. The crude was treated with 1 mL of EtOH and 1 mL of aqueous KOH (50 wt %). The reaction mixture was stirred at 80° C. for 15 h. The mixture was neutralized to pH 7 with 1 N aqueous HCl, and the resulting precipitate was filtered, washed with water, dried in vacuo, and adsorbed on silica gel. Purification on silica gel with a gradient of MeOH/CH2Cl2 afforded 3-[3-(2-pyridin-2-yl-vinyl)-1H-pyrrolo[2,3-b]pyridine-5-yl]-phenol as a yellow solid (17 mg, 35% yield). $^1$H NMR (500 MHz, DMSO-d6) δ 6.78 (dd, J=2.0, 8.0 Hz, 1H), 7.13 (s, 1H), 7.15-7.20 (m, 2H), 7.26 (d, J=16.0 Hz, 1H), 7.29 (t, J=8.0 Hz, 1H), 7.57 (d, J=7.5 Hz, 1H), 7.73 (dt, J=2.0, 8.0 Hz, 1H), 7.90 (d, J=16.0 Hz, 1H), 7.93 (d, J=2.0 Hz, 1H), 8.50 (d, J=2.0 Hz, 1H), 8.52 (d, J=5.0 Hz, 1H), 8.54 (d, J=2.5 Hz, 1H), 9.56 (s, 1H), 12.1 (s, 1H). MS: m/z 314 (M+H+).

Other compounds prepared by method 32:

TABLE 21

| Structure |
| --- |
| 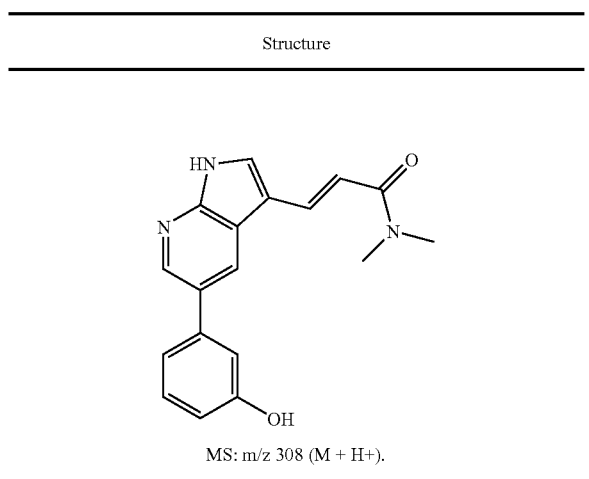 MS: m/z 308 (M + H+). |

Method 33:

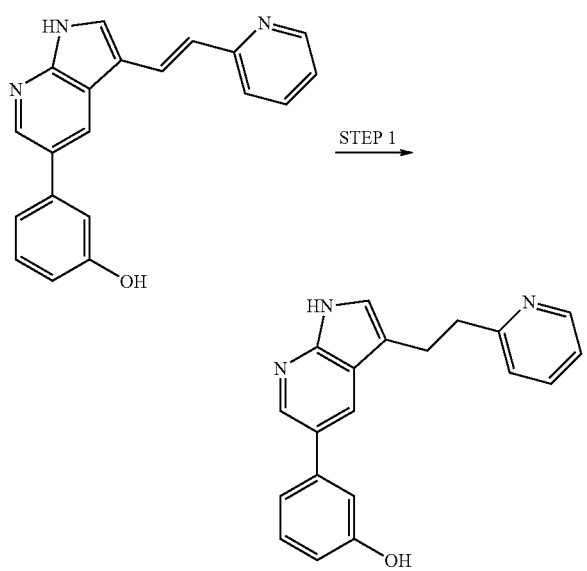

Step 1: Synthesis of 3-[3-(2-pyridin-2-yl-ethyl)-1H-pyrrolo[2,3-b]pyridine-5-yl]-phenol A suspension of 3-[3-(2-pyridin-2-yl-vinyl)-1H-pyrrolo[2,3-b]pyridine-5-yl]-phenol (10 mg, 0.032 mmol) and 10 wt % Pd/C (1.7 mg, 0.0016 mmol) in 0.9 ml of a (1:1:1) mixture of MeOH/CH2Cl2/DMF was stirred for 2 days under $H_2$ atmosphere. The mixture was adsorbed directly on silica gel. Purification on silica gel with a gradient of MeOH/CH2Cl2 afforded 3-[3-(2-pyridin-2-yl-ethyl)-1H-pyrrolo[2,3-b]pyridine-5-yl]-phenol as a yellow solid (6 mg, 60% yield). $^1$H NMR (500 MHz, DMSO-d6) δ 3.22 (t, J=7.5 Hz, 2H), 3.37 (t, J=7.5 Hz, 2H), 6.77 (d, J=7.5 Hz, 1H), 7.07 (s, 1H), 7.11 (d, J=7.0 Hz, 1H), 7.27 (m, 2H), 7.82 (m, 1H), 7.93 (d, J=7.0 Hz, 1H), 8.21 (s, 1H), 8.43 (m, 2H), 8.79 (d, J=5.5 Hz, 1H), 9.54 (broad s, 1H), 11.53 (s, 1H). MS: m/z 316 (M+H+).

Method 34:

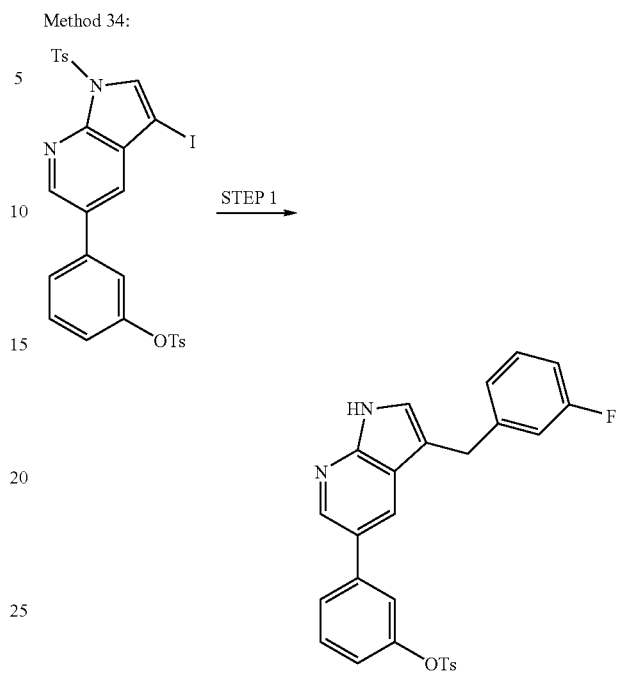

Step 1: Synthesis of 3-[3-(3-fluoro-benzyl)-1H-pyrrolo[2,3-b]pyridine-5-yl]-phenol To a solution of toluene-4-sulfonic acid 3-[3-iodo-1-(toluene-4-sulfonyl)-1H-pyrrolo[2,3-b]pyridine-5-yl]-phenyl ester (50 mg, 0.077 mmol, prepared as exemplified in method 6) in THF (2 mL) at −90° C. under nitrogen atmosphere was added a solution of tBuLi in pentane (1.7 M, 90 uL) dropwise. After stirring for 5 min, 3-fluoro-benzaldehyde (40 uL, 0.38 mmol) was added and the reaction mixture was slowly warmed up to 10° C. over 2 h, then quenched with a saturated solution of ammonium chloride and extracted with EtOAc three times. The extracts were combined and adsorbed on silica gel. Purification on silica gel with a gradient of MeOH/CH2Cl2 afforded 26 mg of toluene-4-sulfonic acid 3-[3-[(3-fluoro-phenyl)-hydroxy-methyl]-1-(toluene-4-sulfonyl)-1H-pyrrolo [2,3-b]pyridine-5-yl]-phenyl ester. The material was dissolved in dichloromethane (0.3 mL) under nitrogen atmosphere. Triethylsilane (24 uL, 0.149 mmol) was added, followed by boron trifluoride etherate (7 μL, 0.149 mmol) dropwise. After stirring for 15 h, the reaction was quenched with a saturated solution of sodium bicarbonate and extracted with dichloromethane three times. The extracts were combined and concentrated under vacuum. The crude was treated with 2 mL of EtOH and 2 mL of aqueous KOH (50 wt %). The reaction mixture was stirred at 70° C. for 1 h. The mixture was acidified to pH 4 with 1 N aqueous HCl, and extracted with EtOAc three times. The extracts were combined and adsorbed on silica gel. Purification on silica gel with a gradient of MeOH/$CH_2Cl_2$ afforded 3-[3-(3-fluoro-benzyl)-1H-pyrrolo[2,3-b]pyridine-5-yl]-phenol as a beige solid (8 mg, 66% yield). $^1$H NMR (500 MHz, DMSO-d6) δ 4.11 (s, 3H), 6.74 (dd, J=2.5, 8.5 Hz, 1H), 6.97 (dt, J=2.0, 8.5 Hz, 1H), 7.00 (s, 1H), 7.05 (d, J=8.0 Hz, 1H), 7.13 (d, J=10.5 Hz, 1H), 7.17 (d, J=8.0 Hz, 1H), 7.25 (t, J=7.5 Hz, 1H), 7.30 (q, J=8.0 Hz, 1H), 7.40 (d, J=2.5 Hz, 1H), 8.07 (d, J=2.0 Hz, 1H), 8.42 (d, J=2.0 Hz, 1H), 9.56 (broads, 1H), 11.6 (s, 1H). MS: m/z 319 (M+H+).

183

Other compounds prepared by Method 34:

TABLE 22

| Structure |
|---|
| 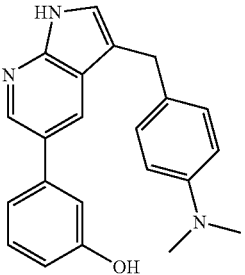 MS: m/z 344 (M + H+). |

Method 35:

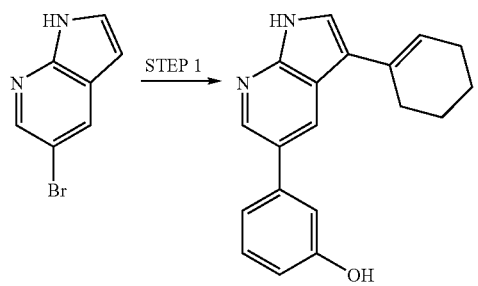

Step 1: Synthesis of 3-(3-cyclohex-1-enyl-1H-pyrrolo[2,3-b]pyridine-5-yl)-phenol To a solution of 5-bromo-1H-pyrrolo[2,3-b]pyridine (100 mg, 0.507 mmol) in MeOH (1 mL) was added cyclohexanone (52 uL, 1.015 mmol). The reaction mixture was stirred at 80° C. for 16 h then concentrated in vacuo. To the residue was added 3-hydroxyphenyl boronic acid (91 mg, 0.66 mmol), dichlorobis (triphenylphosphino)palladium (II) (18 mg, 0.025 mmol), and 2 mL of a 1:1 mixture of acetonitrile, and a 2 M solution of sodium carbonate in water. The reaction was run in a Personal Chemistry® microwave reactor at 150° C. for 600 s. The reaction mixture was diluted with methanol, filtered, and the filtrate was adsorbed on silica gel. Purification on silica gel with a gradient of MeOH/CH$_2$Cl$_2$ afforded 3-(3-cyclohex-1-enyl-1H-pyrrolo[2,3-b]pyridine-5-yl)-phenol as an off-white solid (12.6 mg, 12% yield). $^1$H NMR (500 MHz, DMSO-d6) δ 1.64 (m, 2H), 1.74 (m, 2H), 2.23 (m, 2H), 2.42 (m, 2H), 6.27 (m, 1H), 6.74 (dd, J=2.0, 8.0 Hz, 1H), 7.05 (s, 1H), 7.11 (d, J=7.5 Hz, 1H), 7.26 (t, J=8.0 Hz, 1H), 7.50 (d, J=2.0 Hz, 1H), 8.26 (d, J=2.0 Hz, 1H), 8.42 (d, J=2.0 Hz, 1H), 9.51 (broad s, 1H), 11.7 (s, 1H). MS: m/z 291 (M+H$^+$).

184

Other compounds prepared by Method 35:

TABLE 23

| Structure |
|---|
| 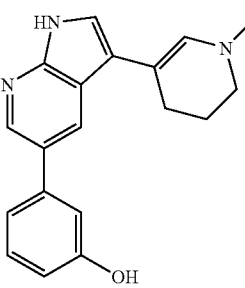 MS: m/z 320 (M + H+). <br><br> MS: m/z 392 (M + H+). |

Method 36:

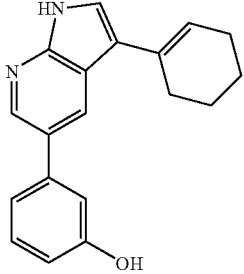

Step 1: Synthesis of 3-(3-cyclohexyl-1H-pyrrolo[2,3-b]pyridine-5-yl)-phenol

A suspension of 3-(3-cyclohex-1-enyl-1H-pyrrolo[2,3-b]pyridine-5-yl)-phenol (6.7 mg, 0.023 mmol) and 10 wt % Pd/C (3 mg) in methanol (0.9 ml) was stirred for 24 h under H$_2$ atmosphere. The reaction mixture was filtered through a silica plug, the solvent was evaporated to give 3-(3-cyclohexyl-1H-pyrrolo[2,3-b]pyridine-5-yl)-phenol as a white solid (2.5 mg, 37% yield). $^1$H NMR (500 MHz, MeOH-d4) δ 1.35 (m, 1H), 1.54 (m, 4H), 1.80 (m, 1H), 1.88 (m, 2H), 2.10 (m, 2H), 2.87 (m, 1H), 6.79 (dd, J=2.5, 8.0 Hz, 1H), 7.06 (t, J=2.0 Hz, 1H), 7.10 (d, J=7.5 Hz, 1H), 7.16 (s, 1H), 7.29 (t, J=8.0 Hz, 1H), 8.14 (d, J=2.0 Hz, 1H), 8.35 (d, J=2.0 Hz, 1H), 9.51 (broad s, 1H), 11.7 (s, 1H). MS: m/e 293 (M+H$^+$).

Other compounds prepared by method 36:

TABLE 24

| Structure |
| --- |
| 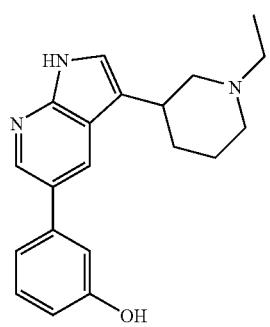 MS: m/z 322 (M + H+). |
| 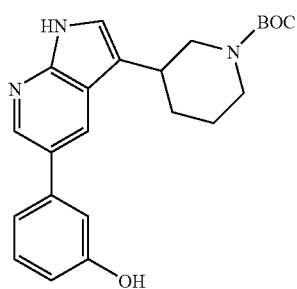 MS: m/z 394 (M + H+). |
| 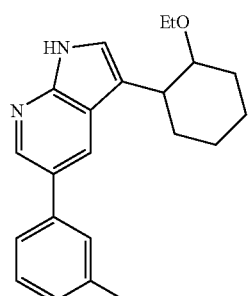 MS: m/z 337 (M + H+). |

Method 37:

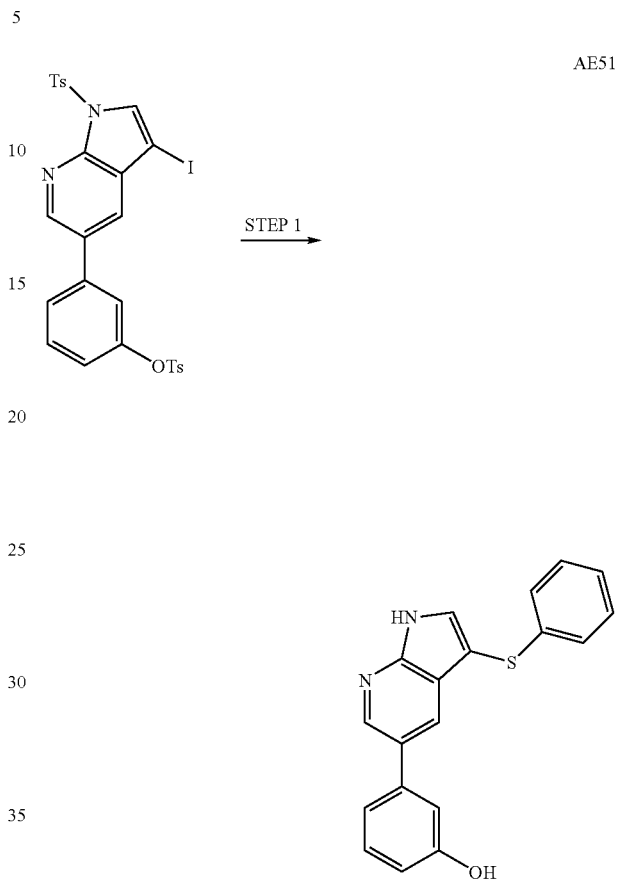

AE51

Step 1: Synthesis of 3-(3-phenylsulfanyl-1H-pyrrolo[2,3-b]pyridine-5-yl)-phenol

To toluene-4-sulfonic acid 3-[3-iodo-1-(toluene-4-sulfonyl)-1H-pyrrolo[2,3-b]pyridine-5-yl]-phenyl ester (50 mg, 0.077 mmol), copper(I) iodide (1.5 mg, 0.004 mmol), and potassium carbonate (16 mg, 0.155 mmol) under nitrogen atmosphere was added isopropanol (0.2 mL), benzenethiol (8 µL, 0.077 mmol), and ethylene glycol (9 uL, 0.155 mmol). The reaction mixture was stirred at 80° C. for 24 h. A (1:1) mixture of 2 M aqueous KOH and MeOh (1 mL) was added, and the reaction mixture was further stirred at 50° C. for 3 h. The mixture was acidified to pH5 with 1N aqueous HCl and extracted with EtOAc twice. Extracts were combined and concentrated under vacuum. Purification by reverse phase chromatography using a gradient of H$_2$O and acetonitrile (with 0.1% formic acid as a modifier) afforded 3-(3-phenylsulfanyl-1H-pyrrolo[2,3-b]pyridine-5-yl)-phenol as a white solid (4.3 mg, 17% yield). $^1$H NMR (500 MHz, DMSO-d6) δ 6.74 (dd, J=2.5, 9.0 Hz, 1H), 6.98 (t, J=2.0 Hz, 1H), 7.08 (m, 4H), 7.23 (m, 3H), 7.85 (d, J=2.5 Hz, 1H), 7.98 (s, 1H), 8.56 (d, J=2.0 Hz, 1H), 9.55 (broad s, 1H), 12.4 (broad s, 1H). MS: m/z 319 (M+H$^+$).

187

Other examples prepared by Method 37:

TABLE 25

| Structure |
|---|
| 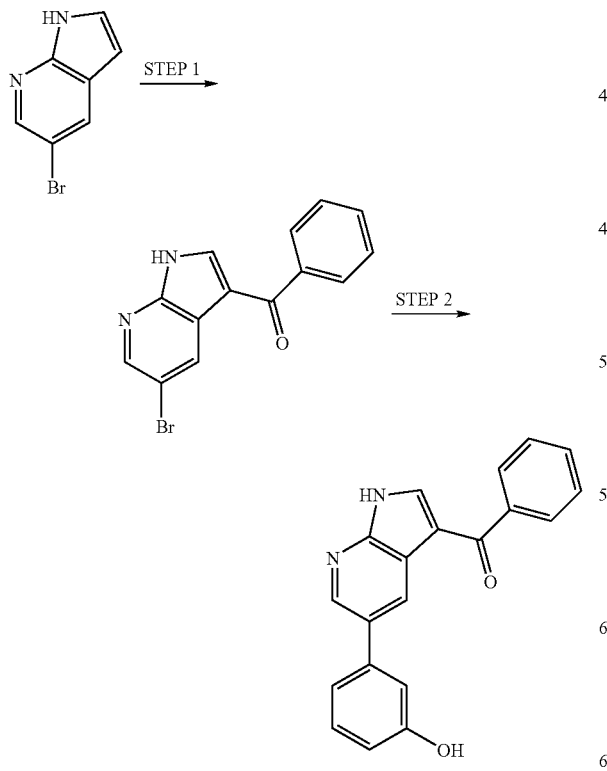  MS: m/z 397 (M + H+). |
| MS: m/z 320 (M + H+). |

Method 38:

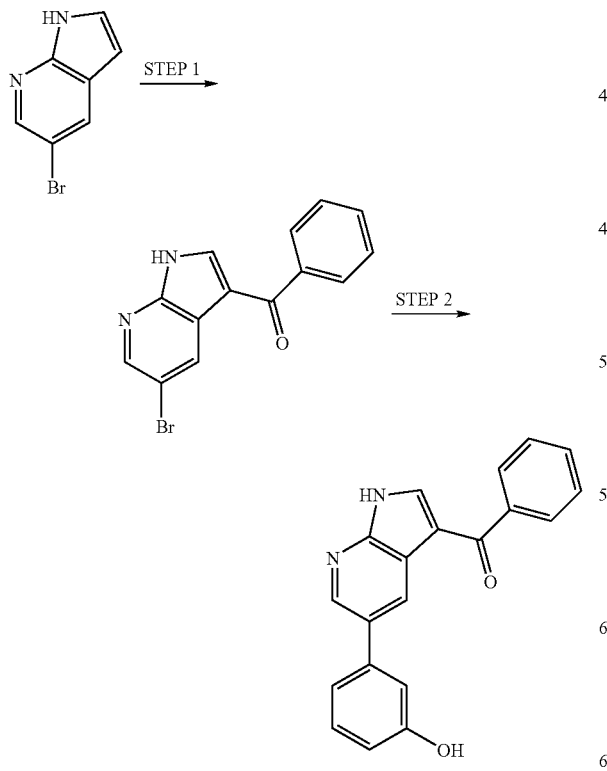

188

Step 1: Synthesis of (5-bromo-1H-pyrrolo[2,3-b]pyridine-3-yl)-phenyl-methanone

To a suspension of AlCl$_3$ (338 mg, 2.54 mmol) in dichloromethane (10 mL) was added 5-bromo-1H-pyrrolo[2,3-b]pyridine (100 mg, 0.507 mmol). After stirring for 45 min, benzoyl chloride (0.3 mL, 2.54 mmol) was added and the reaction mixture was stirred for 3 h, before quenching with MeOH at 0° C. The mixture was concentrated in vacuum, the pH was changed to 4 by addition of 1N aqueous NaOH, and the aqueous layer was extracted twice with EtOAc. The organic layer was dried over MgSO$_4$, filtered and adsorbed on silica gel. Purification on silica gel with a gradient of EtOAc/hexanes afforded (5-bromo-1H-pyrrolo[2,3-b]pyridine-3-yl)-phenyl-methanone as a white solid (61 mg, 40% yield).

Step 2: Synthesis of [5-(3-hydroxy-phenyl)-1H-pyrrolo [2,3-b]pyridine-3-yl]-phenyl-methanone To (5-bromo-1H-pyrrolo[2,3-b]pyridine-3-yl)-phenyl-methanone (50 mg, 0.167 mmol), 3-hydroxyphenyl boronic acid (30 mg, 0.217 mmol), and dichlorobis (triphenylphosphino)palladium (II) (6 mg, 0.0083 mmol) in a Smith process vial was added 1 mL of a 1:1 mixture of acetonitrile, and a 2 M solution of sodium carbonate in water. The reaction was run in a Personal Chemistry® microwave reactor at 150° C. for 1200 s. The mixture was diluted with DMF (ca. 5 mL) and filtered on a silica plug. The filtrate was adsorbed on silica gel. Purification on silica gel with a gradient of MeOH/dichloromethane afforded [5-(3-hydroxy-phenyl)-1H-pyrrolo[2,3-b]pyridine-3-yl]-phenyl-methanone as a yellow solid (37 mg, 71% yield). $^1$H NMR (500 MHz, DMSO-d6) δ 6.80 (dd, J=2.0, 7.5 Hz, 1H), 7.10 (t, J=2.0 Hz, 1H), 7.14 (d, J=9.0 Hz, 1H), 7.31 (t, J=7.5 Hz, 1H), 7.57 (t, J=7.5 Hz, 2H), 7.65 (t, J=7.5 Hz, 1H), 7.84 (d, J=7.0 Hz, 2H), 8.14 (s, 1H), 8.61 (d, J=2.0 Hz, 1H), 8.68 (d, J=2.0 Hz, 1H), 9.65 (broad s, 1H). MS: m/z 315 (M+H$^+$).

Method 39:

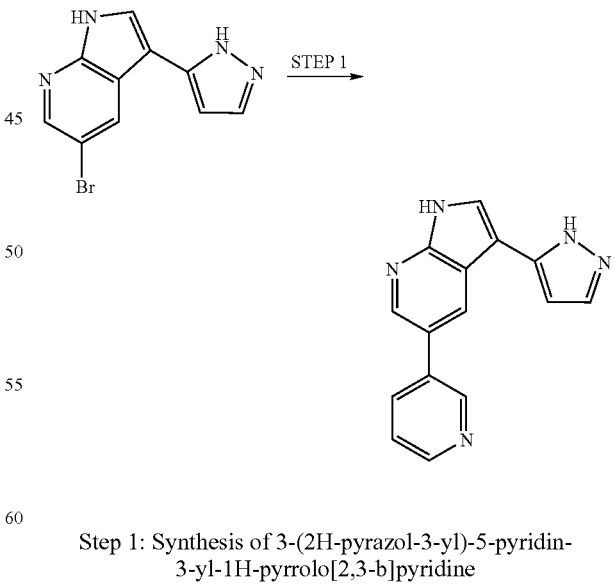

Step 1: Synthesis of 3-(2H-pyrazol-3-yl)-5-pyridin-3-yl-1H-pyrrolo[2,3-b]pyridine To 5-bromo-3-(2H-pyrazol-3-yl)-1H-pyrrolo[2,3-b]pyridine (30 mg, 0.114 mmol), 3-pyridyl boronic acid pinacol ester (30 mg, 0.148 mmol), and dichlorobis (triphenyl-phosphino)palladium (II) (4 mg, 0.0057 mmol) in a Smith process vial was added 1 mL of a 1:1 mixture of acetonitrile, and a 2 M solution of sodium carbonate in water. The reaction was run in a Personal Chemistry® microwave reactor at 150° C. for 900 s. The mixture was diluted with DMF (ca. 5 mL), filtered on a silica plug, and solvent was evaporated. Purification by reverse phase chromatography using a gradient of H$_2$O and acetonitrile (with 0.1% formic acid as a modifier) afforded the formate salt of 3-(2H-pyrazol-3-yl)-5-pyridin-3-yl-1H-pyrrolo[2,3-b]pyridine as a white solid (4.5 mg, 13% yield). $^1$H NMR (500 MHz, DMSO-d6) δ 6.61 (broad s, 1H), 6.73 (broad s, 1H), 7.53 (dd, J=5.5, 7.0 Hz, 1H), 7.71 (broad s, 1H), 7.94 (d, J=2.5 Hz, 1H), 8.18 (broad s, 1H), 8.60 (m, 2H), 8.68 (broad s, 1H), 8.98 (broad s, 1H), 12.0 (broad s, 1H), 12.7 (broad s, 1H). MS: m/z 262 (M+H$^+$).

Other compounds prepared by method 39:

TABLE 26

| Structure |
|---|
| 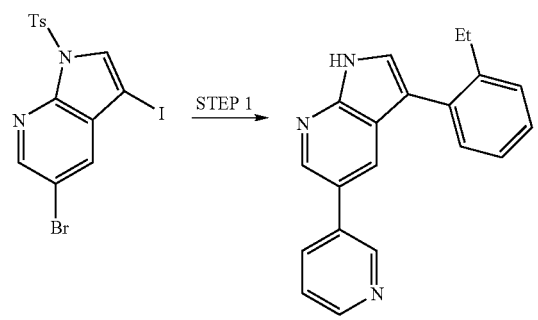 AE52 |
| MS: m/z 300 (M + H+). |

Method 40:

Step 1: Synthesis of 3-(2-ethyl-phenyl)-5-pyridin-3-yl-1H-pyrrolo[2,3-b]pyridine To 5-bromo-3-iodo-1-(toluene-4-sulfonyl)-1H-pyrrolo[2,3-b]pyridine (15 mg, 0.0314 mmol, prepared as described in method 1), 2-ethylphenyl boronic acid (5.2 mg, 0.034 mmol), and dichlorobis (triphenylphosphino)palladium (II) (1.3 mg, 0.0002 mmol) in a Smith process vial was added 0.5 mL of a 1:1 mixture of acetonitrile, and a 2 M solution of sodium carbonate in water. The reaction mixture was stirred for 6 h, then 3-pyridyl boronic acid pinacol ester (8.4 mg, 0.041 mmol) and dichlorobis (triphenylphosphino)palladium (II) (1.3 mg, 0.0002 mmol) were added and the reaction was run in a Personal Chemistry® microwave reactor at 150° C. for 900 s. The mixture was diluted with DMF (2 mL), filtered on a silica plug, and solvent was evaporated. Purification by reverse phase chromatography using a gradient of H$_2$O and acetonitrile (with 0.1% formic acid as a modifier) afforded 3-(2-ethyl-phenyl)-5-pyridin-3-yl-1H-pyrrolo[2,3-b]pyridine as a solid (5.8 mg, 61% yield). $^1$H NMR (500 MHz, DMSO-d6) δ 1.05 (t, J=7.5 Hz, 3H), 2.66 (q, J=7.5 Hz, 2H), 7.27 (t, J=7.0 Hz, 1H), 7.31 (t, J=7.0 Hz, 1H), 7.38 (d, J=7.5 Hz, 2H), 7.45 (dd, J=5.5, 8.5 Hz, 1H), 7.60 (s, 1H), 7.98 (d, J=2.0 Hz, 1H), 8.10 (dd, J=1.5, 8.0 Hz, 1H), 8.54 (d, J=5.0 Hz, 1H), 8.60 (d, J=2.0 Hz, 1H), 8.90 (s, 1H), 12.0 (s, 1H). MS: m/z 300 (M+H$^+$).

Other compounds prepared by Method 40:

TABLE 27

| Structure |
|---|
| 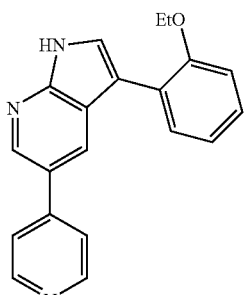 |
| MS: m/z 316 (M + H+). |
| 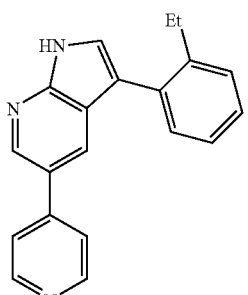 |
| MS: m/z 316 (M + H+). |
| MS: m/z 300 (M + H+). |

TABLE 27-continued
Structure
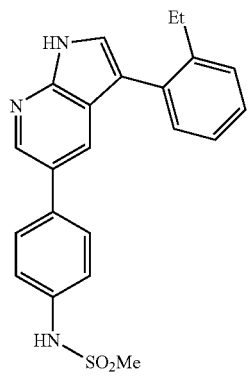
MS: m/z 392 (M + H+).
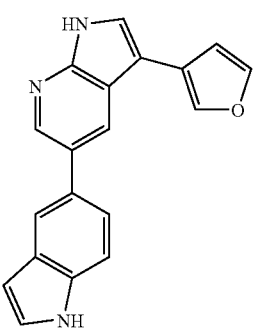
MS: m/z 300 (M + H+).
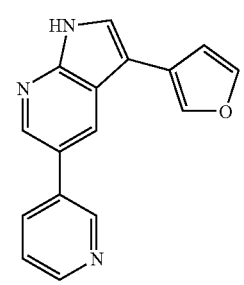
MS: m/z 262 (M + H+).
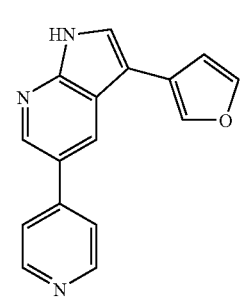
MS: m/z 262 (M + H+).
TABLE 27-continued
Structure
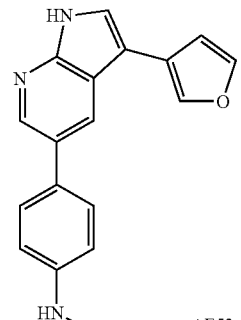
AE53
MS: m/z 354 (M + H+).
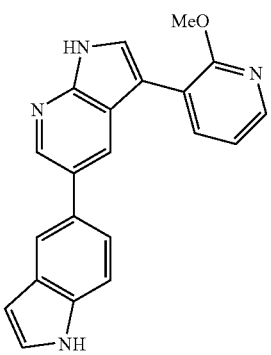
MS: m/z 341 (M + H+).
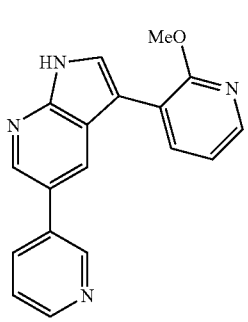
MS: m/z 303 (M + H+).
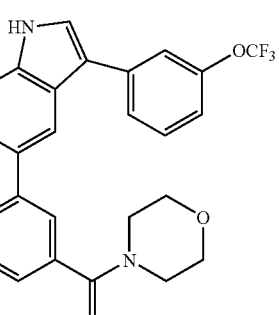
MS: m/z 468 [MH+]

TABLE 27-continued
Structure
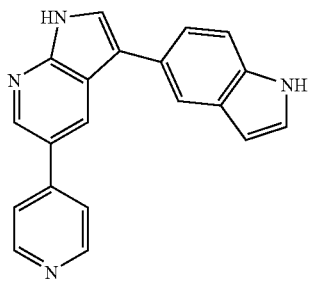
MS: m/z 311 [MH+]
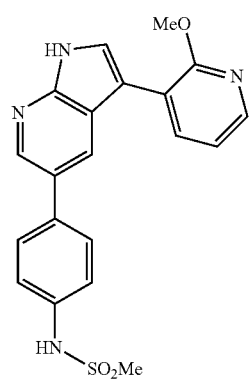
MS: m/z 395 (M + H+).
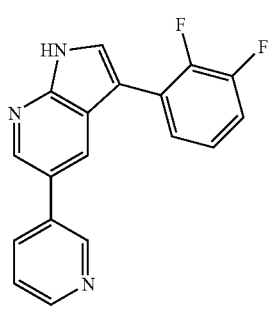
MS: m/z 308 (M + H+).
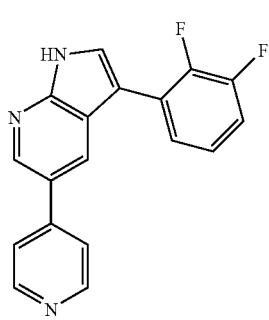
MS: m/z 308 (M + H+).
TABLE 27-continued
Structure
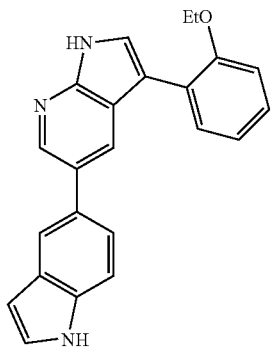
MS: m/z 354 (M + H+).
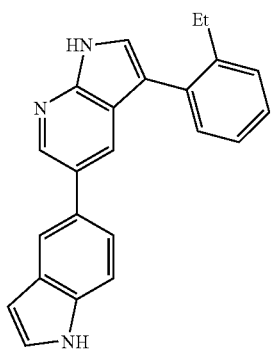
MS: m/z 338 (M + H+).
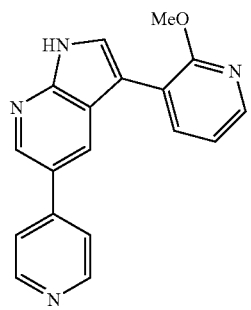
MS: m/z 303 (M + H+).
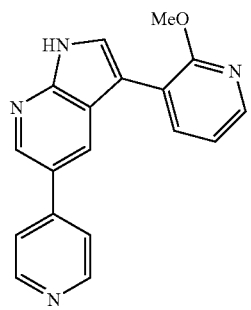
MS: m/z 346 (M + H+).

TABLE 27-continued
| Structure |
|---|
| 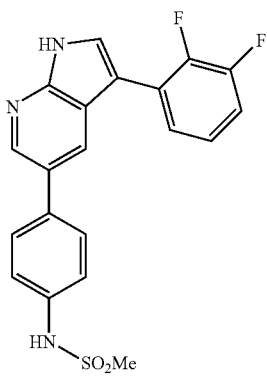<br>MS: m/z 400 (M + H+). |
| 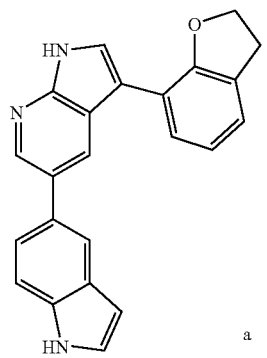<br>MS: m/z 352.1 [MH+]. a |
| 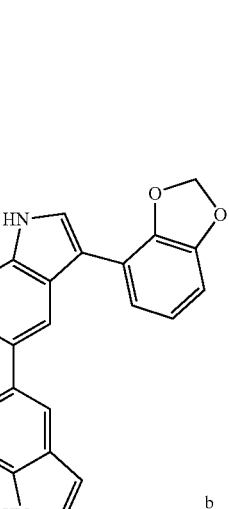<br>MS: m/z 354.1 [MH+]. b |
TABLE 27-continued
| Structure |
|---|
| 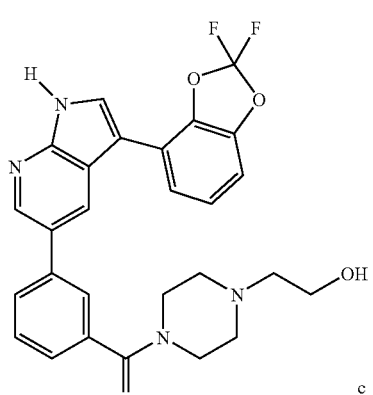<br>MS: m/z 507 [MH+]. c |
| 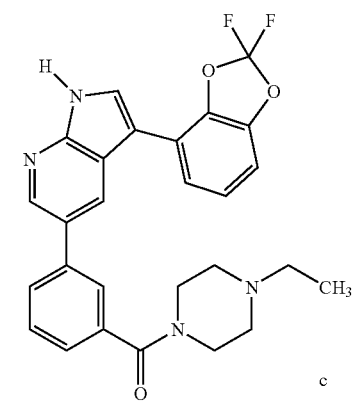<br>MS: m/z 491 [MH+]. c |
| 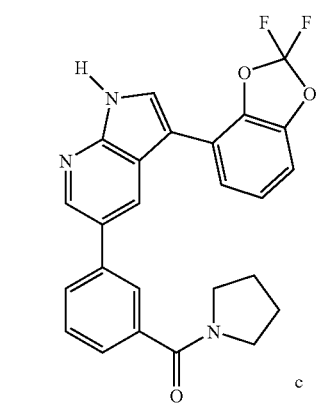<br>MS: m/z 448 [MH+]. c |

TABLE 27-continued
Structure
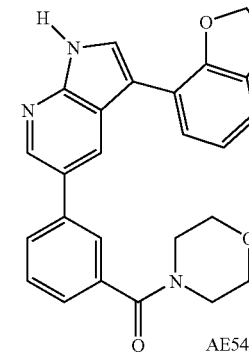
AE54, b
MS: m/z 428 [MH+].
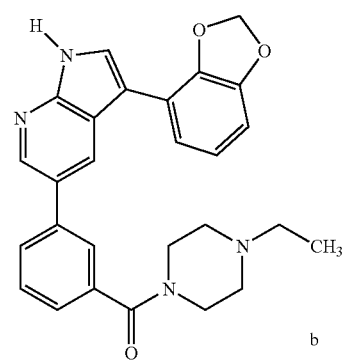
b
MS: m/z 455 [MH+].
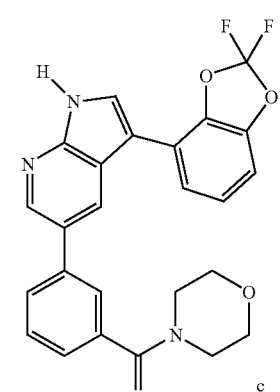
c
MS: m/z 464 [MH+].
TABLE 27-continued
Structure
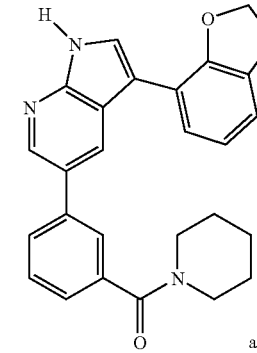
a
MS: m/z 426 [MH+].
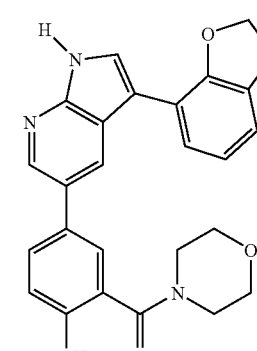
a
MS: m/z 442 [MH+].
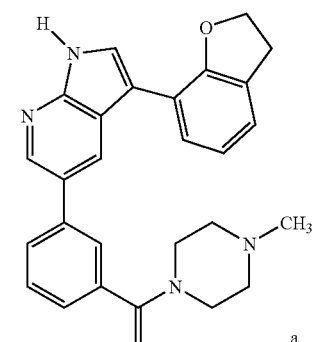
a
MS: m/z 439 [MH+].
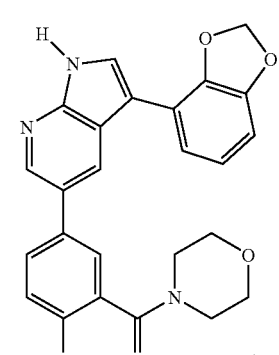
b
MS: m/z 444 [MH+].

TABLE 27-continued

Structure

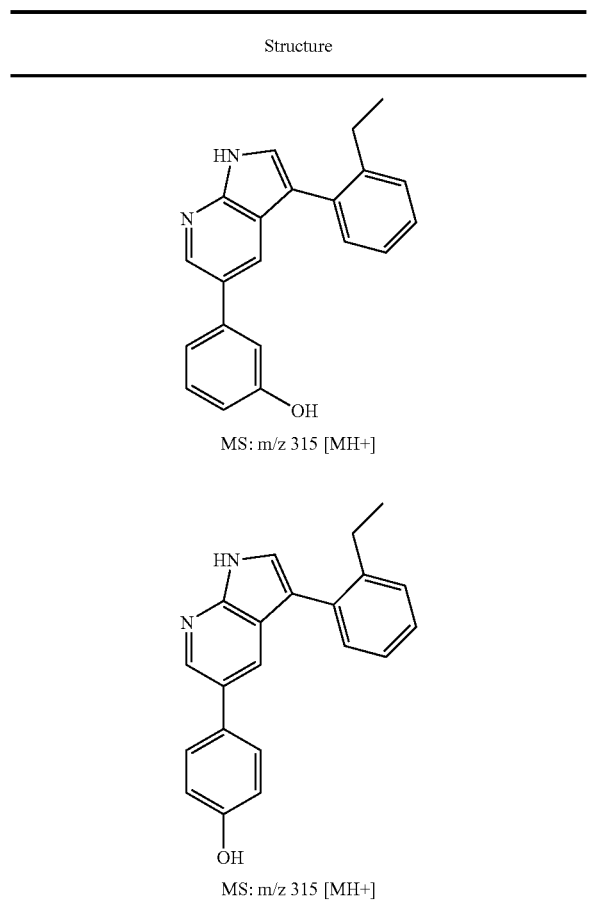

MS: m/z 315 [MH+]

MS: m/z 315 [MH+]

a, b, c 2,3-Dihydro-benzofuran-7-bronic acid, benzo[1,3]dioxole-4-boronic acid and 2,2-difluoro-benzo[1,3]dioxole-4-boronic acid were prepared according to the procedures described below.

Synthesis of 1,3-Dibromo-2-(2-bromo-ethoxy)-benzene

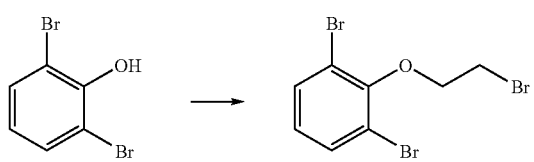

1,2-Dibromoethane (5.0 ml, 58 mmol) was added to a solution of sodium hydroxide (2.5 g, 63 mmol) and 2,6-dibromophenol (14.5 g, 57.6 mmol) in 45 ml of water. The mixture was stirred under reflux for 20 hours and then extracted with ether. The combined organic layers was dried over Na$_2$SO$_4$, filtered and concentrated to give colorless oil. Silica gel chromatography using a gradient of ethyl acetate in hexanes to afforded 1,3-dibromo-2-(2-bromo-ethoxy)-benzene (11.55 g, 57% yield) as a colorless oil.

Synthesis of 7-Bromo-2,3-dihydro-benzofuran

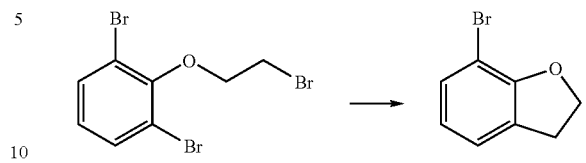

A solution of 2.5M n-BuLi (13.0 ml, 32.5 mmol) was added to a solution of 1,3-dibromo-2-(2-bromo-ethoxy)-benzene (11.5, 32.0 mmol) in 115 ml of THF and 28 ml of hexane at −78° C. over 30 mins. The reaction was continued at −78° C. for 30 minutes, then warmed to 0° C. The mixture was poured into water (100 ml) and the aqueous phase was extracted with ether. The combined organic layers were dried over Na$_2$SO$_4$, filtered, and concentrated to give a pale yellow oil. Silica gel chromatography using a gradient of ethyl acetate in hexanes to give 7-bromo-2,3-dihydro-benzofuran as colorless needles (5.00 g, 78%). $^1$H NMR (500 MHz, DMSO-d6) δ 7.27 (dd, 1 Hz, 8 Hz, 1H), 7.20 (dd, 1 Hz, 7.5 Hz, 1H), 6.75 (t, 7.8 Hz, 1H), 4.59 (t, 9 Hz, 2H), 3.28 (t, 8.8 Hz, 2H).

Synthesis of 2,3-Dihydro-benzofuran-7-bronic acid

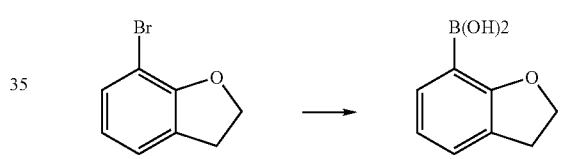

A solution of 1.7M t-BuLi (6.5 ml, 11.1 mmol) in pentane was added to a solution of 7-bromo-2,3-dihydro-benzofuran (2.00 g, 10.1 mmol) in 15 ml of THF at −78° C. over 15 minutes. The mixture was stirred at −78° C. for 30 minutes before trimethyl boroate (1.34 ml, 12.0 mmol) was added. The mixture was slowly warmed to 0° C. and water (100 ml) added. The organic layer was separated and the aqueous phase was extracted with ether. The combined organic layers was dried over Na$_2$SO$_4$, filtered and concentrated to give a white sticky residue. The crude product was then washed with water and then 20% EtOAc in hexanes to afford 2,3-dihydro-benzofuran-7-bronic acid (1.48 g, 90% yield) as a white solid.

Similarly, benzo[1,3]dioxole-4-boronic acid and 2,2-difluoro-benzo[1,3]dioxole-4-boronic acid were prepared.

Method 41:

AE55

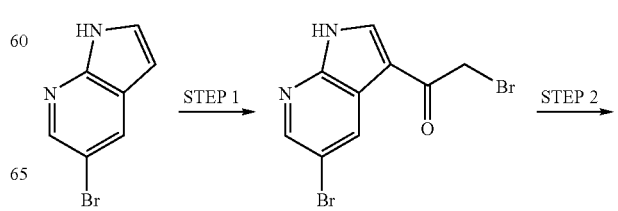

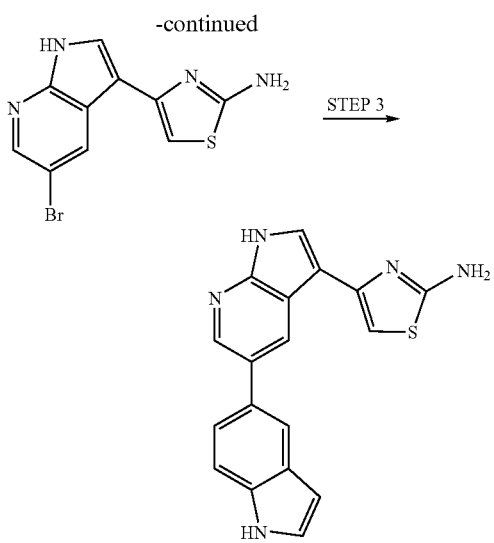

Step 1: Synthesis of 2-bromo-1-(5-bromo-1H-pyrrolo[2,3-b]pyridin-3-yl)-ethanone To a suspension of AlCl₃ (338 mg, 2.54 mmol) in dichloromethane (10 mL) was added 5-bromo-1H-pyrrolo[2,3-b]pyridine (100 mg, 0.507 mmol). After stirring for 30 min, bromoacetyl chloride (0.21 mL, 2.54 mmol) was added and the reaction mixture was stirred for 2 h, before quenching with MeOH at 0° C. The mixture was concentrated in vacuo, the pH was changed to 7 by addition of a saturated solution of aqueous sodium bicarbonate, and the aqueous layer was extracted twice with EtOAc. The organic layer was dried over MgSO₄ and filtered through a plug of silica gel. Solvent was evaporated to dryness to give 2-bromo-1-(5-bromo-1H-pyrrolo[2,3-b]pyridin-3-yl)-ethanone as a light yellow solid (160 mg, quantitative). $^1$H NMR (500 MHz, DMSO-d6) δ 4.70 (s, 2H), 8.44 (d, J=2.0 Hz, 1H), 8.55 (d, J=2.5 Hz, 1H), 8.68 (d, J=3.5 Hz, 1H), 12.9 (s, 1H). MS: m/z 316 (M+H⁺).

Step 2: Synthesis of 4-(5-bromo-1H-pyrrolo[2,3-b]pyridin-3-yl)-thiazol-2-ylamine A solution of 2-bromo-1-(5-bromo-1H-pyrrolo[2,3-b]pyridin-3-yl)-ethanone as a light yellow solid (80 mg, 0.251 mmol) and thiourea (21 mg, 0.276 mmol) in EtOH (1 mL) was stirred at 80° C. for 1.5 h. The resulting precipitate was filtered, washed with MeOH, and dried in vacuo to give 4-(5-bromo-1H-pyrrolo[2,3-b]pyridin-3-yl)-thiazol-2-ylamine hydrobromide salt as a beige solid (66 mg, 70% yield). $^1$H NMR (500 MHz, DMSO-d6) δ 7.11 (s, 1H), 8.00 (d, J=2.5 Hz, 1H), 8.39 (t, J=2.5 Hz, 1H), 8.52 (d, J=2.0 Hz, 1H), 12.4 (s, 1H). MS: m/z 295 (M+H⁺).

Step 3: Synthesis of 4-[5-(1H-indol-5-yl)-1H-pyrrolo[2,3-b]pyridin-3-yl]-thiazol-2-ylamine To 4-(5-bromo-1H-pyrrolo[2,3-b]pyridin-3-yl)-thiazol-2-ylamine hydrobromide salt (20 mg, 0.053 mmol), 5-indolyl boronic acid (13 mg, 0.08 mmol), and [1,1'-bis(diphenylphosphino)ferrocene]dichloropalladium (II), complex with dichloromethane (1:1) (2 mg, 0.0026 mmol) in a Smith process vial was added 0.5 mL of a 1:1 mixture of acetonitrile, and a 2 M solution of sodium carbonate in water. The reaction was run in a Personal Chemistry® microwave reactor at 150° C. for 1200 s. The mixture was diluted with DMF (3 mL), filtered on a silica plug, and solvent was evaporated. Purification by reverse phase chromatography using a gradient of H₂O and acetonitrile (with 0.1% formic acid as a modifier) afforded the formate salt of 4-[5-(1H-indol-5-yl)-1H-pyrrolo[2,3-b]pyridin-3-yl]-thiazol-2-ylamine as an off-white solid (8.5 mg, 42% yield). $^1$H NMR (500 MHz, DMSO-d6) δ 6.44 (m, 1H), 6.82 (s, 1H), 6.91 (s, 2H), 7.32 (t, J=2.5 Hz, 1H), 7.41 (m, 2H), 7.67 (d, J=2.5 Hz, 1H), 7.81 (s, 1H), 8.14 (s, 1H), 8.46 (d, J=2.0 Hz, 1H), 8.49 (d, J=2.0 Hz, 1H), 11.0 (s, 1H), 11.7 (s, 1H). MS: m/z 332 (M+H⁺).

Method 42:

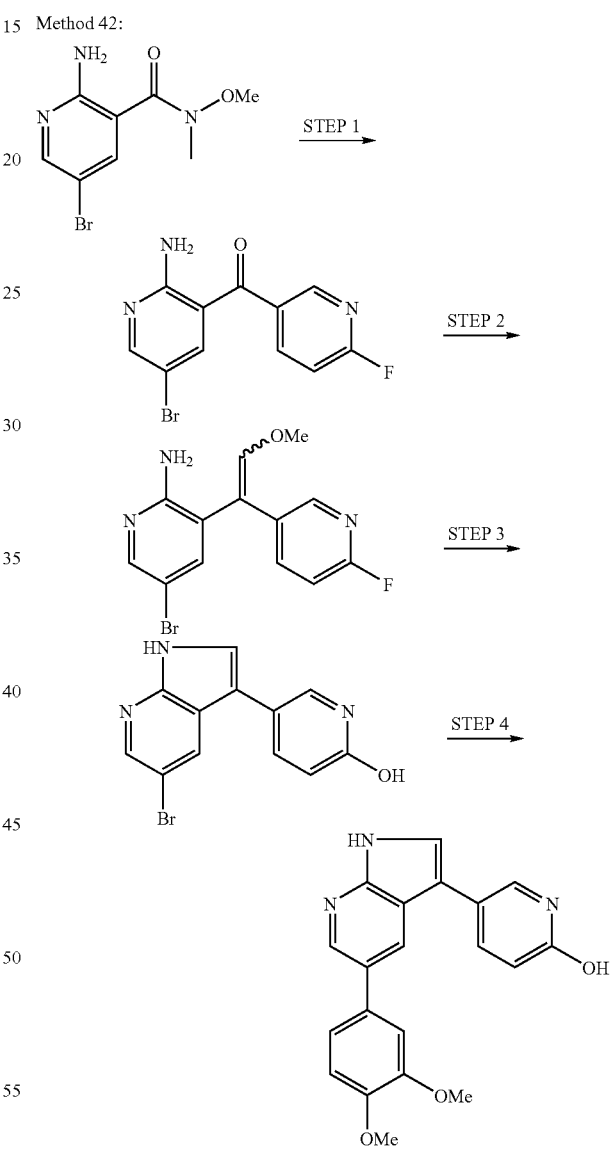

Step 1: Synthesis of (2-Amino-5-bromo-pyridin-3-yl)-(6-fluoro-pyridin-3-yl)-methanone To a solution of 5-bromo-2-fluoropyridine (5.6 ml, 54.2 mmol) in THF (50 ml) at 0° C. under nitrogen was added dropwise a 2 M solution of iso-propylmagnesium chloride in THF (27 ml) over a period of 10 minutes. The ice bath was removed and the reaction mixture was stirred at room temperature for 2 hours. The resulting slurry was added dropwise via cannula to a solution of 2-amino-5-bromo-N-methoxy-N-methyl-nicotinamide hydrochloride (3.0 g, 11.5 mmol) in THF (50 ml) at room temperature under nitrogen over a period of 30 minutes. After stirring for 3 hours, the reaction was quenched by addition of a saturated aqueous solution of ammonium chloride (50 ml) at 0° C. and the mixture was stirred at room temperature for another 20 minutes. Water was added and the mixture was extracted with ethyl acetate (three times). The combined organic layers were dried over sodium sulfate, then filtered and concentrated. Crystallization from methanol (ca. 60 ml) afforded the title compound as dark yellow crystals (1.48 g, 49% yield). $^1$H NMR (DMSO-$d_6$): δ 8.49 (s, 1H), 8.34 (d, J=1.5 Hz, 1H), 8.23 (dt, J=2.5, 8.0 Hz, 1H), 7.81 (d, J=2.5 Hz, 1H), 7.74 (broad s, 2H), 7.36 (dd, J=2.0, 8.0 Hz, 1H); MS: m/z 295.9, 297.9 [MH]$^+$.

Step 2: Synthesis of 5-bromo-3-[1-(6-fluoro-pyridin-3-yl)-2-methoxy-vinyl]-pyridin-2-ylamine To a suspension of (methoxymethyl)triphenylphosphonium chloride (1.16 g, 3.38 mmol) in THF (4 ml) at 0° C. under nitrogen was added dropwise a 1M solution of lithium bis(trimethylsilyl)amide in THF (3.4 ml, 3.4 mmol). The resulting dark red mixture was stirred at 0° C. for 10 minutes to generate the ylide reagent. To a solution of (2-amino-5-bromo-pyridin-3-yl)-(6-fluoro-pyridin-3-yl)-methanone (400 mg, 1.35 mmol) in THF (6 ml) was added dropwise a 1 M solution of tert-butylmagnesium chloride in THF (1.35 ml) at 0° C. under nitrogen. The reaction mixture was stirred at 0° C. for 5 minutes, then the ylide reagent was added dropwise in 5 minutes. The reaction mixture was allowed to warm up to room temperature in 45 minutes before quenching with a saturated aqueous solution of ammonium chloride (50 ml) at 0° C. The mixture was stirred vigorously for 1.5 hours at room temperature. Water was added, followed by extracting ethyl acetate (three times). The combined organic layers were washed with brine, and directly adsorbed on silica gel. Purification on silica gel with a gradient of ethyl acetate/hexane afforded the title compound (single isomer) as a dark foam (220 mg, 50% yield). $^1$H NMR (DMSO-$d_6$): δ 8.15 (d, J=2.5 Hz, 1H), 8.00 (d, J=2.5 Hz, 1H), 7.78 (dt, J=2.5, 8.5 Hz, 1H), 7.48 (d, J=2.5 Hz, 1H), 7.10 (dd, J=3.0, 8.5 Hz, 1H), 6.61 (s, 1H), 5.73 (broad s, 2H), 3.80 (s, 3H); MS: m/z 324, 326 [MH]$^+$.

Step 3: Synthesis of 5-(5-bromo-1H-pyrrolo[2,3-b]pyridin-3-yl)-pyridin-2-ol

To a solution of 5-bromo-3-[1-(6-fluoro-pyridin-3-yl)-2-methoxy-vinyl]-pyridin-2-ylamine (220 mg, 0.678 mmol) in 1,4-dioxane (3 ml) in a Smith process vial was added 0.3 ml of 70% aqueous perchloric acid. The reaction was irradiated in a Personal Chemistry® microwave to 150° C. for 300 s. The reaction mixture was diluted with water and neutralized to pH 7 by addition of an aqueous solution of sodium hydroxide. The resulting precipitate was filtered, washed with water, and dried in vacuo to yield the title compound as a beige solid (152 mg, 77% yield). $^1$H NMR (DMSO-$d_6$): δ 12.1 (broad s, 1H), 11.7 (broad s, 1H), 8.32 (d, J=2.5 Hz, 1H), 8.30 (d, J=2.5 Hz, 1H), 7.83 (dd, J=2.5, 11.5 Hz, 1H), 7.82 (s, 2H), 7.67 (s, 1H), 6.43 (d, J=11.5 Hz, 1H); MS: m/z 290 [MH]$^+$.

Step 4: Synthesis of 5-[5-(3,4-dimethoxy-phenyl)-1H-pyrrolo [2,3-b]pyridin-3-yl]-pyridin-2-ol To 5-(5-bromo-1H-pyrrolo[2,3-b]pyridin-3-yl)-pyridin-2-ol, 3,4-dimethoxyphenyl boronic acid (1.3 equiv.) and dichlorobis (triphenylphosphino)palladium (II) (6 mol %) in a Smith process vial was added a 3:2:1 mixture of acetonitrile, water, and a 2 M solution of sodium carbonate in water to achieve an overall concentration of the starting material of 0.10 M. The reaction was run in a Personal Chemistry® microwave reactor at 165° C. for 1200 s. Water was added and the mixture extracted three times with ethyl acetate. Purification on silica gel with a gradient of MeOH/CH2Cl2 afforded 5-[5-(3,4-dimethoxy-phenyl)-1H-pyrrolo[2,3-b]pyridin-3-yl]-pyridin-2-ol as an off-white solid (34% yield). $^1$H NMR (DMSO-$d_6$): δ 11.86 (broad s, 1H), 11.67 (broad s, 1H), 8.52 (d, J=2.0 Hz, 1H), 8.22 (d, J=2.0 Hz, 1H), 7.89 (dd, J=2.5, 10 Hz, 1H), 7.75 (s, 1H), 7.73 (s, 1H), 7.29 (d, J=2.0 Hz, 1H), 7.23 (dd, J=2.0, 8.0 Hz, 1H), 7.04 (d, J=8.5 Hz, 1H), 6.44 (d, J=9.0 Hz, 1H), 3.85 (s, 3H), 3.79 (s, 3H); MS: m/z 348.1 [MH]$^+$.

Other compounds prepared by method 42:

TABLE 28

Structure

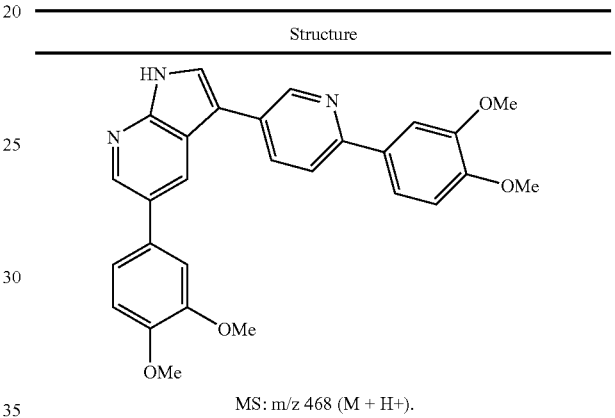

MS: m/z 468 (M + H+).

a) From 5-bromo-3-(6-chloro-pyridin-3-yl)-1H-pyrrolo[2,3-b]pyridine, which was prepared by one of the following ways.

Synthesis of 5-bromo-3-(6-chloro-pyridin-3-yl)-1H-pyrrolo[2,3-b]pyridine from 5-(5-bromo-1H-pyrrolo [2,3-b]pyridin-3-yl)-pyridin-2-ol

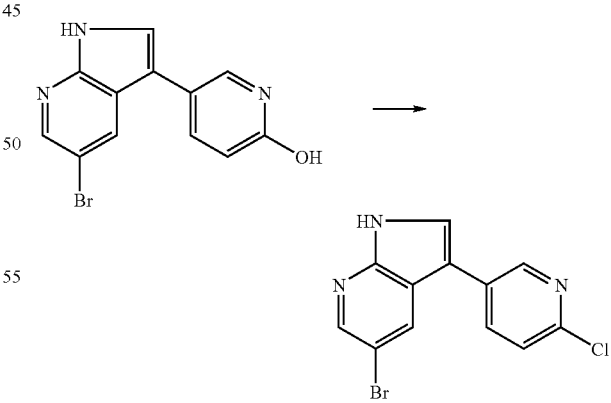

5-(5-bromo-1H-pyrrolo[2,3-b]pyridin-3-yl)-pyridin-2-ol (152 mg, 0.524 mmol) was heated in 2 ml of phosphorus oxychloride in a capped vial. The reaction mixture was stirred at 110° C. for 2 hours, then poured onto ice and neutralized to pH 4 with a 1 N aqueous solution of sodium hydroxide. The precipitate was filtered off, washed with water, and dried in vacuo. The resulting solid was heated in methanol for 30 min, then filtered cold, washed with methanol, and dried in vacuo to yield the title compound as a beige solid (117 mg, 72% yield). $^1$H NMR (DMSO-d$_6$): δ 12.4 (broad s, 1H), 8.80 (d, J=2.5 Hz, 1H), 8.53 (d, J=2.0 Hz, 1H), 8.36 (d, J=1.5 Hz, 1H), 8.23 (dd, J=2.0, 8.0 Hz, 1H), 8.16 (s, 1H), 7.54 (d, J=7.5 Hz, 1H); MS: m/z 307.9, 309.9 [MH]$^+$.

Synthesis of 5-bromo-3-(6-chloro-pyridin-3-yl)-1H-pyrrolo[2,3-b]pyridine from 5-bromo-3-[1-(6-fluoro-pyridin-3-yl)-2-methoxy-vinyl]-pyridin-2-ylamine

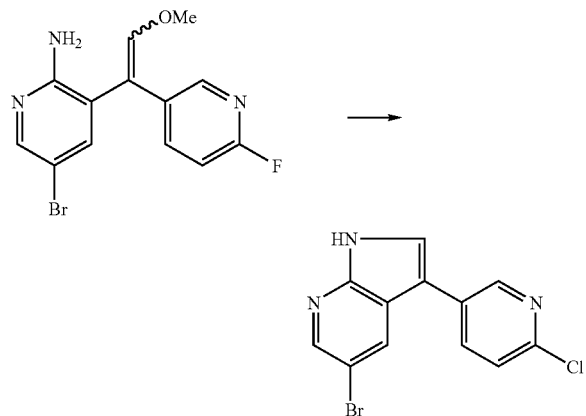

5-bromo-3-[1-(6-fluoro-pyridin-3-yl)-2-methoxy-vinyl]-pyridin-2-ylamine (375 mg, 1.16 mmol) was treated with a 4 M solution of HCl in 1,4-dioxane (5 ml). The reaction mixture was stirred at 110° C. in a sealed tube for 16 hours, then poured onto ice and neutralized to pH 6 with a 1 N aqueous solution of sodium hydroxide. The precipitate was filtered off, washed with water, and dried in vacuo to give 333 mg of a beige solid. The solid was heated with 2 ml of phosphorus oxychloride in a capped vial. The reaction mixture was stirred at 110° C. for 2 hours, then poured onto ice and neutralized to pH 2-3 with a 1 N aqueous solution of sodium hydroxide. The precipitate was filtered off, washed with water, and dried in vacuo. Purification on silica gel using a gradient of methanol in dichloromethane afforded the title compound as a beige solid (241 mg, 67% yield).

Method 43:

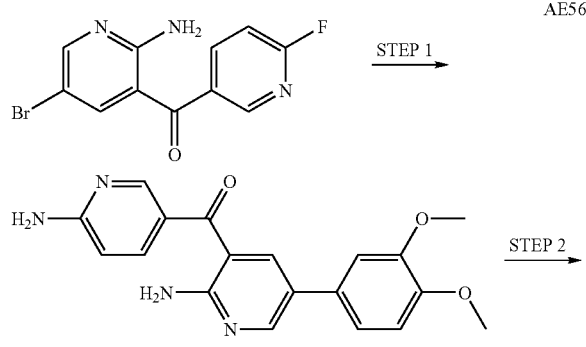

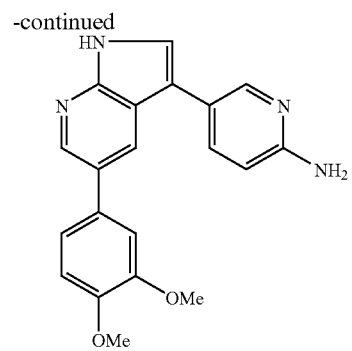

Step 1: Synthesis of [2-amino-5-(3,4-dimethoxy-phenyl)-pyridin-3-yl]-(6-amino-pyridin-3-yl)-methanone A solution of (2-amino-5-bromo-pyridin-3-yl)-(6-fluoro-pyridin-3-yl)-methanone (120 mg, 0.405 mmol), ammonium chloride (5 equiv.), and triethyl amine (5 eq.) in absolute ethanol (0.2 M) was sealed in a Smith process vial. The reaction was heated in a Personal Chemistry® microwave reactor to 200° C. for 25 minutes. The mixture was diluted with water, and the resulting yellow precipitate was filtered off, washed with water, and dried in vacuo. The crude product was mixed with 3,4-dimethoxyphenyl boronic acid (1.3 equiv.), 6 mol % of dichlorbis(triphenylphosphino) palladium (II) and a 3:2:1 mixture of acetonitrile, water, and a 2 M aqueous solution of sodium carbonate (0.11 M). The reaction was run in a Personal Chemistry® microwave reactor at 165° C. for 1200 s. Water was added and the mixture was extracted three times with ethyl acetate. Purification was accomplished by flash chromatography on silica gel with a gradient of ethyl acetate/hexanes and afforded [2-amino-5-(3,4-dimethoxy-phenyl)-pyridin-3-yl]-(6-amino-pyridin-3-yl)-methanone as a yellow solid (37 mg, 31% yield). $^1$H NMR (DMSO-d$_6$): δ 8.50 (d, J=2.5 Hz, 1H), 8.29 (d, J=2.0 Hz, 1H), 7.86 (d, J=2.0 Hz, 1H), 7.75 (dd, J=2.0, 8.5 Hz, 1H), 7.15 (d, J=2.0 Hz, 1H), 7.06 (m, 3H), 6.98 (d, J=8.0 Hz, 1H), 6.92 (broad s, 2H), 6.50 (d, J=9.0 Hz, 1H), 3.80 (s, 3H), 3.75 (s, 3H). HPLC/MS m/z: 351 [MH$^+$].

Step 2: Synthesis of 5-[5-(3,4-dimethoxy-phenyl)-1H-pyrrolo [2,3-b]pyridin-3-yl]-pyridin-2-ylamine To a suspension of (methoxymethyl)triphenylphosphonium chloride (166 mg, 0.485 mmol) in THF (1 ml) at 0° C. under nitrogen was added potassium bis(trimethylsilyl) amide (97 mg, 0.485 mmol). The mixture was stirred at room temperature for 30 min, then it was added to [2-amino-5-(3, 4-dimethoxy-phenyl)-pyridin-3-yl]-(6-amino-pyridin-3-yl)-methanone (34 mg, 0.097 mmol) in one portion. The reaction mixture was stirred for 2 hours, then quenched with wet methanol and concentrated in vacuo. The crude was diluted with 2 ml of 1,4-dioxane and treated with 0.1 ml of aqueous 70% perchloric acid. The mixture was stirred at 80° C. for 19 hours, diluted with THF/methanol (1:1), and treated with 2.0 g of PS-trisamine (Argonaut Technologies, 4 equivalents per equivalent of acid used) for 30 minutes. The resin was filtered off and washed with THF/MeOH (1:1). Purification was accomplished by flash chromatography on silica gel with a gradient of methanol/dichloromethane afforded 5-[5-(3,4-dimethoxy-phenyl)-1H-pyrrolo[2,3-b]pyridin-3-yl]-pyridin-2-ylamine as a yellow solid (9.7 mg, 29% yield). $^1$H NMR (DMSO-d$_6$): δ 11.8 (s, 1H), 8.51 (d, J=2.0 Hz, 1H), 8.31 (d, J=2.0 Hz, 1H), 8.25 (d, J=2.0 Hz, 1H), 7.77 (dd, J=2.0, 10.0

Hz, 1H), 7.70 (d, J=2.5 Hz, 1H), 7.28 (d, J=2.0 Hz, 1H), 7.24 (dd, J=2.0, 7.5 Hz, 1H), 7.04 (d, J=8.5 Hz, 1H), 6.55 (d, J=8.5 Hz, 1H), 5.90 (broad s, 2H), 3.86 (s, 3H), 3.79 (s, 3H). HPLC/MS m/z: 347.1 [MH]$^+$.

Method 44:

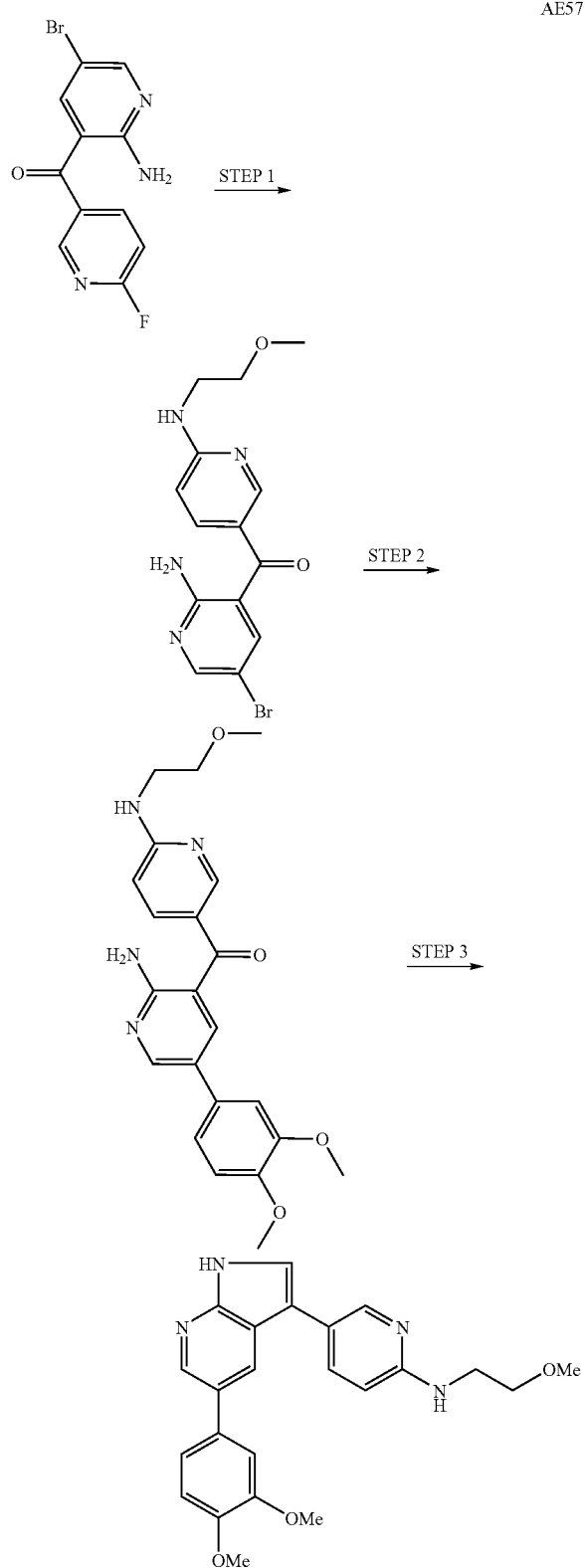

AE57

Step 1: Synthesis of (2-amino-5-bromo-pyridin-3-yl)-[6-(2-methoxy-ethylamino)-pyridin-3-yl]-methanone A solution of (2-amino-5-bromo-pyridin-3-yl)-(6-fluoro-pyridin-3-yl)-methanone, 2-methoxyethylamine (1 equiv.) and triethylamine (1.2 equiv.) in absolute EtOH (0.17 M) was sealed in a Smith process vial. The reaction was run in a Personal Chemistry® microwave reactor at 160° C. for 900 s. The mixture was diluted with water, and the resulting precipitate was filtered off, washed with water, and dried in vacuo to give (2-amino-5-bromo-pyridin-3-yl)-[6-(2-methoxy-ethylamino)-pyridin-3-yl]-methanone as a yellow solid (86% yield). $^1$H NMR (DMSO-d$_6$): δ 8.28 (d, J=2.5 Hz, 1H), 8.23 (d, J=2.5 Hz, 1H), 7.75 (d, J=2.5 Hz, 1H), 7.69 (dd, J=2.0, 9.0 Hz, 1H), 7.64 (broad s, 1H), 7.12 (broad s, 2H), 6.59 (d, J=9.5 Hz, 1H), 3.51 (t, J=4.5 Hz, 2H), 3.47 (t, J=4.5 Hz, 2H), 3.26 (s, 3H); HPLC/MS m/z: 351, 353 [MH]$^+$.

Step 2: Synthesis of [2-amino-5-(3,4-dimethoxy-phenyl)-pyridin-3-yl]-[6-(2-methoxy-ethylamino)-pyridin-3-yl]-methanone To (2-amino-5-bromo-pyridin-3-yl)-[6-(2-methoxy-ethylamino)-pyridin-3-yl]-methanone, 3,4-dimethoxyphenylboronic acid (1.3 equiv.) and dichlorobis (triphenylphosphino) palladium (II) (6 mol %) in a Smith process vial was added a 3:2:1 mixture of acetonitrile, water, and a 2 m solution of sodium carbonate in water to achieve an overall concentration of the starting material of 0.10 m. The reaction was run in a Personal Chemistry® microwave reactor at 165° C. for 1200 s. Water was added and the mixture extracted three times with ethyl acetate. Purification on silica gel with a gradient of MeOH/CH2Cl2 afforded [2-amino-5-(3,4-dimethoxy-phenyl)-pyridin-3-yl]-[6-(2-methoxy-ethylamino)-pyridin-3-yl]-methanone as a yellow solid (74% yield). $^1$H NMR (DMSO-d$_6$): δ 8.49 (d, J=2.0 Hz, 1H), 8.33 (d, J=2.5 Hz, 1H), 7.85 (d, J=2.0 Hz, 1H), 7.73 (d, J=8.5 Hz, 1H), 7.58 (broad s, 1H), 7.14 (s, 1H), 7.05 (m, 3H), 6.98 (d, J=8.5 Hz, 1H), 6.59 (d, J=9.0 Hz, 1H), 3.79 (s, 3H), 3.75 (s, 3H), 3.50 (broad t, J=5.0 Hz, 2H), 3.46 (t, J=5.0 Hz, 2H), 3.26 (s, 3H); HPLC/MS m/z: 409.2 [MH]$^+$.

Step 3: Synthesis of {5-[5-(3,4-dimethoxy-phenyl)-1H-pyrrolo[2,3-b]pyridin-3-yl]-pyridin-2-yl}-(2-methoxy-ethyl)-amine To a suspension of (methoxymethyl)triphenylphosphonium chloride (7-10 equiv.) in THF (0.45 M) at 0° C. under nitrogen was added potassium bis(trimethylsilyl)amide (1 equivalent to phosphonium chloride). The mixture was stirred at room temperature for 30 minutes. The resulting mixture was added to [2-amino-5-(3,4-dimethoxy-phenyl)-pyridin-3-yl]-[6-(2-methoxy-ethylamino)-pyridin-3-yl]-methanone dissolved in THF (0.1-0.2 M) in one portion. The reaction mixture was stirred for 1-16 hours, then diluted with methanol and adsorbed on silica gel. Purification by flash chromatography on silica gel with a gradient of methanol/dichloromethane afforded the corresponding vinyl ether that was used in the next reaction.

The vinyl ether was dissolved in 1,4-dioxane (0.1 M) and treated with 2.6 equivalents of 70% aqueous perchloric acid. The mixture was stirred at 80-100° C. for 19-24 hours, diluted with THF/MeOH (1:1), and treated with PS-trisamine (Argonaut Technologies, 10 equivalents per equivalent of acid used) for 30 minutes. The resin was filtered off and washed with THF/MeOH (1:1). Purification by flash chromatography on silica gel with a gradient of methanol/dichloromethane afforded {5-[5-(3,4-dimethoxy-phenyl)-1H-pyrrolo[2,3-b]pyridin-3-yl]-pyridin-2-yl}-(2-methoxy-ethyl)-amine as a white solid (65% yield). $^1$H NMR (DMSO-$d_6$): using the compound prepared according to example 83 as a starting material. $^1$H-NMR δ 11.8 (s, 1H), 8.51 (d, J=2.0 Hz, 1H), 8.39 (d, J=2.5 Hz, 1H), 8.26 (d, J=2.0 Hz, 1H), 7.77 (dd, J=2.5, 9.0 Hz, 1H), 7.70 (d, J=2.5 Hz, 1H), 7.29 (d, J=2.0 Hz, 1H), 7.25 (dd, J=2.0, 8.5 Hz, 1H), 7.04 (d, J=9.0 Hz, 1H), 6.62 (d, J=8.5 Hz, 1H), 6.55 (t, J=5.5 Hz, 1H), 3.86 (s, 3H), 3.79 (s, 3H), 3.47 (m, 4H), 3.28 (s, 3H). HPLC/MS m/z: 405.2 [MH]$^+$.

The following one-pot procedure was used in some cases:

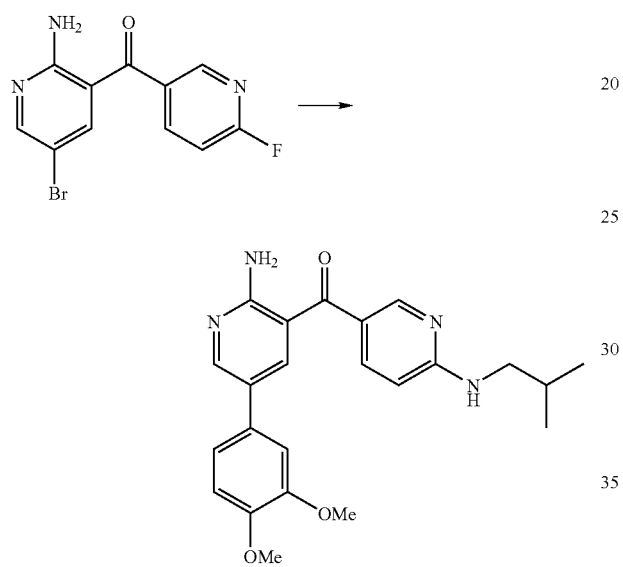

A solution of (2-amino-5-bromo-pyridin-3-yl)-(6-fluoro-pyridin-3-yl)-methanone, 1.1 equivalents of isobutylamine and 1.2 equivalents (or 2.3 equivalents for amines in salt form) of triethyl amine are dissolved in absolute ethanol (overall concentration of the starting material: 0.22 M) and sealed in a Smith process vial. The reaction was run in a Personal Chemistry® microwave reactor at 150° C. for 900 s. The solvent was evaporated and the crude mixed with 1.3 equivalents of 3,4-dimethoxyphenylboronic acid, 6 mol % of dichlorobis (triphenylphosphinol) palladium (II) and a 3:2:1 mixture of acetonitrile, water, and an aqueous 2 M solution of sodium carbonate (overall concentration of starting material: 0.18 M). The reaction was run in a Personal Chemistry® microwave reactor at 165° C. for 1200 s. Water was added and the mixture extracted three times with ethyl acetate Purification by flash chromatography on silica gel with a gradient of ethyl acetate/hexane to afforded [2-Amino-5-(3,4-dimethoxy-phenyl)-pyridin-3-yl]-(6-isobutylamino-pyridin-3-yl)-methanone as a yellow solid (71% yield). $^1$H NMR (DMSO-$d_6$): δ 8.49 (d, J=2.0 Hz, 1H), 8.32 (d, J=2.5 Hz, 1H), 7.86 (d, J=3.0 Hz, 1H), 7.72 (d, J=9.0 Hz, 1H), 7.57 (broad s, 1H), 7.14 (d, J=2.0 Hz, 1H), 7.06 (dd, J=2.0, 8.5 Hz, 1H), 7.03 (broad s, 2H), 6.98 (d, J=8.0 Hz, 1H), 6.56 (d, J=8.5 Hz, 1H), 3.79 (s, 3H), 3.75 (s, 3H), 3.15 (broad s, 2H), 1.83 (m, 1H), 0.89 (d, J=6.5 Hz, 6H); HPLC/MS m/z: 407.2 [MH]$^+$.

Other compounds prepared by Method 44:

TABLE 29

| Structure |
|---|
| MS: m/z 417 (M + H$^+$). |
| MS: m/z 391 (M + H$^+$). a |
| MS: m/z 452 (M + H$^+$). a |
| MS: m/z 332 (M + H+). | a Compounds synthesized by the one-pot procedure.

Method 45:

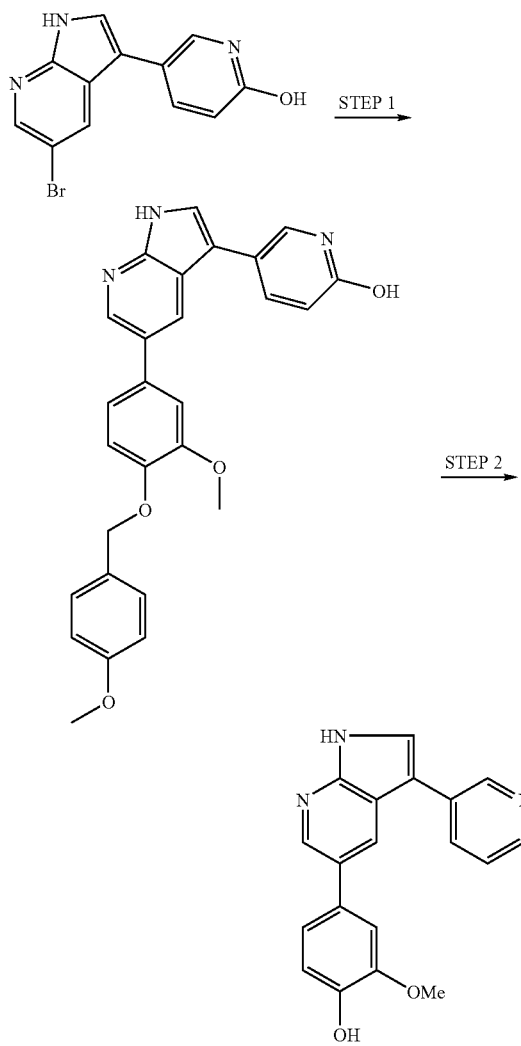

Step 1: Synthesis of 5-{5-[3-methoxy-4-(4-methoxy-benzyloxy)-phenyl]-1H-pyrrolo [2,3-b]pyridin-3-yl}-pyridin-2-ol To the 5-(5-bromo-1H-pyrrolo[2,3-b]pyridin-3-yl)-pyridin-2-ol, 4-(4-methoxyphenylmethoxy)-3-methoxyphenylboronic acid (1.3 equiv.), and 6 mol % of dichlorobis(triiphenylphosphino)palladium (II) in a Smith process vial was added a 3:2:1 mixture of acetonitrile, water and a 2 M aqueous solution of sodium carbonate (0.10 M). The reaction was run in a Personal Chemistry® microwave reactor at 165° C. for 1200 s. Water was added and the mixture was extracted three times with ethyl acetate Purification on silica gel with a gradient or methanol/dichloromethane by flash chromatography afforded 5-{5-[3-methoxy-4-(4-methoxy-benzyloxy)-phenyl]-1H-pyrrolo[2,3-b]pyridin-3-yl}-pyridin-2-ol as a tan solid (46% yield). $^1$H NMR (DMSO-$d_6$): δ 11.86 (broad s, 1H), 11.67 (broad s, 1H), 8.51 (d, J=2.5 Hz, 1H), 8.22 (s, 1H), 7.89 (dd, J=2.5, 9.5 Hz, 1H), 7.75 (d, J=2.5 Hz, 1H), 7.72 (s, 1H), 7.38 (d, J=8.5 Hz, 2H), 7.30 (d, J=2.0 Hz, 1H), 7.20 (dd, J=2.0, 8.5 Hz, 1H), 7.11 (d, J=8.0 Hz, 1H), 6.94 (d, J=8.5 Hz, 2H), 6.44 (d, J=9.5 Hz, 1H), 5.03 (s, 2H), 3.85 (s, 3H), 3.75 (s, 3H); HPLC/MS m/z: 454.1 [MH]$^+$.

Step 2: Synthesis of 5-(5-(4-hydroxy-3-methoxyphenyl)-1H-pyrrolo[2,3-b]pyridin-3-yl)pyridin-2-ol To a suspension of 5-{5-[3-methoxy-4-(4-methoxy-benzyloxy)-phenyl]-1H-pyrrolo[2,3-b]pyridin-3-yl}-pyridin-2-ol (25 mg, 0.055 mmol) in 1.5 ml of dichloromethane was added 78 mg of PS-thiophenol resin (Argonaut Technologies, 1.41 mmol·g$^{-1}$), followed by TFA (0.3 ml). The clear suspension was stirred at room temperature for 1 hour, then the resin was filtered off, washed with ethyl acetate, then methanol. The filtrate was evaporated and the residue was taken up in 2 ml of ethyl acetate and saturated aqueous solution of sodium bicarbonate. The resulting precipitate was filtered off, washed with water, then ethyl acetate and dried in vacuo to afford 5-(5-(4-hydroxy-3-methoxyphenyl)-1H-pyrrolo [2,3-b]pyridin-3-yl)pyridin-2-ol as a light beige solid (15 mg, 80% yield). $^1$H NMR (DMSO-$d_6$): δ 11.83 (broad s, 1H), 11.67 (broad s, 1H), 9.05 (s, 1H), 8.49 (d, J=2.0 Hz, 1H), 8.18 (d, J=2.0 Hz, 1H), 7.88 (dd, J=3.0, 9.5 Hz, 1H), 7.74 (d, J=2.5 Hz, 1H), 7.71 (d, J=2.0 Hz, 1H), 7.26 (d, J=2.0 Hz, 1H), 7.12 (dd, J=2.0, 8.5 Hz, 1H), 6.87 (d, J=8.0 Hz, 1H), 6.44 (d, J=9.0 Hz, 1H), 3.86 (s, 3H); HPLC/MS m/z: 334.1 [MH]$^+$.

Method 46:

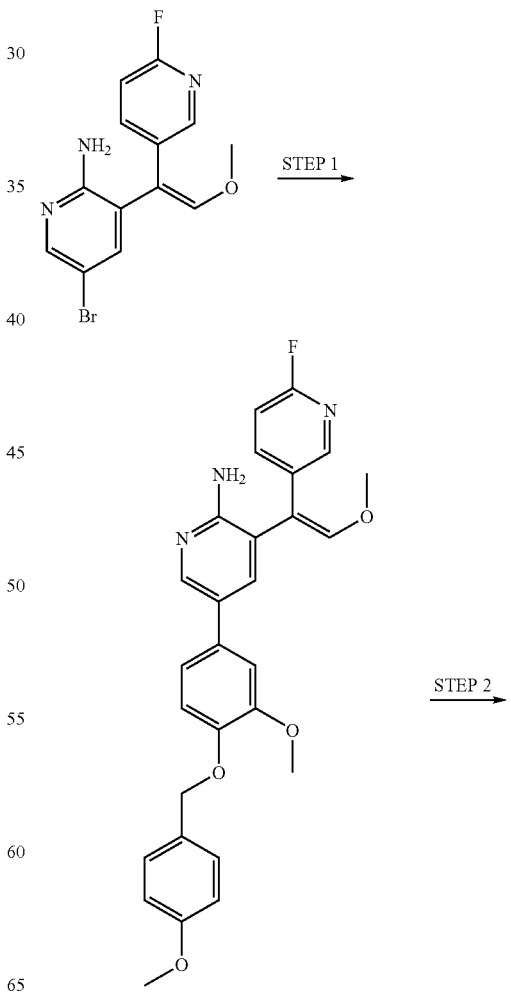

-continued

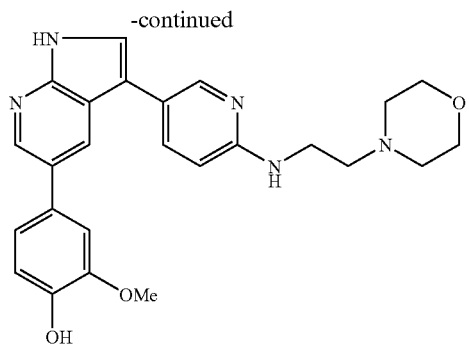

Step 1: Synthesis of 3-[1-(6-fluoro-pyridin-3-yl)-2-methoxy-vinyl]-5-[3-methoxy-4-(4-methoxy-benzyloxy)-phenyl]-pyridin-2-ylamine 5-Bromo-3-[1-(6-fluoro-pyridin-3-yl)-2-methoxy-vinyl]-pyridin-2-ylamine was subjected to method 20, Step 1 to yield 3-[1-(6-fluoro-pyridin-3-yl)-2-methoxy-vinyl]-5-[3-methoxy-4-(4-methoxy-benzyloxy)-phenyl]-pyridin-2-ylamine as a yellow solid (70% yield). $^1$H NMR (DMSO-d$_6$): δ 8.27 (d, J=2.5 Hz, 1H), 8.20 (s, 1H), 7.83 (dt, J=2.5, 8.5 Hz, 1H), 7.61 (d, J=2.0 Hz, 1H), 7.36 (d, J=8.5 Hz, 2H), 7.18 (s, 1H), 7.10 (m, 2H), 7.07 (d, J=8.5 Hz, 1H), 6.94 (d, J=8.5 Hz, 2H), 6.63 (s, 1H), 5.53 (broad s, 2H), 5.00 (s, 2H), 3.82 (s, 3H), 3.81 (s, 3H), 3.75 (s, 3H); HPLC/MS m/z: 488.2 [MH]$^+$.

Step 2: Synthesis of 2-Methoxy-4-{3-[6-(2-morpholin-4-yl-ethylamino)-pyridin-3-yl]-1H-pyrrolo[2,3-b]pyridin-5-yl}-phenol A solution of 3-[1-(6-fluoro-pyridin-3-yl)-2-methoxy-vinyl]-5-[3-methoxy-4-(4-methoxy-benzyloxy)-phenyl]-pyridin-2-ylamine (50 mg, 0.102 mmol) and 2-morpholin-4-yl-ethylamine (0.6 ml, 4.59 mmol) in anhydrous N-methylpyrrolidone (0.5 ml) was sealed in a Smith process vial. The reaction was run in a Personal Chemistry® microwave reactor at 250° C. for 1200 s. The mixture was diluted with a saturated aqueous solution of ammonium chloride (20 ml), the resulting precipitate was filtered off, washed with a saturated aqueous solution of ammonium chloride and water, then dried in vacuo. The solid was transferred to a Smith process vial and dissolved in dioxane (1 ml). Aqueous perchloric acid (70%, 0.1 ml) was added and the reaction was run in a Personal Chemistry® microwave reactor at 150° C. for 300 s. The mixture was diluted with (1:1) THF/methanol (10 ml) and treated with 2.0 g of PS-trisamine (Argonaut Technologies, 3.53 mmol·g$^{-1}$) for 1 hour. The resin was filtered off, washed with (1:1) THF/methanol, and the filtrate evaporated to give 75 mg of a dark oil. Purification on mass-triggered preparative HPLC provided 2-Methoxy-4-{3-[6-(2-morpholin-4-yl-ethylamino)-pyridin-3-yl]-1H-pyrrolo[2,3-b]pyridin-5-yl}-phenol as an off-white fluffy solid (10.7 mg, 21% yield, 0.75 equiv. formate salt). $^1$H NMR (DMSO-d$_6$): δ 11.70 (s, 1H), 8.98 (s, 1H), 8.42 (d, J=2.5 Hz, 1H), 8.32 (d, J=2.0 Hz, 1H), 8.16 (d, J=2.0 Hz, 1H), 8.08 (s, 0.75H, formate), 7.71 (dd, J=2.5, 9.0 Hz, 1H), 7.63 (d, J=2.5 Hz, 1H), 7.19 (d, J=1.5 Hz, 1H), 7.07 (dd, J=2.0, 8.0 Hz, 1H), 6.80 (d, J=8.5 Hz, 1H), 6.53 (d, J=9.5 Hz, 1H), 6.32 (t, J=5.5 Hz, 1H), 3.81 (s, 3H), 3.52 (t, J=4.5 Hz, 4H), 3.33 (m, 2H), 2.44 (m, 2H), 2.36 (broad s, 4H); HPLC/MS m/z: 446.2 [MH]$^+$.

Method 47:

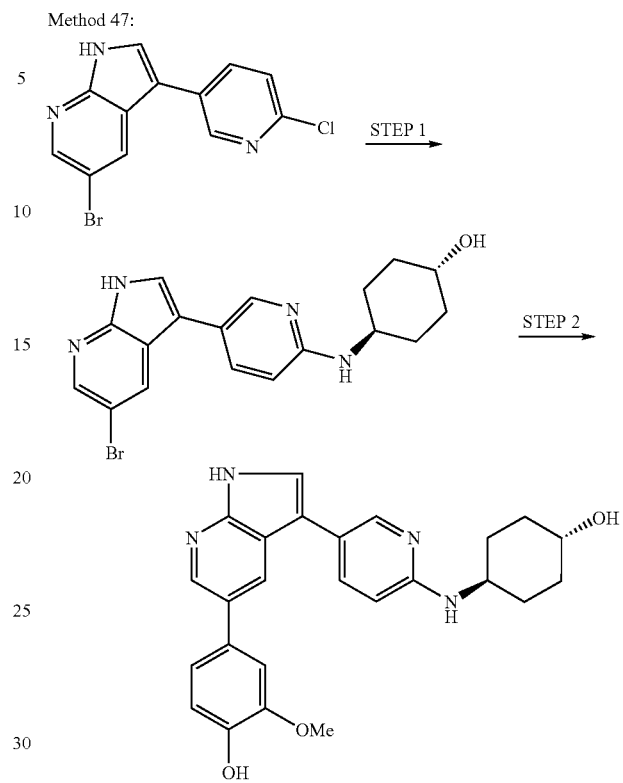

Step 1: Synthesis of trans-4-[5-(5-bromo-1H-pyrrolo[2,3-b]pyridin-3-yl)-pyridin-2-ylamino]-cyclohexanol A solution of 5-bromo-3-(6-chloro-pyridin-3-yl)-1H-pyrrolo[2,3-b]pyridine (100 mg, 0.324 mmol), trans 4-aminocyclohexanol (485 mg, 4.21 mmol), and triethyl amine hydrochloride (134 mg, 0.974 mmol) in anhydrous N-methylpyrrolidone (1 ml) was sealed in a Smith process vial. The reaction was run in a Personal Chemistry® microwave reactor at 250° C. for 1 hour. The mixture was diluted with water (40 ml), and the resulting precipitate was filtered off, washed with water, and dried in vacuo. Purification by flash chromatography on silica gel with a gradient of methanol/dichloromethane afforded trans-4-[5-(5-bromo5-1H-pyrrolo[2,3-b]pyridin-3-yl)-pyridin-2-ylamino]-cyclohexanol as a white solid (82 mg, 66% yield). $^1$H NMR (DMSO-d$_6$): δ 12.00 (s, 1H), 8.32 (d, J=2.5 Hz, 1H), 8.21-8.32 (m, 2H), 7.75 (d, J=11.5, 1H), 7.67 (dt, J=2.5, 9.0 Hz, 1H), 6.51 (d, J=9.0 Hz, 1H), 6.36 (d, J=7.0 Hz, 1H), 4.55 (d, J=5.0 Hz, 1H), 3.64 (m, 1H), 3.42 (m, 1H), 1.95 (m, 2H), 1.82 (m, 2H), 1.22 (m, 4H); HPLC/MS m/z: 387.0, 389.1 [MH]$^+$.

Step 2: Synthesis of trans-4-{3-[6-(4-hydroxy-cyclohexylamino)-pyridin-3-yl]-1H-pyrrolo[2,3-b]pyridin-5-yl}-2-methoxy-phenol To trans-4-[5-(5-bromo-1H-pyrrolo[2,3-b]pyridin-3-yl)-pyridin-2-ylamino]-cyclohexanol (52 mg, 0.134 mmol), 4-(4-methoxyphenylmethoxy)-3-methoxyphenylboronic acid (65 mg, 0.174 mmol), and (6 mg. 6 mol %) dichlorobis(triphenylphosphino)palladium(II) in a Smith process vial was added a 3:2:1 mixture of acetonitrile water and a 2 M aqueous solution of sodium carbonate 0.9 ml. The reaction was run in a Personal Chemistry® microwave reactor at 165° C. for 1200 s. Methanol was added and the mixture was adsorbed on silica gel. Purification by flash chromatography on silica gel with a gradient of methanol/dichloromethane afforded 57 mg of a dark foam. The dark foam was dissolved in dichloromethane (3 ml) and PS-thiophenol resin (150 mg, Argonaut Technologies, 1.41 mmol/g loading) was added, followed by TFA (0.6 ml). The clear suspension was stirred at room temperature for 1 hour, then the resin was filtered off, washed with ethyl acetate, then methanol. The filtrates were evaporated and the residue was treated with saturated aqueous solution of sodium bicarbonate to basic pH and extracted with ethyl acetate. Purification by flash chromotography on silica gel with a gradient of methanol/dichloromethane afforded trans-4-{3-[6-(4-hydroxy-cyclohexylamino)-pyridin-3-yl]-1H-pyrrolo[2,3-b]pyridin-5-yl}-2-methoxy-phenol as a white solid (18 mg, 41% yield). $^1$H NMR (DMSO-$d_6$): δ 11.75 (d, J=2.5 Hz, 1H), 9.03 (s, 1H), 8.47 (d, J=2.5 Hz, 1H), 8.37 (d, J=2.5 Hz, 1H), 8.22 (d, J=2.0 Hz, 1H), 7.73 (dd, J=2.5, 9.0, 1H), 7.66 (d, J=3.0 Hz, 1H), 7.25 (d, J=2.0 Hz, 1H), 7.12 (dd, J=2.0, 8.0 Hz, 1H), 6.86 (d, J=7.5 Hz, 1H), 6.53 (d, J=8.0 Hz, 1H), 6.31 (d, J=7.0 Hz, 1H), 4.55 (d, J=4.5 Hz, 1H), 3.86 (s, 3H), 3.65 (m, 1H), 3.43 (m, 1H), 1.95 (m, 2H), 1.82 (m, 2H), 1.21 (m, 4H); HPLC/MS m/z: 431.2 [MH]$^+$.

Method 48:

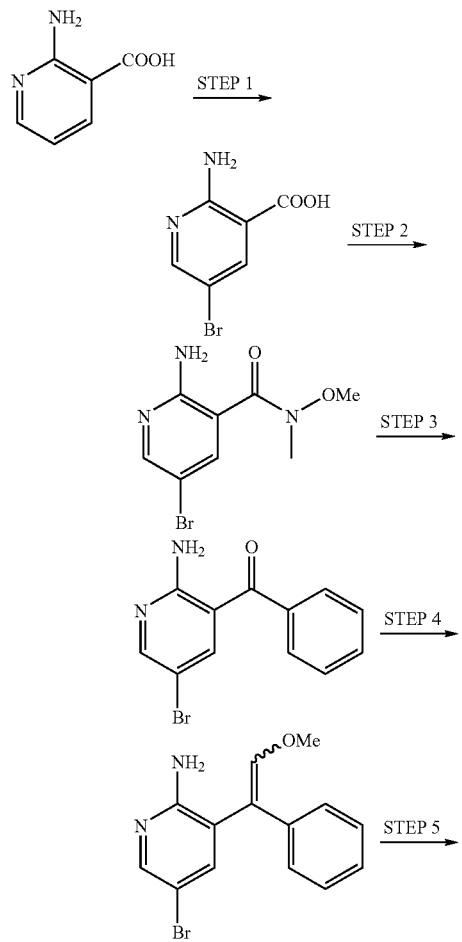

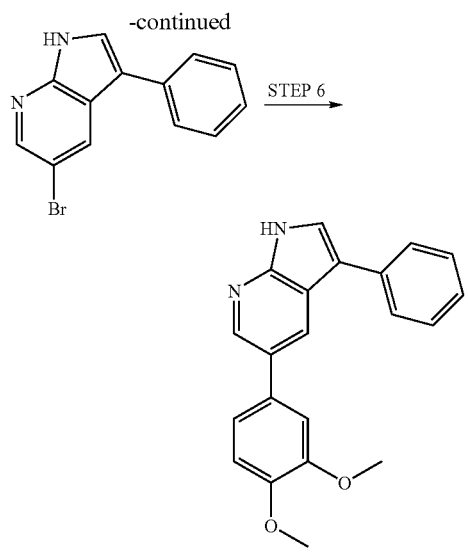

Step 1: Synthesis of 2-amino-5-bromonicotinic acid 25.00 g (0.181 mol) of 2-aminonicotinic acid were dispersed in 100 ml of glacial acetic acid. To this suspension was added a solution of 12.0 ml (0.23 mol) of bromine in 50 ml of glacial acetic acid. The mixture was stirred at room temperature for 20 hours. The precipitate formed was filtered off and washed with 100 ml of glacial acetic acid in several portions until the filtrate remained colorless. The crude was dried by suction and crystallized from boiling methanol to afford 38.63 g (0.178 mol, 98% yield) of 2-amino-5-bromonicotinic acid as slightly greenish to off-white crystalline needles. $^1$H-NMR ($d_6$-DMSO) d: 8.45 [1H] d, 8.34 [1H] d.; MS: m/z 217 [MH]$^+$.

Step 2: Synthesis of N-methoxy-N-methyl-2-amino-5-bromonicotinamide a) Isolated as the Free Base 2-amino-5-bromonicotinic acid (4.000 g, 18.43 mmol), N,O-dimethylhydroxylamine hydrochloride (4.550 g, 46.6 mmol) and PyBOP (1-benzotriazolyloxy-tris(pyrrolidino)phosphonium hexafluorophosphate) (15.00 g, 28.82 mmol) were placed in a nitrogen flushed flask. 150 ml of acetonitrile and 25 ml of di-iso-propylethylamine were added and the mixture was heated to 95° C. for 20 hours. The solvent was then evaporated and the residue distributed between 200 ml of chloroform and 100 ml of a 10% solution of citric acid in water. The organic phase was separated and washed with 100 ml of 1 M aqueous sodium hydroxide and dried over sodium sulfate. The solvent was evaporated and the crude material purified by chromatography on silica gel using a non-linear gradient of ethyl acetate and hexane affording 2.193 g (8.436 mmol, 46% yield) of N-methoxy-N-methyl-2-amino-5-bromonicotinamide as an off-white solid. $^1$H-NMR ($d_6$-DMSO) δ: 8.10 [1H] d, 7.71 [1H] d, 6.35 [2H] s, 3.55 [3H] s, 3.24 [3H] s.; MS: m/z 260 [MH$^+$].

b) Isolated as the Hydrochloride Salt

In a nitrogen flushed flask 3.00 g (30.76 mmol) of N,O-dimetylhydroxylamine hydrochloride and 3.53 g (16.27 mmol) of 2-amino-5-bromonicotinic acid are dissolved in a mixture of 350 ml of dichloromethane, and 30 ml of N-methylmorpholine. 12.70 g (24.40 mmol) of PyBOP (1-benzotriazolyloxy-tris(pyrrolidino)phosphonium hexafluorophosphate) is added and the reaction mixture stirred at room temperature for 5 hours. The mixture is then washed with 150 ml of a 2 M solution of sodium hydroxide in water and then twice with 100 ml of a 10% aqueous citric acid solution and dried over sodium sulfate. The solvent is evaporated and the resulting oil is dissolved in 300 ml of ether. The precipitate formed is filtered off and discarded. The clear filtrate is concentrated to about half its volume and diluted with 30-60 ml of dichloromethane. The resulting solution is stirred vigorously and a 1 M solution of hydrogen chloride in anhydrous ether is added until formation of the resulting precipitate is complete. The precipitate is filtered off, washed with ether and dried by suction to afford 3.15 g (12.04 mmol, 74% yield) of N-methoxy-N-methyl-2-amino-5-bromonicotinamide hydrochloride as an off-white to beige-brown powder. $^1$H-NMR (d$_6$-DMSO) δ: 8.24 [1H] d, 7.97 [1H] d, 3.56 [3H] s, 3.26 [3H] s. MS: m/z 260 [MH$^+$]

The hydrochloride can be conveniently converted into the free base by distributing this product between ethyl acetate and 2 M aqueous sodium hydroxide, washing the aqueous layer three times with ethyl acetate, then drying the combined organic phases over sodium sulfate and evaporation and drying of the residue under vacuum.

Step 3: (2-amino-5-bromo-3-pyridyl)-phenylketone 1.00 g (3.38 mmol) of N-methoxy-N-methyl-2-amino-5-bromonicotinamide hydrochloride was suspended in 50 ml of anhydrous THF under nitrogen. The suspension was cooled to −50° C. and 13.5 ml of a 1.0 M solution of phenylmagnesium bromide in ether was added rapidly to afford an orange solution. The mixture was stirred, and slowly warmed to room temperature. The resulting yellow-orange solution was distributed between 75 ml of a 10% aqueous citric acid solution and 200 ml of ethyl acetate. The organic phase was separated and washed with 75 ml of a 10% aqueous citric acid solution and 75 ml of saturated aqueous sodium bicarbonate solution. The organic phase was then dried over sodium sulfate and evaporated to afford 985 mg of a yellow crystalline solid. $^1$H-NMR (d$_6$-DMSO) δ: 8.34 [1H] d, 7.72 [2H] s, 7.70 [1H] d, 7.65 [1H] t(m), 7.63 [2H] d(m), 7.56 [2H] t(m). MS: m/z 277 [MH$^+$].

Step 4: Synthesis of 5-bromo-3-(2-methoxy-1-phenylvinyl)-2-pyridylamine 2.600 g (8.77 mmol) of N-methoxy-N-methyl-2-amino-5-bromonicotinamide hydrochloride was suspended in 50 ml of anhydrous THF under nitrogen. The suspension was cooled to −50° C. and 32 ml of a 1.0 M solution of phenylmagnesium bromide in ether was added rapidly to afford an orange solution. The mixture was stirred, allowing to slowly warm to room temperature. After 1.5 hours the resulting solution was distributed between 50 ml of 10% aqueous citric acid solution and 400 ml of ethyl acetate. The organic phase was separated and washed with 50 ml of saturated aqueous sodium bromide solution. The organic phase was then dried over sodium sulfate and evaporated to afford 2.676 g of (2-amino-5-bromo-pyridin-3-yl)-phenyl-methanone as a yellow solid. The isolated solid was dissolved in 50 ml of anhydrous THF under nitrogen and added at room temperature to a solution obtained as follows: At 0° C. 3.836 g (19.23 mmol) of potassium bis(trimethylsilyl)amide was dissolved in 100 ml of anhydrous THF under nitrogen. At 0° C. 7.214 g (21.04 mmol) of methoxymethyltriphenylphosphonium chloride was added and the resulting mixture stirred at room temperature for 75 minutes.

Upon addition of (2-amino-5-bromo-pyridin-3-yl)-phenyl-methanone to the solution, the resulting mixture was stirred at room temperature for 75 minutes. The reaction mixture was then quenched by addition of a saturated aqueous solution of ammonium chloride and distributed between 100 ml of water and 250 ml of ethyl acetate. The aqueous phase was extracted three times with 100 ml of ethyl acetate, each. The combined organic phases were dried over sodium sulfate and evaporated. The crude material was purified by flash chromatography on silica gel using an ethyl acetate/hexane mixture and a non-linear gradient to afford 1.718 g (5.630 mmol, 64% yield over 2 steps) of 5-bromo-3-(2-methoxy-1-phenylvinyl)-2-pyridylamine. $^1$H-NMR (d$_6$-DMSO) (E)-isomer δ: 8.00 [1H] d, 7.44 [1H] d, 7.34 [2H] d(m), 7.29 [2H] t(m), 7.18 [1H] t(m), 6.51 [1H] s, 5.50 [2H] s, 3.78 [3H] s; (Z)-isomer δ: 7.97 [1H] d, 7.28 [1H] d, 7.27 [2H] t(m), 7.17 [1H] t(m), 7.14 [1H] d(m), 6.95 [1H] s, 5.60 [2H] s, 3.73 [3H] s. MS: m/z 305 [MH$^+$].

Step 5: 5-bromo-3-phenylpyrrolo[2,3-b]pyridine 1.093 g (3.582 mmol) of 5-bromo-3-(2-methoxy-1-phenylvinyl)-2-pyridylamine was dissolved in 60 ml of anhydrous 1,4-dioxane. 800 µl of 70% aqueous perchloric acid was added and the mixture heated to 100° C. for 13 hours. The mixture was then cooled to room temperature and 3 ml of triethylamine was added and the mixture evaporated to dryness. The resulting crude was crystallized from hot ethanol to afford 763 mg (2.79 mmol, 78% yield) of 5-bromo-3-phenylpyrrolo[2,3-b]pyridine as a beige-brown to brown crystalline solid. $^1$H-NMR (d$_6$-DMSO) δ: 12.19 [1H] s, 8.44 [1H] d, 8.34 [1H] d, 7.97 [1H] d, 7.72 [2H] d(m), 7.45 [2H] t, 7.27 [1H] t(m). MS: m/z 273 [MH$^+$].

Step 6: Synthesis of 5-(3,4-dimethoxyphenyl)-3-phenylmethylpyrrolo[2,3-b]pyridine A vial was charged with 50 mg (0.18 mmol) of 5-bromo-3-phenylpyrrolo[2,3-b]pyridine, 43 mg (0.24 mmol) of 3,4-dimethoxyphenylboronic acid and 6.5 mg (9.3 µmol, 5 mol %) of dichlorobis(triphenylphosphino)palladium(II). To this mixture was added 1 ml of acetonitrile and 1 ml of a 2 M aqueous solution of sodium carbonate. The vial was sealed and irradiated in a Personal Chemistry® microwave reactor with a temperature setting of 165° C. for 20 minutes. The resulting mixture was distributed between 75 ml of dichloromethane and 20 ml of a saturated aqueous solution of sodium bicarbonate in water. The organic phase was dried over sodium sulfate and evaporated. The residue obtained was recrystallized from a hot mixture of acetonitrile and ethanol to afford 20 mg (61 µmol, 34% yield) of 5-(3,4-dimethoxyphenyl)-3-phenylmethylpyrrolo[2,3-b]pyridine as a colorless crystalline solid. $^1$H-NMR (d$_6$-DMSO) δ: 11.97 [1H] s, 8.55 [1H] d, 8.38 [1H] d, 7.90 [1H] d, 7.79 [2H] d, 7.45 [2H] t, 7.30 [1H] d, 7.26 [2H] t(m), 7.06 [1H] d, 3.87 [3H] s, 3.81 [3H] s. MS, m/z: 331 [MH$^+$].

Other compounds prepared by Method 48:
TABLE 30
Structures
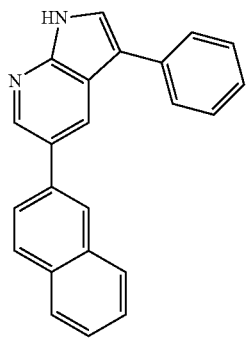
MS: m/z 321 [MH+]
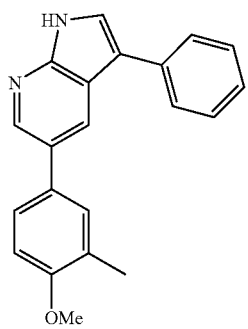
MS: m/z 315 [MH+]
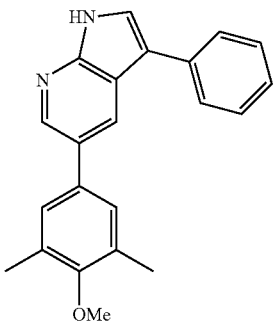
MS: m/z 329 [MH+]
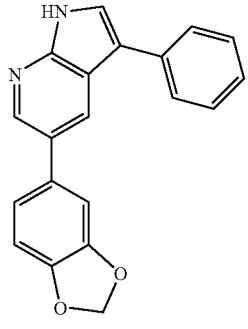
MS: m/z 315 [MH+]
TABLE 30-continued
Structures
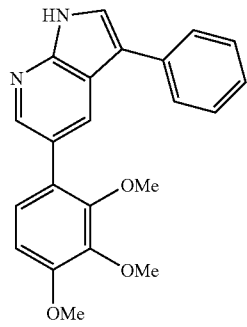
MS: m/z 361 [MH+]
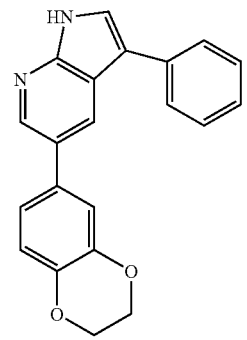
MS: m/z 329 [MH+]
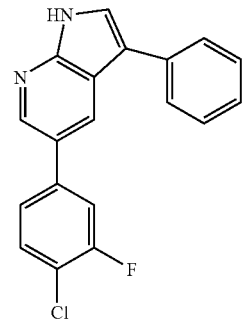
MS: m/z 323 [MH+]
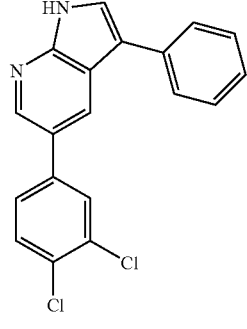
MS: m/z 339 [MH+]

TABLE 30-continued

Structures

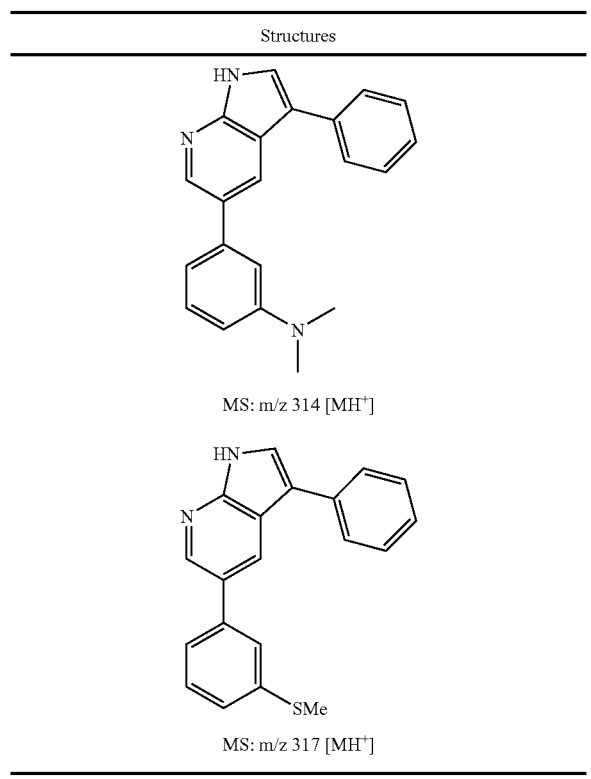

MS: m/z 314 [MH+]

MS: m/z 317 [MH+]

Method 49:

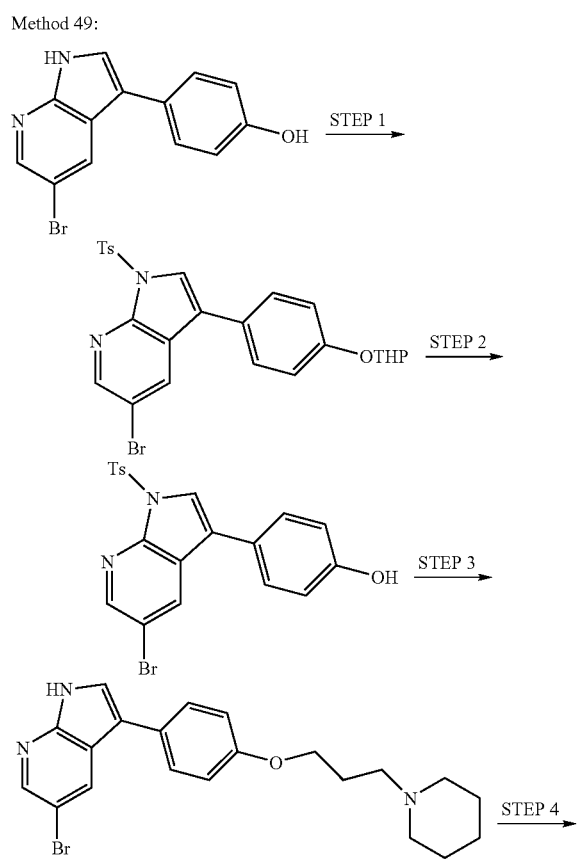

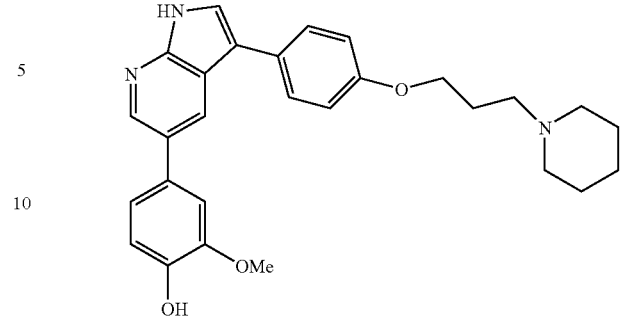

Step 1: Synthesis of 5-bromo-3-[4-(tetrahydro-pyran-2-yloxy)-phenyl]-1-(toluene-4-sulfonyl)-1H-pyrrolo[2,3-b]pyridine 1.092 g (3.77 mmol) of 5-bromo-3-[4-hydroxyphenyl]-1H-pyrrolo[2,3-b]pyridine and 200 mg of para-toluenesulfonic acid monohydrate were dissolved in 180 ml of dichloromethane. 10 ml of dihydro-1H-pyran was added and the mixture was heated to reflux for 4 hours. The mixture was then cooled to room temperature and an excess of triethylamine was added. The mixture was evaporated and 2.50 g (13.11 mmol) of para-toluenesulfonyl chloride was added. The mixture was dissolved in 150 ml of THF and the resulting solution was cooled to 0° C. An excess of sodium hydride powder was added until further addition did not result in the formation of more hydrogen gas and the mixture was stirred for 16 hours at room temperature. The resulting mixture was cooled to 0° C. and another 2.5 g (13.11 mmol) of para-toluenesulfonyl chloride along with more sodium hydride was added. The mixture was then quenched by addition of a saturated aqueous solution of ammonium chloride and distributed between 500 ml of ether and water. The organic phase was washed three times with a saturated aqueous solution of sodium bicarbonate, dried over sodium sulfate and evaporated. The crude product was purified by flash chromatography on silica gel using a gradient of ethyl acetate in hexanes to afford 1.163 g (2.21 mmol, 58% yield) of 5-bromo-3-[4-(tetrahydro-pyran-2-yloxy)-phenyl]-1-(toluene-4-sulfonyl)-1H-pyrrolo[2,3-b]pyridine as a pale yellow or pink solid. $^1$H-NMR (d$_6$-DMSO) δ: 8.53 [1H] d, 8.46 [1H] d, 8.20 [1H] s, 8.03 [2H] d(m), 7.71 [2H] d(m), 7.43 [2H] d, 7.14 [2H] d(m), 5.54 [1H] t, 3.78 [1H] m, 3.57 [1H] m, 2.35 [3H] s, 1.95-1.74 [2H] (m), 1.68-1.52 [4H] (m). MS, m/z: 527 [MH+].

Step 2: Synthesis of 4-[5-bromo-1-(toluene-4-sulfonyl)-1H-pyrrolo[2,3-b]pyridin-3-yl]-phenol 575 g (1.09 mmol) of 5-bromo-3-[4-(tetrahydro-pyran-2-yloxy)-phenyl]-1-(toluene-4-sulfonyl)-1H-pyrrolo[2,3-b]pyridine was dissolved in 250 ml of dichloromethane. To this solution was added 2.50 g (3.53 mmol) of PS-thiophenol (Argonaut Technologies) and 1.5 ml of a 2 M solution of hydrochloric acid in ether. The mixture was stirred at room temperature for 3 hours before the resin was filtered off, washing extensively with dichloromethane. The filtrate was evaporated to afford 389 mg (877 µmol, 81%) of 4-[5-bromo-1-(toluene-4-sulfonyl)-1H-pyrrolo[2,3-b]pyridin-3-yl]-phenol as a pale yellow solid. $^1$H-NMR (d$_6$-DMSO) δ: 9.67 [1H]

s, 8.52 [1H] d, 8.43 [1H] d, 8.11 [1H] s, 8.03 [2H] d, 7.58 [2H] d(m), 7.43 [2H] d, 6.89 [2H] d(m), 2.35 [3H] s. MS, m/z: 443 [MH$^+$].

Step 3: Synthesis of 5-bromo-3-[4-(3-piperidin-1-yl-propoxy)-phenyl]-1H-pyrrolo[2,3-b]pyridine hydrochloride 200 mg (0.45 mmol) of 4-[5-bromo-1-(toluene-4-sulfonyl)-1H-pyrrolo[2,3-b]pyridin-3-yl]-phenol and 1.20 g (2.80 mmol) of PS-triphenylphosphine (2.33 mmol·g$^{-1}$, Argonaut Technologies) were dissolved in 30 ml of anhydrous toluene. 325 mg (2.27 mmol) of 3-(1-piperidinyl)propanol and 300 μl (1.52 mmol) of di-iso-propylazodicarboxylate were added at room temperature and the mixture stirred for 72 hours.

The resin was filtered off and washed repeatedly with dichloromethane and ether. The filtrates were combined and evaporated. The residual beige oil was dissolved in 20 ml of methanol together with an excess of potassium hydroxide. The mixture was stirred for 48 hours at room temperature. The resulting suspension was distributed between dichloromethane and a saturated solution of sodium bicarbonate in water. The phases were separated and the aqueous layer was extracted twice with dichloromethane. The combined organic phases were dried over sodium sulfate and evaporated. The crude was purified by flash chromatography on an amine functionalized silica gel (ISCO RediSep® amine column) using a gradient of ethyl acetate in hexanes. The isolated material was dispersed in 75 ml of ether and the insoluble part filtered off. To the clear filtrate was added an excess of a 2 M solution of hydrochloric acid in ether. The precipitate was filtered off and dried in vacuo to afford 133 mg (0.30 mmol, 66% yield) of 5-bromo-3-[4-(3-piperidin-1-yl-propoxy)-phenyl]-1H-pyrrolo[2,3-b]pyridine hydrochloride as a yellow solid. $^1$H-NMR (d$_6$-DMSO) δ: 12.17 [1H] (d), 10.68 [1H] s,br, 8.39 [1H] d, 8.33 [1H] d, 7.87 [1H] d, 7.65 [2H] d, 7.03 [2H] d, 4.10 [2H] t, 8.46 [2H] d, 3.18 [2H] m, 2.89 [2H] m, 2.24 [2H] m, 1.89-1.76 [4H] (m), 1.71 [1H] m, 1.39 [1H] m. MS, m/z: 414 [MH$^+$].

Step 4: Synthesis of 2-methoxy-4-{3-[4-(3-piperidin-1-yl-propoxy)-phenyl]-1H-pyrrolo[2,3-b]pyridin-5-yl}-phenol 100 mg (0.24 mmol) of 5-bromo-3-[4-(3-piperidin-1-yl-propoxy)-phenyl]-1H-pyrrolo[2,3-b]pyridine hydrochloride, 120 mg (0.33 mmol) of 2-[3-Methoxy-4-(4-methoxy-benzyloxy)-phenyl]-4,4,5,5-tetramethyl-[1,3,2]dioxaborolane and 10 mg (5 mol %) of dichlorobis(triphenylphosphino)palladium(II) were placed in a vial and 1.5 ml of acetonitrile and 1.5 ml of a 2 M aqueous solution of sodium carbonate were added. The mixture was irradiated in a Personal Chemistry® microwave reactor to 165° C. for 1200 sec. The resulting mixture was distributed between dichloromethane and a saturated aqueous solution of sodium bicarbonate. The aqueous layer was extracted three times with dichloromethane and the combined organic phases were dried over sodium sulfate and evaporated. The crude product was purified by flash chromatography on amine functionalized silica gel (ISCO RediSep® amine column) using a gradient of ethyl acetate in hexanes. The resulting intermediate was dissolved in 30 ml of dichloromethane and 750 mg (1.06 mmol) of PS-thiophenol (Argonaut Technologies) was added. To this was added 1.5 ml of trifluoroacetic acid and the mixture was stirred at room temperature for 2 hours. The resin was filtered off and washed with dichloromethane. The filtrate was washed with a saturated aqueous solution of sodium sulfate and evaporated. The residue was triturated with 20 ml of dichloromethane and dried by suction to afford 9 mg (20 μmol, 8% yield) of 2-methoxy-4-{3-[4-(3-piperidin-1-yl-propoxy)-phenyl]-1H-pyrrolo[2,3-b]pyridin-5-yl}-phenol as a beige powder. $^1$H-NMR (d$_6$-DMSO) δ: 11.83 [1H] d, 9.06 [1H] s, 8.50 [1H] d, 8.28 [1H] d, 7.76 [1H], 7.67 [2H] d(m), 7.25 [1H] d, 7.12 [1H] dd, 7.01 [2H] d(m), 6.88 [1H] d, 4.02 [2H] t, 3.87 [3H] s, 2.39 [2H] t, 2.34 [4H] (m), br, 1.88 [2H] t, 1.50 [4H] qui, 1.38 [2H] (m). MS, m/z: 458 [MH$^+$].

Method 50:

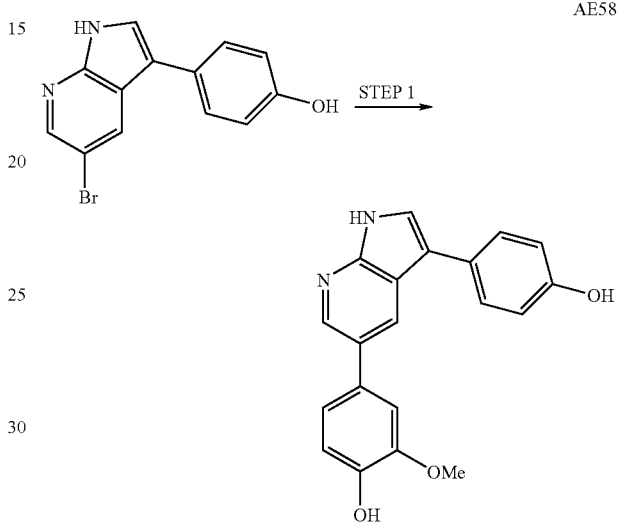

AE58

Step 1: Synthesis of 4-{5-[3-methoxy-4-hydroxy-phenyl]-1H-pyrrolo[2,3-b]pyrazin-3-yl}-phenol 145 mg (0.44 mmol) of 5-bromo-3-[4-hydroxyphenyl]-1H-pyrrolo[2,3-b]pyridine, 240 mg (0.65 mmol) of 2-[3-Methoxy-4-(4-methoxy-benzyloxy)-phenyl]-4,4,5,5-tetramethyl-[1,3,2]dioxaborolane and 25 mg (8 mol %) of dichlorobis(triphenylphosphino) palladium(II) were placed in a vial and 1.5 ml of acetonitrile and 1.5 ml of a 2 M aqueous solution of sodium carbonate were added. The mixture was irradiated in a Personal Chemistry® microwave reactor to 165° C. for 1200 sec. The resulting mixture was distributed between dichloromethane and a saturated aqueous solution of sodium bicarbonate. The aqueous layer was extracted twice with dichloromethane and the combined organic phases were dried over sodium sulfate and evaporated. The crude was purified by flash chromatography on silica gel using a gradient of ethyl acetate in hexanes. The resulting intermediate was dissolved in 70 ml of dichloromethane and 2.00 g (2.82 mmol) of PS-thiophenol (Argonaut Technologies) was added. To this was added 1 ml of trifluoroacetic acid and the mixture stirred at room temperature for 1 hour. The resin was filtered off and washed with dichloromethane. The filtrate was washed with a saturated aqueous solution of sodium bicarbonate. The phases were separated and the aqueous layer extracted twice with ethyl acetate. All organic phases were combined, dried over sodium sulfate and evaporated. The residue was heated up with acetonitrile, cooled down to room temperature and the supernatant was removed. The residue was dried in vacuo to afford 72 mg (0.22 mmol, 50% yield) of 4-{5-[3-methoxy-4-hydroxy-phenyl]-1 H-pyrrolo[2,3-b]

pyrazin-3-yl}-phenol as a beige powder. ¹H-NMR (d₆-DMSO) δ: 11.77 [1H] d, 9.37 [1H] s, br, 9.06 [1H] s, br, 8.49 [1H] d, 8.27 [1H] d, 7.69 [1H] d, 7.56 [2H] d(m), 7.25 [1H] d, 7.12 [1H] dd, 6.88 [1H] d, 6.86 [2H] d(m), 3.87 [3H] s. MS, m/z: 333 [MH⁺].

Method 51:

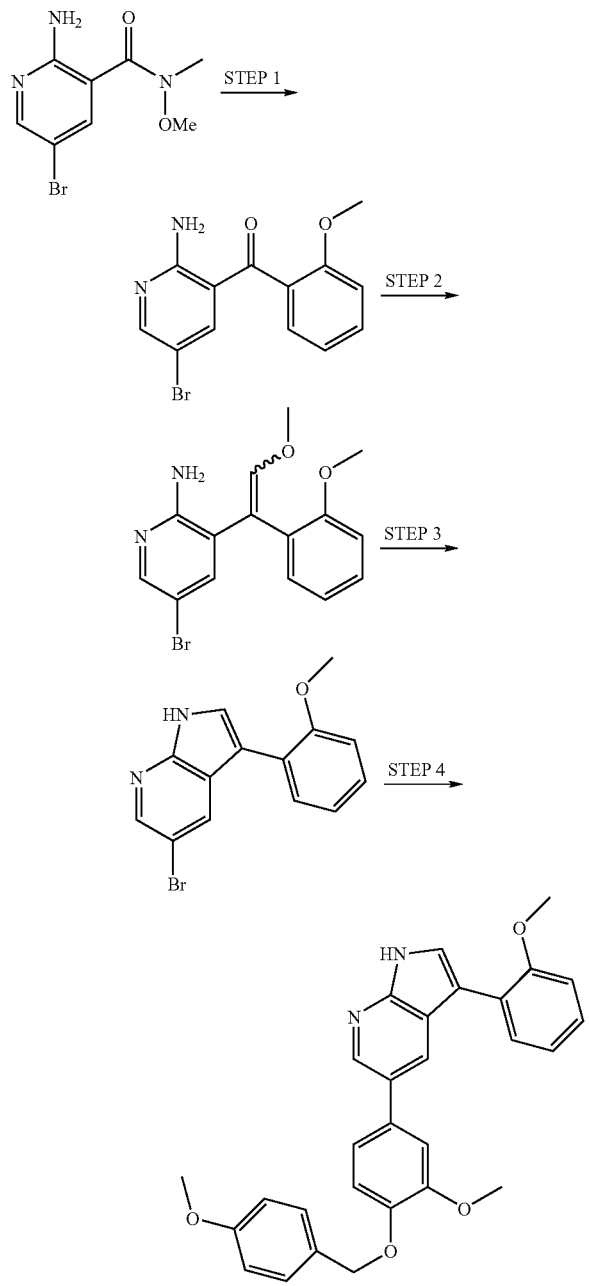

Step 1: Synthesis of 5-bromo-3-(2-methoxy-phenyl)-1H-pyrrolo[2,3-b]pyridine

To a flame-dried 100 ml round bottomed flask were added 2-amino-5-bromo-N-methoxy-N-methyl-nicotinamide (661 mg, 2.54 mmol) and anhydrous THF (15 ml). The solution was stirred at −55° C. for 5 minutes under nitrogen, then a 0.5 M solution of 2-methoxyphenyl magnesium bromide in THF (18 ml, 9.0 mmol) was added dropwise over 3 minutes. The resulting solution was allowed to warm to room temperature over 2 hours then quenched by addition of 1 M citric acid. (25 ml). Ethyl acetate (50 ml) was added, and the layers were separated. The aqueous fraction was extracted three times with ethyl acetate, and the combined organic fractions were washed with brine, dried (Na₂SO₄), filtered and concentrated to give a sticky yellow solid. Recrystallization from ethanol provided 619.5 mg (79%) of (2-amino-5-bromo-pyridin-3-yl)-(2-methoxy-phenyl)-methanone as yellow needles. MS m/z: 308 [MH]⁺.

Step 2: Synthesis of 5-bromo-3-[2-methoxy-1-(2-methoxy-phenyl)-vinyl]-pyridin-2-ylamine Into a 50 ml flame-dried round bottomed flask were added potassium bis(trimethylsilyl)amide (832 mg, 39.2 mmol) and anhydrous THF (10 ml). The slurry was cooled to 0° C. for 5 minutes under nitrogen, then (methoxymethyl)triphenylphosphonium chloride (1.53 g, 4.47 mmol) was added. The resulting red-orange solution was stirred at room temperature for 45 min, then a solution of (2-amino-5-bromo-pyridin-3-yl)-(2-methoxy-phenyl)-methanone (601 mg, 1.95 mmol in 10 ml THF) was added all at once. The reaction was stirred under nitrogen for 4 hours then quenched by addition of a saturated aqueous solution of ammonium chloride (25 ml). Ethyl acetate (100 ml) was added, and the layers were separated. The aqueous fraction was extracted three times with ethyl acetate, and the combined organic fractions were washed with brine, dried (Na₂SO₄), filtered and concentrated to give a brown, sticky oil. Purification by flash chromatography on silica gel using a gradient of ethyl acetate in hexanes gave 554 mg (84%) of 5-bromo-3-[2-methoxy-1-(2-methoxy-phenyl)-vinyl]-pyridin-2-ylamine as a mixture of E- and Z-isomers.

Step 3: Synthesis of 5-bromo-3-(2-methoxy-phenyl)-1H-pyrrolo[2,3-b]pyridine

A 50 ml round bottomed flask was charged with 403 mg of 5-bromo-3-[2-methoxy-1-(4-methoxy-phenyl)-vinyl]-pyridin-2-ylamine (1.2 mmol; combined E- and Z-isomers), 1,4-dioxane (5 ml), and 70% aqueous perchloric acid (250 μl). The flask was fitted with a reflux condenser and nitrogen inlet adapter and heated in an oil bath to 100° C. for 8 hours. The reaction mixture was concentrated, then treated with 15 ml of a saturated aqueous solution of sodium bicarbonate followed by ethyl acetate (20 ml). The layers were separated, and the aqueous fraction was extracted twice with ethyl acetate. The combined organic fractions were washed with brine, dried (Na₂SO₄), filtered, and concentrated. The residue was triturated with ether to afford 300 mg (82%) of 5-bromo-3-(2-methoxy-phenyl)-1H-pyrrolo[2,3-b]pyridine as a tan powder. ¹H-NMR (d₆-DMSO) δ=12.16 (br. s, 1H), 8.36 (d, 1H), 8.18 (d, 1H), 7.82 (d, 1H), 7.58 (d, 1H), 7.36 (t, 1H), 7.19 (d, 1H),7.10 (t, 1H), 3.88 (s, 3H); MS m/z: 303 [MH]⁺.

Step 4: Synthesis of 5-[3-methoxy-4-(4-methoxy-benzyloxy)-phenyl]-3-(2-methoxy-phenyl)-1H-pyrrolo[2,3-b]pyridine 2-[3-Methoxy-4-(4-methoxy-benzyloxy)-phenyl]-4,4,5,5-tetramethyl-[1,3,2]dioxaborolane was prepared as follows. To a flame-dried 50 ml round bottomed flask were added 2-methoxy-4-(4,4,5,5-tetramethyl-[1,3,2]dioxaborolan-2-yl)-phenol (1.00 g, 4.00 mmol) and anhydrous DMF (20 ml). Sodium hydride (251 mg, 6.29 mmol; 60% dispersion in mineral oil) was added in three portions, and the suspension was stirred under nitrogen for 30 minutes para-Methoxy benzyl chloride (655 μl, 3.62 mmol) and tetrabutyl ammonium iodide (10 mg, 0.03 mmol) were added, and the reaction mixture was stirred for an additional 16 hours. The reaction mixture was concentrated, then cooled in an ice-bath, and 50 ml of 1 M citric acid was added followed by 100 ml ethyl acetate. The layers were separated, and the aqueous phase was extracted three times with ethyl acetate. The combined organic fractions were washed with brine, dried ($Na_2SO_4$), filtered and concentrated to give a tan powder. Trituration with diethyl ether gave 1.34 g (91%) of 2-[3-Methoxy-4-(4-methoxy-benzyloxy)-phenyl]-4,4,5,5-tetramethyl-[1,3,2]dioxaborolane as a tan powder. $^1$H-NMR ($CDCl_3$) δ=7.35 (m, 2H), 7.29 (s, 1H), 7.26 (s, 1H), 6.89 (m, 3H), 5.11 (s, 2H), 3.91 (s, 3H), 3.80 (s, 3H), 1.33 (s, 12H); MS m/z: 393 [M+Na]$^+$.

A Personal Chemistry® microwave vial (2-5 ml size) was charged with 5-bromo-3-(2-methoxy-phenyl)-1H-pyrrolo[2,3-b]pyridine (98 mg, 0.33 mmol), 2-[3-methoxy-4-(4-methoxy-benzyloxy)-phenyl]-4,4,5,5-tetramethyl-[1,3,2]dioxaborolane (148 mg, 0.400 mmol), 6.5 mg (9.3 μmol, 5 mol %) of dichlorobis(triphenylphosphino)palladium(II), 1 ml of acetonitrile and 1 ml of a 2 M aqueous solution of sodium carbonate. The vial was sealed, evacuated and purged three times with nitrogen, then irradiated in a Personal Chemistry® microwave reactor with a temperature setting of 150° C. for 30 minutes. Ethyl acetate (50 ml) was added, and the layers were separated. The aqueous fraction was extracted three times with ethyl acetate, and the combined organic fractions were washed with brine, dried ($Na_2SO_4$), filtered and concentrated. Purification by flash chromatography on silica gel using a gradient of ethyl acetate in hexanes gave 75 mg (50%) of 5-[3-methoxy-4-(4-methoxy-benzyloxy)-phenyl]-3-(2-methoxy-phenyl)-1H-pyrrolo[2,3-b]pyridine as a light yellow solid. $^1$H-NMR ($d_6$-DMSO) δ=12.12 (br.s, 1H), 8.51 (d, 1H), 8.11 (d, 1H), 7.70 (d, 1H), 7.57 (dd, 1H), 7.38 (d, 2H), 7.27 (t, 1H), 7.25 (d, 1H), 7.18 (dd, 1H), 7.11 (m, 2H), 7.02 (t, 1H), 6.95 (d, 2H), 5.03 (s, 2H), 3.85 (s, 3H), 3.82 (s, 3H), 3.75 (s, 3H); MS m/z: 467 [MH]$^+$.

Other compounds prepared by Method 51:

TABLE 31

| Structure |
| --- |
| 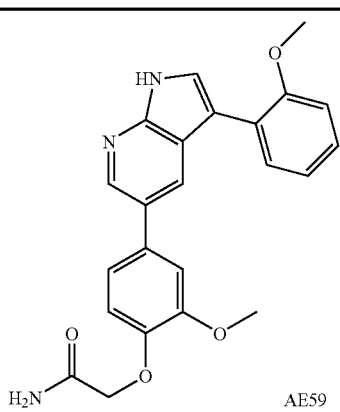 AE59<br>MS: m/z 404 [MH]$^+$. |

TABLE 31-continued

| Structure |
| --- |
| 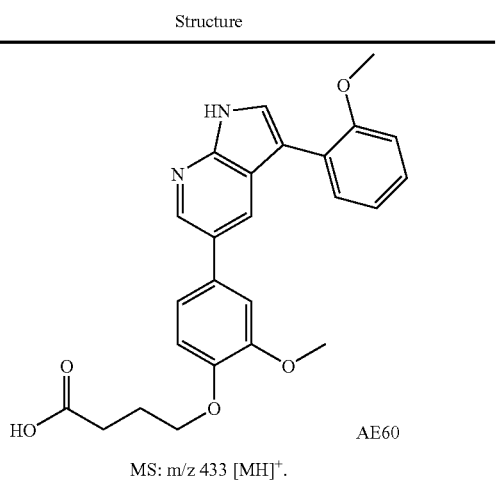 AE60<br>MS: m/z 433 [MH]$^+$. |
| 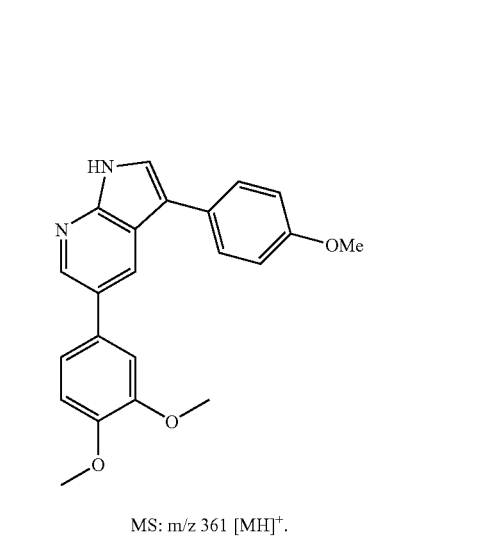<br>MS: m/z 361 [MH]$^+$. |
| 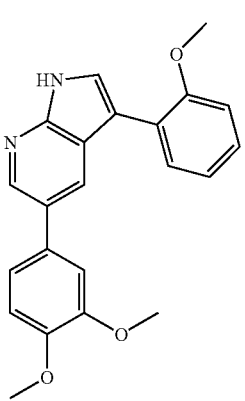<br>MS: m/z 361 [MH]$^+$. |

TABLE 31-continued
Structure
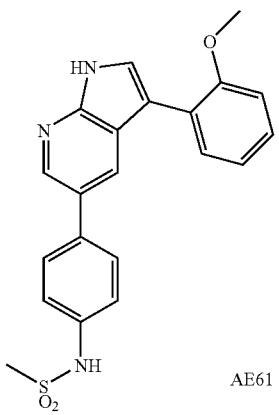
AE61
MS: M/Z 394 [MH]+.
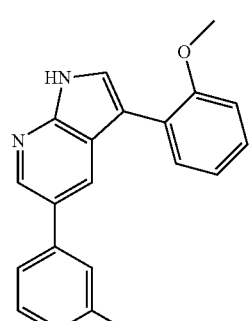
MS: M/Z 317 [MH]+.
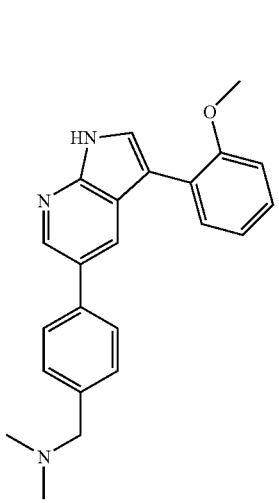
MS: m/z 358 [MH]+.
TABLE 31-continued
Structure
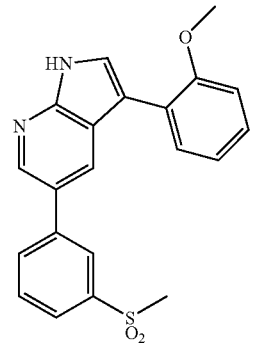
MS: M/Z 379 [MH]+.
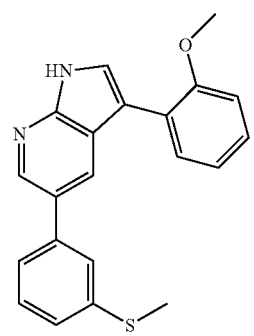
MS: M/Z 347 [MH]+.
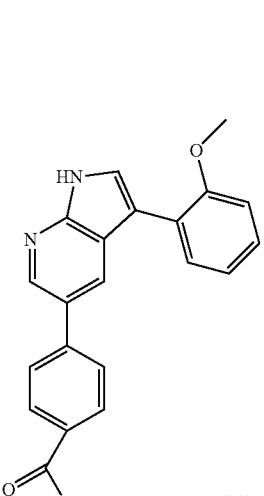
AE62
MS: m/z 344 [MH]+.

TABLE 31-continued

Structure

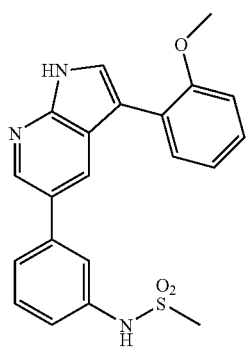

MS: M/Z 394 [MH]⁺.

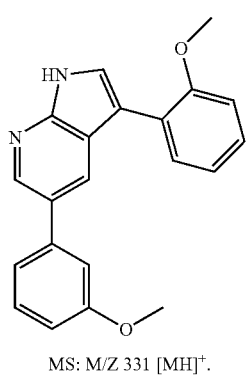

MS: M/Z 331 [MH]⁺.

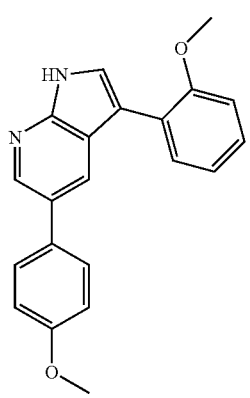

MS: m/z 331 [MH]⁺.

TABLE 31-continued

Structure

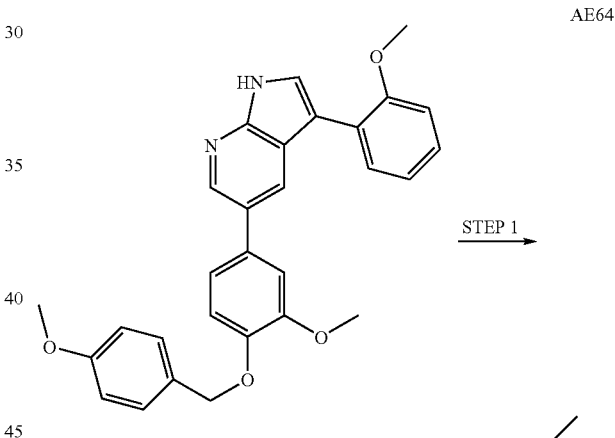

AE63 *

MS: M/Z 403 [MH]⁺.

* obtained from 7-Bromo-4,5-dihydro-3H-benzo[b]oxepin-2-one (obtained via Baeyer-Villiger reaction).

Method 52:

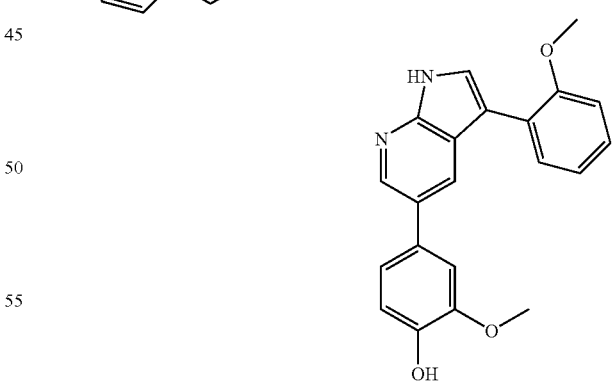

AE64

Step 1: Synthesis of 2-Methoxy-4-[3-(2-methoxyphenyl)-1H-pyrrolo[2,3-b]pyridin-5-yl]-phenol To a 50 ml round bottomed flask were added 5-[3-methoxy-4-(4-methoxy-benzyloxy)-phenyl]-3-(2-methoxy-phenyl)-1H-pyrrolo[2,3-b]pyridine (48 mg, 0.10 mmol), methylene chloride (2.5 ml) and 396 mg (0.28 mmol) PS-thiophenol (1.41 mmol·g⁻¹; Argonaut Technologies). Trifluoroacetic acid (500 µl) was added and the suspension was shaken in a orbital shaker for 1 hour. The yellow reaction mixture was filtered, and the resin was washed three times with dichloromethane and ether, then twice with dichloromethane. The combined filtrate was concentrated to obtain a yellow residue, which was distributed between ethyl acetate and saturated aqueous solution of sodium bicarbonate. The layers were separated, and the aqueous phase was extracted three times with ethyl acetate. The combined organic fractions were washed with brine, dried (Na$_2$SO$_4$), filtered and concentrated. Purification by flash chromatography on silica gel using a gradient of ethyl acetate and hexanes gave 31 mg (86%) of 2-methoxy-4-[3-(2-methoxy-phenyl)-1H-pyrrolo[2,3-b]pyridin-5-yl]-phenol as a light yellow powder. ¹H-NMR (d$_6$-DMSO) δ=11.87 (br.s, 1H), 9.04 (br.s, 1H), 8.48 (d, 1H), 8.07 (d, 1H), 7.68 (dd, 1H), 7.57 (dd, 1H), 7.27 (t, 1H), 7.20 (d, 1H), 7.13 (d, 1H), 7.08 (dd, 1H), 7.02 (t, 1H), 6.85 (d, 1H), 3.85 (s, 3H), 3.82 (s, 3H); MS m/z: 347 [MH]⁺.

Other compounds prepared by Method 52:

TABLE 32

Structure

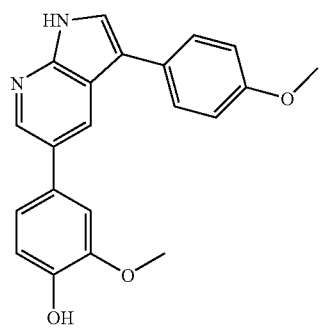

MS: m/z 347 [MH]⁺.

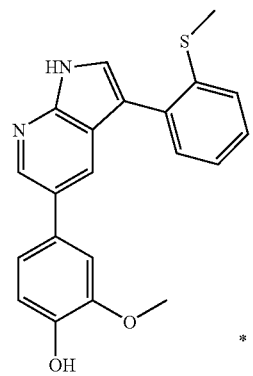

MS: m/z 363 [MH]⁺.

TABLE 32-continued

Structure

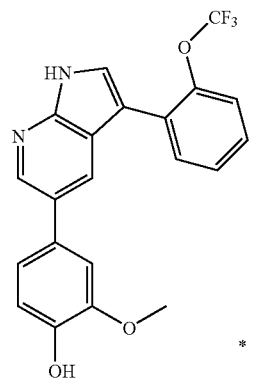

MS: m/z: 400 [MH]⁺.

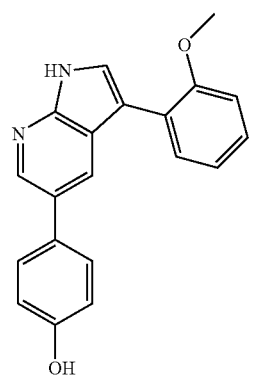

MS: m/z 317 [MH]⁺.

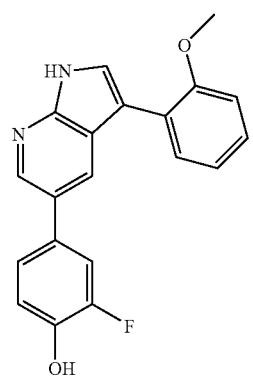

MS: m/z 334 [MH]⁺.

* (2-amino-5-bromopyridin-3-yl)(2-(trifluoromethoxy)phenyl)methanone and (2-amino-5-bromopyridin-3-yl)(2-(methylthio)phenyl)methanone needed in these cases were prepared by the method illustrated below.

235

Synthesis of (2-amino-5-bromo-pyridin-3-yl)-(2-trifluoromethoxy-phenyl)-methanone

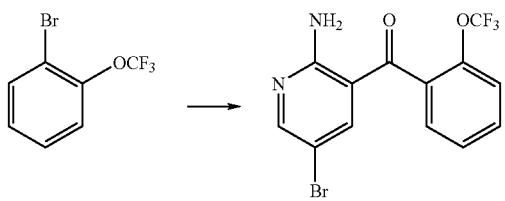

To a flame-dried 100 ml round bottomed flask was added 1-bromo-2-(trifluoromethoxy)benzene (2.39 g, 9.9 mmol). The flask was fitted with a rubber septum, purged with nitrogen then charged with anhydrous THF (20 ml). The solution was cooled to −78° C. for 10 min, then a 2.5 M solution of n-butyl lithium in hexanes (3.9 ml, 9.8 mmol) was added dropwise over 3 minutes. The resulting solution was stirred at −78 ° C. for 40 minutes under nitrogen, then a solution of 739 mg (2.84 mmol) of 2-amino-5-bromo-N-methoxy-N-methyl-nicotinamide in 5 ml of THF was added dropwise over 3 minutes. The resulting red solution was allowed to warm to room temperature over 5 hours, then the reaction was quenched by addition of 10 ml of a saturated aqueous solution of ammonium chloride. Ethyl acetate (50 ml) was added, and the layers were separated. The aqueous fraction was extracted three times with ethyl acetate, and the combined organic fractions were washed with brine, dried ($Na_2SO_4$), filtered and concentrated. Purification by flash chromatography on silica gel using a gradient of ethyl acetate in hexanes gave 530 mg (52%) of (2-amino-5-bromo-pyridin-3-yl)-(2-trifluoromethoxy-phenyl)-methanone as a yellow-orange solid. $^1$H-NMR (CDCl$_3$) δ=8.29 (d, 1H), 7.60 (m, 2H,), 7.45 (t, 1H), 7.42 (m, 3H), 1.79 (br. s, 2H); MS m/z: 361 [MH]$^+$.

Method 53:

AE65

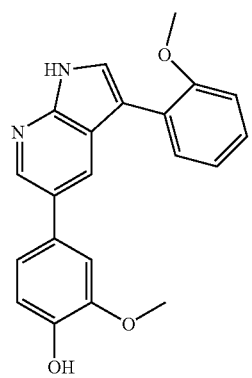

STEP 1

236

Step 1: Synthesis of 3-(2-Methoxy-phenyl)-5-[3-methoxy-4-(2-pyrrolidin-1-yl-ethoxy)-phenyl]-1H-pyrrolo[2,3-b]pyridine To an 8 ml borosilicate reaction vial were added 150 mg (0.350 mmol) of PS-triphenylphosphine (2.33 mmol·g$^{-1}$; Argonaut Technologies) and anhydrous methylene chloride (5 ml). The vial was fitted with a rubber septum and the suspension was stirred for 5 minutes in an ice-bath (0° C.). Diisopropyl azodicarboxylate (68 µL, 0.35 mmol) was added dropwise, and the mixture was allowed to warm to room temperature over 20 minutes. To the reaction vial was added 2-pyrrolidin-1-yl-ethanol (54 mg, 0.47 mmol) and 2-methoxy-4-[3-(2-methoxy-phenyl)-1H-pyrrolo[2,3-b]pyridin-5-yl]phenol (60 mg, 0.17 mmol), and the suspension was stirred at room temperature for 8 hours. The yellow reaction mixture was filtered, and the resin was washed three times with DCM and ether, then twice with DCM. The combined filtrate was concentrated to obtain a yellow residue, which was purified by flash chromatography on amine functionalized silica gel (ISCO RediSep® amine column) using a gradient of ethyl acetate in hexanes to afford 12 mg (8%) of 3-(2-methoxy-phenyl)-5-[3-methoxy-4-(2-pyrrolidin-1-yl-ethoxy)-phenyl]-1H-pyrrolo[2,3-b]pyridine as a light yellow powder. $^1$H-NMR(d$_6$-DMSO) δ=11.87 (br.s, 1H), 8.51 (d, 1H), 8.18 (s, 1H), 8.11 (d, 1H), 7.70 (d, 1H), 7.57 (dd, 1H), 7.27 (m, 1H), 7.24 (d, 1H), 7.17 (dd, 1H), 7.12 (dd, 1H), 7.06 (s, 1H), 7.04 (m, 1H), 4.08 (t, 2H), 3.85 (s, 3H), 3.83 (s, 3H), 2.82 (t, 2H), 2.55 (m, 4H), 1.69 (m, 4H); MS m/z: 444 [MH]$^+$.

Other compounds prepared according to Method 53:

TABLE 33

| Structure |
| --- |
| 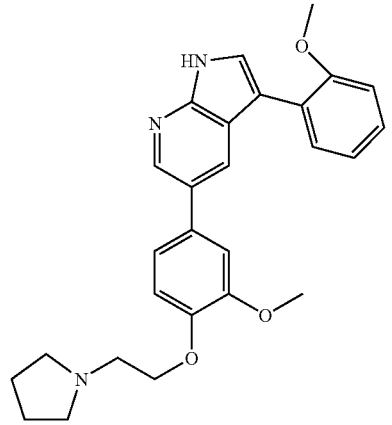 |
| 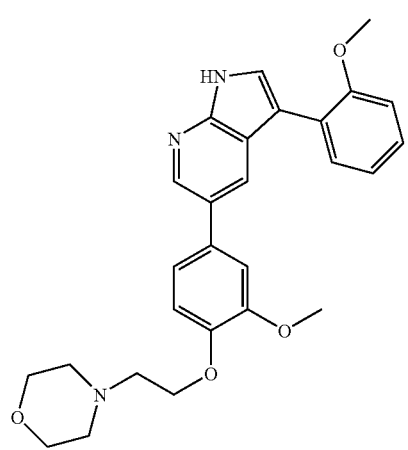<br>MS: m/z 460 [MH]$^+$. |

TABLE 33-continued
Structure
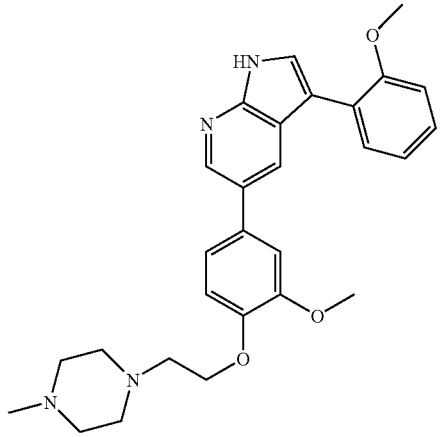
MS: m/z 473 [MH]+.
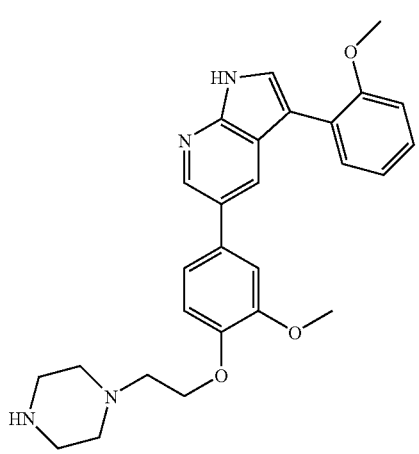
MS: m/z 459 [MH]+.
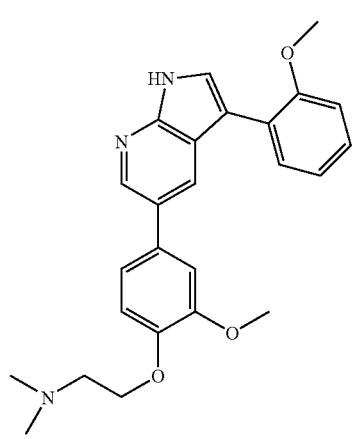
MS: m/z 418 [MH]+.
TABLE 33-continued
Structure
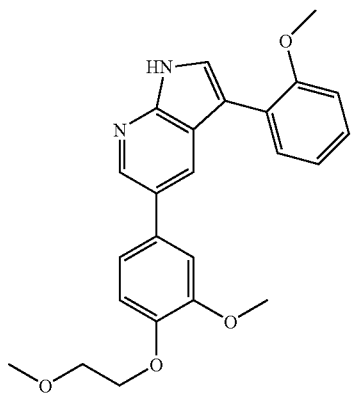
MS: m/z 405 [MH]+.
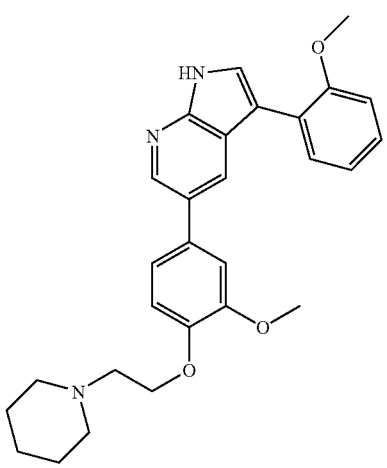
MS: m/z 458 [MH]+.
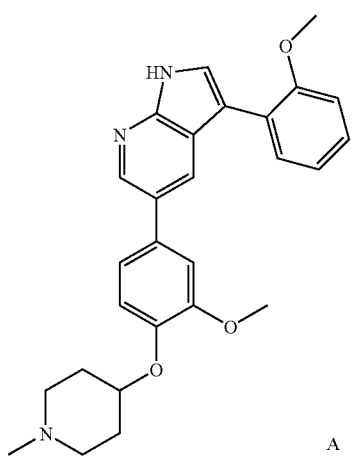
E66
MS: m/z 444 [MH]+.

TABLE 33-continued

Structure

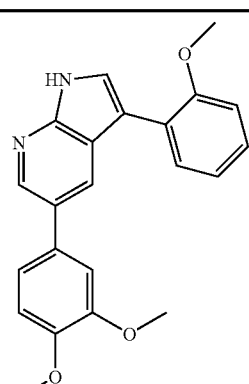

MS: m/z 405 [MH]⁺.

The purification of the compounds in above table was accomplished using reverse phase HPLC (C18; 5-95% gradient solvent A: 0.1% formic acid aq. containing 5% ACN, solvent B: 0.1% formic acid in ACN, with mass-triggered collection).

Method 54:

AE67

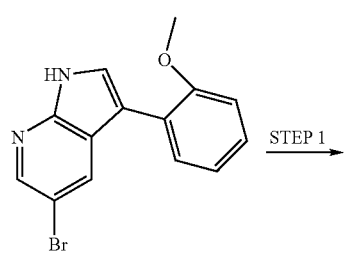

STEP 1 →

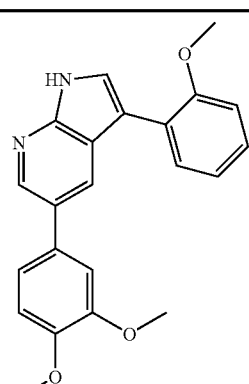

Step 1: Synthesis of 3-(2-Methoxy-phenyl)-5-(1H-pyrrol-2-yl)-1H-pyrrolo[2,3-b]pyridine To a Personal Chemistry® microwave vial (2-5 ml size) were added 5-bromo-3-(2-methoxy-phenyl)-1H-pyrrolo[2,3-b]pyridine (96 mg, 0.32 mmol), 1-N-(BOC)pyrrole-2-boronic acid (103 mg, 0.487 mmol) and 12 mg (5 mol %) of dichloro[1,1'-bis(diphenylphoshino)ferrocene]palladium(II) dichloromethane adduct, 1 ml of acetonitrile and 1 ml of a 2 M aqueous solution of sodium carbonate. The vial was sealed, evacuated and purged three times with nitrogen, then irradiated in a Personal Chemistry® microwave reactor with a temperature setting of 150° C. for 15 minutes. Ethyl acetate (50 ml) was added, and the layers were separated. The aqueous fraction was extracted three times with ethyl acetate, and the combined organic fractions were washed with brine, dried (Na₂SO₄), filtered and concentrated. Purification by flash chromatography on silica gel using a gradient of ethyl acetate in hexanes gave 28.1 mg (30%) of 3-(2-methoxy-phenyl)-5-(1H-pyrrol-2-yl)-1H-pyrrolo[2,3-b]pyridine as a tan solid. ¹H-NMR (d₆-DMSO) δ=11.78 (br.s, 1H), 11.32 (br. s, 1H), 8.56 (d, 1H), 8.20 (d, 1H), 7.66 (d, 1H), 7.59 (dd, 1H), 7.29 (dd, 1H), 7.12 (d, 1H), 7.07 (t, 1H), 6.83 (m, 1H), 6.49 (m, 1H), 6.10 (m, 1H), 3.82 (s, 3H); MS m/z: 290 [MH]⁺.

Other compounds prepared according to Method 54:

TABLE 34

Structure

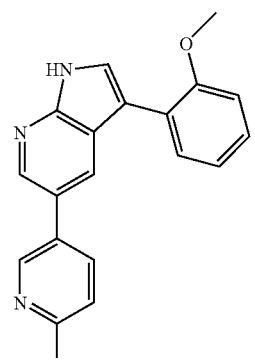

MS: m/z 332 [MH]⁺.

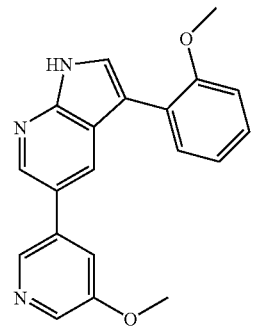

MS: m/z 332 [MH]⁺.

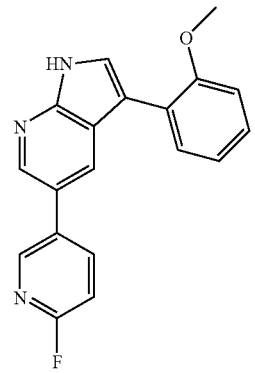

MS: m/z 320 [MH]⁺.

TABLE 34-continued

| Structure |
|---|
| 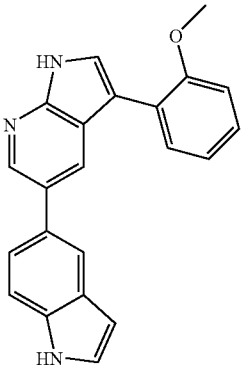<br>MS: m/z 340 [MH]+. |
| 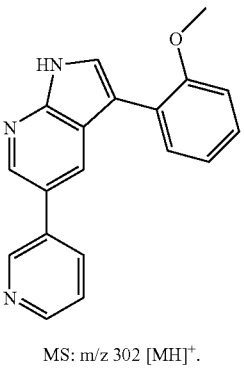<br>MS: m/z 302 [MH]+. |
| 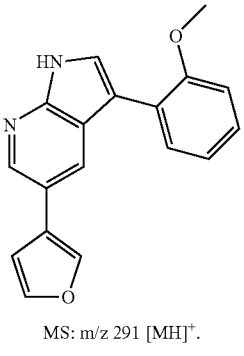<br>MS: m/z 291 [MH]+. |

Method 55:

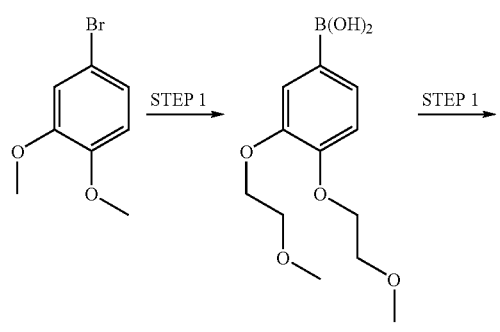

AE68

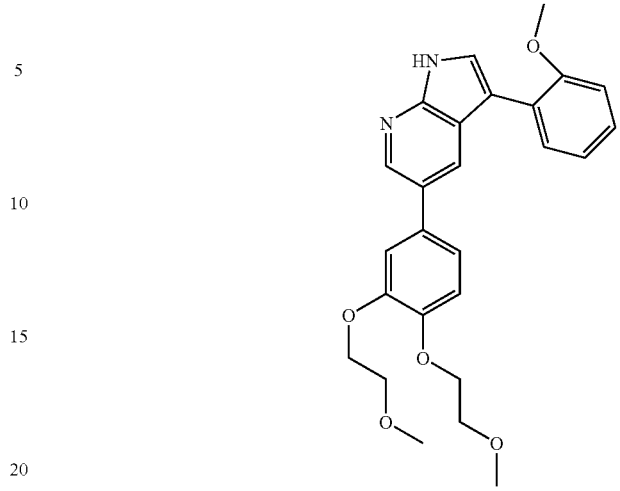

Step 1: Synthesis of 3,4-bis(2-methoxyethoxy)phenylboronic acid 6.51 g (0.0300 mol) of 4-bromoveratrole is dissolved in 50 ml of dichloromethane. To this suspension is added 37.6 g (0.150 mol) of boron tribromide at 0° C. The mixture was stirred for 3 hours at room temperature. Solvents were removed under reduced pressure. The resulting brown oil was dissolved in ethyl acetate and filtered through a pad of silica gel. The filtrate was concentrated to afford 5.45 g of 4-bromo catechol as a light brown oil.

1.89 g (10.0 mmol) of this oil is dissolved in 50 ml of anhydrous DMF and 576 mg (24.0 mmol) of sodium hydride was added. To the resulting solution was added 5.56 g (40.0 mmol) of bromoethyl methyl ether at 0° C. over 25 minutes. The mixture was stirred overnight from 0° C. to room temperature. 5 ml of water was added to quench the reaction. After removal of the solvent, the black oily residue was adsorbed on celite, and the resulting solid washed with ethyl acetate. The filtrate was then concentrated to give 3,4-bis (2-methoxyethoxy)bromobenzene as a yellowish solid.

The solid was dissolved in anhydrous THF and the resulting solution cooled to –78° C. To the solution was added 4.8 ml of a 2.5 M solution of n-butyl lithium in hexanes at –78° C. over 10 minutes. The mixture was then stirred for 30 minutes at –78° C. 2.77 ml (12 mmol) of tri-iso-propyl borate was then added. The reaction was stirred for another 30 minutes at –78° C. and then warmed to 0° C. over 2 hours. The mixture was then cooled to –20° C. and 10 ml of aqueous 2 N hydrochloric acid was added to the mixture. After stirring for 20 minutes, the reaction mixture was transferred to a separating funnel and extracted three times with 100 ml of ethyl acetate. The combined organic layers were dried over sodium sulfate and concentrated to afford 2.85 g of a brown oil. The oil was titurated with ether to afford 625 mg (2.44 mmol; 8% overall yield) of 3,4-bis (2-methoxyethoxy)phenylboronic acid as a colorless powder. $^1$H-NMR (d$_4$-methanol) δ: 7.36 [2H] m, 7.23 [2H] m, 6.98 [1H] d (7.5 Hz), 6.94 [1H] d (8.5 Hz), 4.16 [4H] m, 3.75 [4H] m, 3.43 [3H] s, 3.42 [3H] s. MS m/z: 271.1 [MH+], 293.1 [MNa+].

Step 2: Synthesis of 5-[3,4-Bis-(2-methoxy-ethoxy)-phenyl]-3-(2-methoxy-phenyl)-1H-pyrrolo[2,3-b]pyridine A vial is charged with 81.0 mg (0.300 mmol) of 3,4-bis(2-methoxyethoxy)phenylboronic acid, 60.6 mg (0.200 mmol) of 5-bromo-3-(2-methoxyphenyl)-1H-pyrrolo[2,3-b]pyridine and 8.3 mg (5 mol %) of bis(triphenylphosphino)palladium(II)-dichloride. 1.5 ml of acetonitrile and 1.5 ml of a 2 M aqueous solution of sodium carbonate were added and the mixture irradiated in a Personal Chemistry® microwave reactor to 150° C. for 15 minutes. The mixture was extracted with three times with 15 ml of ethyl acetate. The combined organic layers were dried over anhydrous sodium sulfate and concentrated. The dark brown residue (187 mg) was purified by flash chromatography on silicon using a gradient of ethyl acetate in hexane to give 57 mg of 5-[3,4-bis-(2-methoxy-ethoxy)-phenyl]-3-(2-methoxy-phenyl)-1H-pyrrolo[2,3-b]pyridine as a colorless powder. $^1$H-NMR (d$_4$-methanol) δ: 8.41 [1H] d (2.0 Hz), 8.17 [1H] d (2.0 Hz), 7.63 [1H] s, 7.56 [1H] dd (1.5 Hz, 7.5 Hz), 7.30 [1H] m, 7.26 [1H] d (2.5 Hz), 7.20 [1H] dd (2.3 Hz, 8.3 Hz), 7.11 [1H] d (8 Hz), 7.08 [1H] d (8.5 Hz), 7.05 [1H] dt (1 Hz, 7.5 Hz) 4.24 [2H] m, 4.19 [2H] m, 3.77 [4H] m, 3.44 [3H] s, 3.43 [3H] s. MS m/z: 449.2 [MH$^+$], 471.1.1 [MNa+].

Method 56:

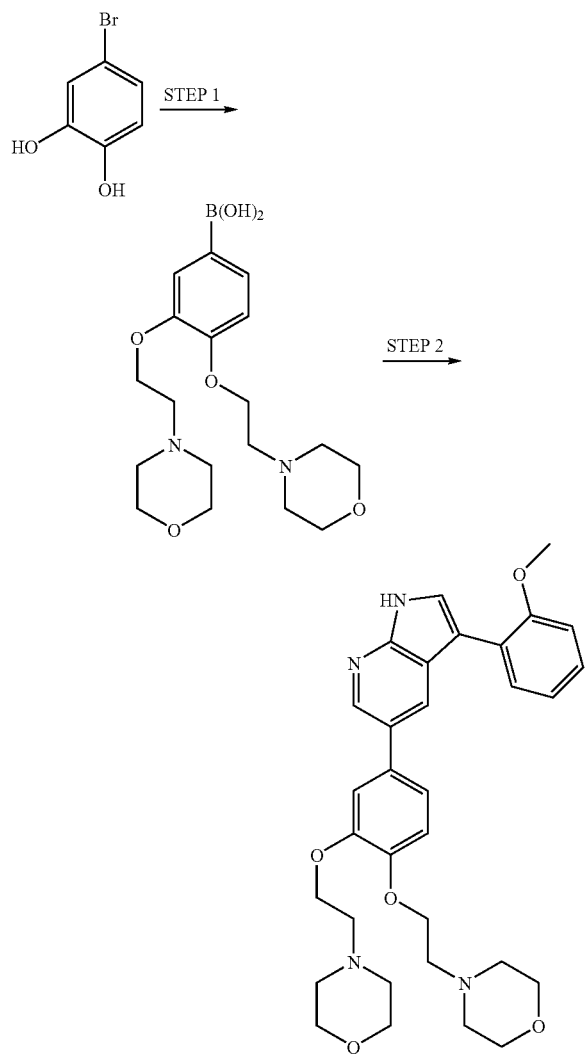

Step 1: Synthesis of 3,4-bis(2-morpholinoethoxy)phenylboronic acid 864 mg (36.0 mmol) of sodium hydride was added to a suspension of 900 mg (5.0 mmol) of 4-bromocatechol and 3.72 g (20.0 mmol) of 2-chloroethylmorpholine hydrochloride in 50 ml of anhydrous DMF at 0° C. over 25 minutes. The mixture was stirred for 3 days at room temperature. 5 ml water was added to quench the reaction. After removal of the solvent, the black oily residue was adsorbed onto celite and the resulting solid washed with ethyl acetate. The filtrate was then concentrated to give 0.75 g (1.81 mmol; 36% yield) of 3,4-bis(2-morpholinoethoxy)bromobenzene as a hygroscopic yellow solid. $^1$H-NMR (CD3OD) δ: 8.42 [1H] d (2.0 Hz), 8.18 [1H] d (1.5 Hz), 7.64 [1H] s, 7.56 [1H] dd (1.5 Hz, 7.5 Hz), 7.30 [1H] dt (1.5 Hz, 7.5 Hz), 7.25 [1H] d (2.5 Hz), 7.19 [1H] dd (2.5 Hz, 8.5 Hz), 7.12 [1H] d (8.5 Hz), 7.08 [1H] d (8.5 Hz), 7.05 [1H] dt (1 Hz, 7.5 Hz) 4.25 [2H] t (5.75 Hz), 4.20 [2H] t (5.5 Hz), 3.72 [8H] m, 2.84 [4H] m, 2.66 [8H] m. MS: 559.2 [MH$^+$].

2.4 ml of a 2.5 M solution of n-buthyl lithium in hexanes was added at −78° C. to a solution of 2.08 g (5.0 mmol) 3,4-bis(2-morpholinoethoxy)bromobenzene in THF over 10 minutes. The mixture was stirred for 30 minutes at −78° C. before 1.39 ml (6.0 mmol) of tri-n-isopropyl borate was added. The mixture was stirred for another 30 minutes at −78° C. and then warmed to 0° C. over 2 hours. The mixture was cooled to −20° C. and 5 ml of aqueous 2 N hydrochloric acid was added. After stirring for 20 minutes the reaction mixture was transferred to a separating funnel and extracted three times with 100 ml of ethyl acetate. The combined organic layers were dried over sodium sulfate and concentrated to give a brown oil. The oil was titurated with ether to give 925 mg of a very hygroscopic dark brown oil, which was about 50% pure by LC/MS and used directly without further purification.

Step 2: Synthesis of 5-[3,4-bis-(2-morpholin-4-yl-ethoxy)-phenyl]-3-(2-methoxy-phenyl)-1H-pyrrolo[2,3-b]pyridine A vial is charged with 228 mg (approx. 0.3 mmol of pure boronic acid) of the crude boronic acid, 60.6 mg (0.20 mmol) of 5-bromo-3-(2-methoxy-phenyl)-1H-pyrrolo[2,3-b]pyridine and 8.3 mg (5 mol %) of dichlororbis(triphenylphosphino)palladium(II). 1.5 ml of acetonitrile and 1.5 ml of a 2 M aqueous solution of sodium carbonate were added and the mixture irradiated in a Personal Chemistry® microwave reactor to 150° C. for 15 minutes. The resulting mixture was extracted three times with 15 ml of ethyl acetate and the combined organic layers were dried over anhydrous sodium sulfate and concentrated. The resulting dark brown residue was purified by flash chromatography on silica gel using a gradient of ethyl acetate in hexanes to give 9.4 mg (16 µmol; 8% yield) of 5-[3,4-bis-(2-morpholin-4-yl-ethoxy)-phenyl]-3-(2-methoxy-phenyl)-1H-pyrrolo[2,3-b]pyridine as a light yellow solid.

$^1$H-NMR (d$_4$-methanol) δ: 8.42 [1H] d (2.0 Hz), 8.18 [1H] d (1.5 Hz), 7.64 [1H] s, 7.56 [1H] dd (1.5 Hz, 7.5 Hz), 7.30 [1H] dt (1.5 Hz, 7.5 Hz), 7.25 [1H] d (2.5 Hz), 7.19 [1H] dd (2.5 Hz, 8.5 Hz), 7.12 [1H] d (8.5 Hz), 7.08 [1H] d (8.5 Hz), 7.05 [1H] dt (1 Hz, 7.5 Hz) 4.25 [2H] t (5.75 Hz), 4.20 [2H] t (5.5 Hz), 3.72 [8H] m, 2.84 [4H] m, 2.66 [8H] m. MS m/z: 559.2 [MH$^+$].

Method 57

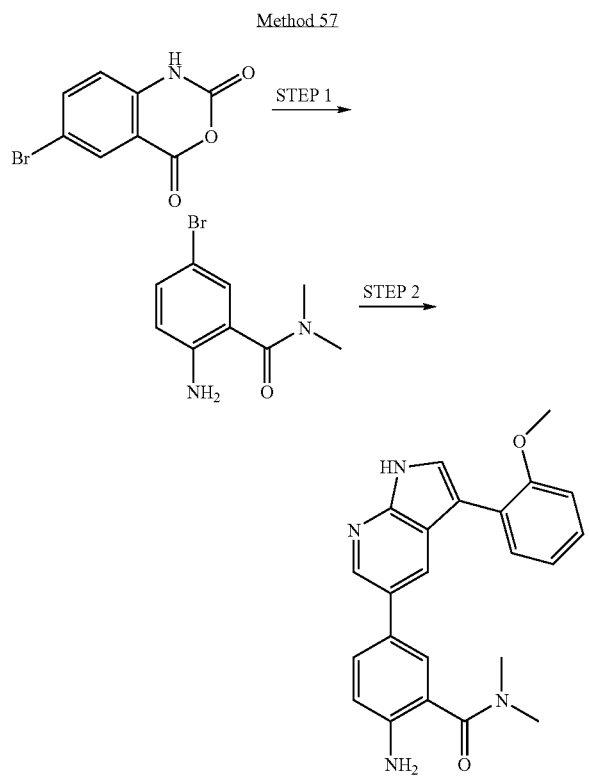

Step 1: Synthesis of 2-Amino-5-bromo-N,N-dimethyl-benzamide

Into an 15 mL high pressure glass vial (with Teflon screw cap) were added 5-bromoisatoic anhydride (0.401 g, 1.66 mmol), DMAP (20 mg, 0.16 mmol), and dimethylamine (2 M in THF; 5.0 mL, 10.0 mmol). The vial was sealed and placed in an oil bath at 70° C. for 8 h after which it was concentrated under vacuum. The crude product was dissolved in EtOAc and washed 2× with water followed by brine. The organic phase was dried ($Na_2SO_4$), filtered and concentrated to afford 0.428 g of 2-Amino-5-bromo-N,N-dimethyl-benzamide as a pink solid, which was used directly for the next step. $^1$H-NMR (500 MHz, $d_6$-DMSO) δ=7.19 (dd, J=2.0, 8.5 Hz, 1H), 7.08 (d, J=2.0 Hz, 1H), 6.63 (d, J=8.5 Hz, 1H), 5.31 (br. s, 2H), 2.89 (br. s, 6H). MS: m/z 198/200 [C=O$^+$].

Step 2: Synthesis of 2-Amino-5-[3-(2-methoxy-phenyl)-1H-pyrrolo[2,3-b]pyridin-5-yl]-N,N-dimethyl-benzamide Into a 5 mL Personal Chemistry microwave reaction vial were added 3-(2-methoxy-phenyl)-5-(4,4,5,5-tetramethyl-[1,3,2]dioxaborolan-2-yl)-1-(toluene-4-sulfonyl)-1H-pyrrolo[2,3-b]pyridine (0.167 g, 0.331 mmol), 2-amino-5-bromo-N,N-dimethyl-benzamide (0.088 g, 0.364 mmol), 1,1'-bis(diphenylphosphino)ferrocenepalladium(II)-dichloride dichloromethane adduct (14 mg, 0.017 mmol), acetonitrile (5 mL) and saturated aqueous $NaHCO_3$ (5 mL). The vial was sealed, purged with $N_2$, and irradiated in a Personal Chemistry Optimizer at 90° C. for 5 min. The layers were separated, and the aqueous phase was extracted 3× with EtOAc. The combined organic phase was treated with brine, dried ($Na_2SO_4$), filtered and adsorbed onto silica gel. The crude material was purified by silica gel chromatography in an EtOAc (containing 10% MeOH) and hexane gradient. The purified material was dissolved in a MeOH/acetone solution (5 mL) and 200 uL of a 50% KOH solution was added and the solution was stirred at room temperature for 3 hours. The reaction was quenched by adding 1 M citric acid dropwise until pH=5. The quenched reaction mixture was partitioned between EtOAc and water, the layers were separated, and the aqueous phase was extracted 2× with EtOAc. The combined organic phase was treated with brine, dried ($Na_2SO_4$), filtered and adsorbed onto silica gel. The material was purified on amino silica in an EtOAc (containing 10% MeOH) and hexane gradient to afford the title compound as a pale yellow powder (13.5 mg, 11% yield). $^1$H-NMR (500 MHz, $d_6$-DMSO) δ=11.80 (br. s, 1H), 8.42 (d, J=2.0 Hz, 1H), 8.02 (d, J=2.0 Hz, 1H), 7.68 (d, J=2.5 Hz, 1H), 7.58 (dd, J=1.5, 6.0 Hz, 1H), 7.44 (dd, J=2.0, 6.0 Hz, 1H), 7.31 (d, J=2.0 Hz, 1H), 7.27 (t, J=7.5 Hz, 1H), 7.12 (d, J=7.5 Hz, 1H), 7.04 (t, J=7.0 Hz, 1H), 6.80 (d, J=9.0 Hz, 1H), 5.26 (s, 2H), 3.80 (s, 3H), 2.95 (s, 6H). MS: m/z 387.1 [MH$^+$].

Other compounds prepared by Method 57:

TABLE 35

| Structure |
| --- |
| 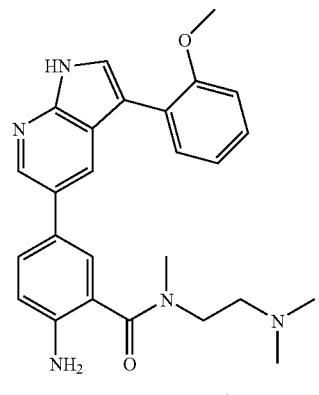<br>MS: m/z 444 [MH$^+$]. |
| 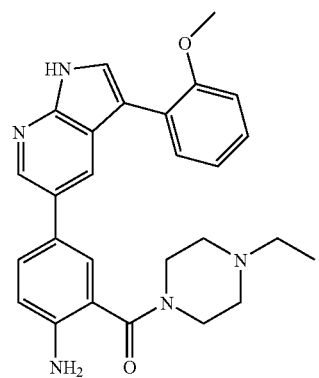<br>MS: m/z 456 [MH$^+$]. |

TABLE 35-continued
Structure
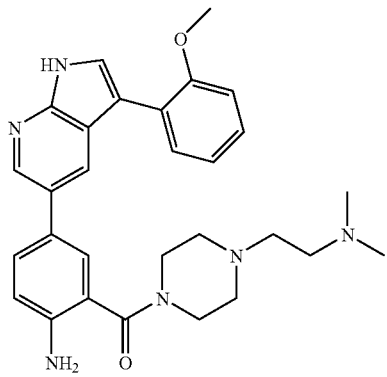
MS: m/z 499 [MH+].
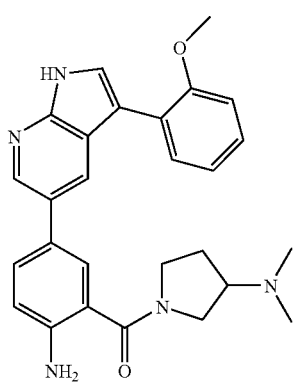
MS: m/z 456 [MH+].
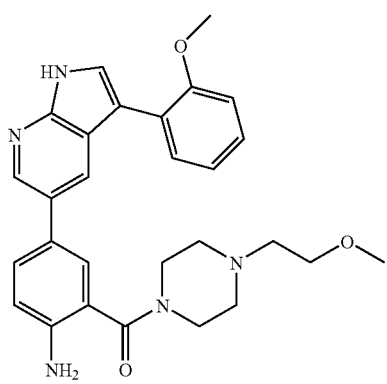
MS: m/z 486 [MH+].
TABLE 35-continued
Structure
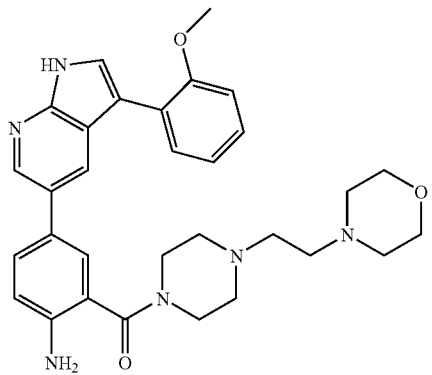
MS: m/z 541 [MH+].
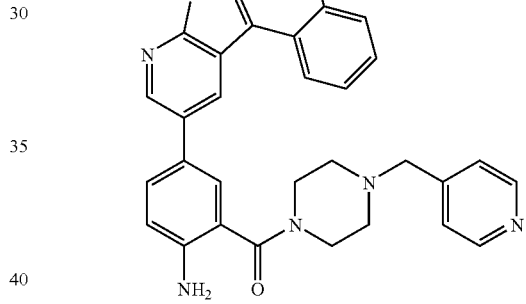
MS: m/z 519 [MH+].
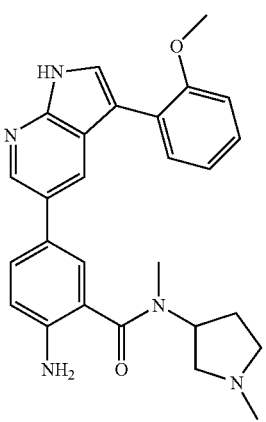
MS: m/z 556 [MH+].

Method 58:

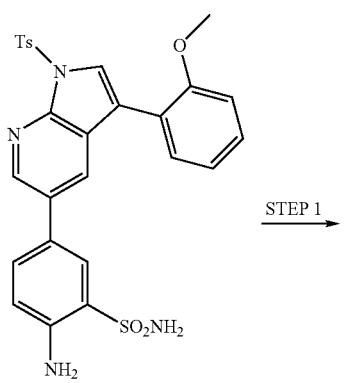

STEP 1

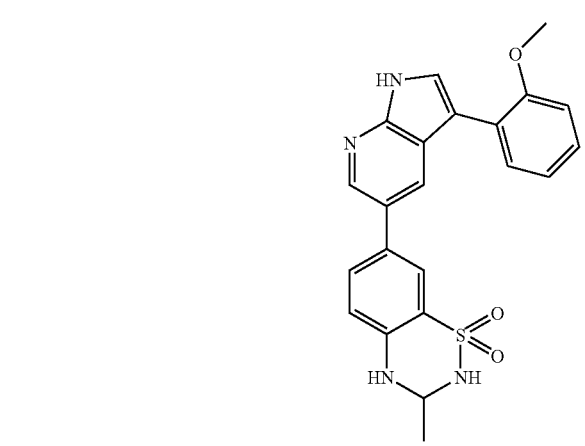

Step 1: Synthesis of 7-[3-(2-Methoxy-phenyl)-1H-pyrrolo[2,3-b]pyridin-5-yl]-3-methyl-3,4-dihydro-2H-benzo[1,2,4]thiadiazine 1,1-dioxide Into an 8 mL screw-cap vial were added 2-Amino-5-[3-(2-methoxy-phenyl)-1-(toluene-4-sulfonyl)-1H-pyrrolo[2,3-b]pyridin-5-yl]-benzenesulfonamide (0.0492 g, 0.090 mmol), acetaldehyde (200 μL, 3.54 mmol), and acetonitrile (700 μL). The vial was sealed and placed in a heat block at 90° C. for 1 h. The reaction mixture was concentrated under vacuum then dissolved in THF (1 mL), and 500 μL of 50% w/w KOH aq. was added to the resulting solution. After 2 h, the reaction was quenched by addition of glacial acetic acid then concentrated under vacuum to afford a brown residue. Purification by flash chromatography on $SiO_2$ gel, eluting with ethyl acetate and hexanes (0-100% gradient) afforded the title compound as a yellow powder (23.3 mg, 61%). $^1$H-NMR (500 MHz, $d_6$-DMSO) δ=11.88 (br.s, 1H), 8.44 (d, J=2.0 Hz, 1H), 8.04 (d, J=2.0 Hz, 1H), 7.71 (m, 2H), 7.68 (dd, J=2.5, 8.6 Hz, 1H), 7.59 (dd, J=2.5, 8.5 Hz, 1H), 7.54 (br.d, 1H), 7.29 (m, 1H), 7.26 (br.s, 1H), 7.12 (dd, J=8.5, 1 Hz, 1H), 7.05 (t, J=7.5 Hz, 1H), 6.89 (d, J=9.0 Hz, 1H), 4.86 (m, 1H), 3.81 (s, 3H), 1.44 (d, J=5.5.0 Hz, 3H). MS: m/z 421.1 [MH$^+$].

Other compounds prepared by Method 58:

TABLE 36

| Structure |
| --- |
| 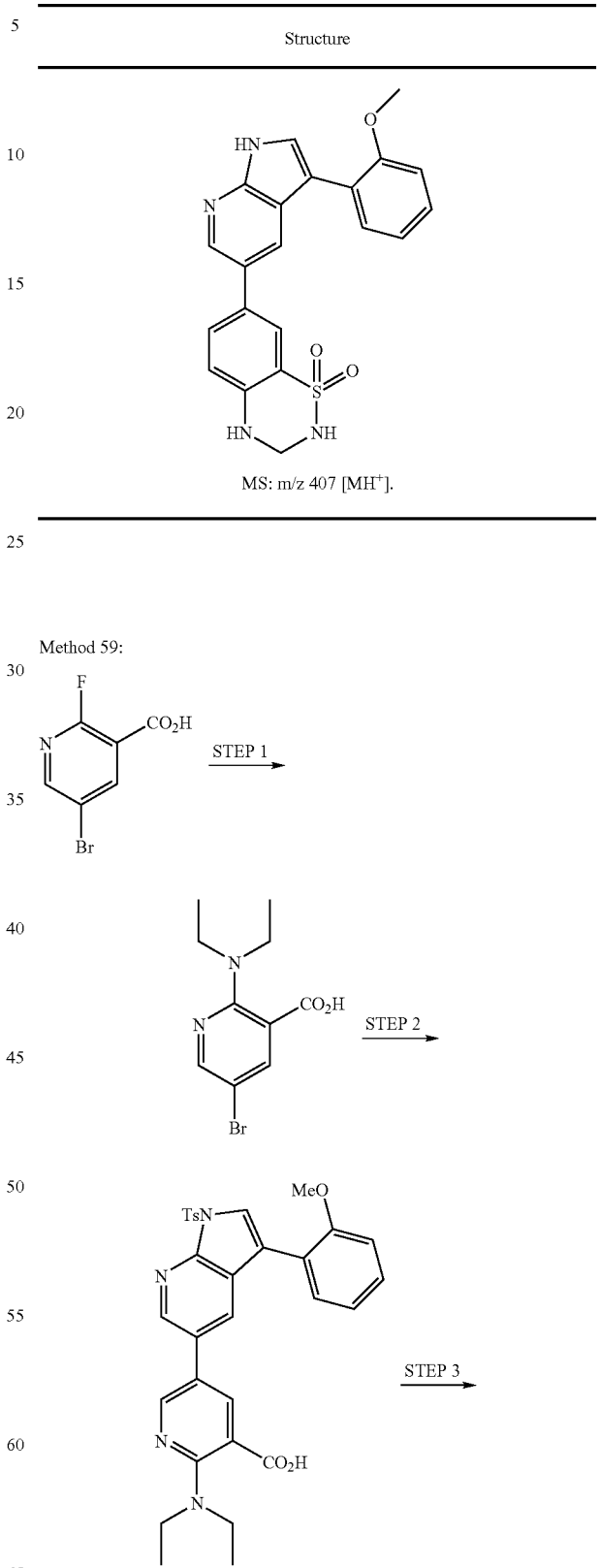 MS: m/z 407 [MH$^+$]. |

Method 59:

-continued

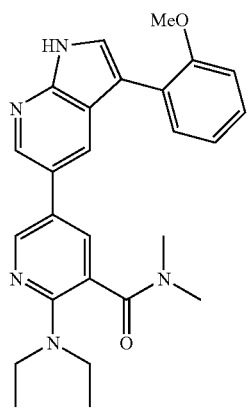

Step 1: Synthesis of 5-bromo-2-diethylamino-nicotinic acid 880 mg (4.00 mmol) of 5-bromo-2-fluoronicotinic acid was dissolved in 3 ml of acetonitrile. 1.0 ml (9.7 mmol) of diethylamine was added and the resulting mixture heated to 80° C. for 18 h. The mixture was evaporated and the resulting brown oil used without further purification. MS: m/z 273 [MH⁺].

Step 2: Synthesis of 2-diethylamino-5-[3-(2-methoxy-phenyl)-1-(toluene-4-sulfonyl)-1H-pyrrolo[2,3-b]pyridin-5-yl]-nicotinic acid 230 mg (0.45 mmol) of 3-(2-methoxy-phenyl)-5-(4,4,5,5-tetramethyl-[1,3,2]dioxaborolan-2-yl)-1-(toluene-4-sulfonyl)-1H-pyrrolo[2,3-b]pyridine, 137 mg (0.50 mmol) of 5-bromo-2-diethylamino-nicotinic acid and 16 mg (23 μmol) of 1,1'-bis(diphenylphosphino)ferrocenepalladium(II)-dichloride dichloromethane adduct were dissolved in a mixture of 2.5 ml of acetonitrile and 2 ml of a 2 M aqueous solution of sodium carbonate. The reaction mixture was heated for 1.5 h to 100° C.

The resulting mixture was distributed between brine and ethyl acetate and the aqueous phase extracted three times with ethyl acetate. The combined organic phases were washed with brine, dried over sodium sulfate and evaporated. The crude was then purified by flash chromatography on silica gel using a gradient of ethyl acetate and a solvent mixture of ethyl actetae, dichloromethane and methanol (4:4:1) containing 1% v/v of 35% w/w aqueous ammonia solution to afford 150 mg of 2-diethylamino-5-[3-(2-methoxy-phenyl)-1-(toluene-4-sulfonyl)-1H-pyrrolo[2,3-b]pyridin-5-yl]-nicotinic acid as a brown solid. MS: m/z 571 [MH⁻].

Step 3: Synthesis of 2-diethylamino-5-[3-(2-methoxy-phenyl)-1H-pyrrolo[2,3-b]pyridin-5-yl]-N,N-dimethyl-nicotinamide 40 mg (0.07 mmol) of 2-diethylamino-5-[3-(2-methoxy-phenyl)-1-(toluene-4-sulfonyl)-1H-pyrrolo[2,3-b]pyridin-5-yl]-nicotinic acid was dissolved in 1.5 ml of dichloromethane. 40 mg (0.11 mmol) of O-(7-azabenzotriazol-1-yl)-N,N,N', N'-tetramethyluronium hexafluorophosphate, 55 μl (0.11 mmol) of 2 M dimethylamine in THF, and 1 ml of DMF were added and the resulting mixture was stirred for 1 h. The solvent was completely evaporated.

The residue was dissolved in a mixture of methanol and DMSO and 1.1 ml of 2 M aqueous sodium hydroxide added in three portions over the period of 24 h. After stirring at ambient temperature for 48 h total the mixture was evaporated and the residue acidified by addition of glacial acetic acid and the resulting material purified by mass triggered reverse phase HPLC to afford 6.8 mg (14 μmol; 20% yield) of 2-diethylamino-5-[3-(2-methoxy-phenyl)-1H-pyrrolo[2,3-b]pyridin-5-yl]-N,N-dimethyl-nicotinamide as a brown solid. ¹H-NMR (d₆-DMSO): δ 11.94 (s, 1H), 8.52 (d, 1H), 8.50 (d, 1H), 8.14 (d, 1H), 7.73 (d, 1H), 7.73 (s, 1H), 7.63 (dd, 1H), 7.29 (ddd, 1H), 7.13 (d(d), 1H), 7.05 (dd(d), 1H), 3.83 (s, 3H), 3.3.46-3.28 (m, 4H), 3.00 (s, 3H), 2.87 (s, 3H), 1.10 (t, 6H). MS: m/z 444 [MH⁺].

Other compounds prepared by Method 59:

TABLE 37

| Structure |
| --- |
| 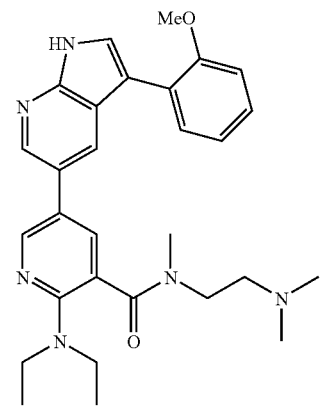<br>MS: m/z 487 [MH⁺]. |
| <br>MS: m/z 501 [MH⁺]. |

TABLE 37-continued
| Structure |
|---|
| 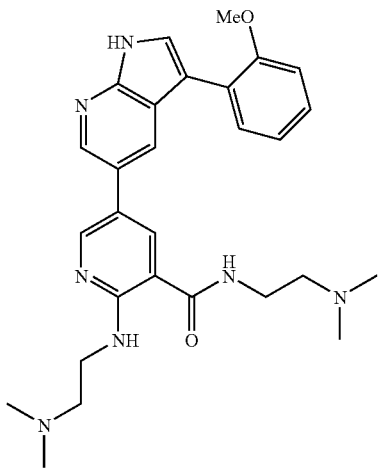<br>MS: m/z 502 [MH+]. |
| 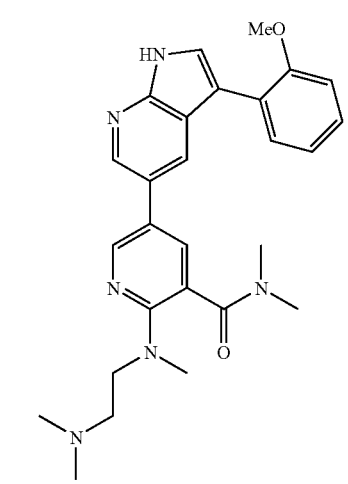<br>MS: m/z 473 [MH+]. |
| 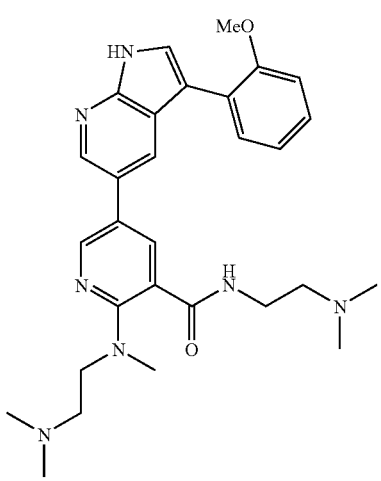<br>MS: m/z 516 [MH+]. |
TABLE 37-continued
| Structure |
|---|
| 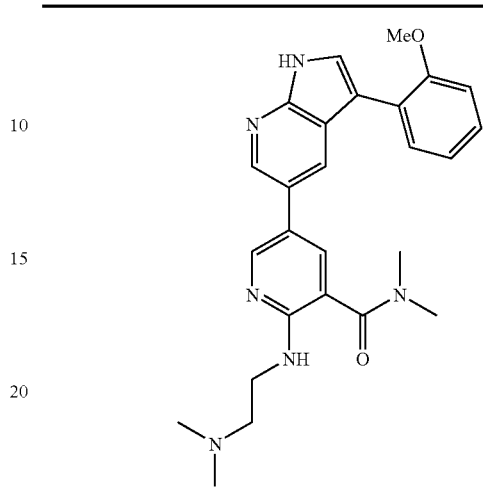<br>MS: m/z 459 [MH+]. |
Method 60:
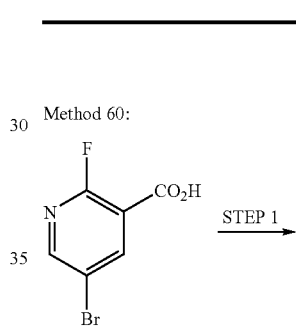 STEP 1
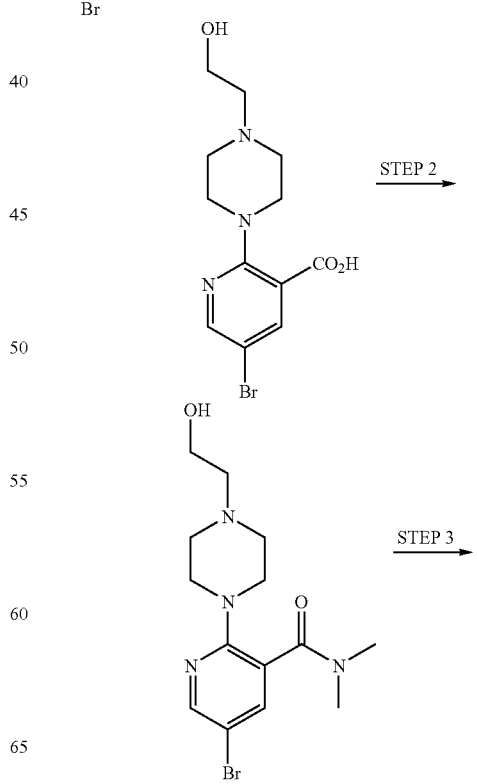

-continued

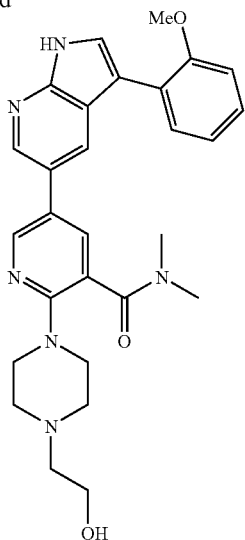

Step 1: Synthesis of 5-bromo-2-[4-(2-hydroxy-ethyl)-piperazin-1-yl]-nicotinic acid 500 mg (4.00 mmol) of 5-bromo-2-fluoronicotinic acid was dissolved in 3 ml of acetonitrile. 620 µl of 1-(2-hydroxyethyl)piperazine was added and the resulting mixture heated to 70° C. for 24 h. The mixture was distributed between ethyl acetate and water containing 35% w/w aqueous ammonia solution to adjust the pH to about 12. The aqueous phase is extracted twice with ethyl acetate. The aqueous phase was then lyophyllized to afford a beige residue.

The residue was dissolved in a mixture of dichloromethane, acetonitrile and methanol and treated with an excess of MP-isocyanate resin (Argonaut Technologies®). The resin was then filtered off and the filtrate evaporated to afford 632 mg (1.91 mmol; 84% yield) of 5-bromo-2-[4-(2-hydroxy-ethyl)-piperazin-1-yl]-nicotinic acid as a beige, partially crystalline residue. MS: m/z 330 [MH$^+$].

Step 2: Synthesis of 5-bromo-2-[4-(2-hydroxy-ethyl)-piperazin-1-yl]-N,N-dimethyl-nicotinamide 630 mg (1.90 mmol) of 5-bromo-2-[4-(2-hydroxy-ethyl)-piperazin-1-yl]-nicotinic acid was suspended in 50 ml of dichloromethane. 6 ml of 2 M dimethylamine in THF and 850 mg (1.63 mmol) of benzotriazol-1-yl-oxytripyrrolidinophosphonium hexafluorophosphate were added and the resulting mixture was stirred for 18 h at ambient temperature. The resulting mixture was diluted with dichloromethane and washed with water. The aqueous phase was extracted with dichloromethane and the organic phases were combined, dried over sodium sulfate and evaporated to afford crude 5-bromo-2-[4-(2-hydroxy-ethyl)-piperazin-1-yl]-N,N-dimethyl-nicotinamide as a pale brown oil containing tris(pyrrolidinyl)phosphoramidate as a contaminant. MS: m/z 357 [MH$^+$].

Step 3: 2-[4-(2-hydroxy-ethyl)-piperazin-1-yl]-5-[3-(2-methoxy-phenyl)-1H-pyrrolo[2,3-b]pyridin-5-yl]-N,N-dimethyl-nicotinamide 50 mg (99 µmol) of 3-(2-methoxy-phenyl)-5-(4,4,5,5-tetramethyl-[1,3,2]dioxaborolan-2-yl)-1-(toluene-4-sulfonyl)-1H-pyrrolo[2,3-b]pyridine, 215 mg of the crude 5-bromo-2-[4-(2-hydroxy-ethyl)-piperazin-1-yl]-N,N-dimethyl-nicotinamide obtained from step 2 and 5 mg (6 µmol) of 1,1'-bis(diphenylphosphino)ferrocenepalladium(II)-dichloride dichloromethane adduct were dissolved in a mixture of 3 ml of acetonitrile and 2 ml of a saturated aqueous solution of sodium bicarbonate. The reaction mixture was heated to 120° C. for 4 h.

The resulting mixture was distributed between water and ethyl acetate and the aqueous phase extracted twice with ethyl acetate. The combined organic phases were washed with brine, dried over sodium sulfate and evaporated. The residue was dissolved in methanol and 400 µl of 50% w/v aqueous potassium hydroxide was added. The resulting mixture was left at ambient temperature for 3 h. The crude solution was directly purified by mass triggered reverse phase HPLC purification to afford 14.7 mg (29 µmol; 29% yield) of 2-[4-(2-hydroxy-ethyl)-piperazin-1-yl]-5-[3-(2-methoxy-phenyl)-1H-pyrrolo[2,3-b]pyridin-5-yl]-N,N-dimethyl-nicotinamide as a colorless solid. $^1$H-NMR (d$_6$-DMSO): δ 11.93 (s, 1H), 8.59 (d, 1H), 8.52 (d, 1H), 8.17 (d, 1H), 7.85 (d, 1H), 7.74 (s, 1H), 7.63 (dd, 1H), 7.29 (ddd, 1H), 7.12 (d(d), 1H), 7.05 (dd(d), 1H), 3.83 (s, 3H), 3.55 (m, 2H), 3.4-3.3 (m, 4H), 3.01 (s, 3H), 2.88 (s, 3H), 2.58 (m, 4H), 2.54-2.46 (m, 2H) MS: m/z 501 [MH$^+$].

Other compounds prepared by Method 60:

TABLE 38

| Structure |
| --- |
| 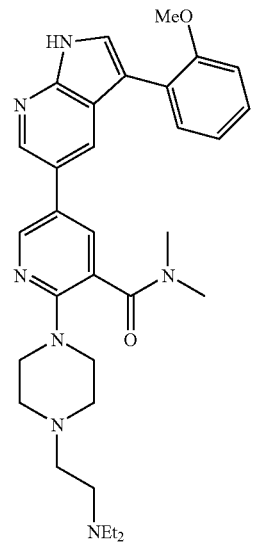 |
| MS: m/z 556 [MH$^+$]. |

Method 61:

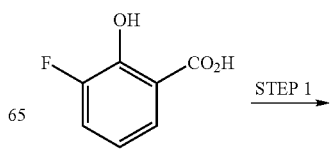

STEP 1

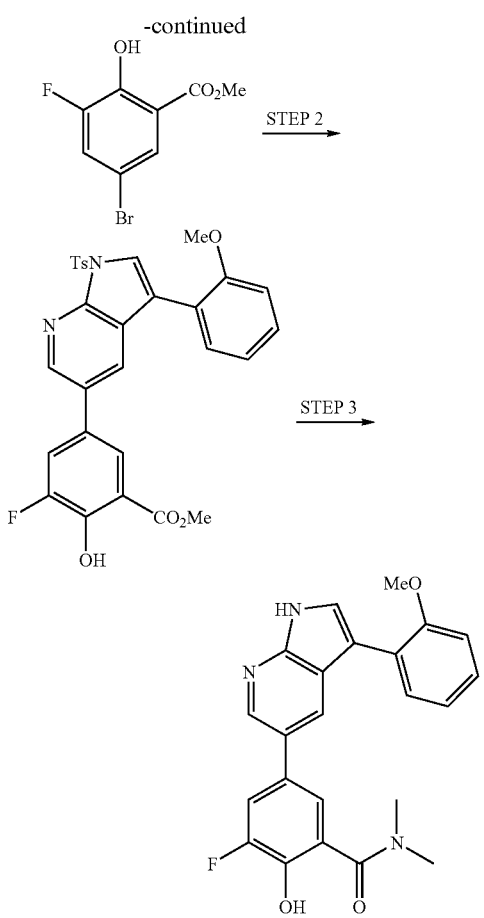

Step 1: Synthesis of 5-bromo-3-fluoro-2-hydroxybenzoic acid methyl ester 5.00 g (32 mmol) of 3-fluorosalicylci acid was suspended in 50 ml of glacial acetic acid. 2.2 ml of bromine were added and the mixture was stirred at ambient temperature for 48 h. The resulting suspension was diluted with 500 ml of water and the precipitate filtered off and dried by suction to afford 9.394 g of 5-bromo-3-fluoro-2-hydroxybenzoic acid as an ivory solid.

4.08 g (13.9 mmol max.) of the crude was dissolved in a mixture of 70 ml of toluene and 30 ml of methanol. 9 ml of a 2 M solution of trimethylsilyl diazomethane was added until the mixture remains yellow. 200 µl of glacial acetic acid was added until the mixture was colorless and the solvent was evaporated to afford 3.037 g (12.20 mmol; 88% over both steps) of 5-bromo-3-fluoro-2-hydroxybenzoic acid methyl ester. $^1$H-NMR (d$_6$-DMSO): δ 10.57 (s, br., 1H), 7.83 (dd, 1H), 7.67 (d(d), 1H), 3.90 (s, 3H).

Step 2: Synthesis of 3-fluoro-2-hydroxy-5-[3-(2-methoxy-phenyl)-1-(toluene-4-sulfonyl)-1H-pyrrolo[2,3-b]pyridin-5-yl]-benzoic acid methyl ester 600 mg (1.19 mmol) of 3-(2-methoxy-phenyl)-5-(4,4,5,5-tetramethyl-[1,3,2]dioxaborolan-2-yl)-1-(toluene-4-sulfonyl)-1H-pyrrolo[2,3-b]pyridine, 509 mg (2.04 mmol) of 5-bromo-3-fluoro-2-hydroxybenzoic acid methyl ester and 43 mg (60 µmol) of 1,1'-bis(diphenylphosphino)ferrocene-palladium(II)-dichloride dichloromethane adduct were dissolved in a mixture of 10 ml of toluene and 10 ml of a saturated aqueous solution of sodium bicarbonate. The reaction mixture was heated to 70° C. for 2.5 h and then to 90° C. for an additional 1.5 h.

The crude was distributed between dichloromethane and a saturated aqueous solution of sodium bicarbonate. The aqueous phase was extracted three times with dichloromethane and the combined organic phases were dried over sodium sulfate and evaporated. The crude was purified by flash chromatography on silica gel using a gradient of ethyl acetate in hexanes to afford 427 mg (0.79 mmol; 66% yield) of 3-fluoro-2-hydroxy-5-[3-(2-methoxy-phenyl)-1-(toluene-4-sulfonyl)-1H-pyrrolo[2,3-b]pyridin-5-yl]-benzoic acid methyl ester. MS: m/z 547 [MH$^+$].

Step 3: Synthesis of 3-fluoro-2-hydroxy-5-[3-(2-methoxy-phenyl)-1H-pyrrolo[2,3-b]pyridin-5-yl]-N,N-dimethyl-benzamide 22 mg (40 µmol) of 3-fluoro-2-hydroxy-5-[3-(2-methoxy-phenyl)-1-(toluene-4-sulfonyl)-1H-pyrrolo[2,3-b]pyridin-5-yl]-benzoic acid methyl ester was dissolved in 2 ml of a 2 M solution of dimethylamine in THF. The solution was heated to 100° C. in a closed vial for 24 h and then concentrated. The residue was dissolved in 2 ml of methanol and 350 µl of 50% w/v aqueous potassium hydroxide added. The mixture was left at ambient temperature for 1 h and then neutralized by addition of glacial acetic acid. The crude was directly purified by mass triggered reverse phase HPLC purification to afford 6.0 mg (14 µmol; 37% yield) of 3-fluoro-2-hydroxy-5-[3-(2-methoxy-phenyl)-1H-pyrrolo[2,3-b]pyridin-5-yl]-N,N-dimethyl-benzamide as an ivory solid. $^1$H-NMR (d$_6$-DMSO): δ 11.91 (s, 1H), 8.51 (d, 1H), 8.14 (d, 1H), 7.73 (d, 1H), 7.64 (d, 1H), 7.62 (dd, 1H), 7.32-7.25 (m, 2H), 7.14 (d, 1H), 7.05 (m, 1H), 3.82 (s, 3H), 2.99 (s, 3H), 2.87 (s, 3H). MS: m/z 406 [MH$^+$].

Other compounds prepared by Method 61:

TABLE 39

| Structure |
| --- |
| 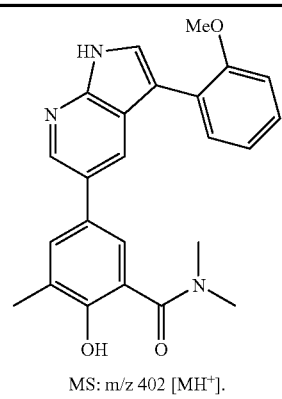<br>MS: m/z 402 [MH$^+$]. |

TABLE 39-continued

Structure

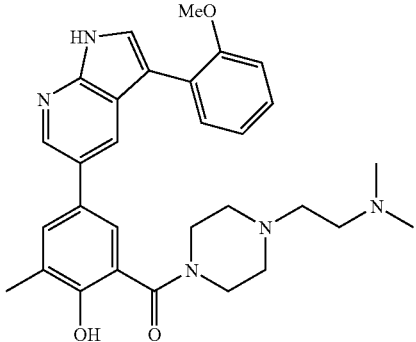

MS: m/z 514 [MH+].

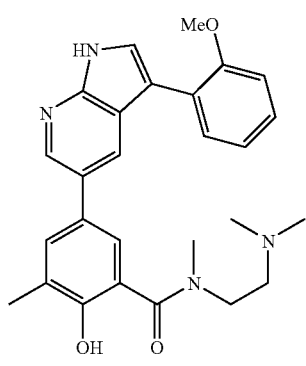

MS: m/z 459 [MH+].

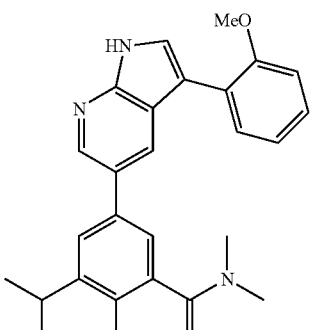

MS: m/z 430 [MH+].

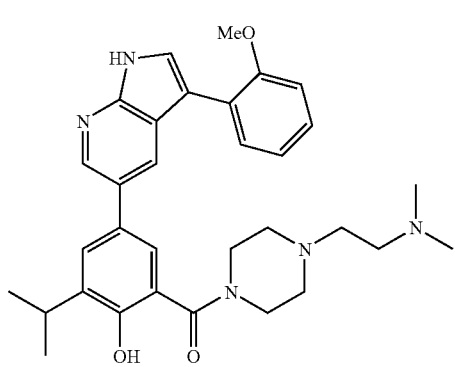

MS: m/z 542 [MH+].

TABLE 39-continued

Structure

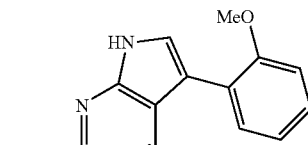
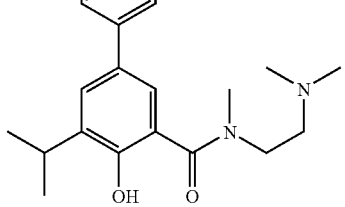

MS: m/z 487 [MH+].

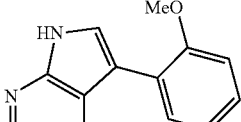
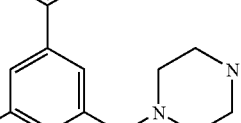
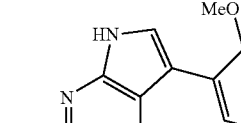

MS: m/z 518 [MH+].

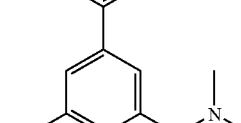
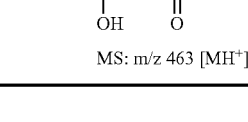
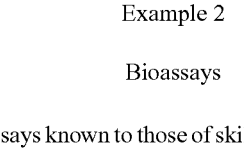
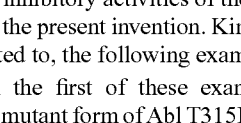

MS: m/z 463 [MH+].

Example 2

Bioassays

Kinase assays known to those of skill in the art may be used to assay the inhibitory activities of the compounds and compositions of the present invention. Kinase assays include, but are not limited to, the following examples.

Although the first of these examples uses the kinase domain of a mutant form of Abl T315I ("Abl T315I KD"), the kinase assays may use various forms of mutant and wild type enzymes, including, for example, the entire protein, the kinase domain, or a portion thereof (e.g. Abl Y393F). The kinases used in the assays may also be of varying phosphorylation states. In the c-Abl example, a mutant kinase at a zero phosphorylation state was used.

c-Abl Pyruvate Kinase/Lactate Dehydrogenase Coupled Enzyme Assay

In the c-Abl Pyruvate Kinase (PK)/Lactate Dehydrogenase (LDH) Coupled Assay the protein kinase dependant phosphorylation of a substrate peptide was coupled to the oxidation of NADH. The oxidation of NADH to NAD+ was detected by monitoring a decrease in absorbance at 340 nm.

Materials: Abl substrate peptide=EAIYAAPFAKKK (SEQ ID NO: 1) —OH (Biopeptide, San Diego, Calif.); βNADH (Sigma Cat#N-8129, FW=709.4); 2M $MgCl_2$; 1M HEPES buffer, pH 7.5; Phosphoenolpyruvate (PEP) (Sigma Cat#P-7002, FW=234); Lactate dehydrogenase (LDH) (Worthington Biochemical Cat#2756); Pyruvate Kinase (PK) (Sigma Cat#P-9136); ATP (Sigma Cat#A-3377, FW=551); Greiner 384-well UV star plate; and purified and unphosphorylated T315I Abl kinase domain.

Stock Solutions: 10 mM NADH (7.09 mg/ml in miliQ$H_2$O) made fresh daily; 10 mM Abl substrate peptide (13.4 mg/ml in miliQ$H_2$O) stored at −20° C.; 100 mM HEPES buffer, pH 7.5 (5 ml 1M stock+45 ml miliQ$H_2$O); 100 mM $MgCl_2$ (5 ml 2M $MgCl_2$+95 ml d$H_2$O); 100 mM PEP (23.4 mg/ml in d$H_2$O) stored at −20° C.; 10 mM ATP (5.51 mg/ml in d$H_2$O) stored at −20° C. (diluted 50 µl into total of 10 ml miliQ$H_2$O daily=50 µM ATP working stock); 1000 U/ml PK (U/mg varies with lot) flash-frozen under liquid $N_2$ and stored at −80° C.; and 1000 U/ml LDH (U/mg varies with lot) flash-frozen under liquid $N_2$ and stored at −80° C.

Standard Assay Setup for 384-well format (50 µl reaction): 300 µM NADH; 10 mM $MgCl_2$; 2 mM PEP; 45 U/ml PK; 60 U/ml LDH; 200 µM Abl substrate peptide; 2.5 µl test compound (in DMSO); 2 µg/ml Abl kinase domain; 10 µM ATP; 100 mM HEPES buffer. Positive controls contained DMSO with no test compound. Negative controls contained 5 µl of 0.5M EDTA (50 mM in the assay). The dephosphorylated form of the c-Abl T315I mutant was used in the biochemical screening assays. The kinase reaction was initiated at time t=0 by the addition of ATP.

Activity was measured by following the time-dependent loss of NADH by absorbance spectroscopy at 340 nm. The linear portion of the resulting progress curve was then analyzed by linear regression to get the activity in absorbance units/time, reported as the slope of that best fit line (moles/unit time can be calculated from using molar extinction coefficient for NADH at 340 nm, 6250 $M^{-1}cm^{-1}$).

Data was evaluated using the equation: $Z'=1-[3*(\sigma_+ + \sigma_-)/|\mu_+ - \mu_-|]$ (Zhang, et al., 1999 J Biomol Screening 4(2) 67-73), where µ denotes the mean and σ the standard deviation. The subscript designates positive or negative controls. The Z' score for a robust screening assay should be ≧0.50. The typical threshold=$\mu_+ - 3*\sigma_+$. Any value that falls below the threshold was designated a "hit".

Dose response was analyzed using the equation: y=min+ {(max−min)/(1+$10^{[Compound]-logIC50}$)}, where y is the observed initial slope, max=the slope in the absence of inhibitor, min=the slope at infinite inhibitor, and the $IC_{50}$ is the [compound] that corresponds to ½ the total observed amplitude (Amplitude=max−min).

To measure modulation, activation, or inhibition of Abl KD, a test compound was added to the assay at a range of concentrations. Inhibitors may inhibit Abl KD activity at an $IC_{50}$ in the micromolar range, the nanomolar range, or, for example, in the subnanomolar range.

Additional Kinase Assays

In addition to the c-Abl PK/LDH coupled assay (above), homogeneous luminescence-based inhibitor screening assays were developed for c-Abl, MET, AurA, and PDK1 kinases (among others). Each of these assays made use of an ATP depletion assay (Kinase-Glo™, Promega Corporation, Madison, Wis.) to quantitate kinase activity. The Kinase-Glo™ format uses a thermostable luciferase to generate luminescent signal from ATP remaining in solution following the kinase reaction. The luminescent signal is inversely correlated with the amount of kinase activity.

cAbl Luminescence-based Enzyme Assay

Materials: Abl substrate peptide=EAIYAAPFAKKK (SEQ ID NO: 1) —OH (Biopeptide, San Diego, Calif.), ATP (Sigma Cat#A-3377, FW=551), HEPES buffer, pH 7.5, Bovine serum albumin (BSA) (Roche 92423420), $MgCl_2$, Staurosporine (*Streptomyces* sp. Sigma Cat#85660-1MG), white Costar 384-well flat-bottom plate (VWR Cat#29444-088), Abl kinase (see below), Kinase-Glo™ (Promega Cat#V6712).

Stock Solutions: 10 mM Abl substrate peptide (13.4 mg/ml in miliQ$H_2$O) stored at −20° C.; 100 mM HEPES buffer, pH 7.5 (5 ml 1M stock+45 ml miliQ$H_2$O); 10 mM ATP (5.51 mg/ml in d$H_2$O) stored at −20° C. (diluted 50 µl into total of 10 ml miliQ$H_2$O daily=50 µM ATP working stock); 1% BSA (1 g BSA in 100 ml 0.1 M HEPES, pH 7.5, stored at −20° C.), 100 mM $MgCl_2$; 200 µM Staurosporine, 2× Kinase-Glo™ reagent (made fresh or stored at −20° C.).

Standard Assay Setup for 384-well format (20 µl kinase reaction, 40 µl detection reaction): 10 mM $MgCl_2$; 100 µM Abl substrate peptide; 0.1% BSA; 1 µl test compound (in DMSO); 0.4 µg/ml Abl kinase domain; 10 µM ATP; 100 mM HEPES buffer. Positive controls contained DMSO with no test compound. Negative controls contained 10 µM staurosporine. The kinase reactions were initiated at time t=0 by the addition of ATP. Kinase reactions were incubated at 21° C. for 30 min, then 20 µl of Kinase-Glo™ reagent were added to each well to quench the kinase reaction and initiate the luminescence reaction. After a 20 min incubation at 2° C., the luminescence was detected in a plate-reading luminometer.

MET Luminescence-based Enzyme Assay

Materials: Poly Glu-Tyr (4:1) substrate (Sigma Cat# P-0275), ATP (Sigma Cat#A-3377, FW=551), HEPES buffer, pH 7.5, Bovine serum albumin (BSA) (Roche 92423420), $MgCl_2$, Staurosporine (Streptomyces sp. Sigma Cat#85660-1MG), white Costar 384-well flat-bottom plate (VWR Cat#29444-088). MET kinase (see below), Kinase-Glo™ (Promega Cat#V6712).

Stock Solutions: 10 mg/ml poly Glu-Tyr in water, stored at −20° C.; 100 mM HEPES buffer, pH 7.5 (5 ml 1M stock+45 ml miliQ$H_2$O); 10 mM ATP (5.51 mg/ml in d$H_2$O) stored at −20° C. (diluted 50 µl into total of 10 ml miliQ$H_2$O daily=50 µM ATP working stock); 1% BSA (1 g BSA in 100 ml 0.1M HEPES, pH 7.5, stored at −20° C.), 100 mM $MgCl_2$; 200 µM Staurosporine, 2× Kinase-Glo™ reagent (made fresh or stored at −20° C.).

Standard Assay Setup for 384-well format (20 µl kinase reaction, 40 µl detection reaction): 10 mM $MgCl_2$; 0.3 mg/ml poly Glu-Tyr; 0.1% BSA; 1 µl test compound (in DMSO); 0.4 µg/ml MET kinase; 10 µM ATP; 100 mM HEPES buffer. Positive controls contained DMSO with no test compound. Negative controls contained 10 µM staurosporine. The kinase reactions were initiated at time t=0 by the addition of ATP. Kinase reactions were incubated at 21° C. for 60 min, then 20 µl of Kinase-Glo™ reagent were added to each well to quench the kinase reaction and initiate the luminescence reaction.

After a 20 min incubation at 21° C., the luminescence was detected in a plate-reading luminometer.

AurA Luminescence-based Enzyme Assay

Materials: Kemptide peptide substrate=LRRASLG (SEQ ID NO: 2) (Biopeptide, San Diego, Calif.), ATP (Sigma Cat#A-3377, FW=551), HEPES buffer, pH 7.5, 10% Brij 35 (Calbiochem Cat#203728), MgCl$_2$, Staurosporine (*Streptomyces* sp. Sigma Cat#85660-1MG), white Costar 384-well flat-bottom plate (VWR Cat#29444-088), Autophosphorylated AurA kinase (see below), Kinase-Glo™ (Promega Cat#V6712).

Stock Solutions: 10 mM Kemptide peptide (7.72 mg/ml in water), stored at −20° C.; 100 mM HEPES buffer+0.015% Brij 35, pH 7.5 (5 ml 1M HEPES stock+75 µL 10% Brij 35+45 ml miliQH$_2$O); 10 mM ATP (5.51 mg/ml in dH$_2$O) stored at −20° C. (diluted 50 µl into total of 10 ml miliQH$_2$O daily=50 µM ATP working stock); 100 mM MgCl$_2$; 200 µM Staurosporine, 2× Kinase-Glo™ reagent (made fresh or stored at −20° C.).

AurA Autophosphorylation Reaction: ATP and MgCl$_2$ were added to 1-5 mg/ml AurA at final concentrations of 10 mM and 100 mM, respectively. The autophosphorylation reaction was incubated at 21° C. for 2-3 h. The reaction was stopped by the addition of EDTA to a final concentration of 50 mM, and samples were flash frozen with liquid N$_2$ and stored at −80° C.

Standard Assay Setup for 384-well format (20 µl kinase reaction, 40 µl detection reaction): 10 mM MgCl$_2$; 0.2 mM Kemptide peptide; 1 µl test compound (in DMSO); 0.3 µg/ml Autophosphorylated AurA kinase; 10 µM ATP; 100 mM HEPES+0.015% Brij buffer. Positive controls contained DMSO with no test compound. Negative controls contained 5 µM staurosporine. The kinase reactions were initiated at time t=0 by the addition of ATP. Kinase reactions were incubated at 21° C. for 45 min, then 20 µl of Kinase-Glo™ reagent were added to each well to quench the kinase reaction and initiate the luminescence reaction. After a 20 min incubation at 21° C., the luminescence was detected in a plate-reading luminometer.

PDK1 Luminescence-based Enzyme Assay

Materials: PDKtide peptide substrate=KTFCGTPEYLAPEVRREPRILSEEEQEMFRDFDYIADWC (SEQ ID NO: 3) (Upstate Cat#12-401), ATP (Sigma Cat#A-3377, FW=551), HEPES buffer, pH 7.5, 10% Brij 35 (Calbiochem Cat#203728), MgCl$_2$, Staurosporine (*Streptomyces* sp. Sigma Cat#85660-1MG), white Costar 384-well flat-bottom plate (VWR Cat#29444-088), PDK1 kinase (see below), Kinase-Glo™ (Promega Cat#V6712).

Stock Solutions: 1 mM PDKtide substrate (1 mg in 200 µl, as supplied by Upstate), stored at −20° C.; 100 mM HEPES buffer, pH 7.5 (5 ml 1M HEPES stock+45 ml miliQH$_2$O); 10 mM ATP (5.51 mg/ml in dH$_2$O) stored at −20° C. (diluted 25 µl into total of 10 ml miliQH$_2$O daily=25 µM ATP working stock); 100 mM MgCl$_2$; 10% Brij 35 stored at 2-8° C.; 200 µM Staurosporine, 2× Kinase-Glo™ reagent (made fresh or stored at −20° C.).

Standard Assay Setup for 384-well format (20 µl kinase reaction, 40 µl detection reaction): 10 mM MgCl$_2$; 0.01 mM PDKtide; 1 µl test compound (in DMSO); 0.1 µg/ml PDK1 kinase; 5 µM ATP; 10 mM MgCl$_2$; 100 mM HEPES+0.01% Brij buffer. Positive controls contained DMSO with no test compound. Negative controls contained 10 µM staurosporine. The kinase reactions were initiated at time t=0 by the addition of ATP. Kinase reactions were incubated at 21° C. for 40 min, then 20 µl of Kinase-Glo™ reagent were added to each well to quench the kinase reaction and initiate the luminescence reaction. After a 20 min incubation at 21° C., the luminescence was detected in a plate-reading luminometer.

Preparation of Co-expression Plasmid

A lambda phosphatase co-expression plasmid was constructed as follows.

An open-reading frame for Aurora kinase was amplified from a *Homo sapiens* (human) HepG2 cDNA library (ATCC HB-8065) by the polymerase chain reaction (PCR) using the following primers:

```
                                       (SEQ ID NO: 4)
    Forward primer: TCAAAAAAGAGGCAGTGGGCTTTG (SEQ ID NO: 5)
    Reverse primer: CTGAATTTGCTGTGATCCAGG.
```

The PCR product (795 base pairs expected) was gel purified as follows. The PCR product was purified by electrophoresis on a 1% agarose gel in TAE buffer and the appropriate size band was excised from the gel and eluted using a standard gel extraction kit. The eluted DNA was ligated for 5 minutes at room temperature with topoisomerase into pSB2-TOPO. The vector pSB2-TOPO is a topoisomerase-activated, modified version of pET26b (Novagen, Madison, Wis.) wherein the following sequence has been inserted into the NdeI site: CATAATGGGCCATCATCATCATCATCACGGT GGTCATATGTCCCTT (SEQ ID NO: 6) and the following sequence inserted into the BamHI site: AAGGGGGATCCTAAACTGCAGAGATCC (SEQ ID NO: 7). The sequence of the resulting plasmid, from the Shine-Dalgarno sequence through the "original" NdeI site, the stop site and the "original" BamHII site is as follows:

```
                                       (SEQ ID NO: 8)
AAGGAGGAGATATACATAATGGGCCATCATCATCATCATCACGGTGGTCA

TATGTCCCTT (SEQ ID NO: 9)
AAGGGGGATCCTAAACTGCAGAGATCC.
```

The Aurora kinase expressed using this vector has 14 amino acids added to the N-terminus (MetGlyHisHisHisHisHisHisGlyGlyHisMetSerLeu) (SEQ ID NO: 10) and four amino acids added to the C-terminus (GluGlyGlySer) (SEQ ID NO: 11).

The phosphatase co-expression plasmid was then created by inserting the phosphatase gene from lambda bacteriophage into the above plasmid (Matsui T, et al., Biochem. Biophys. Res. Commun., 2001, 284:798-807). The phosphatase gene was amplified using PCR from template lambda bacteriophage DNA (HinDIII digest, New England Biolabs) using the following oligonucleotide primers:

```
Forward primer (PPfor):
                                       (SEQ ID NO: 12)
GCAGAGATCCGAATTCGAGCTCCGTCGACGGATGGAGTGAAAGAGATGCG

C

Reverse primer (PPrev):
                                       (SEQ ID NO: 13)
GGTGGTGGTGCTCGAGTGCGGCCGCAAGCTTTCATCATGCGCCTTCTCCC

TGTAC.
```

The PCR product (744 base pairs expected) was gel purified. The purified DNA and non-co-expression plasmid DNA were then digested with SacI and XhoI restriction enzymes. Both the digested plasmid and PCR product were then gel purified and ligated together for 8 h at 16° C. with T4 DNA ligase and transformed into Top 10 cells using standard procedures. The presence of the phosphatase gene in the co-expression plasmid was confirmed by sequencing. For standard molecular biology protocols followed here, see also, for example, the techniques described in Sambrook et al, Molecular Cloning: A Laboratory Manual, Cold Spring Harbor Laboratory, NY, 2001, and Ausubel et al., Current Protocols in Molecular Biology, Greene Publishing Associates and Wiley Interscience, NY, 1989.

This co-expression plasmid contains both the Aurora kinase and lambda phosphatase genes under control of the lac promoter, each with its own ribosome binding site. By cloning the phosphatase into the middle of the multiple cloning site, downstream of the target gene, convenient restriction sites are available for subcloning the phosphatase into other plasmids. These sites include SacI, SalI and EcoRI between the kinase and phosphatase and HinDIII, NotI and XhoI downstream of the phosphatase.

Protein Kinase Expression

An open-reading frame for c-Abl was amplified from a *Mus musculus* (mouse) cDNA library prepared from freshly harvested mouse liver using a commercially available kit (Invitrogen) by PCR using the following primers:

```
                                          (SEQ ID NO: 14)
Forward primer: GACAAGTGGGAAATGGAGC (SEQ ID NO: 15)
Reverse primer: CGCCTCGTTTCCCCAGCTC.
```

The PCR product (846 base pairs expected) was purified from the PCR reaction mixture using a PCR cleanup kit (Qiagen). The purified DNA was ligated for 5 minutes at room temperature with topoisomerase into pSGX3-TOPO. The vector pSGX3-TOPO is a topoisomerase-activated, modified version of pET26b (Novagen, Madison, Wis.) wherein the following sequence has been inserted into the NdeI site: CATATGTCCCTT (SEQ ID NO: 16) and the following sequence inserted into the BamHI site: AAGGGCAT-CATCACCATCACCACTGATCC (SEQ ID NO: 17). The sequence of the resulting plasmid, from the Shine-Dalgarno sequence through the stop site and the BamHI, site is as follows: AAGGAGGA GATATACATATGTC CCTT (SEQ ID NO: 18) AAGGGCATCAT CACCATCACCACTGATCC (SEQ ID NO: 19). The c-Abl expressed using this vector had three amino acids added to its N-terminus (Met Ser Leu) and 8 amino acids added to its C-terminus (GluGlyHisHisHisHisHisHis) (SEQ ID NO: 20).

A c-Abl /phosphatase co expression plasmid was then created by subcloning the phosphatase from the Aurora co-expression plasmid of Example 1 into the above plasmid. Both the Aurora co-expression plasmid and the Abl non-co-expression plasmid were digested 3 hrs with restriction enzymes EcoRI and NotI. The DNA fragments were gel purified and the phosphatase gene from the Aurora plasmid was ligated with the digested c-Abl plasmid for 8 h at 16° C. and transformed into Top10 cells. The presence of the phosphatase gene in the resulting construct was confirmed by restriction digestion analysis.

This plasmid codes for c-Abl and lambda phosphatase co expression. It has the additional advantage of two unique restriction sites, XbaI and NdeI, upstream of the target gene that can be used for subcloning of other target proteins into this phosphatase co-expressing plasmid.

The plasmid for Abl T315I was prepared by modifying the Abl plasmid using the Quick Change mutagenesis kit (Stratagene) with the manufacturer's suggested procedure and the following oligonucleotides:

```
Mm05582dS4
                                          (SEQ ID NO: 21)
5'-CCACCATTCTACATAATCATTGAGTTCATGACCTATGGG-3'

Mm05582dA4
                                          (SEQ ID NO: 22)
5'-CCCATAGGTCATGAACTCAATGATTATGTAGAATGGTGG-3'.
```

Protein from the phosphatase co-expression plasmids was purified as follows. The non-co-expression plasmid was transformed into chemically competent BL21(DE3)Codon+ RIL (Stratagene) cells and the co-expression plasmid was transformed into BL21(DE3) pSA0145 (a strain that expresses the lytic genes of lambda phage and lyses upon freezing and thawing (Crabtree S, Cronan J E Jr. J Bacteriol 1984 April; 158(1):354-6)) and plated onto petri dishes containing LB agar with kanamycin. Isolated single colonies were grown to mid-log phase and stored at −80° C. in LB containing 15% glycerol. This glycerol stock was streaked on LB agar plates with kanamycin and a single colony was used to inoculate 10 ml cultures of LB with kanamycin and chloramphenicol, which was incubated at 30° C. overnight with shaking. This culture was used to inoculate a 2 L flask containing 500 ml of LB with kanamycin and chloramphenicol, which was grown to mid-log phase at 37° C. and induced by the addition of IPTG to 0.5 mM final concentration. After induction flasks were incubated at 21° C. for 18 h with shaking.

The c-Abl T315I KD (kinase domain) was purified as follows. Cells were collected by centrifugation, lysed in diluted cracking buffer (50 mM Tris HCl, pH 7.5, 500 mM KCl, 0.1% Tween 20, 20 mM Imidazole, with sonication, and centrifuged to remove cell debris. The soluble fraction was purified over an IMAC column charged with nickel (Pharmacia, Uppsala, Sweden), and eluted under native conditions with a gradient of 20 mM to 500 mM imidazole in 50 mM Tris, pH7.8, 500 mM NaCl, 10 mM methionine, 10% glycerol. The protein was then further purified by gel filtration using a Superdex 75 preparative grade column equilibrated in GF5 buffer (10 mM HEPES, pH7.5, 10 mM methionine, 500 mM NaCl, 5 mM DTT, and 10% glycerol). Fractions containing the purified c-Abl T315I KD kinase domain were pooled. The protein obtained was 98% pure as judged by electrophoresis on SDS polyacrylamide gels. Mass spectroscopic analysis of the purified protein showed that it was predominantly singly phosphorylated. The protein was then dephosphorylated with Shrimp Alkaline Phosphatase (MBI Fermentas, Burlington, Canada) under the following conditions: 100U Shrimp Alkaline Phosphatase/mg of c-Abl T315I KD, 100 mM MgCl$_2$, and 250 mM additional NaCl. The reaction was run overnight at 23° C. The protein was determined to be unphosphorylated by Mass spectroscopic analysis. Any precipitate was spun out and the soluble fraction was separated from reactants by gel filtration using a Superdex 75 preparative grade column equilibrated in GF4 buffer (10 mM HEPES, pH7.5, 10 mM methionine, 150 mM NaCl, 5 mM DTT, and 10% glycerol).

Purification of Met:

The cell pellets produced from half of a 12 L Sf9 insect cell culture expressing the kinase domain of human Met were resuspended in a buffer containing 50 mM Tris-HCl pH 7.7 and 250 mM NaCl, in a volume of approximately 40 ml per 1

L of original culture. One tablet of Roche Complete, EDTA-free protease inhibitor cocktail (Cat# 1873580) was added per 1 L of original culture. The suspension was stirred for 1 hour at 4° C. Debris was removed by centrifugation for 30 minutes at 39,800×g at 4° C. The supernatant was decanted into a 500 ml beaker and 10 ml of 50% slurry of Qiagen Ni-NTA Agarose (Cat# 30250) that had been pre-equilibrated in 50 mM Tris-HCl pH 7.8, 50 mM NaCl, 10% Glycerol, 10 mM Imidazole, and 10 mM Methionine, were added and stirred for 30 minutes at 4° C. The sample was then poured into a drip column at 4° C. and washed with 10 column volumes of 50 mM Tris-HCl pH 7.8, 500 mM NaCl, 10% Glycerol, 10 mM Imidazole, and 10 mM Methionine. The protein was eluted using a step gradient with two column volumes each of the same buffer containing 50 mM, 200 mM, and 500 mM Imidazole, sequentially. The 6× Histidine tag was cleaved overnight using 40 units of TEV protease (Invitrogen Cat# 10127017) per 1 mg of protein while dialyzing in 50 mM Tris-HCl pH 7.8, 500 mM NaCl, 10% Glycerol, 10 mM Imidazole, and 10 mM Methionine at 4° C. The 6× Histidine tag was removed by passing the sample over a Pharmacia 5 ml IMAC column (Cat# 17-0409-01) charged with Nickel and equilibrated in 50 mM Tris-HCl pH 7.8, 500 mM NaCl, 10% Glycerol, 10 mM Imidazole, and 10 mM Methionine. The cleaved protein bound to the Nickel column at a low affinity and was eluted with a step gradient. The step gradient was run with 15% and then 80% of the B-side (A-side=50 mM Tris-HCl pH 7.8, 500 mM NaCl, 10% Glycerol, 10 mM Imidazole, and 10 mM Methionine; B-side=50 mM Tris-HCl pH 7.8, 500 mM NaCl, 10% Glycerol, 500 mM Imidazole, and 10 mM Methionine) for 4 column volumes each. The Met protein eluted in the first step (15%), whereas the non-cleaved Met and the cleaved Histidine tag eluted in the 80% fractions. The 15% fractions were pooled after SDS-PAGE gel analysis confirmed the presence of cleaved Met; further purification was done by gel filtration chromatography on an Amersham Biosciences HiLoad 16/60 Superdex 200 prep grade (Cat# 17-1069-01) equilibrated in 50 mM Tris-HCl pH 8.5, 150 mM NaCl, 10% Glycerol and 5 mM DTT. The cleanest fractions were combined and concentrated to ~10.4 mg/ml by centrifugation in an Amicon Ultra-15 10,000 Da MWCO centrifugal filter unit (Cat# UFC901024).

Purification of AurA:

The Sf9 insect cell pellets (18 g) produced from 6 L of cultured cells expressing human Aurora-2 were resuspended in 50 mM Na Phosphate pH 8.0, 500 mM NaCl, 10% glycerol, 0.2% n-octyl-β-D-glucopyranoside (BOG) and 3 mM β-Mercaptoethanol (BME). One tablet of Roche Complete, EDTA-free protease inhibitor cocktail (Cat# 1873580) and 85 units Benzonase (Novagen Cat#70746-3)) were added per 1 L of original culture. Pellets were resuspended in approximately 50 ml per 1 L of original culture and were then sonicated on ice with two 30-45 sec bursts (100% duty cycle). Debris was removed by centrifugation and the supernatant was passed through a 0.8 µm syringe filter before being loaded onto a 5 ml Ni$^{2+}$ HiTrap column (Pharmacia). The column was washed with 6 column volumes of 50 mM Na Phosphate pH 8.0, 500 mM NaCl, 10% glycerol, 3 mM BME. The protein was eluted using a linear gradient of the same buffer containing 500 mM Imidazole. The eluant (24 ml) was cleaved overnight at 4° C. in a buffer containing 50 mM Na Phosphate pH 8.0, 500 mM NaCl, 10% glycerol, 3 mM BME and 10,000 units of TEV (Invitrogen Cat# 10127-017). The protein was passed over a second nickel affinity column as described above; the flow-through was collected. The cleaved protein fractions were combined and concentrated using spin concentrators. Further purification was done by gel filtration chromatography on a S75 sizing column in 50 mM Na Phosphate (pH 8.0), 250 mM NaCl, 1 mM EDTA, 0.1 mM AMP-PNP or ATP buffer, and 5 mM DTT. The cleanest fractions were combined and concentrated to approximately 8-11 mg/ml, and were either flash frozen in liquid nitrogen in 120 µl aliquots and stored at −80° C., or stored at 4° C.

Purification of PDK1:

Cell pellets produced from 6 L of Sf9 insect cells expressing human PDK1 were resuspended in a buffer containing 50 mM Tris-HCl pH 7.7 and 250 mM NaCl in a volume of approximately 40 mL per 1 L of original culture. One tablet of Roche Complete, EDTA-free protease inhibitor cocktail (Cat# 1873580) and 85 units Benzonase (Novagen Cat#70746-3)) were added per 1 L of original culture. The suspension was stirred for 1 hour at 4° C. Debris was removed by centrifugation for 30 minutes at 39,800×g at 4° C. The supernatant was decanted into a 500 mL beaker and 10 ml of a 50% slurry of Qiagen Ni-NTA Agarose (Cat# 30250) that had been pre-equilibrated in 50 mM Tris-HCl pH 7.8, 500 mM NaCl, 10% Glycerol, 10 mM Imidazole, and 10 mM Methionine, were added and stirred for 30 minutes at 4° C. The sample was then poured into a drip column at 4° C. and washed with 10 column volumes of 50 mM Tris-HCl pH 7.8, 500 mM NaCl, 10% Glycerol, 10 mM Imidazole, and 10 mM Methionine. The protein was eluted using a step gradient with two column volumes each of the same buffer containing 50 mM, and 500 mM Imidazole, sequentially. The 6× Histidine tag was cleaved overnight using 40 units of TEV protease (Invitrogen Cat# 10127017) per 1 mg of protein while dialyzing in 50 mM Tris-HCl pH 7.8, 500 mM NaCl, 10% Glycerol, 10 mM Imidazole, and 10 mM Methionine at 4° C. The 6× Histidine tag was removed by passing the sample over a Pharmacia 5 ml IMAC column (Cat# 17-0409-01) charged with Nickel and equilibrated in 50 mM Tris-HCl pH 7.8, 500 mM NaCl, 10% Glycerol, 10 mM Imidazole, and 10 mM Methionine. The cleaved protein eluted in the flow-through, whereas the uncleaved protein and the His-tag remained bound to the Ni-column. The cleaved protein fractions were combined and concentrated using spin concentrators. Further purification was done by gel filtration chromatography on an Amersham Biosciences HiLoad 16/60 Superdex 200 prep grade (Cat# 17-1069-01) equilibrated in 25 mM Tris-HCl pH 7.5, 150 mM NaCl, and 5 mM DTT. The cleanest fractions were combined and concentrated to ~15 mg/ml by centrifugation in an Amicon Ultra-15 10,000 Da MWCO centrifugal filter unit (Cat# UFC901024).

Example 3

Cell Assays

MV4-11 and THP cells were maintained in Iscove's Modified Dulbecco's Medium supplemented with 10% fetal bovine serum (FBS) and penicillin/streptomycin, Ba/F3 cells were maintained in RPMI 1640 supplemented with 10% FBS, penicillin/streptomycin and 5 ng/ml recombinant mouse IL-3.

Cell Survival Assays

Compounds were tested in the following assays in duplicate.

96-well XTT assay: Cells were grown in growth media containing various concentrations of compounds (duplicates) on a 96-well plate for 72 hours at 37° C. The starting cell number was 5000-8000 cells per well and volume was 120 µl. At the end of the 72-hour incubation, 40 µl of XTT labeling mixture (50:1 solution of sodium 3'-[1-(phenylamino-carbonyl)-3,4-tetrazolium]-bis (4-methoxy-6-nitro) benzene sulfonic acid hydrate and Electron-coupling reagent: PMS (N-methyl dibenzopyrazine methyl sulfate) were added to each well of the plate. After an additional 2-6 hours of incubation at 37° C., the absorbance reading at 405 nm with background correction at 650 nm was measured with a spectrophotometer.

384-well AlamarBlue assay: 90 µl of cell suspension were plated onto each well of a 384-well plate preprinted with 0.5 µl of compound in DMSO or DMSO only. The starting cell number was 4000 cells per well. After a 72-hour incubation, 10 µl of AlamarBlue solution (440 µM resazurin in PBS) were then added to each well of the plate. After an additional 2-hour incubation at 37° C., fluorescence was measured using a TECAN plate reading fluorometer with excitation at 535 nm and emission at 591 nm.

BCR-ABL Phospho-ELISA Assay

The following table shows the reagents that were typically used in the BCR-ABL phospho-ELISA ("P-ELISA") assay.

TABLE 40

BCR-ABL phospho-ELISA(p-ELISA) Typical Reagent List

| Description | Vendor | Catalog # |
|---|---|---|
| RPMI 1640 | Invitrogen | 11875-135 |
| 10% Fetal Bovine Serum, characterized, heat inactivated | VWR | 16777-014 |
| Human Plasma, Anticoagulant = EDTA | Bioreclamation Inc. | HMPLEDTA |
| c-Abl (Ab-3) monoclonal antibody | VWR | 80001-286 |
| Recombinant Mouse Interleukin-3 | Chemicon | IL015 |
| Adhesive Plate Seals | | |
| 96 well PP 325 µl round bottom plate w/ lid TC | Thompson Instrument Co | 932465 |
| 96 well Nunc Maxisorp plate (for colorimetric assay) | Fisher Scientific | 12-565-136 |
| 96 well white flat-bottom plate (for luminescent assay) | Matrix | 4923 |
| Lysis buffer components | | |
| Tris-Cl pH 7.4 (20 mM) | | |
| NP-40 (1%) | | |
| EDTA (5 mM) | | |
| Sodium pyrophosphate (NaPP; 5 mM) | | |
| NaF (5 mM) | | |
| NaCl (150 mM) | | |
| Protease Inhibitor Cocktail | Sigma | P2714 |
| PMSF (1 mM) | | |
| Sodium vanadate (NaVO$_4$; 2 mM) | | |
| PBS, ice cold | | |
| Anti-Phosphotyrosine (4G10 ™), HRP conjugate or unconjugated | Upstate | 16-105 or 05-321 |
| Goat Anti-Mouse IgG, HRP conjugate (if unconjugated 4G10 is used) | Upstate | 12-349 |
| BD OptEIA Reagent Set B | BD Biosciences | 550534 |
| Coating Buffer (0.1M Na-carbonate, pH 9.5) | | |
| Assay Diluent | | |
| Wash buffer (.05% Tween/PBS) | | |
| Stop Solution (2N sulfuric acid) | | |
| Substrate Reagents A&B | | |
| SuperSignal ELISA Pico Chemiluminescent Substrate (may be used instead of Substrate Reagents A&B) | Pierce | 37070 |

Cells (Ba/F$_3$ cells transfected with WT BCR-ABL, other kinases, or T315I, Y253F, or other mutant forms of BCR-ABL) were grown in the absence of IL-3 at least ½ week before the assay. The day before assay, the cells were fed with fresh media so that at the time of assay the cells were in log phase. Ba/F3 cells that had been grown in the absence of IL-3 for at least ½ week were resuspended in RPMI 1640 so that each well of a 96-well plate would contain approximately 200,000 cells. Cells were distributed in a 96-well plate containing serially diluted concentrations of test compounds. Cells were typically incubated with or without test compounds for 60-120 minutes at 5% $CO_2$, 37° C. The incubation was performed with or without other additives such as 10% FCS or 50% human plasma. After incubation of compounds, lysis buffer was added and incubated for 10-15 minutes; the lysate was cleared by centrifugation.

To make the ELISA plate, commercially available Anti-ABL antibodies (e.g. (Ab-3, Calbiochem OP20) were prepared at a concentration of 0.125 µg/ml in coating buffer (0.1M Na-carbonate, pH 9.5), and plated at 10 ml per plate (12.5 µl 100 µg/ml Ab/10 ml). In a high binding multi-well plate, 100 µl Ab in coating buffer were added to each well, and each plate was covered with a plate seal and incubated overnight at 4° C.

Excess antibody was removed and the ELISA plate was washed 3-4 times with 200 µl of wash buffer (0.05% Tween in PBS, pH 7.4). 150 µl of lysate (see above) were transferred to the ELISA plate. Plates were sealed and incubated 2 hours at room temperature. The detection antibody (e.g. HRP conjugated anti-pTyr or unconjugated α-p-Y 4G10, Upstate) was prepared in assay diluent. The antibody was diluted 1:1000 (stock=2 µg/µl, 200 µg in 100 µl; f.c.=2 µg/ml) in assay diluent and 10 ml of diluted antibody per plate were added. The lysate was removed from the ELISA plates, and wells were washed four times with 200 µl of wash buffer per well. 100 µl of detection antibody was added to each well; the plate was covered, and incubated 1 hr at room temperature (21° C.). Excess detection antibody was removed from the ELISA plates, and the wells were washed four times with 200 µl of wash buffer per well.

If necessary, (i.e. for unconjugated anti-pTyr antibody) secondary antibody (goat anti-rabbit HRP) was diluted 1:3000 in assay diluent (3.33 µl per 10 ml diluent) and added at 10 ml of diluted antibody per plate. Excess secondary antibody was removed from the ELISA plate, and the plate was washed four times with 200 µl per well of wash buffer.

Substrate Reagent A and Substrate Reagent B (Pierce Cat#37070 SuperSignal ELISA Pico Chemiluminescent Substrate) were added immediately before use (10 ml resultant solution per plate). 100 µl substrate were added per well, mixed for 1 minute, and chemiluminescent signal was measured with a luminometer.

Assay Results on Selected Compounds:

Abl_T315 Bioassay:

$IC_{50}$<0.05 µM: AE1, AE2, AE3, AE4, AE5, AE6, AE7, AE8, AE9, AE10, AE11, AE12, AE13, AE14, AE15, AE16, AE17, AE18, AE19, AE20, AE21, AE22, AE23, AE24, AE25, AE27, AE28, AE29, AE30, AE31, AE32, AE33, AE34, AE35, AE37, AE40, AE41, AE42, AE43, AE44, AE47, AE48, AE49, AE50, AE52, AE55, AE58, AE59, AE60, AE61, AE64, AE62, AE63, AE65, AE66, AE67 and AE68.

0.05 µM<$IC_{50}$<0.2 µM: AE26, AE36, AE38, AE39, AE45, AE46, AE51, AE53 and AE54.

Abl_T315 p-ELISA Cellular Assay:

$IC_{50}$<0.1 µM: AE1, AE3, AE5, AE6, AE7, AE14, AE20, AE25, AE26, AE30, AE31, AE37, AE41, AE42, AE44, AE54, AE55, AE58 and AE64.

0.1 µM<$IC_{50}$<1 µM: AE2, AE4, AE9, AE11, AE13, AE15, AE16, AE18, AE19, AE22, AE29, AE32, AE34, AE35, AE48, AE49, AE52, AE61, AE62 and AE63.

AurA Bioassay:

$IC_{50}$<0.5 µM: AE6, AE7, AE15, AE30, AE31, AE32, AE34, AE35, AE47, AE51, AE52, AE53, AE54, AE55 and AE60.

0.5 µM<$IC_{50}$<5 µM: AE1, AE11, AE13, AE33, AE59, AE62, AE67, AE68.

Met Bioassay:

$IC_{50}$<1 µM: AE8, AE14, AE40, AE42, AE43, AE48, AE53, AE56 and AE66.

1 µM<$IC_{50}$<5 µM: AE22, AE26, AE41, AE46, AE52, AE57, AE58 and AE65.

PDK1 Bioassay:

$IC_{50}$<1 µM: AE50, AE55 and AE58.

1 µM<$IC_{50}$<5 µM: AE2, AE3, AE9, AE10, AE11, AE20, AE21, AE38, AE44, AE45, AE46, AE48, AE49, AE52, AE53, AE59, AE60, AE61, AE63 and AE64.

What is claimed is:

1. A method of modulating the activity of a protein kinase comprising contacting said protein kinase with a compound of Formula IV:

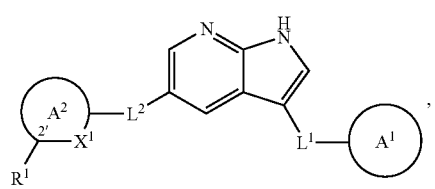

(IV)

wherein
L$^1$ and L$^2$ are bonds;
A$^1$ is substituted or unsubstituted phenyl;
A$^2$ is substituted or unsubstituted pyridinyl;

R$^1$ is halogen, —OR$^5$, —NR$^6$R$^7$, —C(Z)R$^8$, —S(O)$_w$R$^9$, —CN, —NO$_2$, —CF$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein w is an integer from 0 to 2;

X$^1$ is —C(R$^2$)=, or —N=;

R$^2$ is independently hydrogen, halogen, —OR$^5$, —NR$^6$R$^7$, —C(Z)R$^8$, —S(O)$_w$R$^9$, —CN, —NO$_2$, —CF3, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein w is an integer from 0 to 2;

Z is N(R$^{23}$), S, or O, wherein R$^{23}$ is hydrogen, substituted or unsubstituted alkyl, or substituted or unsubstituted heteroalkyl;

R$^5$ is independently hydrogen, —CF$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^6$ and R$^7$ are independently hydrogen, —C(O)R$^{10}$, —S(O)$_2$R$^{11}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^8$ is independently hydrogen, —NR$^{14}$R$^{15}$, —OR$^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is independently hydrogen, —NR$^{17}$R$^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl R$^{10}$ and R$^{11}$ are independently hydrogen, —NR$^{12}$R$^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{12}$ and R$^{13}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{14}$, R$^{15}$, and R$^{16}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{17}$ and R$^{18}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or wherein R$^6$ and R$^7$, R$^{12}$ and R$^{13}$, R$^{14}$ and R$^{15}$, and R$^{17}$ and R$^{18}$ are independently joined with the nitrogen to which they are attached to form substituted or unsubstituted heterocycloalkyl, or substituted or unsubstituted 5-membered heteroaryl.

2. The method of claim 1, wherein A$^1$ is substituted phenyl.

3. The method of claim 2, wherein A$^1$ is substituted with a halogen.

4. The method of claim 1, wherein A$^1$ has formula II:

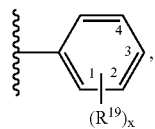

(II)

wherein x is an integer from 1 to 5;

R$^{19}$ is independently halogen, —OR$^5$, —NR$^6$R$^7$, —C(Z)R$^8$, —S(O)$_w$R$^9$, —CN, —NO$_2$, —CF$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or wherein two R$^{19}$ groups are combined to form a substituted or unsubstituted ring with the carbons to which they are attached.

5. The method of claim 4, wherein an R$^{19}$ attached at position 1 is combined with an R$^{19}$ attached at position 2 to form a substituted or unsubstituted ring.

6. The method of claim 4, wherein an R$^{19}$ attached at position 2 is combined with an R$^{19}$ attached at position 3 to form a substituted or unsubstituted ring.

7. The method of claim 4, wherein two R$^{19}$ groups are combined to form a substituted or unsubstituted ring with the carbons to which they are attached, wherein the substituted or unsubstituted ring is substituted or unsubstituted heterocycloalkyl or substituted or unsubstituted heteroaryl.

8. The method of claim 4, wherein R$^{19}$ is independently halogen, —NR$^6$R$^7$, OR$^5$, or substituted or unsubstituted alkyl.

9. The method of claim 4, wherein R$^5$, R$^6$, and R$^7$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or wherein R$^6$ and R$^7$ are joined with nitrogen to which they are attached to form substituted or unsubstituted heterocycloalkyl, or substituted or unsubstituted 5-membered heteroaryl.

10. The method of claim 8, wherein R$^5$, R$^6$, and R$^7$ are independently hydrogen, or substituted or unsubstituted alkyl.

11. The method of claim 8, wherein R$^5$, R$^6$, and R$^7$ are independently hydrogen, or substituted or unsubstituted C$_1$-C$_6$ alkyl.

12. The method of claim 4, wherein x is 1; and R$^{19}$ is attached at position 2.

13. The method of claim 4, wherein x is 1; and R$^{19}$ is attached at position 1.

14. The method of claim 4, wherein x is an integer from 2 to 5; and at least one R$^{19}$ is attached at position 1.

15. The method of claim 4, wherein x is an integer from 2 to 5; and at least one R$^{19}$ is attached at position 2.

16. The method of claim 1, wherein A$^2$ has formula VI:

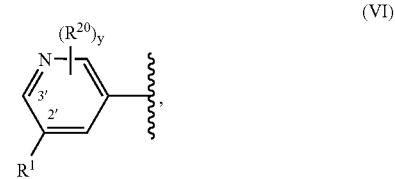

(VI)

wherein y is an integer from 0 to 3;

R$^{20}$ is independently —OR$^5$, —NR$^6$R$^7$, —C(Z)R$^8$, —S(O)$_w$R$^9$, —CN, —NO$_2$, —CF$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or wherein one $R^{20}$ and $R^1$ are combined to form a substituted or unsubstituted ring with the carbons to which they are attached.

17. The method of claim 16, wherein y is 1; and $R^{20}$ is attached at position 3'.

18. The method of claim 1, wherein $R^1$ is —C(O)NR$^{14}$R$^{15}$.

19. The method of claim 16, wherein $R^1$ is —C(O)NR$^{14}$R$^{15}$.

20. The method of claim 2, wherein $R^1$ is —C(O)NR$^{14}$R$^{15}$.

21. The method of claim 1, wherein
   $R^1$ is —C(O)NR$^{14}$R$^{15}$; and
   $R^{14}$ and $R^{15}$ are independently substituted or unsubstituted alkyl, substituted or unsubstituted heteroalkyl, or wherein $R^{14}$ and $R^{15}$ are combined with the nitrogen to which they are attached to form substituted or unsubstituted piperidinyl, or substituted or unsubstituted piperazinyl, substituted or unsubstituted pyrrolidinyl, or substituted or unsubstituted morpholino.

22. The method of claim 21, wherein y is 0.

23. The method of claim 18, wherein $R^{14}$ and $R^{15}$ are combined with the nitrogen to which they are attached to form a piperazinyl substituted with a substituted or unsubstituted alkyl or substituted or unsubstituted heteroalkyl.

24. The method of claim 23, wherein the piperazinyl is substituted with —(CH$_2$)$_t$—NR$^{21}$R$^{22}$, wherein
   t is an integer from 0 to 6; and
   $R^{21}$ and $R^{22}$ are independently hydrogen, substituted or unsubstituted alkyl;
   substituted or unsubstituted heteroalkyl, substituted or unsubstituted cycloalkyl, substituted or unsubstituted heterocycloalkyl, substituted or unsubstituted aryl, or substituted or unsubstituted heteroaryl, or wherein $R^{21}$ and $R^{22}$ are combined with the nitrogen to which they are attached to form a substituted or unsubstituted heterocycloalkyl or substituted or unsubstituted heteroaryl.

25. The method of claim 24, wherein $R^{21}$ and $R^{22}$ are combined with the nitrogen to which they are attached to form a substituted or unsubstituted piperazinyl, substituted or unsubstituted piperidinyl, or substituted or unsubstituted morpholino.

26. The method of claim 24, wherein $R^{21}$ and $R^{22}$ are independently hydrogen, substituted or unsubstituted alkyl, or substituted or unsubstituted aminoalkyl.

27. The method of claim 1, wherein $A^1$ is substituted with at least one —OR$^5$, wherein $R^5$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

28. The method of claim 4, wherein A2 has formula VI:

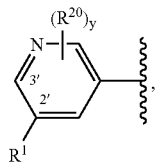

(VI)

wherein
   y is an integer from 0 to 3; and
   $R^{20}$ is halogen, —OR$^5$, —NR$^6$R$^7$, —C(Z)R$^8$, —S(O)$_w$R$^9$, —CN, —CF$_3$, —NO$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

29. The method of claim 28, wherein y is 1; and $R^{20}$ is attached at position 3'.

30. The method of any of claims 1; or 2-29 wherein the protein kinase is selected from the group consisting of Abelson tyrosine kinase, Ron receptor tyrosine kinase, Met receptor tyrosine kinase, Ems-like tyrosine kinase-3, Aurora kinases, p21-activated kinase-4, and 3-phosphoinositide-dependent kinase-1.

31. The method of claim any of claims 1 or 2-29, wherein said protein kinase is a Bcr-Abl kinase having a mutation selected from the group consisting of M244V, L248V, G250E, G250A, Q252H, Q252R, Y253F, Y253H, E255K, E255V, D276G, F311L, T315I, T315N, T315A, F317V, F317L, M343T, M351T, E355G, F359A, F359V, V379I, F382L, L387M, H396P, H396R, S417Y, E459K and F486S.

32. The method of claim any of claims 1 or 2-29, wherein said protein kinase is a Bcr-Abl kinase having a mutation selected from the group consisting of, wherein said mutation is T315I.

* * * * *

UNITED STATES PATENT AND TRADEMARK OFFICE
CERTIFICATE OF CORRECTION

| | | |
|---|---|---|
| PATENT NO. | : 7,582,637 B2 | Page 1 of 1 |
| APPLICATION NO. | : 12/040527 | |
| DATED | : September 1, 2009 | |
| INVENTOR(S) | : William D. Arnold et al. | |

It is certified that error appears in the above-identified patent and that said Letters Patent is hereby corrected as shown below:

On the Title Page, Item (56), replace "Perspectivesin" with -- Perspectives in --

On the Title Page, Item (74), replace "Wilson Sonsini Goorich & Rosati" with -- Wilson Sonsini Goodrich & Rosati --

In line 62 of column 284 (Claim 1) in the Claims section of the patent, replace "-CF3" with -- —CF3 --

In line 1 of column 285 (Claim 1) in the Claims section of the patent, replace "N($R^{23}$)" with -- N(R23) --

In line 25 of column 285 (Claim 1) in the Claims section of the patent, replace "het-eroaryl" with -- heteroaryl --

In line 23 of column 286 (Claim 8) in the Claims section of the patent, replace "$OR^5$" with -- OR5 --

In line 5 of column 288 (Claim 28) in the Claims section of the patent, replace "A2" with -- $A^2$ --

In line 27 of column 288 (Claim 30) in the Claims section of the patent, replace "1;" with -- 1 --

In line 30 of column 288 (Claim 30) in the Claims section of the patent, replace "Ems-ike" with -- FMS-like --

In line 33 of column 288 (Claim 31) in the Claims section of the patent, replace "method of claim any of claims 1" with -- method of any of claims 1 --

In line 40 of column 288 (Claim 32) in the Claims section of the patent, replace "method of claim any of claims 1" with -- method of any of claims 1 --

Signed and Sealed this

Thirteenth Day of April, 2010

David J. Kappos
*Director of the United States Patent and Trademark Office*

SEQUENCE LISTING

```
<160> NUMBER OF SEQ ID NOS: 23

<210> SEQ ID NO 1
<211> LENGTH: 12
<212> TYPE: PRT
<213> ORGANISM: Artificial Sequence
<220> FEATURE:
<223> OTHER INFORMATION: Synthetic construct - AB1 substrate peptide

<400> SEQUENCE: 1

Glu Ala Ile Tyr Ala Ala Pro Phe Ala Lys Lys Lys
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic construct - Kemptide peptide
      substrate

<400> SEQUENCE: 2

Leu Arg Arg Ala Ser Leu Gly
1               5

<210> SEQ ID NO 3
<211> LENGTH: 39
<212> TYPE: PRT
<213> ORGANISM: Artificial Sequence
<220> FEATURE:
<223> OTHER INFORMATION: Synthetic construct - PDKtide peptide substrate

<400> SEQUENCE: 3

Lys Thr Phe Cys Gly Thr Pro Glu Tyr Leu Ala Pro Glu Val Arg Arg
1               5                   10                  15

Glu Pro Arg Ile Leu Ser Glu Glu Glu Gln Glu Met Phe Arg Asp Phe
            20                  25                  30

Asp Tyr Ile Ala Asp Trp Cys
        35

<210> SEQ ID NO 4
<211> LENGTH: 24
<212> TYPE: DNA
<213> ORGANISM: Artificial Sequence
<220> FEATURE:
<223> OTHER INFORMATION: Forward primer

<400> SEQUENCE: 4
tcaaaaaaga ggcagtgggc tttg                                           24

<210> SEQ ID NO 5
<211> LENGTH: 21
```

```
<212> TYPE: DNA
<213> ORGANISM: Artificial Sequence
<220> FEATURE:
<223> OTHER INFORMATION: Reverse primer

<400> SEQUENCE: 5
ctgaatttgc tgtgatccag g                                               21

<210> SEQ ID NO 6
<211> LENGTH: 46
<212> TYPE: DNA
<213> ORGANISM: Artificial Sequence
<220> FEATURE:
<223> OTHER INFORMATION: Synthetic construct - sequence inserted into
      NdeI site of vector pSB2-TOPO

<400> SEQUENCE: 6
cataatgggc catcatcatc atcatcacgg tggtcatatg tccctt                    46

<210> SEQ ID NO 7
<211> LENGTH: 27
<212> TYPE: DNA
<213> ORGANISM: Artificial Sequence
<220> FEATURE:
<223> OTHER INFORMATION: Synthetic construct - sequence inserted into
      BamHI site of vector pSB2-TOPO

<400> SEQUENCE: 7 aaggggatc ctaaactgca gagatcc                                          27

<210> SEQ ID NO 8
<211> LENGTH: 60
<212> TYPE: DNA
<213> ORGANISM: Artificial Sequence
<220> FEATURE:
<223> OTHER INFORMATION: Synthetic construct - portion of resulting
      plasmid sequence upstr eam of ORF

<400> SEQUENCE: 8
aaggaggaga tatacataat gggccatcat catcatcatc acggtggtca tatgtccctt     60

<210> SEQ ID NO 9
<211> LENGTH: 27
<212> TYPE: DNA
<213> ORGANISM: Artificial Sequence
<220> FEATURE:
<223> OTHER INFORMATION: Synthetic construct - portion of resulting
      plasmid sequence downs tream of ORF

<400> SEQUENCE: 9 aaggggatc ctaaactgca gagatcc                                          27

<210> SEQ ID NO 10
<211> LENGTH: 14
<212> TYPE: PRT
<213> ORGANISM: Artificial Sequence
<220> FEATURE:
<223> OTHER INFORMATION: Synthetic construct - amino acids added to
      N-terminus of expresse d Aurora kinase

<400> SEQUENCE: 10

Met Gly His His His His His His Gly Gly His Met Ser Leu
1               5                   10

<210> SEQ ID NO 11
<211> LENGTH: 4
<212> TYPE: PRT
```

```
<213> ORGANISM: Artificial Sequence
<220> FEATURE:
<223> OTHER INFORMATION: Synthetic construct - amino acids added to
      C-terminus of expressed Aurora kinase

<400> SEQUENCE: 11

Glu Gly Gly Ser
1

<210> SEQ ID NO 12
<211> LENGTH: 51
<212> TYPE: DNA
<213> ORGANISM: Artificial Sequence
<220> FEATURE:
<223> OTHER INFORMATION: Forward primer - PPfor

<400> SEQUENCE: 12
gcagagatcc gaattcgagc tccgtcgacg gatggagtga aagagatgcg c            51

<210> SEQ ID NO 13
<211> LENGTH: 55
<212> TYPE: DNA
<213> ORGANISM: Artificial Sequence
<220> FEATURE:
<223> OTHER INFORMATION: Reverse primer - PPrev

<400> SEQUENCE: 13
ggtggtggtg ctcgagtgcg gccgcaagct ttcatcatgc gccttctccc tgtac        55

<210> SEQ ID NO 14
<211> LENGTH: 19
<212> TYPE: DNA
<213> ORGANISM: Artificial Sequence
<220> FEATURE:
<223> OTHER INFORMATION: Forward primer

<400> SEQUENCE: 14
gacaagtggg aaatggagc                                                19

<210> SEQ ID NO 15
<211> LENGTH: 19
<212> TYPE: DNA
<213> ORGANISM: Artificial Sequence
<220> FEATURE:
<223> OTHER INFORMATION: Reverse primer

<400> SEQUENCE: 15
cgcctcgttt ccccagctc                                                19

<210> SEQ ID NO 16
<211> LENGTH: 12
<212> TYPE: DNA
<213> ORGANISM: Artificial Sequence
<220> FEATURE:
<223> OTHER INFORMATION: Synthetic construct - sequence inserted into
      NdeI site of vector pSGX3-TOPO

<400> SEQUENCE: 16
catatgtccc tt                                                       12

<210> SEQ ID NO 17
<211> LENGTH: 29
<212> TYPE: DNA
<213> ORGANISM: Artificial Sequence
<220> FEATURE:
<223> OTHER INFORMATION: Synthetic construct - sequence inserted into
      the BamHI site of vector pSGX3-TOPO
```

```
<400> SEQUENCE: 17
aagggcatca tcaccatcac cactgatcc                                    29

<210> SEQ ID NO 18
<211> LENGTH: 26
<212> TYPE: DNA
<213> ORGANISM: Artificial Sequence
<220> FEATURE:
<223> OTHER INFORMATION: Synthetic construct - portion of resulting
      plasmid sequence upstream of ORF

<400> SEQUENCE: 18
aaggaggaga tatacatatg tccctt                                       26

<210> SEQ ID NO 19
<211> LENGTH: 29
<212> TYPE: DNA
<213> ORGANISM: Artificial Sequence
<220> FEATURE:
<223> OTHER INFORMATION: Synthetic construct - portion of resulting
      plasmid sequence downstream of ORF

<400> SEQUENCE: 19
aagggcatca tcaccatcac cactgatcc                                    29

<210> SEQ ID NO 20
<211> LENGTH: 8
<212> TYPE: PRT
<213> ORGANISM: Artificial Sequence
<220> FEATURE:
<223> OTHER INFORMATION: Synthetic construct - amino acids added to
      C-terminus of expressed c-AB1

<400> SEQUENCE: 20

Glu Gly His His His His His His
1               5

<210> SEQ ID NO 21
<211> LENGTH: 39
<212> TYPE: DNA
<213> ORGANISM: Artificial Sequence
<220> FEATURE:
<223> OTHER INFORMATION: Synthetic construct - Mm05582dS4
      oligonucleotide used to modify Abl plasmid

<400> SEQUENCE: 21
ccaccattct acataatcat tgagttcatg acctatggg                         39

<210> SEQ ID NO 22
<211> LENGTH: 39
<212> TYPE: DNA
<213> ORGANISM: Artificial Sequence
<220> FEATURE:
<223> OTHER INFORMATION: Synthetic construct - Mm05582dA4
      oligonucleotide used to modify Abl plasmid

<400> SEQUENCE: 22
cccataggtc atgaactcaa tgattatgta gaatggtgg                         39

<210> SEQ ID NO 23
<211> LENGTH: 1130
<212> TYPE: PRT
<213> ORGANISM: Homo sapiens

<400> SEQUENCE: 23
```

```
Met Leu Glu Ile Cys Leu Lys Leu Val Gly Cys Lys Ser Lys Lys Gly
1               5                   10                  15

Leu Ser Ser Ser Ser Cys Tyr Leu Glu Glu Ala Leu Gln Arg Pro
            20                  25                  30

Val Ala Ser Asp Phe Glu Pro Gln Gly Leu Ser Glu Ala Ala Arg Trp
            35                  40                  45

Asn Ser Lys Glu Asn Leu Leu Ala Gly Pro Ser Glu Asn Asp Pro Asn
        50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
                85                  90                  95

Gly Glu Trp Cys Glu Ala Gln Thr Lys Asn Gly Gln Gly Trp Val Pro
                100                 105                 110

Ser Asn Tyr Ile Thr Pro Val Asn Ser Leu Glu Lys His Ser Trp Tyr
            115                 120                 125

His Gly Pro Val Ser Arg Asn Ala Ala Glu Tyr Leu Leu Ser Ser Gly
        130                 135                 140

Ile Asn Gly Ser Phe Leu Val Arg Glu Ser Glu Ser Ser Pro Gly Gln
145                 150                 155                 160

Arg Ser Ile Ser Leu Arg Tyr Glu Gly Arg Val Tyr His Tyr Arg Ile
                165                 170                 175

Asn Thr Ala Ser Asp Gly Lys Leu Tyr Val Ser Ser Glu Ser Arg Phe
            180                 185                 190

Asn Thr Leu Ala Glu Leu Val His His Ser Thr Val Ala Asp Gly
        195                 200                 205

Leu Ile Thr Thr Leu His Tyr Pro Ala Pro Lys Arg Asn Lys Pro Thr
210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gly Gln Tyr Gly Glu Val
            245                 250                 255

Tyr Glu Gly Val Trp Lys Lys Tyr Ser Leu Thr Val Ala Val Lys Thr
                260                 265                 270

Leu Lys Glu Asp Thr Met Glu Val Glu Glu Phe Leu Lys Glu Ala Ala
        275                 280                 285

Val Met Lys Glu Ile Lys His Pro Asn Leu Val Gln Leu Leu Gly Val
        290                 295                 300

Cys Thr Arg Glu Pro Pro Phe Tyr Ile Ile Thr Glu Phe Met Thr Tyr
305                 310                 315                 320

Gly Asn Leu Leu Asp Tyr Leu Arg Glu Cys Asn Arg Gln Glu Val Asn
                325                 330                 335

Ala Val Val Leu Leu Tyr Met Ala Thr Gln Ile Ser Ser Ala Met Glu
            340                 345                 350

Tyr Leu Glu Lys Lys Asn Phe Ile His Arg Asp Leu Ala Ala Arg Asn
        355                 360                 365

Cys Leu Val Gly Glu Asn His Leu Val Lys Val Ala Asp Phe Gly Leu
370                 375                 380

Ser Arg Leu Met Thr Gly Asp Thr Tyr Thr Ala His Ala Gly Ala Lys
385                 390                 395                 400

Phe Pro Ile Lys Trp Thr Ala Pro Glu Ser Leu Ala Tyr Asn Lys Phe
                405                 410                 415

Ser Ile Lys Ser Asp Val Trp Ala Phe Gly Val Leu Leu Trp Glu Ile
```

-continued

```
              420             425             430
Ala Thr Tyr Gly Met Ser Pro Tyr Pro Gly Ile Asp Leu Ser Gln Val
    435                 440                 445

Tyr Glu Leu Leu Glu Lys Asp Tyr Arg Met Glu Arg Pro Glu Gly Cys
    450                 455                 460

Pro Glu Lys Val Tyr Glu Leu Met Arg Ala Cys Trp Gln Trp Asn Pro
465                 470                 475                 480

Ser Asp Arg Pro Ser Phe Ala Glu Ile His Gln Ala Phe Glu Thr Met
                    485                 490                 495

Phe Gln Glu Ser Ser Ile Ser Asp Glu Val Lys Glu Leu Gly Lys
                500                 505                 510

Gln Gly Val Arg Gly Ala Val Ser Thr Leu Leu Gln Ala Pro Glu Leu
            515                 520                 525

Pro Thr Lys Thr Arg Thr Ser Arg Ala Ala Glu His Arg Asp Thr
        530                 535                 540

Thr Asp Val Pro Glu Met Pro His Ser Lys Gly Gln Gly Glu Ser Asp
545                 550                 555                 560

Pro Leu Asp His Glu Pro Ala Val Ser Pro Leu Leu Pro Arg Lys Glu
                565                 570                 575

Arg Gly Pro Pro Glu Gly Gly Leu Asn Glu Asp Glu Arg Leu Leu Pro
                580                 585                 590

Lys Asp Lys Lys Thr Asn Leu Phe Ser Ala Leu Ile Lys Lys Lys Lys
                595                 600                 605

Lys Thr Ala Pro Thr Pro Pro Lys Arg Ser Ser Ser Phe Arg Glu Met
            610                 615                 620

Asp Gly Gln Pro Glu Arg Arg Gly Ala Gly Glu Glu Gly Arg Asp
625                 630                 635                 640

Ile Ser Asn Gly Ala Leu Ala Phe Thr Pro Leu Asp Thr Ala Asp Pro
                    645                 650                 655

Ala Lys Ser Pro Lys Pro Ser Asn Gly Ala Gly Val Pro Asn Gly Ala
                660                 665                 670

Leu Arg Glu Ser Gly Gly Ser Gly Phe Arg Ser Pro His Leu Trp Lys
            675                 680                 685

Lys Ser Ser Thr Leu Thr Ser Ser Arg Leu Ala Thr Gly Glu Glu Glu
            690                 695                 700

Gly Gly Gly Ser Ser Ser Lys Arg Phe Leu Arg Ser Cys Ser Ala Ser
705                 710                 715                 720

Cys Val Pro His Gly Ala Lys Asp Thr Glu Trp Arg Ser Val Thr Leu
                    725                 730                 735

Pro Arg Asp Leu Gln Ser Thr Gly Arg Gln Phe Asp Ser Ser Thr Phe
                740                 745                 750

Gly Gly His Lys Ser Glu Lys Pro Ala Leu Pro Arg Lys Arg Ala Gly
            755                 760                 765

Glu Asn Arg Ser Asp Gln Val Thr Arg Gly Thr Val Thr Pro Pro Pro
            770                 775                 780

Arg Leu Val Lys Lys Asn Glu Glu Ala Ala Asp Glu Val Phe Lys Asp
785                 790                 795                 800

Ile Met Glu Ser Ser Pro Gly Ser Ser Pro Pro Asn Leu Thr Pro Lys
                    805                 810                 815

Pro Leu Arg Arg Gln Val Thr Val Ala Pro Ala Ser Gly Leu Pro His
                820                 825                 830

Lys Glu Glu Ala Glu Lys Gly Ser Ala Leu Gly Thr Pro Ala Ala Ala
            835                 840                 845
```

-continued

```
Glu Pro Val Thr Pro Thr Ser Lys Ala Gly Ser Gly Ala Pro Gly Gly
    850             855             860

Thr Ser Lys Gly Pro Ala Glu Glu Ser Arg Val Arg Arg His Lys His
865             870             875             880

Ser Ser Glu Ser Pro Gly Arg Asp Lys Gly Lys Leu Ser Arg Leu Lys
            885             890             895

Pro Ala Pro Pro Pro Pro Ala Ala Ser Ala Gly Lys Ala Gly Gly
        900             905             910

Lys Pro Ser Gln Ser Pro Ser Gln Glu Ala Ala Gly Glu Ala Val Leu
    915             920             925

Gly Ala Lys Thr Lys Ala Thr Ser Leu Val Asp Ala Val Asn Ser Asp
930             935             940

Ala Ala Lys Pro Ser Gln Pro Gly Glu Gly Leu Lys Lys Pro Val Leu
945             950             955             960

Pro Ala Thr Pro Lys Pro Gln Ser Ala Lys Pro Ser Gly Thr Pro Ile
            965             970             975

Ser Pro Ala Pro Val Pro Ser Thr Leu Pro Ser Ala Ser Ser Ala Leu
        980             985             990

Ala Gly Asp Gln Pro Ser Ser Thr Ala Phe Ile Pro Leu Ile Ser Thr
        995             1000            1005

Arg Val Ser Leu Arg Lys Thr Arg Gln Pro Pro Glu Arg Ile Ala
    1010            1015            1020

Ser Gly Ala Ile Thr Lys Gly Val Val Leu Asp Ser Thr Glu Ala
    1025            1030            1035

Leu Cys Leu Ala Ile Ser Arg Asn Ser Glu Gln Met Ala Ser His
    1040            1045            1050

Ser Ala Val Leu Glu Ala Gly Lys Asn Leu Tyr Thr Phe Cys Val
    1055            1060            1065

Ser Tyr Val Asp Ser Ile Gln Gln Met Arg Asn Lys Phe Ala Phe
    1070            1075            1080

Arg Glu Ala Ile Asn Lys Leu Glu Asn Asn Leu Arg Glu Leu Gln
    1085            1090            1095

Ile Cys Pro Ala Thr Ala Gly Ser Gly Pro Ala Ala Thr Gln Asp
    1100            1105            1110

Phe Ser Lys Leu Leu Ser Ser Val Lys Glu Ile Ser Asp Ile Val
    1115            1120            1125

Gln Arg
    1130
```